(12) United States Patent
Rogers et al.

(10) Patent No.: US 10,333,069 B2
(45) Date of Patent: Jun. 25, 2019

(54) PURIFICATION OF CARBON NANOTUBES VIA SELECTIVE HEATING

(71) Applicants: THE BOARD OF TRUSTEES OF THE UNIVERSITY OF ILLINOIS, Urbana, IL (US); NORTHWESTERN UNIVERSITY, Evanston, IL (US); UNIVERSITY OF MIAMI, Miami, FL (US)

(72) Inventors: John A. Rogers, Champaign, IL (US); William L. Wilson, Champaign, IL (US); Sung Hun Jin, Urbana, IL (US); Simon N. Dunham, Atlanta, GA (US); Xu Xie, Urbana, IL (US); Ahmad Islam, Beavercreek, OH (US); Frank Du, Urbana, IL (US); Yonggang Huang, Glencoe, IL (US); Jizhou Song, Zhejiang (CN)

(73) Assignees: The Board of Trustees of The University of Illinois, Urbana, IL (US); Northwestern University, Evanston, IL (US); University of Miami, Miami, FL (US)

( * ) Notice: Subject to any disclaimer, the term of this patent is extended or adjusted under 35 U.S.C. 154(b) by 0 days.

(21) Appl. No.: 15/354,951

(22) Filed: Nov. 17, 2016

(65) Prior Publication Data
US 2017/0291817 A1 Oct. 12, 2017

Related U.S. Application Data

(63) Continuation of application No. 14/772,312, filed as application No. PCT/US2014/032848 on Apr. 3, 2014, now Pat. No. 9,825,229.
(Continued)

(51) Int. Cl.
*H01L 51/00* (2006.01)
*H01L 21/02* (2006.01)
(Continued)

(52) U.S. Cl.
CPC .......... *H01L 51/0048* (2013.01); *B82Y 30/00* (2013.01); *C01B 32/17* (2017.08);
(Continued)

(58) Field of Classification Search
None
See application file for complete search history.

(56) References Cited

U.S. PATENT DOCUMENTS 7,195,733 B2  3/2007  Rogers et al.
7,521,292 B2  4/2009  Rogers et al.
(Continued)

OTHER PUBLICATIONS

U.S. Appl. No. 11/465,317, filed Aug. 17, 2006.
(Continued)

*Primary Examiner* — Benjamin P Sandvik
(74) *Attorney, Agent, or Firm* — Leydig, Voit & Mayer, Ltd.

(57) ABSTRACT

The present invention provides methods for purifying a layer of carbon nanotubes comprising providing a precursor layer of substantially aligned carbon nanotubes supported by a substrate, wherein the precursor layer comprises a mixture of first carbon nanotubes and second carbon nanotubes; selectively heating the first carbon nanotubes; and separating the first carbon nanotubes from the second carbon nanotubes, thereby generating a purified layer of carbon nanotubes. Devices benefiting from enhanced electrical properties enabled by the purified layer of carbon nanotubes are also described.

13 Claims, 72 Drawing Sheets

Related U.S. Application Data

(60) Provisional application No. 61/808,572, filed on Apr. 4, 2013.

(51) Int. Cl.
    *C01B 32/17*         (2017.01)
    *B82Y 30/00*         (2011.01)
    *G01N 21/62*         (2006.01)
    *H01M 4/1393*       (2010.01)

(52) U.S. Cl.
    CPC ....... *G01N 21/62* (2013.01); *H01L 21/02606* (2013.01); *H01L 51/0004* (2013.01); *H01M 4/1393* (2013.01); *C01B 2202/22* (2013.01); *C01B 2202/34* (2013.01); *H01L 51/0025* (2013.01)

(56) References Cited

U.S. PATENT DOCUMENTS

| | | |
|---|---|---|
| 7,557,367 B2 | 7/2009 | Rogers et al. |
| 7,622,367 B1 | 11/2009 | Nuzzo et al. |
| 7,704,684 B2 | 4/2010 | Rogers et al. |
| 7,705,280 B2 | 4/2010 | Nuzzo et al. |
| 7,776,764 B2 | 8/2010 | Cho et al. |
| 7,799,699 B2 | 9/2010 | Nuzzo et al. |
| 7,932,123 B2 | 4/2011 | Rogers et al. |
| 7,943,491 B2 | 5/2011 | Nuzzo et al. |
| 7,972,875 B2 | 7/2011 | Rogers et al. |
| 7,982,296 B2 | 7/2011 | Nuzzo et al. |
| 8,039,847 B2 | 10/2011 | Nuzzo et al. |
| 8,198,621 B2 | 6/2012 | Rogers et al. |
| 8,217,381 B2 | 7/2012 | Rogers et al. |
| 8,367,035 B2 | 2/2013 | Rogers et al. |
| 8,394,706 B2 | 3/2013 | Nuzzo et al. |
| 8,440,546 B2 | 5/2013 | Nuzzo et al. |
| 8,470,701 B2 | 6/2013 | Rogers et al. |
| 8,552,299 B2 | 10/2013 | Rogers et al. |
| 8,562,095 B2 | 10/2013 | Alleyene et al. |
| 8,664,699 B2 | 3/2014 | Nuzzo et al. |
| 8,666,471 B2 | 3/2014 | Rogers et al. |
| 8,679,888 B2 | 3/2014 | Rogers et al. |
| 8,722,458 B2 | 5/2014 | Rogers et al. |
| 8,729,524 B2 | 5/2014 | Rogers et al. |
| 8,754,396 B2 | 6/2014 | Rogers et al. |
| 8,865,489 B2 | 10/2014 | Rogers et al. |
| 8,895,406 B2 | 11/2014 | Rogers et al. |
| 8,905,772 B2 | 12/2014 | Rogers et al. |
| 8,934,965 B2 | 1/2015 | Rogers et al. |
| 8,946,683 B2 | 2/2015 | Rogers et al. |
| 9,057,994 B2 | 6/2015 | Rogers et al. |
| 9,061,494 B2 | 6/2015 | Rogers et al. |
| 9,105,555 B2 | 8/2015 | Rogers et al. |
| 9,105,782 B2 | 8/2015 | Rogers et al. |
| 9,117,940 B2 | 8/2015 | Rogers et al. |
| 9,278,522 B2 | 3/2016 | Rogers et al. |
| 9,324,733 B2 | 4/2016 | Rogers et al. |
| 9,349,900 B2 | 5/2016 | Rogers et al. |
| 9,442,285 B2 | 9/2016 | Rogers |
| 9,450,043 B2 | 9/2016 | Nuzzo et al. |
| 9,487,002 B2 | 11/2016 | Rogers et al. |
| 9,496,229 B2 | 11/2016 | Rogers et al. |
| 9,515,025 B2 | 12/2016 | Rogers et al. |
| 9,554,484 B2 | 1/2017 | Rogers et al. |
| 9,555,644 B2 | 1/2017 | Rogers et al. |
| 9,601,671 B2 | 3/2017 | Rogers et al. |
| 9,613,911 B2 | 4/2017 | Rogers et al. |
| 9,647,171 B2 | 5/2017 | Rogers et al. |
| 9,691,873 B2 | 6/2017 | Rogers et al. |
| 2002/0085968 A1 | 7/2002 | Smalley et al. |
| 2004/0043219 A1 | 4/2004 | Ito et al. |
| 2007/0273264 A1 | 11/2007 | Choi et al. |
| 2008/0055581 A1 | 3/2008 | Rogers et al. |
| 2011/0081770 A1* | 4/2011 | Tombler, Jr. ........... B82Y 10/00 438/466 |
| 2011/0136304 A1* | 6/2011 | Wong ..................... B82Y 10/00 438/167 |
| 2011/0147715 A1 | 6/2011 | Rogers et al. |
| 2011/0262772 A1 | 10/2011 | Hauge et al. |
| 2011/0290648 A1 | 12/2011 | Majlof et al. |
| 2011/0316120 A1 | 12/2011 | Rogers et al. |
| 2012/0157804 A1 | 6/2012 | Rogers et al. |
| 2012/0165759 A1 | 6/2012 | Rogers et al. |
| 2012/0261551 A1 | 10/2012 | Rogers et al. |
| 2012/0320581 A1 | 12/2012 | Rogers et al. |
| 2012/0321785 A1* | 12/2012 | Rogers ................... B82Y 10/00 427/249.1 |
| 2013/0036928 A1 | 2/2013 | Rogers et al. |
| 2013/0041235 A1 | 2/2013 | Rogers et al. |
| 2013/0140649 A1 | 6/2013 | Rogers et al. |
| 2013/0181189 A1* | 7/2013 | Bertin .................... B82Y 10/00 257/29 |
| 2013/0333094 A1 | 12/2013 | Rogers et al. |
| 2014/0163390 A1 | 6/2014 | Rogers et al. |
| 2014/0191236 A1 | 7/2014 | Nuzzo et al. |
| 2014/0220422 A1 | 8/2014 | Rogers et al. |
| 2014/0305900 A1 | 10/2014 | Rogers et al. |
| 2014/0323968 A1 | 10/2014 | Rogers et al. |
| 2014/0361409 A1 | 12/2014 | Rogers et al. |
| 2014/0374872 A1 | 12/2014 | Rogers et al. |
| 2015/0001462 A1 | 1/2015 | Rogers et al. |
| 2015/0080695 A1 | 3/2015 | Rogers et al. |
| 2015/0132873 A1 | 5/2015 | Rogers et al. |
| 2015/0141767 A1 | 5/2015 | Rogers et al. |
| 2015/0181700 A1 | 6/2015 | Rogers et al. |
| 2015/0207012 A1 | 7/2015 | Rogers et al. |
| 2015/0237711 A1 | 8/2015 | Rogers et al. |
| 2015/0290938 A1 | 10/2015 | Rogers et al. |
| 2015/0373831 A1 | 12/2015 | Rogers et al. |
| 2015/0380355 A1 | 12/2015 | Rogers et al. |
| 2016/0005700 A1 | 1/2016 | Rogers et al. |
| 2016/0027737 A1 | 1/2016 | Rogers et al. |
| 2016/0066789 A1 | 3/2016 | Rogers et al. |
| 2016/0072027 A1 | 3/2016 | Rogers et al. |
| 2016/0133843 A1 | 5/2016 | Rogers et al. |
| 2016/0136877 A1 | 5/2016 | Rogers et al. |
| 2016/0284544 A1 | 9/2016 | Nuzzo et al. |
| 2016/0293794 A1 | 10/2016 | Nuzzo et al. |
| 2016/0381789 A1 | 12/2016 | Rogers et al. |
| 2017/0020402 A1 | 1/2017 | Rogers et al. |
| 2017/0128015 A1 | 5/2017 | Rogers et al. |
| 2017/0164482 A1 | 6/2017 | Rogers et al. |
| 2017/0179085 A1 | 6/2017 | Rogers et al. |
| 2017/0179356 A1 | 6/2017 | Rogers et al. |
| 2017/0181704 A1 | 6/2017 | Rogers et al. |
| 2017/0200679 A1 | 7/2017 | Rogers et al. |
| 2017/0200707 A1 | 7/2017 | Rogers et al. |

OTHER PUBLICATIONS

U.S. Appl. No. 12/372,605, filed Feb. 17, 2009.
U.S. Appl. No. 13/095,502, filed Apr. 27, 2011.
U.S. Appl. No. 15/354,951, filed Nov. 17, 2016.
U.S. Appl. No. 15/374,926, filed Dec. 9, 2016.
U.S. Appl. No. 15/402,684, filed Jan. 10, 2017.
U.S. Appl. No. 15/501,364, filed Feb. 2, 2017.
U.S. Appl. No. 15/501,373, filed Feb. 2, 2017.
U.S. Appl. No. 15/501,379, filed Feb. 2, 2017.
U.S. Appl. No. 15/515,494, filed Mar. 29, 2017.
U.S. Appl. No. 15/477,865, filed Apr. 3, 2017.
U.S. Appl. No. 15/625,087, filed Jun. 16, 2017.
U.S. Appl. No. 15/632,004, filed Jun. 23, 2017.
U.S. Appl. No. 15/640,206, filed Jun. 30, 2017.
PCT/US16/35331, Jun. 1, 2016, WO 2016/196673, Dec. 8, 2016.
PCT/US16/35336, Jun. 1, 2016, WO 2016/196675, Dec. 8, 2016.
PCT/US16/40717, Jul. 1, 2016, WO 2017/004531, Jan. 5, 2017.
PCT/US16/40814, Jul. 1, 2016, WO 2017/004576, Jan. 5, 2017.
Arnold et al. (2006) "Sorting carbon nanotubes by electronic structure using density differentiation," Nature Nanotechnol. 1:60-65.
Assael et al. (2005) "Thermal conductivity of polymethyl methacrylate (PMMA) and borosilicate crown glass BK7," Int. J. Thermophys. 26:1595-1605.

(56) References Cited

OTHER PUBLICATIONS

Balasubramanian et al. (2004) "A Selective Electrochemical Approach to Carbon Nanotube Field-Effect Transistors," Nano Lett. 4:827-830.
Banerjee et al. (2004) "Demonstration of Diameter-Selective Reactivity in the Sidewall Ozonation of SWNTs by Resonance Raman Spectroscopy," Nano Lett. 4:1445-1450.
Beck et al. (1978) "Lattice conductivities of single-crystal and polycrystalline materials at mantle pressures and temperatures," Physics of the Earth and Planetary Interiors. 17:35-53.
Blech et al. (1982) "Effects of Humidity on Stress in Thin Silicon Dioxide Films," J. Appl. Phys. 53:4202-4207.
Cao et al. (2008) "Medium-scale carbon nanotube thin-film integrated circuits on flexible plastic substrates," Nature. 454:495-500.
Cao et al. (2009) "Ultrathin Films of Single-Walled Carbon Nanotubes for Electronics and Sensors: A Review of Fundamental and Applied Aspects," J. Advanced Materials. 21:29-53.
Cassell et al. (1999) "Large Scale CVD Synthesis of Single-Walled Carbon Nanotubes," J. Phys. Chem. B. 103(31):6484-6492.
Che et al. (Jul. 31, 2012) "Selective synthesis and device applications of semiconducting single-walled carbon nanotubes using isopropyl alcohol as feedstock," ACS Nano. 6(8):7454-7462.
Cheng et al. (1998) "Large-Scale and Low-Cost Synthesis of Single-Walled Carbon Nanotubes by the Catalytic Pyrolysis of Hydrocarbons," Appl. Phys. Lett. 72(25:3282-3284.
Chiang et al. (2001) "Purification and Characterization of Single-Wall Carbon Nanotubes (SWNTs) Obtained from the Gas-Phase Decomposition of CO (HiPco Process)," J. Phys. Chem. B. 105:8297-8301.
Chou et al. (1997) "Imprint lithography with sub-10 nm feature size and high throughput," Microelectron. Eng. 35:237-240.
Collins et al. (2001) "Engineering Carbon Nanotubes and Nanotube Circuits Using Electrical Breakdown," Science. 292:706-709.
Dai et al. (2006) "Molecular Glass Resists for High-Resolution Patterning," Chem. Mat. 18:3404-3411.
Davis (1987) "Thermocapillary Instabilities. Annual Review Fluid Mechanics," 19:403-435.
Ding et al. (2009) "Selective Growth of Well-Aligned Semiconducting Single-Walled Carbon Nanotubes," Nano Letters. 9:800-805.
Duesberg et al. (1998) "Chromatographic size separation of single-wall carbon nanotubes," Appl. Phys. A. 67:117-119.
Engel et al. (2008) "Thin Film Nanotube Transistors Based on Self-Assembled, Aligned, Semiconducting Carbon Nanotube Arrays," ACS Nano 2:2445-2452.
Felts et al. (May 3, 2012) "Nanometer-scale flow of molten polyethylene from a heated atomic force microscope tip," Nanotechnology. 23:215301.
Feng et al. (2003) "Removal of Some Impurities from Carbon Nanotubes," Chem. Phys. Lett. 375:645-648.
Ferkl et al. (Jun. 28, 2013) "Heat transfer in one-dimensional micro- and nano-cellular foams," Chemical Eng. Sci. 97:50-58.
Franklin et al. (2010) "Current Scaling in Aligned Carbon Nanotube Array Transistors With Local Bottom Gating," IEEE Electron Dev. Lett. 31:644-646.
Green et al. (2011) "Nearly Single-Chirality Single-Walled Carbon Nanotubes Produced via Orthogonal Iterative Density Gradient Ultracentrifugation," Adv. Mater. 23:2185-2190.
Grosse et al. (2011) "Nanoscale Joule heating, Peltier cooling and current crowding at graphene-metal contacts," Nature Nanotechnol. 6:287-290.
Hafner et al. (1998) "Catalytic growth of single-wall carbon nanotubes from metal particles," Chem. Phys. Lett. 296(1-2):195-202.
Holzinger et al. (2000) "A new purification method for single-wall carbon nanotubes (SWNTs)," Applied Physics A. 70:599-602.
Hu et al. (2003) "Sidewall Functionalization of Single-Walled Carbon Nanotubes by Addition of Dichlorocarbene," J. Am. Chem. Soc. 125:14893-14900.

Huang et al. (2003) "Preferential Destruction of Metallic Single-Walled Carbon Nanotubes by Laser Irradiation," J. Phys. Chem. B. 110:7316-7320.
Hur et al. (2005) "Organic Nanodielectrics for Low Voltage Carbon Nanotube Thin Film Transistors and Complementary Logic Gates," J. Am. Chem. Soc. 127:13808-13809.
International Search Report with Written Opinion corresponding to International Patent Application No. PCT/US2014/032848, dated Aug. 22, 2014.
Ishiyama et al. (2002) "Effects of humidity on Young's modulus in poly(methyl methacrylate)," J. Polym. Sci. Pol. Phys. 40:460-465.
Islam et al. (Mar. 9, 2012) "Effect of variations in diameter and density on the statistics of aligned array carbon-nanotube field effect transistors," J. Appl. Phys. 111:054511.
Javey et al. (2004) "High-Field Quasiballistic Transport in Short Carbon Nanotubes," Phy. Rev. Lett. 92:106804.
Jin et al. (2004) "Pentacene OTFTs with PVA Gate Insulators on a Flexible Substrate," J. Kor. Phy. Soc. 44:181-184.
Jin et al. (2011) "Localized Temperature and Chemical Reaction Control in Nanoscale Space by Nanowire Array," Nano Lett. 11:4818-4825.
Jin et al. (Mar. 2012) "Sources of Hysteresis in Carbon Nanotube Field-Effect Transistors and Their Elimination Via Methylsiloxane Encapsulants and Optimized Growth Procedures," Adv. Func. Mat. 22:2276-2284.
Jin et al. (Feb. 7, 2014) "Fundamental effects in nanoscale thermocapillary flow," J. Appl. Phys. 115:054315.
Jin et al. (Apr. 28, 2013) "Using nanoscale thermocapillary flows to create arrays of purely semiconducting single-walled carbon nanotubes," Nature Nanotech. 8:347-355.
Journet et al. (1997) "Large-scale production of single-walled carbon nanotubes by the electric-arc technique," Nature. 388:756-758.
Ju et al. (1999) "Process-dependent thermal transport properties of silicon-dioxide films deposited using low-pressure chemical vapor deposition," J. Appl. Phys. 85:7130-7134.
Kang et al. (2007) "High-performance Electronics Using Dense, Perfectly Aligned Arrays of Single-Walled Carbon Nanotubes," Nature Nanotechnology 2:230-236.
Kang et al. (2007) "Printed Multilayer Superstructures of Aligned Single-Walled Carbon Nanotubes for Electronic Applications," Nano Lett. 7:3343-3348.
Kim (1996) "Influence of substrates on the elastic reaction of films for the microindentation tests," Thin Solid Films. 283:12-16.
Kim et al. (2003) "Hysteresis Caused by Water Molecules in Carbon Nanotube Field-Effect Transistors," Nano Lett. 3:193-198.
Kitiyanan et al. (2000) "Controlled production of single-wall carbon nanotubes by catalytic decomposition of CO on bimetallic Co—Mo catalysts," Chem. Phys. Lett. 317(3-5):497-503.
Kocabas et al. (2007) "Improved Synthesis of Aligned Arrays of Single-Walled Carbon Nanotubes and Their Implementation in Thin Film Type Transistors," J. Phys. Chem. C. 111:17879-17886.
Kocabas et al. (2008) "Radio frequency analog electronics based on carbon nanotube transistors," Proc. Natl. Acad. Sci. USA 105:1405-1409.
Kocabas et al. (2009) "High-Frequency Performance of Submicrometer Transistors That Use Aligned Arrays of Single-Walled Carbon Nanotubes," Nano Lett 9(5):1937-1943.
Krupke et al. (2003) "Separation of Metallic from Semiconducting Single-Walled Carbon Nanotubes," Science. 301:344-347.
Lan et al. (2011) "Physics and applications of aligned carbon nanotubes," Advances in Physics. 60(4):553-678.
Lee et al. (2006) "Electrical, thermal, and mechanical characterization of silicon microcantilever heaters," J. Microelectromech. Syst. 15:1644-1655.
LeMieux et al. (2008) "Self-Sorted, Aligned Nanotube Networks for Thin-Film Transistors," Science. 321:101-104.
Li et al. (2007) "Langmuir—Blodgett Assembly of Densely Aligned Single-Walled Carbon Nanotubes from Bulk Materials," J. Am. Chem. Soc. 129:4890-4891.
Liao et al. (2008) "Avalanche-Induced Current Enhancement in Semiconducting Carbon Nanotubes," Phy. Rev. Lett. 101:256804.

(56) References Cited

OTHER PUBLICATIONS

Liao et al. (2010) "Thermal dissipation and variability in electrical breakdown of carbon nanotube devices," Phy. Rev. B. 82:205406.
Liu et al. (1998) "Fullerene Pipes," Science 280:1253-1256.
Liu et al. (2006) "Modeling and data for thermal conductivity of ultrathin single-crystal SOI layers at high temperature," IEEE Trans. Electron Dev. 53:1868-1876.
Liu et al. (2011) "Large-scale single-chirality separation of single-wall carbon nanotubes by simple gel chromatography," Nature Commun. 2:1-8.
Lundstrom (2000) *Fundamentals of Carrier Transport*. Cambridge University Press. p. 235.
Majeste et al. (1998) "Viscoelasticity of low molecular weight polymers and the transition to the entangled regime," Rheol. Acta. 37:486-499.
Maria et al. (2006) "Experimental and computational studies of phase shift lithography with binary elastomeric masks," J. Vac. Sci. & Technol. B: Microelectronics and Nanometer Structures. 24:828-835.
McKenna et al. (1987) "Dilute solution characterization of cyclic polystyrene molecules and their zero-shear viscosity in the melt," Macromolecules 20:498-512.
Moreira et al. (2001) "Influence of temperature, molecular weight, and molecular weight dispersity on the surface tension of PS, PP, and PE. I. Experimental," Journal of Appl. Polymer Sci. 82:1907-1920.
Nougaret et al. (2009) "80 GHz field-effect transistors produced using high purity semiconducting single-walled carbon nanotubes," Appl. Phys. Lett. 94:243505.
Okada et al. (1984) "Precise Determination of Lattice-Parameter and Thermal-Expansion Coefficient of Silicon between 300-K and 1500-K," J. Appl. Phys. 56:314-320.
Paddock et al. (1986) "Transient thermoreflectance from thin metal films," J. Appl. Phys. 60:285-290.
Park et al. (2007) "Selective Surface Functionalization of Silicon Nanowires via Nanoscale Joule Heating," Nano Lett. 7:3106-3111.
Patil et al. (2009) "Wafer-Scale Growth and Transfer of Aligned Single-Walled Carbon Nanotubes," IEEE Trans. Nanotech. 8:498-504.
Perebeinos et al. (2006) "Mobility in Semiconducting Carbon Nanotubes at Finite Carrier Density," Nano Lett. 6:205-208.
Pesetski et al. (2008) "A 500 MHz Carbon Nanotube Transistor Oscillator," Applied Physics Letters. 93:123506.
Pop (2008) "The role of electrical and thermal contact resistance for Joule breakdown of single-wall carbon nanotubes," Nanotechnology. 19:295202.
Rinzler et al. (1998) "Large-scale purification of single-wall carbon nanotubes: process, product, and characterization," Appl. Phys. A. 67:29-37.
Rutherglen et al. (2009) "Nanotube electronics for radiofrequency applications," Nature Nanotechnology. 4:811-819.
Ryu et al. (2008) "CMOS-Analogous Wafer-Scale Nanotube-on-Insulator Approach For Submicrometer Devices and Integrated Circuits Using Aligned Nanotubes," Nano Lett. 9:189-197.
Shulaker et al. (2011) "Linear Increases in Carbon Nanotube Density Through Multiple Transfer Technique," Nano Lett. 11:1881-1886.
Snow et al. (2005) "Chemical Detection with a Single-Walled Carbon Nanotube Capacitor," Science. 307:1942-1945.
Su et al. (2000) "A scalable CVD method for the synthesis of single-walled carbon nanotubes with high catalyst productivity," Chem. Phys. Lett. 322(5):321-326.
Sun et al. (2011) "Flexible high-performance carbon nanotube integrated circuits," Nature Nanotechnol. 6:156-161.
Tada et al. (2000) "Thermal expansion coefficient of polycrystalline silicon and silicon dioxide thin films at high temperatures," J. Appl. Phys. 87:4189-4193.
Takenobu et al. (2003) "Hydrogen storage in $C_{70}$ encapsulated single-walled carbon nanotube," Synthetic Metals. 135-136:787-788.
Thess et al. (1996) "Crystalline Ropes of Metallic Carbon Nanotubes," Science 273:483-487.
Tsutsumi et al. (1988) "Measurement of Thermal-Diffusivity for Polymer Film by Flash Radiometry," Appl. Phys. Lett. 52:442-444.
Tu et al. (2009) "DNA sequence motifs for structure-specific recognition and separation of carbon nanotubes," Nature. 460:250-253.
Varesi et al. (1998) "Scanning Joule expansion microscopy at nanometer scales," App. Phys. Lett. 72:37-39.
Wahab et al. (Jan. 16, 2013) "Electrostatic Dimension of Aligned-Array Carbon Nanotube Field-Effect Transistors," ACS Nano. 7:1299-1308.
Wang et al. (2010) "Macroelectronic Integrated Circuits Using High-Performance Separated Carbon Nanotube Thin-Film Transistors," ACS Nano 4:7123-7132.
Wang et al. (2010) "Synthesis and device applications of high-density aligned carbon nanotubes using low-pressure chemical vapor deposition and stacked multiple transfer," Nano Research. 3:831-842.
Wang et al. (2011) "Metal Contact Engineering and Registration-Free Fabrication of Complementary Metal-Oxide Semiconductor Integrated Circuits Using Aligned Carbon Nanotubes," ACS Nano. 5:1147-1153.
Wang et al. (Feb. 7, 2012) "Extremely Bendable, High-Performance Integrated Circuits Using Semiconducting Carbon Nanotube Networks for Digital, Analog, and Radio-Frequency Applications," Nano Lett. 12:1527-1533.
Weitz et al. (2007) "High-Performance Carbon Nanotube Field Effect Transistors with a Thin Gate Dielectric Based on a Self-Assembled Monolayer," Nano Lett. 7:22-27.
Wortman et al. (1965) "Youngs Modulus Shear Modulus and Poissons Ratio in Silicon and Germanium," J. Appl. Phys. 36:153.
Wu et al. (1995) "Film Thickness Dependent Thermal-Expansion in Ultrathin Poly(Methyl Methacrylate) Films on Silicon," Macromolecules. 28:771-774.
Wu et al. (May 6, 2012) "Short channel field-effect transistors from highly enriched semiconducting carbon nanotubes," Nano Research. 5:388-394.
Wulf et al. (1999) "A new method for the simultaneous determination of surface tension and density of polymer melts," Phy. Chem. Chemical Phys. 1:3899-3903.
Xiao et al. (2009) "Alignment Controlled Growth of Single-Walled Carbon Nanotubes on Quartz Substrates," Nano Lett. 9:4311-4319.
Xie et al. (Aug. 6, 2012) "Electroluminescence in Aligned Arrays of Single-Wall Carbon Nanotubes with Asymmetric Contacts," ACS Nano. 6:7981-7988.
Xie et al. (Oct. 12, 2012) Quantitative Thermal Imaging of Single-Walled Carbon Nanotube Devices by Scanning Joule Expansion Microscopy, ACS Nano 6, 10267-10275.
Xiong et al. (Dec. 21, 2012) "Self-Aligned Nanotube—Nanowire Phase Change Memory," Nano Lett. 13:464.
Zhang et al. (2010) "Self-aligned nanolithography by selective polymer dissolution," Nanoscale. 2:2302-2306.
Zhao et al. (2009) "Multiband Mobility in Semiconducting Carbon Nanotubes," IEEE Electron Dev. Lett. 30:1078-1080.
Zheng et al. (2002) "CVD synthesis and purification of single-walled carbon nanotubes on aerogel-supported catalyst," Applied Physics A. 74:345-348.
Zheng et al. (2007) "Enrichment of Single Chirality Carbon Nanotubes," J. Am. Chem. Soc. 129:6084-6085.
Zhou et al. (2005) "Band Structure, Phonon Scattering, and the Performance Limit of Single-Walled Carbon Nanotube Transistors," Phys. Rev. Lett. 95:146805.
Zhou et al. (2008) "Wafer scale synthesis of dense aligned arrays of single-walled carbon nanotubes," Nano Research. 1:158-165.

\* cited by examiner

Providing a precursor layer of substantially aligned carbon nanotubes comprising a mixture of first carbon nanotubes (e.g., a first subset of nanotubes having one or more selected physical or chemical property) and second carbon nanotubes (e.g., a second subset).

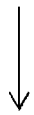

Covering the precursor layer with a thermocapillary resist provided in thermal contact (optionally in physical contact) with the carbon nanotubes including at least a portion of the first carbon nanotubes.

Selectively heating the first carbon nanotubes to generate a thermocapillary flow of the thermocapillary resist away from the first carbon nanotubes, thereby exposing at least a portion of the first carbon nanotubes of the precursor layer.

Separating at least a portion of the first carbon nanotubes (e.g. exposed first nanotubes) from the second carbon nanotubes to generate a purified layer of carbon nanotubes, for example, via removal or transfer of said first carbon nanotubes.

Fig. 1A a b of Trenches Formed: 8
# of Tubes: 28
Selectivity = ~28%

PURIFICATION OF CARBON NANOTUBES VIA SELECTIVE HEATING

CROSS-REFERENCE TO RELATED APPLICATIONS

This application is a continuation of U.S. application Ser. No. 14/772,312, filed Sep. 2, 2015, which is a U.S. National Stage Application under 35 U.S.C. § 371 of International Application No. PCT/US2014/032848, filed Apr. 3, 2014, which claims the benefit of priority to U.S. provisional Patent Application 61/808,572 filed Apr. 4, 2013, each of which is hereby incorporated by reference in its entirety.

STATEMENT REGARDING FEDERALLY SPONSORED RESEARCH OR DEVELOPMENT

This invention was made with government support awarded by the following agency: U.S. Department of Energy Grant DEFG02-91 ER45439. The United States government has certain rights in the invention.

BACKGROUND OF INVENTION

Since their discovery in the early 1990s, a great deal has been learned about the composition and properties of carbon nanotube materials. This research has demonstrated that carbon nanotubes exhibit extraordinary mechanical, electronic and chemical properties, which has stimulated substantial interest in developing applied technologies exploiting these properties. Accordingly, substantial research is directed at developing techniques for organizing, arranging and incorporating carbon nanotube materials into useful functional devices.

Carbon nanotubes are allotropes of carbon comprising one or more cylindrically configured graphene sheets and are classified on the basis of structure as either single walled carbon nanotubes (SWNTs) or multiwalled carbon nanotubes (MWNTs). Typically having small diameters ($\approx$1-30 nanometers) and large lengths (up to several microns), SWNTs and MWNTs commonly exhibit length to diameter ratios of $\approx 10^2$ to about $10^7$. Carbon nanotubes exhibit either metallic or semiconductor electrical behavior, and the energy band structure of nanotube materials varies considerably depending on their precise molecular structure and diameter.

Single walled carbon nanotubes (SWNTs), in particular, are identified as candidates for functional materials in a new generation of high performance passive and active nanotube based electronic devices. SWNTs are made up of a single, contiguous graphene sheet joined with itself to form a hollow, seamless tube, in some cases with capped ends similar in structure to smaller fullerenes. SWNTs typically have very small diameters ($\approx$1 nanometer) and are often present in curled, looped and bundled configurations. SWNTs are chemically versatile materials capable of functionalization of their exterior surfaces and encapsulation of materials within their hollow cores, such as gases or molten materials.

A number of unique properties of SWNTs make these materials particularly attractive for a variety of emerging applied technologies, including sensors, light emissive systems, flexible electronics and novel composite materials. First, SWNTs are believed to have remarkable mechanical properties, such as tensile strengths at least 50 times that of steel. Second, the electron transport behavior in SWNTs is predicted to be essentially that of a quantum wire, and the electrical properties of SWNTs have been observed to vary upon charge transfer doping and intercalation, opening up an avenue for potentially tuning the electrical properties of nanotube materials. Finally, SWNTs have also been demonstrated to have very high intrinsic field affect mobilities (e.g., about 10,000 $cm^2V^{-1}s^{-1}$) making them interesting for possible applications in nanoelectronics.

Despite substantial progress in developing a SWNT-based electronic device platform, several factors impede commercialization of these systems. First, the device mobilities that have been achieved with these networks are far below the intrinsic tube mobilities inferred from measurements of transistors that incorporate an individual tube (or small number of tubes) spanning the gap between the source and drain electrodes. Second, films comprising SWNT networks are typically a mixture of metallic tubes and semiconducting tubes. The presence of metallic tubes in the network often results in a significant extent of purely metallic conductive pathways between the source/drain (S/D) electrodes of SWNT-based thin-film transistor (TFT) devices. Such metallic conductive pathways decrease the device on/off ratio attainable and generally increase the static power consumption, thereby preventing their applications for important classes of electronics systems.

It will be appreciated from the foregoing that there is currently a need in the art for improved device geometries, components, and fabrication methods to enable carbon nanotube electronic devices.

SUMMARY OF THE INVENTION

The present invention provides device component geometries and fabrication strategies for enhancing the electronic performance of electronic devices based on thin films of semiconducting carbon nanotubes. The invention provides, for example, processes utilizing selective heating of a subset of carbon nanotubes having one or more selected physical and/or chemical properties so as to selectively separate nanotubes of the subset from a precursor layer containing nanotubes, such as a layer containing substantially aligned carbon nanotubes. In some embodiments, for example, a flow of a thermocapillary resists is generated via selective heating of carbon nanotubes so as to expose nanotubes having one or more selected physical and/or chemical properties, thereby allowing subsequent separation from the precursor layer, for example via removal or transfer processes. Examples of processes useful in the present invention for achieving selective heating and separation of carbon nanotubes based on one or more selected physical and/or chemical properties include absorption of electromagnetic radiation (e.g., via laser or microwave source), application of an electromagnetic field, electric field, magnetic field and/or application or a voltage. In some embodiments, for example, one or more of the following are applied simultaneously, electromagnetic radiation, electromagnetic field, electric field, magnetic field and/or application or a voltage.

In certain aspects, devices and methods of the present invention provide for the purification of mixtures of metallic and semiconducting carbon nanotubes. For example, mixtures of substantially aligned single-walled carbon nanotubes may be purified by methods involving selective heating of one class of nanotubes, which may be separated from the mixture. In an embodiment, metallic nanotubes are selectively heated to induce flow of a thermocapillary resist away from the metallic nanotubes to expose the metallic nanotubes while semiconducting nanotubes remain covered by the resist. Separation of the exposed and unexposed nanotubes may be carried out, for example, by etching, ablation, transfer printing, and other known methods. In an embodiment, additional processing may be carried out to protect the exposed nanotubes followed by removal of the thermocapillary resist, and optionally the nanotubes underlying the thermocapillary resist.

The present purification methods are versatile, thereby providing a platform enabling improved nanotube-based electronic devices and systems well suited for a range of device applications, including thin film electronics, large area electronics (e.g., macroelectronics), flexible electronics, and sensing. Methods and devices of the present invention are compatible with low temperature processing and assembly on a wide range of device substrates, including mechanically flexible substrates such as polymer substrates. Processing methods and design strategies of the present invention are complementary to conventional microfabrication and nanofabrication platforms, and can be effectively integrated into existing photolithographic, etching and thin film deposition patterning strategies, systems and infrastructure. In specific embodiments, methods of the present invention enable low cost fabrication of high performance nanotube based semiconductor devices, such as thin film transistors, transistor arrays, and integrated electronic circuits.

In an aspect, a method for purifying a layer of carbon nanotubes comprises: providing a precursor layer of substantially aligned carbon nanotubes supported by a substrate, wherein the precursor layer comprises a mixture of first carbon nanotubes and second carbon nanotubes; covering the precursor layer of carbon nanotubes with a thermocapillary resist, wherein the thermocapillary resist is in thermal contact with at least a portion of the carbon nanotubes; selectively heating the first carbon nanotubes, thereby causing thermocapillary flow of the thermocapillary resist away from the first carbon nanotubes to expose the first carbon nanotubes; and separating the first carbon nanotubes from the second carbon nanotubes, thereby generating a purified layer of carbon nanotubes.

In an aspect, a method for making an electronic device comprises: providing a precursor layer of substantially aligned carbon nanotubes supported by a substrate, wherein the precursor layer comprises a mixture of first carbon nanotubes and second carbon nanotubes; covering the precursor layer of carbon nanotubes with a thermocapillary resist, wherein the thermocapillary resist is in thermal contact with at least a portion of the carbon nanotubes; selectively heating the first carbon nanotubes, thereby causing thermocapillary flow of the thermocapillary resist away from the first carbon nanotubes to expose the first carbon nanotubes; separating the first carbon nanotubes from the second carbon nanotubes, thereby generating a purified layer of carbon nanotubes; and providing one or more device component structures in electrical or physical contact with the purified layer of carbon nanotubes, thereby making the electronic device.

In an embodiment, first carbon nanotubes can be a first set of nanotubes, a first class of nanotubes, or a first distribution of nanotubes. Second carbon nanotubes can be a second set of nanotubes, a second class of nanotubes, or a second distribution of nanotubes. Each type, set, class or distribution of nanotubes may be characterized by an electronic, optical, physical, chemical or other property in common. In an embodiment, the precursor layer comprises an array of substantially longitudinally aligned carbon nanotubes, such as an array generated using a guide growth substrate or guided deposition substrate.

In an embodiment, the selective heating results from absorption of electromagnetic radiation, electronic resistance, mobility, direct thermal contact or electromagnetic induction.

Carbon nanotubes of the present invention may be single walled carbon nanotubes, multiwalled carbon nanotubes or a mixture of both. Use of single walled nanotubes (SWNTs) is preferred for some applications given their particularly useful semiconducting properties. In an embodiment, the precursor layer is a monolayer or sub-monolayer of carbon nanotubes. As used herein, the terms "nanotube surface concentration" and "nanotube density" are used interchangeably and refer to the number of nanotubes per area of substrate having the nanotubes. In an embodiment, carbon nanotubes of the precursor layer are a mixture of semiconducting nanotubes and metallic nanotubes, wherein there are more semiconducting nanotubes than metallic nanotubes. For example, the first carbon nanotubes may be metallic carbon nanotubes and the second carbon nanotubes may be semiconducting carbon nanotubes. Conventional sources of carbon nanotubes, such as SWNTs, typically generate mixtures having more semiconducting nanotubes than metallic nanotubes, for example mixtures having between 60-80% semiconducting nanotubes and 40-20% metallic nanotubes or mixtures having between 65-75% semiconducting nanotubes and 35-25% metallic nanotubes. In an embodiment, carbon nanotubes of the precursor layer are a mixture of semiconducting nanotubes and metallic nanotubes, wherein there are more semiconducting nanotubes than metallic nanotubes, for example a mixture wherein there are at least 1.5 times more semiconducting nanotubes than metallic nanotubes, and in some embodiments wherein there are 1.5-4 times more semiconducting nanotubes than metallic nanotubes. Carbon nanotubes of the precursor layer can be generated by a range of synthetic methods including, chemical vapor deposition, pyrolysis, arc discharge, catalytic methods and laser ablation methods. Precursor layers of carbon nanotubes of the present invention may further comprise additional components, such as dopants or components enhancing the mechanical properties of the nanotube layer.

A precursor layer of the present invention comprises one or more carbon nanotubes in a selected geometry. In an embodiment, the precursor layer may be provided by growing substantially aligned carbon nanotubes on a substrate comprising a guided growth substrate or by printing substantially aligned carbon nanotubes onto a substrate. Suitable methods for printing the substantially aligned carbon nanotubes may for example be selected from ink jet printing, thermal transfer printing, contact printing, dry transfer printing or screen printing.

The carbon nanotubes of the precursor layer generally have an average length selected from a range of 20 nanometers to 100 microns, or 50 nanometers to 10 microns, or 75 nanometers to 1 micron, or 100 nanometers to 500 nanometers. Further, an average spacing between adjacent carbon nanotubes of the precursor layer is typically selected from a range of 2 nm to 100 µm, or 5 nm to 10 µm, or 10 nm to 1 µm, or 20 nm to 500 nm, or 30 nm to 250 nm. In an embodiment, an average spacing between adjacent carbon nanotubes of the precursor layer is at least 2 nm, or at least 5 nm or at least 10 nm, or at least 20 nm, or at least 30 nm.

A surface concentration of carbon nanotubes of the precursor layer is typically selected from a range of 0.2 carbon nanotubes micron$^{-2}$ to 100 carbon nanotubes micron$^{-2}$, or 0.5 carbon nanotubes micron$^{-2}$ to 50 carbon nanotubes micron$^{-2}$, or 1 carbon nanotube micron$^{-2}$ to 25 carbon nanotubes micron$^{-2}$, or 2 carbon nanotubes micron$^{-2}$ to 15 carbon nanotubes micron$^{-2}$. In an embodiment, the precursor layer of substantially aligned carbon nanotubes includes less than 100 carbon nanotube crossings per square micron, or less than 50 carbon nanotube crossings per square micron, or less than 25 carbon nanotube crossings per square micron, or less than 10 carbon nanotube crossings per square micron.

The layer of substantially aligned carbon nanotubes typically has a thickness less than or equal to 10 nanometers, or less than or equal to 5 nanometers, or less than or equal to 2 nanometers. In an embodiment, the layer of substantially aligned carbon nanotubes is a monolayer film or a substantially monolayer film.

Carbon nanotubes of the present invention may be covered by a thermocapillary resist. Useful thermocapillary resists for covering the nanotubes, and optionally a portion of a substrate, include but are not limited to thermocapillary resists having a room temperature viscosity selected from a range of 0.5 Pa·s to 50 Pa·s, or 1 Pa·s to 30 Pa·s, or 3 Pa·s to 15 Pa·s.

Generally, the thermocapillary resist comprises a conformal layer on and between the carbon nanotubes, where the thermocapillary resist is in physical contact with the carbon nanotubes. In an embodiment, the thermocapillary resist comprises a substantially uniform layer. The substantially uniform layer may, for example, have a thickness selected from a range of 1 nm to 10 µm, or 5 nm to 1 µm, or 10 nm to 500 nm, or 10 nm to 50 nm, or a thickness less than or equal to 500 nm, or less than or equal to 250 nm, or less than or equal to 100 nm, or less than or equal to 50 nm. In an embodiment, the substantially uniform layer is a continuous layer.

In an embodiment, the thermocapillary resist comprises a molecular organic species. For example, the thermocapillary resist may be selected from the group consisting of α,α,α'-Tris(4-hydroxyphenyl)-1-ethyl-4-isopropylbenzene polymethylmethacrylate (PMMA), polystyrene (PS), and low molecular weight silicon containing polymers such as poly(styrene-dimethylsiloxane) (PS-PDMS); oligosaccharide-trimethylsilylstyrene, and polyhedral oligomeric silsesquioxane (POSS). In an embodiment, the thermocapillary resist comprises a molecular weight selected from a range of 50 g/mol to 1000 kg/mol, or 500 g/mol to 500 kg/mol, or 1 kg/mol to 100 kg/mol.

In an embodiment, at least 1%, 5%, 10%, 20%, 50% or 75% of a lateral cross section of each of the first carbon nanotubes is exposed by the step of selectively heating the first carbon nanotubes.

In an embodiment, the step of separating the first carbon nanotubes from the second carbon nanotubes may include: etching exposed carbon nanotubes, transfer printing the exposed carbon nanotubes, transfer printing the carbon nanotubes covered by the thermocapillary resist, removing the exposed carbon nanotubes from the precursor layer, or removing the covered carbon nanotubes from the precursor layer (e.g., by performing steps of applying a protective layer to the exposed nanotubes, removing the thermocapillary resist and separating the previously covered carbon nanotubes from the precursor layer).

As a further processing step, any of the methods described herein may include a step of removing the thermocapillary resist after the step of separating.

Carbon nanotubes and devices or device components of the present invention may be supported by a substrate. Useful substrates for supporting the nanotubes, devices and device components of the present invention include but are not limited to mechanically flexible substrates such as polymer substrates, rigid substrates, dielectric substrates, metal substrates, ceramic substrates, glass substrates, semiconductor substrates and functional substrates prepatterned with one or more device components. The present invention also includes devices and device components provided on (i.e. supported by) contoured substrates, including curved substrates, curved rigid substrates, concave substrates, and convex substrates.

The step of selectively heating a type, set, class or distribution of nanotubes may be carried out by application of electromagnetic energy, current, an electric field, a magnetic field, microwave energy or laser radiation to the nanotubes of the precursor layer. In an embodiment, selective heating comprises absorption of energy by metallic carbon nanotubes, wherein the energy is insufficient to overcome the Schottky barrier of semiconducting carbon nanotubes.

In an embodiment, a ratio of a temperature increase of the first carbon nanotubes to a temperature increase of the second carbon nanotubes during the step of selective heating is 1.25 or greater, or 1.7 or greater, or 2 or greater, or 2.5 or greater.

In an embodiment, an average temperature gradient within the thermocapillary resist proximate to the first carbon nanotubes is at least 1 K/µm, or at least 1.5 K/µm, or at least 2 K/µm In an embodiment, the selective heating is provided by one or more of an optical source, a microwave source, a laser source, a DC source, an AC source, or an acoustic source. The source may be pulsed or continuous.

In an embodiment, selective heating of the nanotubes occurs in a transistor configuration, where the carbon nanotubes of the precursor layer are in electrical contact with a source electrode, a drain electrode and a gate electrode. The selective heating is provided by one or more of a DC source and an AC source delivering a power per carbon nanotube selected from a range of 5 µW/µm/tube to 50 µW/µm/tube, or 10 µW/µm/tube to 30 µW/µm/tube, to the source electrode. In an embodiment, the source is pulsed at a frequency selected from a range of CW (i.e., 0 Hz) to 100 MHz, or CW (i.e., 0 Hz) to 10 MHz, or CW (i.e., 0 Hz) to 1 MHz, or CW (i.e., 0 Hz) to 500 Hz, and the source is activated for a duration selected from a range of 1 ns to 100 minutes, or 10 ns to 10 minutes, or 100 ns to 1 minute.

In an embodiment, selective heating of the nanotubes occurs via laser irradiation using a laser source producing radiation having an energy selected from a range of 100 nJ to 100 mJ, or 1 µJ to 10 mJ and a power less than 1 kJ/m$^2$, or less than 0.5 kJ/m$^2$. In an embodiment, the laser source produces radiation having a wavelength selected from a range of 1 µm to 10 µm, or 1.5 µm to 8 µm, or 2 µm to 5 µm. The laser source may be pulsed at a frequency selected from a range of 1 Hz to 100 MHz, or 1 Hz to 1000 KHz or 1 Hz to 100 KHz, or 1 Hz to 10 KHz. In an embodiment, the laser source is activated for a duration selected from a range of 1 nm to 300 minutes, or 10 ns to 200 minutes, or 100 ns to 100 minutes, or 1 µs to 10 minutes, or 1 ms to 1 minute.

In an embodiment, selective heating of the nanotubes occurs in a microwave configuration, where the carbon nanotubes of the precursor layer are in electromagnetic communication with at least one microwave antennae. The electromagnetic communication may involve physical contact, electrical contact or both physical and electrical contact. In an embodiment, the electromagnetic communication does not comprise physical contact.

In an embodiment, the microwave source produces radiation having an energy selected from a range of 50 J/sec to 10 kJ/sec, or 100 J/sec to 1 kJ/sec. In an embodiment, the microwave source is pulsed at a frequency selected from a range of CW (i.e., 0 Hz) to 100 MHz, or CW (i.e., 0 Hz) to 10 MHz, or CW (i.e., 0 Hz) to 1 MHz, or CW (i.e., 0 Hz) to 500 Hz. In an embodiment, the microwave source is activated for a duration selected from a range of 0.1 µs to 300 minutes, or 1 µs to 300 minutes, or of 0.1 µs to 100 minutes or 1 µs to 100 minutes, or 1 ms to 10 minutes.

In some embodiments, the selective heating comprises differential absorption of a preselected wavelength of radiation between the first carbon nanotubes and the second carbon nanotubes, wherein the first carbon nanotubes absorb more than 1.25 times, or more than 1.5 times as much energy as the second carbon nanotubes. The preselected wavelength may, for example, be selected from a range of 100 nm to 20 µm, or 300 nm to 20 µm, or 0.5 µm to 10 µm, or 1 µm to 5 µm.

In an embodiment, selective heating of the nanotubes occurs in a two-terminal configuration, where the first and second carbon nanotubes of the precursor layer are in electrical contact with a first electrode and a second electrode. An electrode bias voltage between the first electrode and the second electrode may, for example, be selected from a range of 0.01 V to 500 V, or 0.1 V to 500 V, or 0.01 V to 100 V, or 1 V to 50 V, or 5 V to 25 V. In an embodiment, the first and second electrodes are interdigitated. The selective heating may be provided, for example, by one or more of a DC source and an AC source delivering a current selected from a range of 0.01 mA to 100 A, or 0.1 mA to 10 A, or 1 mA to 1 A, or 10 mA to 1 A. In an embodiment, the DC or AC source is pulsed at a frequency selected from a range of 1 Hz to 500 MHz, or 1 Hz to 100 MHz, or 10 Hz to 500 MHz, or 100 Hz to 50 MHz, or 1 MHz to 5 MHz. In an embodiment, the DC or AC source is activated for a duration selected from a range of 0.1 µs to 100 minutes, or 1 µs to 10 minutes, or 1 ms to 1 minute.

In an aspect, a method for purifying a layer of carbon nanotubes comprises: providing a precursor layer of substantially aligned carbon nanotubes supported by a substrate, wherein the precursor layer comprises a mixture of first carbon nanotubes and second carbon nanotubes; and selectively heating the first carbon nanotubes to separate the first carbon nanotubes from the second carbon nanotubes, thereby providing a purified layer of carbon nanotubes comprising at least 50%, 60%, 70%, 80%, or 90% of the first or the second carbon nanotubes.

In an embodiment, the present invention provides a transistor wherein the nanotube layer provides a semiconductor channel between first and second electrodes comprising source and drain electrodes. Transistors of the present invention may further comprise a gate electrode and dielectric layer; wherein the dielectric layer is provided between the gate electrode and the precursor layer. In some embodiments, the gate electrode is electrically isolated from, and positioned close enough to, the semiconductor channel such that electron transport through the channel is modulated by application of an electric potential to the gate electrode. In some embodiments, the layer has a strip geometry and comprises a plurality of strips of interconnected carbon nanotube networks, wherein strips of interconnected carbon nanotubes extend lengths from source to drain electrodes and are aligned in the electron transport direction of the transistor, optionally in a parallel strip orientation. In an embodiment, a transistor of this aspect is a thin film transistor. In an embodiment, a transistor of this aspect has an on/off ratio greater than or equal to 100, and preferably for some applications greater than or equal to 1000. In an embodiment, a transistor of this aspect has a field effect mobility greater than or equal to 0.1 cm$^2$ V$^{-1}$ s$^{-1}$, and preferably for some applications a field effect mobility greater than or equal to 10 cm$^2$ V$^{-1}$ s$^{-1}$. The invention provides nanotube-based transistor arrays and integrated circuits comprising a plurality of nanotube-based transistors.

In another aspect, the invention provides an electronic device comprising: a first electrode; a second electrode; and a layer of substantially aligned carbon nanotubes positioned between and in electrical contact with the first electrode and the second electrode, wherein the layer of substantially aligned carbon nanotubes comprises at least 90% semiconducting carbon nanotubes. In an embodiment, fabrication of the electronic device does not include a fluidic assembly step.

Electronic devices of the present invention include a range of nanotube-based devices. Electronic devices of the present invention include for example, transistors, diodes, light emitting diodes, integrated circuits and photodetectors comprising one or more layers of carbon nanotubes. For example, when the electronic device is a transistor, the first electrode may be a source electrode, the second electrode may be a drain electrode and the layer of substantially aligned semiconducting carbon nanotubes may be a semiconductor channel of the transistor. In an embodiment, the layer of substantially aligned semiconducting carbon nanotubes provides a semiconductor channel between first and second electrodes, wherein the semiconductor channel has a length selected from a range of 50 nanometers and 1000 microns.

In an embodiment, contact printing of carbon nanotubes is achieved using soft lithography methods, such as dry transfer printing techniques using a conformable transfer device such as an elastomeric stamp.

Without wishing to be bound by any particular theory, there can be discussion herein of beliefs or understandings of underlying principles or mechanisms relating to the invention. It is recognized that regardless of the ultimate correctness of any explanation or hypothesis, an embodiment of the invention can nonetheless be operative and useful.

BRIEF DESCRIPTION OF THE DRAWINGS

FIG. 1A provides a schematic flow diagram illustrating a method of the present invention for purifying carbon nanotubes, for example, by separation of a first class of nanotubes having one or more selected physical or chemical properties from other nanotubes in a nanotube precursor layer.

FIG. 76a shows the schematic illustration of this process. To do the purification, the SWNTs are first grown on the quartz substrate, then followed by patterning strips of metal contacts on the SWNTs. Metals with relatively low work-function respect to the middle gap energy of the SWNTs, as well as good wettability to the SWNTs are typically good choices for the contacts. After the deposition of the thermocapillary resist (T$_c$ resist), a DC voltage is applied across the metal contacts, which selectively induces the Joule heating on the m-SWNTs, causing the flows of the T$_c$ resist to open trenches above the m-SWNTs. Reactive ion etching is then used to etch away the exposed m-SWNTs, leaving the s-SWNTs well protected by the $T_c$ resist. FIG. 76b shows the SEM image of a pristine array of SWNTs and the corresponding AFM topography image of the induced trenches. Such well-defined, uniform trenches along the SWNTs are the key for the successful removal. Statistics of the trench depth associated with each SWNT in a device with total 171 SWNTs are shown in FIG. 76c. The depths are arranged in an ascending manner (x axis is the accumulated differential fraction of the SWNTs), showing that ~37% of the SWNTs creates trenches deep enough to etch away. This statistics matches that ~⅓ of the SWNTs are metallic types.

DETAILED DESCRIPTION OF THE INVENTION

Figure 1B:
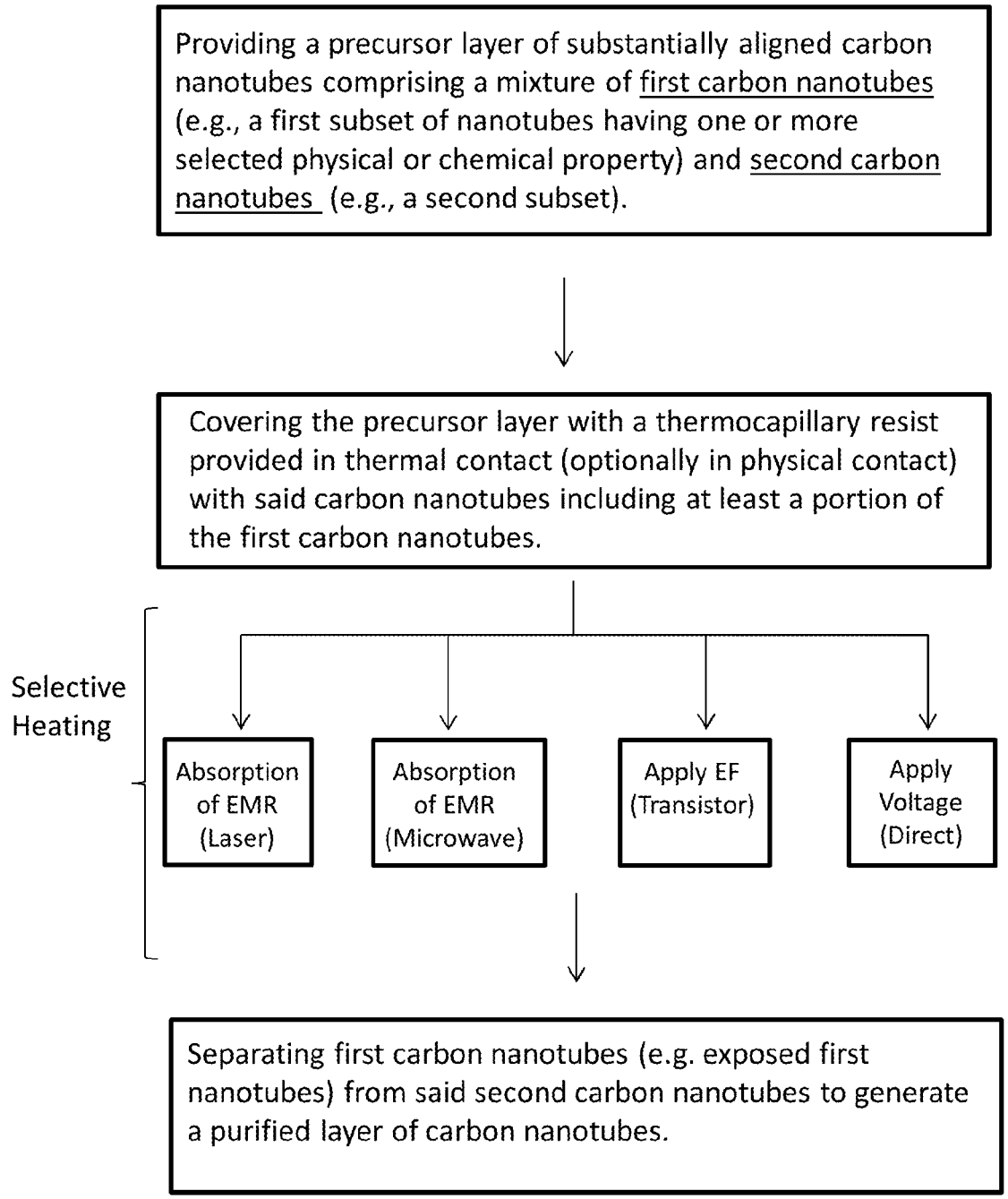
FIG. 1B provides a schematic flow diagram corresponding to a method of the present invention further illustrating various process approaches for selective heating the first carbon nanotubes having one or more selected physical or chemical properties.

In general, the terms and phrases used herein have their art-recognized meaning, which can be found by reference to standard texts, journal references and contexts known to those skilled in the art. The following definitions are provided to clarify their specific use in the context of the invention.

"Carbon nanotube" and "nanotube" are used synonymously and refer to allotropes of carbon comprising one or more cylindrically configured graphene sheets. Carbon nanotubes include single walled carbon nanotubes (SWNTs) and multiwalled carbon nanotubes (MWNTs). Carbon nanotubes typically have small diameters (≈1-10 nanometers) and large lengths (up to several microns), and therefore may exhibit length to diameter ratios≈$10^2$ to about $10^7$. The longitudinal dimension of a nanotube is its length and the cross sectional dimension of a nanotube is its diameter (or radius). Carbon nanotubes include semiconducting carbon nanotubes, metallic carbon nanotubes, semi-metallic carbon nanotubes and mixtures of these. In some embodiments, the compositions and methods of the present invention include a mixture of semiconducting and metallic carbon nanotubes, for example, wherein the ratio of semiconducting nanotubes to metallic nanotubes is selected from a range of 9-0.5. In some embodiments, the compositions and methods of the present invention include a mixture of semiconducting and metallic carbon nanotubes, for example, wherein the ratio of semiconducting nanotubes to metallic nanotubes is greater than or equal to 1, preferably for some application greater than or equal to 2. In some embodiments, the compositions and methods of the present invention include a mixture of semiconducting and metallic carbon nanotubes, for example, wherein the extent of semiconducting nanotubes is enriched, for example using fractionation or other purification techniques.

"Supported by a substrate" refers to a structure that is present at least partially on a substrate surface or present at least partially on one or more intermediate structures positioned between the structure and the substrate surface. The term "supported by a substrate" may also refer to structures partially or fully embedded in a substrate, structures partially or fully immobilized on a substrate surface via an encapsulating layer (e.g., polymer layer) and structures partially or fully laminated on a substrate surface.

"Substantially aligned nanotubes" have lengths extending in longitudinal directions that are aligned with respect to each other but not provided in an absolutely parallel configuration. In some embodiments, for example, substantially aligned nanotubes have a partially linear geometry wherein their lengths assume a configuration with deviations from absolute linearity greater than about 10%, and in some embodiments with deviations from absolute linearity greater than about 20%. As used in this context, the term "parallel" refers to a geometry in which the lengths of carbon nanotubes are equidistant from each other for at least a portion of the points along their respective lengths and have the same direction or curvature. In one embodiment, for example substantially aligned nanotubes are aligned relative to each other with deviations from absolute parallelism that are greater than or equal to 20 degrees, and in some embodiments deviations from absolute parallelism that are greater than or equal to 10 degrees. In some embodiments, compositions and methods of the invention include carbon nanotube networks comprising substantially aligned nanotubes having at least one nanotube crossing. Alternatively, compositions and methods of the invention include carbon nanotube networks comprising randomly oriented nanotubes having at least one nanotube crossing.

"Monolayer of nanotubes" refers to a layer of nanotubes on a substrate surface wherein the coverage of the area of the surface of the substrate having nanotubes is less than 100%, preferably for some embodiments substantially less than 100%. In some embodiments, for example, a monolayer refers to a layer of nanotubes wherein the coverage of the area of the surface of the substrate having nanotubes is less than 10%, preferably for some applications less than 2%, and preferably for some applications less than 1%. In some embodiments, for example, a monolayer refers to a layer of nanotubes wherein the coverage of the area of the surface of the substrate having nanotubes is selected over the range of 0.1-10%, or preferably for some embodiments selected over the range of 0.5-2%. In some embodiments a monolayer of carbon nanotubes has a thickness less than or equal to 20 nanometers, preferably for some applications less than or equal to 10 nanometers and preferably for some applications less than or equal to 5 nanometers. Use of monolayers of carbon nanotubes in some embodiments of the invention are useful for achieving effective gate modulation in a nanotube-based electronic devices.

"Flexible" refers to a property of an object, such as a substrate, which is deformable in a reversible manner such that the object or material does not undergo damage when deformed, such as damage characteristic of fracturing, breaking, or inelastically deforming. Flexible polymers are useful with the methods described herein. Specific flexible polymers include, but are not limited to: rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin, elastomers and other flexible polymers known to those of skill in the art. In certain embodiments, flexible objects or materials can undergo strain levels selected over the range of 1% to 1300%, 10% to 1300%, or 100% to 1300% without resulting in mechanical failure (e.g., breaking, fracturing or inelastically deforming). In some embodiments, flexible objects or materials can be deformed to a radius of curvature selected over the range of 100 µm to 3 m without resulting in mechanical failure (e.g., breaking, fracturing or inelastically deforming).

A "Schottky barrier" is a potential energy barrier for electrons formed at a metal-semiconductor junction. In some cases, thermally excited electrons may absorb sufficient energy to overcome the barrier.

A "thermocapillary resist" is an material capable of responding to a localized temperature increase by migrating away from a heat source. This occurs when the material has a higher affinity for itself than for the surface material of the heated object. A "thermocapillary resist" also protects objects against at least one chemical and/or physical challenge applied to the resist. A thermocapillary resist may comprise an encapsulating material, a coating material and/or a conformal material.

"Substantially uniform" refers to a continuous, pinhole free layer of material.

"Nanotube crossings" in this context refers to a configuration wherein two or more nanotubes are in electrical contact, physical contact and/or in an overlapping configuration. For example, nanotube crossings in some embodiments refers to a configuration with two, three or four different nanotubes are provided on top of or underneath each other.

"Electronic device" generally refers to a device incorporating a plurality of components, and includes large area electronics, printed wire boards, integrated circuits, component arrays, biological and/or chemical sensors, physical sensors (e.g., temperature, strain, etc.), nanoelectromechanical systems, microelectromechanical systems, photovoltaic devices, communication systems, medical devices, optical devices and electro-optic devices.

"Semiconductor" refers to any material that is an insulator at a very low temperature, but which has an appreciable electrical conductivity at a temperature of about 300 Kelvin. In the present description, use of the term semiconductor is intended to be consistent with use of this term in the art of microelectronics and electronic devices.

A "component" is used broadly to refer to an individual part of a device. Components include, but are not limited to, thin film transistors (TFTs), transistors, diodes, electrodes, integrated circuits, circuit elements, control elements, photovoltaic elements, photovoltaic elements (e.g. solar cell), sensors, light emitting elements, actuators, piezoelectric elements, receivers, transmitters, microprocessors, transducers, islands, bridges and combinations thereof. Components may be connected to other components such as one or more contact pads as known in the art, such as by metal evaporation, wire bonding, and application of solids or conductive pastes, for example. Electronic devices of the invention may comprise one or more components, optionally provided in an interconnected configuration.

The terms "directly and indirectly" describe the actions or physical positions of one component relative to another component. For example, a component that "directly" acts upon or touches another component does so without intervention from an intermediary. Contrarily, a component that "indirectly" acts upon or touches another component does so through an intermediary (e.g., a third component).

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50% or optionally 90%, of the external surfaces of the structure are surrounded by one or more structures. "Completely encapsulated" refers to the orientation of one structure such that it is completely surrounded by one or more other structures.

"Contiguous" refers to materials or layers that are touching or connected throughout in an unbroken sequence. In one embodiment, a contiguous layer of an implantable biomedical device has not been etched to remove a substantial portion (e.g., 10% or more) of the originally provided material or layer.

"Substrate" refers to a material, layer or other structure having a surface, such as a receiving surface, that is capable of supporting one or more components or devices. A component that is "bonded" to the substrate refers to a component that is in physical contact with the substrate and unable to substantially move relative to the substrate surface to which it is bonded. Unbonded components or portions of a component, in contrast, are capable of substantial movement relative to the substrate and may be referred to herein as in physical contact with the substrate.

"Processing" is used broadly to refer to treatment of a device or surface to obtain one or more desired functional attributes, including a functional attribute such as electrical interconnection. Examples of processing include providing a material such as by deposition of one or more components, including active electronic components, structural, barrier, or encapsulating layer(s), removal or partial removal of materials, or transformation or partial transformation of materials to obtain a desired physical parameter.

"Dielectric" refers to a non-conducting or insulating material. In an embodiment, an inorganic dielectric comprises a dielectric material substantially free of carbon. Specific examples of inorganic dielectric materials include, but are not limited to, silicon nitride, silicon dioxide, silk, silk composite, elastomers and polymers.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomeric stamp" and "elastomeric transfer device" are used interchangeably and refer to an elastomeric material having a surface that can receive as well as transfer a material. Exemplary conformal transfer devices useful in some methods of the invention include elastomeric transfer devices such as elastomeric stamps, molds and masks. The transfer device affects and/or facilitates material transfer from a donor material to a receiver material. In an embodiment, a method of the invention uses a conformal transfer device, such as an elastomeric transfer device (e.g. elastomeric stamp) in a microtransfer printing process, for example, to transfer one or more single crystalline inorganic semiconductor structures, one or more dielectric structures and/or one or more metallic conductor structures from a fabrication substrate to a device substrate. Stamp is used broadly herein to refer to a substrate that can pick up components from one surface and transfer them to another surface. Accordingly, in an aspect the stamp may be a material having an adhesive surface that facilitates pick-up by adhesive forces, wherein the adhesive forces are less than subsequent contact forces when the stamp is brought into contact with a receiving surface. In an embodiment, the transfer printing may be direct surface-to-surface contact, from donor to a receiving surface.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. In some embodiments, an elastomeric stamp comprises an elastomer. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly (phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt any desired contour profile, for example a contour profile allowing for conformal contact with a surface having a pattern of relief features. In certain embodiments, a desired contour profile is that of a tissue in a biological environment.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. In an embodiment, a method of the invention comprises establishing conformal contact between a conformal transfer device and one or more single crystalline inorganic semiconductor structures, one or more dielectric structures and/or one or more metallic conductor structures, for example, in a microtransfer printing process, such as dry transfer contact printing. The receiving surface may functionally correspond to a release layer that is later used to release the components from a substrate that supports the release layer.

"Young's modulus" is a mechanical property of a material, device or layer which refers to the ratio of stress to strain for a given substance. Young's modulus may be provided by the expression:

$$E = \frac{\text{(stress)}}{\text{(strain)}} = \left(\frac{L_0}{\Delta L}\right)\left(\frac{F}{A}\right), \quad (1)$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \quad (2)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components, such as substrate, encapsulating layer, inorganic semiconductor structures, dielectric structures and/or metallic conductor structures, having a low Young's modulus. In an embodiment, a device of the invention has an overall low Young's modulus.

"Low modulus" refers to materials having a Young's modulus less than or equal to 10 MPa, less than or equal to 5 MPa or less than or equal to 1 MPa.

"Guided growth" refers to growth of carbon nanotubes on a substrate wherein growth of individual nanotubes occurs along nanotube growth axes having selected spatial orientations, such as an orientation that is parallel to at least a portion of the growth axes of other nanotubes in the array and/or an orientation that is parallel to a principle guided growth axis of the guided growth substrate. Guided growth in the present invention arises from electrostatic, energetic and/or steric interactions between the nanotubes and or catalyst with the guided growth substrate. For example, guided growth of nanotubes may occur via a mechanism involving energetically favorable van der Waals interactions between growing nanotubes and/or catalyst particles with the lattice arrangement of the guided growth substrate. Guided growth of nanotubes may also occur via interaction of the nanotubes and/or catalyst particles with step edges, microfacets, nanofacets or other surface features of the receiving surface of the guided growth substrate.

"Guided deposition" refers to assembling and/or positioning materials, such as carbon nanotubes, on a substrate via a concerted process providing for spatial orientation, position and/or organization selected with good accuracy and precision. In some embodiments, guided deposition methods of the present invention provide a means of assembling and/or positioning carbon nanotubes in spatial orientations and positions selected such that their longitudinal axes are parallel to a principle guided deposition axis of a guided deposition substrate. In some embodiments, guided deposition methods of the present invention provide a means of assembling and/or positioning carbon nanotubes in orientations and positions wherein their longitudinal axes are parallel to each other.

"Parallel to a principle guided growth axis" refers to a spatial configuration of one or more carbon nanotubes wherein the length of the carbon nanotube is substantially equidistant to the principle guided growth axis of a guided growth substrate for at least some points along the length of the nanotube. "Parallel to a principle guided deposition axis" refers to a spatial configuration of one or more carbon nanotubes wherein the length of the carbon nanotube is substantially equidistant to the principle guided deposition axis of a guided deposition substrate for at least some points along the length of the nanotube. As used in this context, the term parallel is intended to encompass some deviation from absolute parallelism. Nanotubes parallel to a principle guided growth or deposition axis may have parallel spatial orientations with deviations from absolute parallelism that are less than or equal to 20 degrees, preferably deviations from absolute parallelism that are less than or equal to 10 degrees for some applications, and preferably deviations from absolute parallelism that are less than 1 degrees for some applications. The present invention provides nanotube arrays and related methods of making nanotube arrays wherein at least 95% of the nanotubes in the array extend lengths that are parallel to each other and/or parallel to a principle guided growth or deposition axis with deviations from absolute parallelism of less than or equal to 20 degrees.

FIG. 1A provides a schematic flow diagram illustrating a method of the present invention for purifying carbon nanotubes, for example, by separation of a first subset of nanotubes having one or more selected physical or chemical properties from other nanotubes in a nanotube precursor layer. Aspects of this method are particularly useful for purifying carbon nanotubes on the basis of optical and/or electronic properties, such as optical absorption, electronic conductivity, interaction with an electromagnetic field, electric field, magnetic field, etc. In an embodiment, for example, the aspect of the invention provides a means of selectively removing or transferring metallic nanotubes from a precursor layer comprising a mixture of longitudinally aligned metallic and semiconducting carbon nanotubes. Aspects of the methods of the present invention are particularly well suited for purification of SWNTs, including layers and thin films containing SWNTs such as monolayer and submonolayer SWNT layers.

As shown in FIG. 1A, a precursor layer of substantially aligned carbon nanotubes is provided comprising a mixture of first carbon nanotubes (e.g., a first subset of nanotubes having one or more selected physical or chemical property) and second carbon nanotubes (e.g., a second subset different from the first subset), for example, providing as a layer or film of substantially aligned carbon nanotubes including both metallic and semiconducting carbon nanotubes. Next, the precursor layer is covered with a thermocapillary resist provided in thermal contact, and optionally in physical contact, with the carbon nanotubes, for example, in thermal contact with at least a portion of, and optionally all of, the first carbon nanotubes. The process further includes selectively heating the first carbon nanotubes to generate a thermocapillary flow of the thermocapillary resist away from the first carbon nanotubes, thereby exposing at least a portion of the first carbon nanotubes of the precursor layer. In an embodiment, for example, metallic nanotubes are selectively heated in a manner such that semiconducting nanotubes in the precursor layer do not undergo an equivalent increase in temperature. The process further includes separating at least a portion of the first carbon nanotubes, such as the exposed first nanotubes, from the second carbon nanotubes to generate a purified layer of carbon nanotubes. In some embodiments, the exposed first nanotubes are separated via removal from the precursor layer, for example via chemical degradation or transfer processing.

FIG. 1B provides a schematic flow diagram corresponding to a method of the present invention further illustrating various process approaches for selective heating the first carbon nanotubes having one or more selected physical or chemical properties. As shown in this figure, selective heating is achieved in some embodiments via absorption of electromagnetic radiation (EMR), for example, via absorption of continuous or pulsed EMR from a laser source or a microwave source. Alternatively, selective heating is achieved in some embodiments via applying a voltage and/or electric field so as to selectively generate current in the first carbon nanotubes having one or more selected physical or chemical properties. In some embodiments, for example, a transistor or direct two terminal device structure is used for applying an electromagnetic field or voltage to the carbon nanotubes undergoing processing, thereby selectively generating an increase in temperature for the first carbon nanotubes relative to the second carbon nanotubes. In an embodiment, for example, a voltage applied across the nanotubes and an electric field is simultaneously applied, for example, using a gate electrode positioned proximate to carbon nanotubes extending from source and drain electrodes.

Figure 1C:
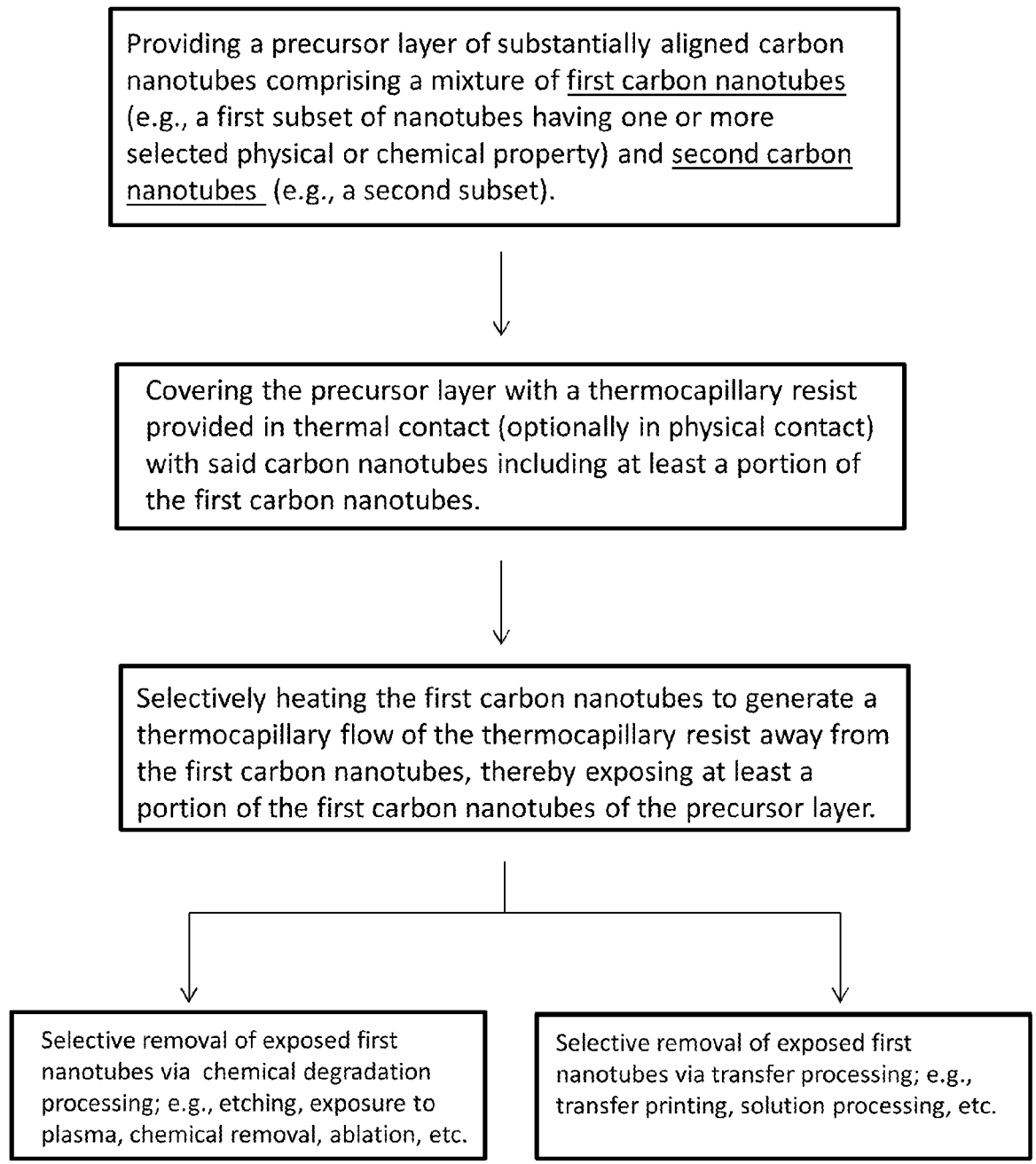
FIG. 1C provides a schematic flow diagram corresponding to a method of the present invention further illustrating various process approaches for selective removal of the first carbon nanotubes that undergo selective heating.

FIG. 1C provides a schematic flow diagram corresponding to a method of the present invention further illustrating various process approaches for selective removal of the first carbon nanotubes that undergo selective heating. In some embodiments, for example, exposure of the first nanotubes allows access for subsequent removal via a range of processes. As shown in this figure, exposed carbon nanotubes are removed in some embodiments by chemical degradation processing that optionally destroy the carbon nanotubes, for example, via etching, exposure to a plasma, chemical removal or ablation. Alternatively, selective removal is achieved in some embodiments via transfer processing that optionally does not result in degradation of the first carbon nanotubes, for example, via transfer printing (e.g., dry transfer printing) or via solution processing, such as by contacting the exposed nanotubes with a solution, dissolution and subsequent transfer away from the precursor layer. In some embodiments, for example, transfer is achieved via transfer printing via contacting the exposed first carbon nanotubes with an elastomeric stamp.

Figure 1D:
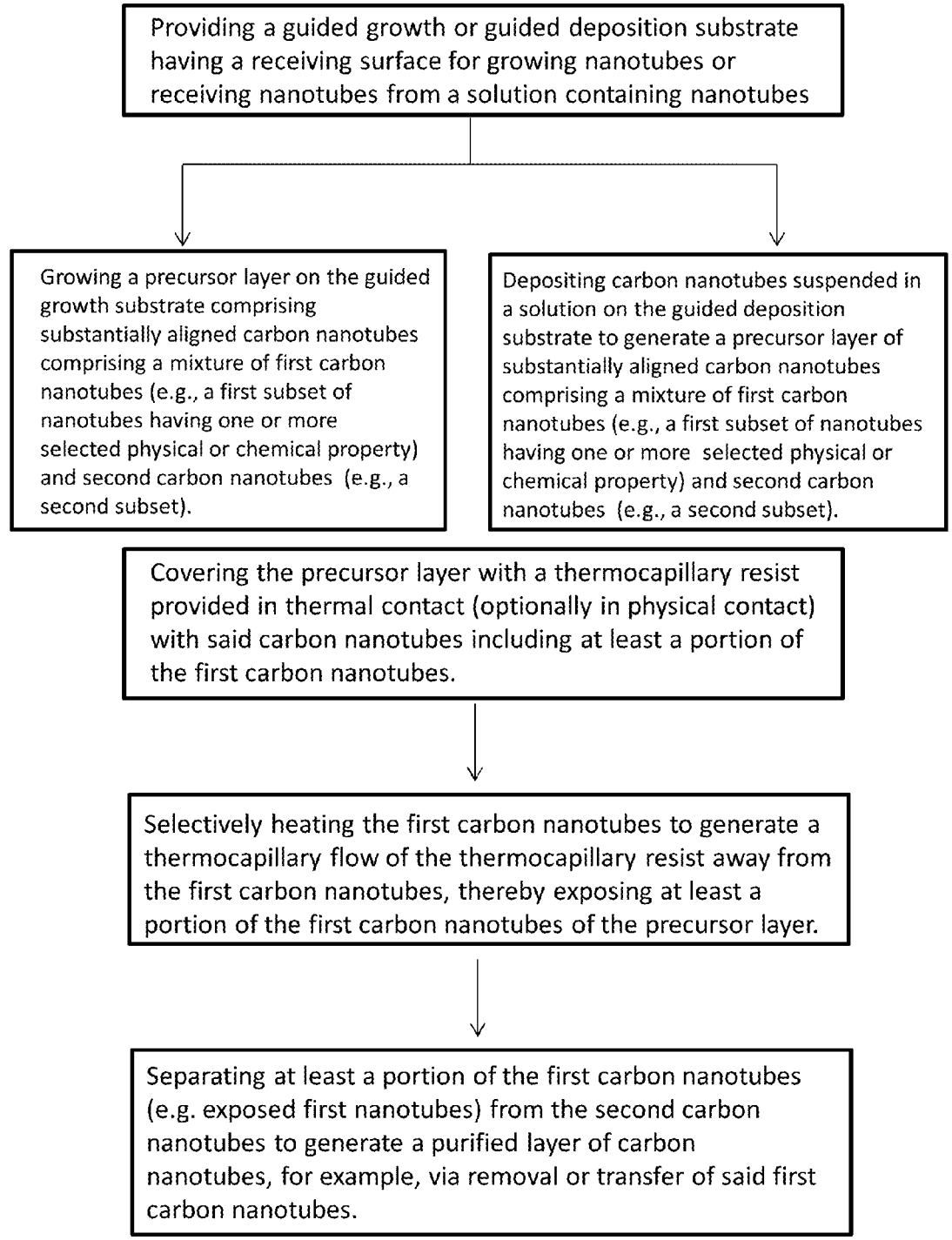
FIG. 1D provides a schematic flow diagram corresponding to a method of the present invention further illustrating various process approaches for generating a precursor layer comprising substantially aligned carbon nanotubes.

FIG. 1D provides a schematic flow diagram corresponding to a method of the present invention further illustrating various process approaches for generating a precursor layer comprising substantially aligned carbon nanotubes. As shown in this figure, a guide growth substrate is provided in some embodiments, and substantially longitudinally aligned carbon nanotubes are grown on a receiving surface of the guided drown substrate. Alternatively, the precursor layer comprising substantially longitudinally aligned carbon nanotubes is achieved in some embodiments via contacting the receiving surface of a guided deposition substrate with a solution containing suspended carbon nanotubes, which optionally undergo self assembly to form the precursor layer.

Devices and methods of making and using the devices will now be described with reference to the figures. For clarity, multiple items within a figure may not be labeled and the figures may not be drawn to scale.

EXAMPLE 1

Using Nanoscale Thermocapillary Flows to Create Purely Semiconducting Arrays of Single Walled Carbon Nanotubes Among the remarkable variety of semiconducting nanomaterials that have been discovered over the past two decades, single walled carbon nanotubes (SWNTs) remain uniquely well suited for applications in high performance electronics, sensors and other technologies. The most advanced opportunities demand the ability to form perfectly aligned, horizontal arrays of purely semiconducting, chemically pristine SWNTs. Here, we present strategies that provide this capability, in which nanoscale thermocapillary flows in thin film organic coatings serve as highly efficient means for selectively removing metallic SWNTs from electronically heterogeneous aligned arrays grown on quartz substrates. The low temperatures and unusual physics associated with this process enable robust, scalable operation, with clear potential for practical use. Detailed experimental and theoretical studies reveal all of the essential attributes of the underlying thermophysical phenomena. Demonstrations include use of purified arrays in transistors with mobilities and on/off switching ratios that can exceed ~1000 cm$^2$/Vs and ~10,000, respectively, and with current outputs in the mA range; simple logic gates built using such devices represent first steps toward integration into circuits.

Exploiting the exceptional electrical properties[1,2] of arrays of SWNTs in advanced applications[3-9] requires an ability to meet demanding requirements on degrees of alignment and purity in semiconducting behavior. Because direct, selective growth of purely semiconducting SWNTs (s-SWNTs) remains a topic of continuing study, the synthetic strategies that offer the greatest near-term potential fall into two categories: (1) purify the SWNTs and then assemble them into arrays; and (2) assemble the SWNTs into arrays and then purify them. The first has the advantage that it can build on recently developed wet chemical methods (ultra-centrifugation[10,11], chromatograph[12-14] and others[15,16]) for purification. The disadvantages are that the resulting SWNTs are typically short (~1 μm), chemically modified and/or coated, and difficult to assemble into arrays with high degrees of alignment[15,17-19]. The second approach overcomes these limitations through the use of chemical vapor deposition techniques that, when used with quartz substrates, can yield nearly perfectly linear (>99.9% of SWNTs within 0.01° of perfect alignment), aligned arrays of long (100 μm and up to ~millimeters) and chemically pristine SWNTs[3,20-23]. The main difficulty is in removing the m-SWNTs from such arrays. Techniques based on optical[24], electrical[25], or chemical[26-28] effects involve some combination of drawbacks, including incomplete removal of the m-SWNTs, partial removal and/or degradation of the s-SWNTs, inability to operate on aligned arrays and/or reliance on uncertain underlying mechanisms. Among these methods, electrical breakdown is noteworthy because it operates directly on the basis of relevant distinguishing characteristics in charge transport[25]. This scheme, however, has two critical disadvantages. First, the required high power operation (~90 μW/μm for channel lengths>1 μm, increasing as channel length decreases to values>1 mW/μm)[29-31] leads to shifts in threshold voltage, avalanche effects[32], band-to-band tunneling, failure in gate dielectrics, and significant heat sinking at the contacts[29], all of which can prevent proper operation of the process. More significantly, breakdown only removes the m-SWNTs in isolated, narrow regions (~100 nm lengths), with positions that are not well controlled[34]. As a result, the vast majority of the m-SWNTs remain in the arrays, thereby preventing generalized use in subsequently fabricated devices.

Purification Based on Thermocapillary Flow and Etching

Figure 2I:
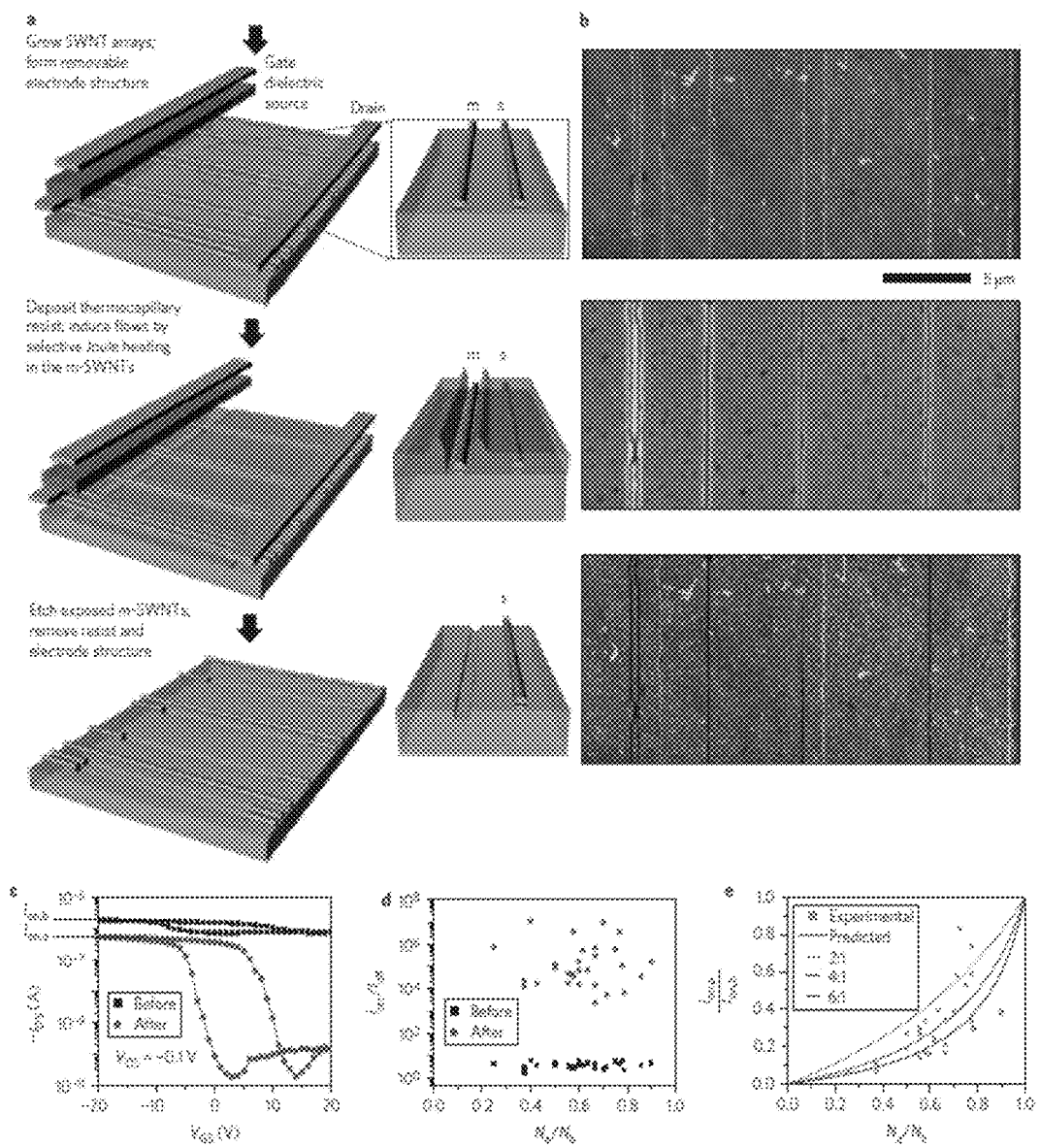
FIG. 2(i). Thermocapillary effects provide the basis for a process that enables selective and complete elimination of m-SWNTs from electronically heterogeneous arrays of SWNTs. (a,b) Schematic illustration and corresponding atomic force microscope images of various stages of the process applied to an array of five m-SWNTs and three s-SWNTs. Uniform thermal evaporation forms a thin, amorphous organic coating that functions as a thermocapillary resist. A series of processing steps defines a collection of electrodes and dielectric layers for selective injection of current into the m-SWNTs. The Joule heating that results from this process induces thermal gradients that drive flow of thermocapillary resist away from the m-SWNT, to form open trenches with widths, measured near the substrate, of ~100 nm. Reactive ion etching physically eliminates the m-SWNT exposed in this fashion, while leaving the coated s-SWNTs unaltered. Removing the thermocapillary resist and electrode structures completes the process, to yield arrays comprised only of s-SWNTs. (c) Typical transfer characteristics for a transistor built with an array of SWNTs in a partial gate geometry, evaluated before and after purification. The quantities $I_{on,b}$ and $I_{on,a}$ correspond to currents measured in the on states before and after purification, respectively. Here, the on/off ratio improves by $2\times10^4$ times, while $I_{on,a}/I_{on,b}$ remains relatively large, i.e. ~0.25. (d) Ratios between currents in the on and off states before and after purification ($I_{on,b}$ and $I_{off,a}$ respectively) as a function of the ratio of the number of SWNTs after purification ($N_a$) to the number of SWNT before purification ($N_b$). All devices show on/off ratios>$2\times10^3$, with most >$1\times10^4$. This result is consistent with complete removal of all m-SWNT. (e) Ratio of $I_{on,a}$ to $I_{on,b}$ as a function of $N_a/N_b$, for the entire set of devices with $N_b$>7. The result s are consistent with modeling (lines) that assumes complete retention of s-SWNTs through the purification process, expected relative populations of s-SWNTs and m-SWNTs in the arrays, and ratios of conductivities of m-SWNTs and s-SWNTs (in the their on state) that lie in an experimentally expected range.
Figure 8:
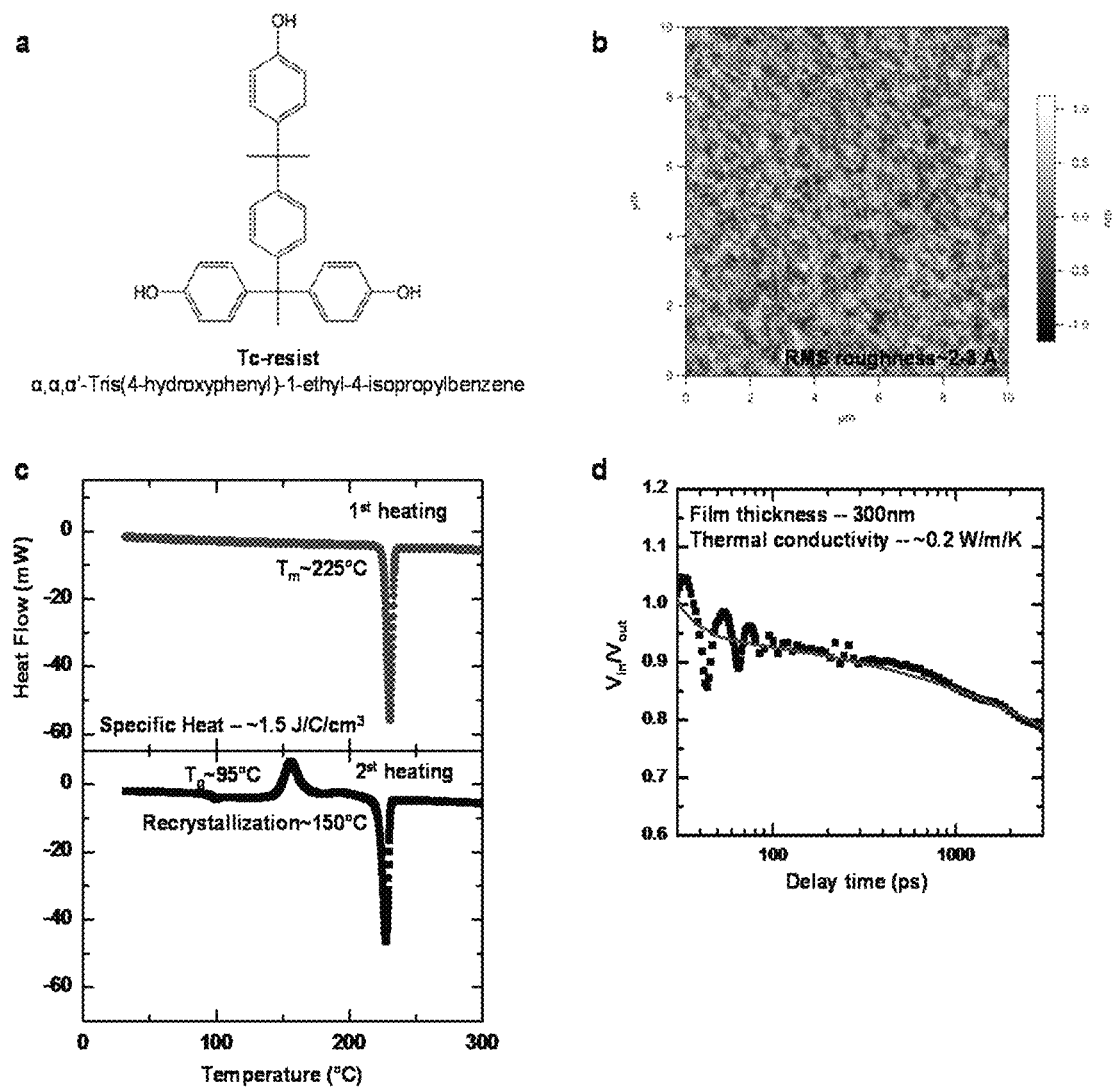
FIG. 8. Tc-resist characterization. (a) Chemical structure for Tc-resist. (b) AFM of a pristine film deposited by thermal evaporation (25 nm, ~1 Å/s) showing a very smooth surface (2-3 Å RMS roughness, similar to underlying Si substrate). (c) DSC of Tc-resist showing specific heat (~1.5 J/C/cm³), melting temperature (~225° C.), recrystallization (~150° C.), and glass transition (~95° C.) for a bulk sample. (d) Thermoreflectance for a 300 nm thick film of Tc-resist. Fitting yields thermal conductivities of ~0.2 W/m/K.

We introduce an approach for eliminating m-SWNTs in which thermocapillary effects in thin organic coatings allow their use as selective, self-aligned etch resists. Here, physical mass transport occurs by surface tension gradients generated through spatial variations in temperature[35] associated with selective heating in the m-SWNTs. We illustrate these concepts through the complete physical removal of all m-SWNTs from linear, horizontally aligned arrays that contain both m-SWNTs and s-SWNTs, without any measurable adverse effects on the latter. FIG. 2(i)a,b shows schematic illustrations and corresponding atomic force microscope images of the process applied to a heterogeneous collection of SWNTs grown on quartz. Arrays formed in this fashion consist of individual, isolated SWNTs, with very few multi-walled nanotubes or bundles of SWNTs, but with a distribution of diameters between ~0.6 and ~2.0 nm and a range of chiralities[23,31]. The key element in the purification process is an ultrathin (~25 nm) amorphous layer of a small molecule organic species, in this example α,α,α'-Tris(4-hydroxyphenyl)-1-ethyl-4-isopropylbenzene[36], deposited uniformly over the arrays of SWNTs by thermal evaporation. We refer to this film (FIG. 8) as a thermocapillary resist. Besides its favorable thermophysical properties, the particular material used here is well suited for present purposes because it combines hydroxyl and phenyl moieties to facilitate formation of uniform, continuous coatings on the surfaces of both the quartz and the SWNTs. This behavior is critical for its role as an effective etch resist at extremely small thicknesses.

Metal and dielectric layers patterned at the edges of an area of interest enable current injection primarily into only the m-SWNTs, due to controlled electrostatically induced increases in the heights and widths of the Schottky barriers at the source ends of s-SWNTs (FIGS. 1a, 10 and 31-33). These layers represent removable, transistor structures in which the gates extend beyond the source electrodes by a distance small (~5 μm) compared to the separation between the source and drain (~30 μm). Applying a positive voltage to the gate (~20 V) and a negative voltage to the drain (−40 to −50 V), while holding the source at electrical ground leads to selective Joule heating only in the m-SWNTs, due to approximately unipolar p-type behavior in the s-SWNTs. (FIGS. S27 and 28 illustrate good stability in the current outputs.) This set of bias conditions produces small increases in temperature only in the vicinity of the m-SWNTs. The large thermal gradients associated with nanoscale localization of these heat sources, in turn, drive mass transport in the thermocapillary resist. In typical experiments (fields of $V_{DS}/L_{ch}$~1.33-1.66 V/μm along the SWNTs for 5 min, with substrate heating to 60° C. in vacuum; $V_{DS}$ is the drain-source bias and $L_{ch}$ is the distance between these electrodes), the resulting flows yield trenches centered at the m-SWNTs and extending throughout the thickness of the thermocapillary resist (FIG. 1b). Although most experiments were performed in vacuum ($1\times10^{-4}$ torr), inert environments can also be used (e.g. dry nitrogen, or argon). Excluding oxygen can help to prevent electrical breakdown in extreme cases of hot spots along the lengths of the SWNTs with localized defects. Reactive ion etching ($O_2/CF_4$) after thermocapillary flow eliminates only the m-SWNTs. Removing the residual thermocapillary resist and the metal/dielectric structures leaves a purified array of s-SWNTs, in a configuration well suited for planar integration into diverse classes of devices and sensors.

Efficiency of the Purification Process

A key feature of this process is its exceptional efficiency in removing the m-SWNTs completely and exclusively. Such operation is important because most envisioned applications of s-SWNTs in electronics require purity at the level of 99.99% or better. For present purposes, we define a SWNT as metallic (semiconducting) if the ratio between the on ($I_{on}$) and off ($I_{off}$) currents (i.e. on/off ratio) in a well-designed transistor structure that incorporates this SWNT is less than (greater than) ~100. This definition places SWNTs that are sometimes referred to as quasi-metallic into the m-SWNT classification. (In all cases, we observe a clear distinction between the behavior of m-SWNTs and s-SWNTs defined in this way, for populations of SWNTs grown on quartz. In particular, of the hundreds of SWNTs studied here and elsewhere, none exhibit on/off ratios between ~50 and ~1000.)[37] Detailed electrical characterization (i.e. $I_{on}$ and $I_{off}$ before and after purification) and assessment of statistics (i.e. total numbers of SWNTs before and after) performed on significant numbers of devices (35 devices, each with an active area of ~30×30 μm to enable full visualization by atomic force microscopy; 377 SWNTs in total) provide quantitative insights into the effectiveness. FIG. 2(i)c shows a representative transfer characteristic for a device before and after purification, measured in air using the same metal/dielectric structures that enable selective Joule heating. The results illustrate a dramatic reduction in $I_{off}$ (from 0.7 pA to $2\times10^{-5}$ pA), thereby improving the on/off ratio from 2.7 to $3\times10^4$. All devices showed on/off ratios<10 (median=3.7) before and >$2\times10^3$ (median=6.6×$10^4$) after purification, independent of the number of SWNTs removed (FIG. 1d). The relatively small numbers (<30) of SWNTs in each device used to examine the statistics lead to the conclusion that the observed on/off ratios correspond to complete removal (i.e. 100%) of the m-SWNTs.

Figure 7:
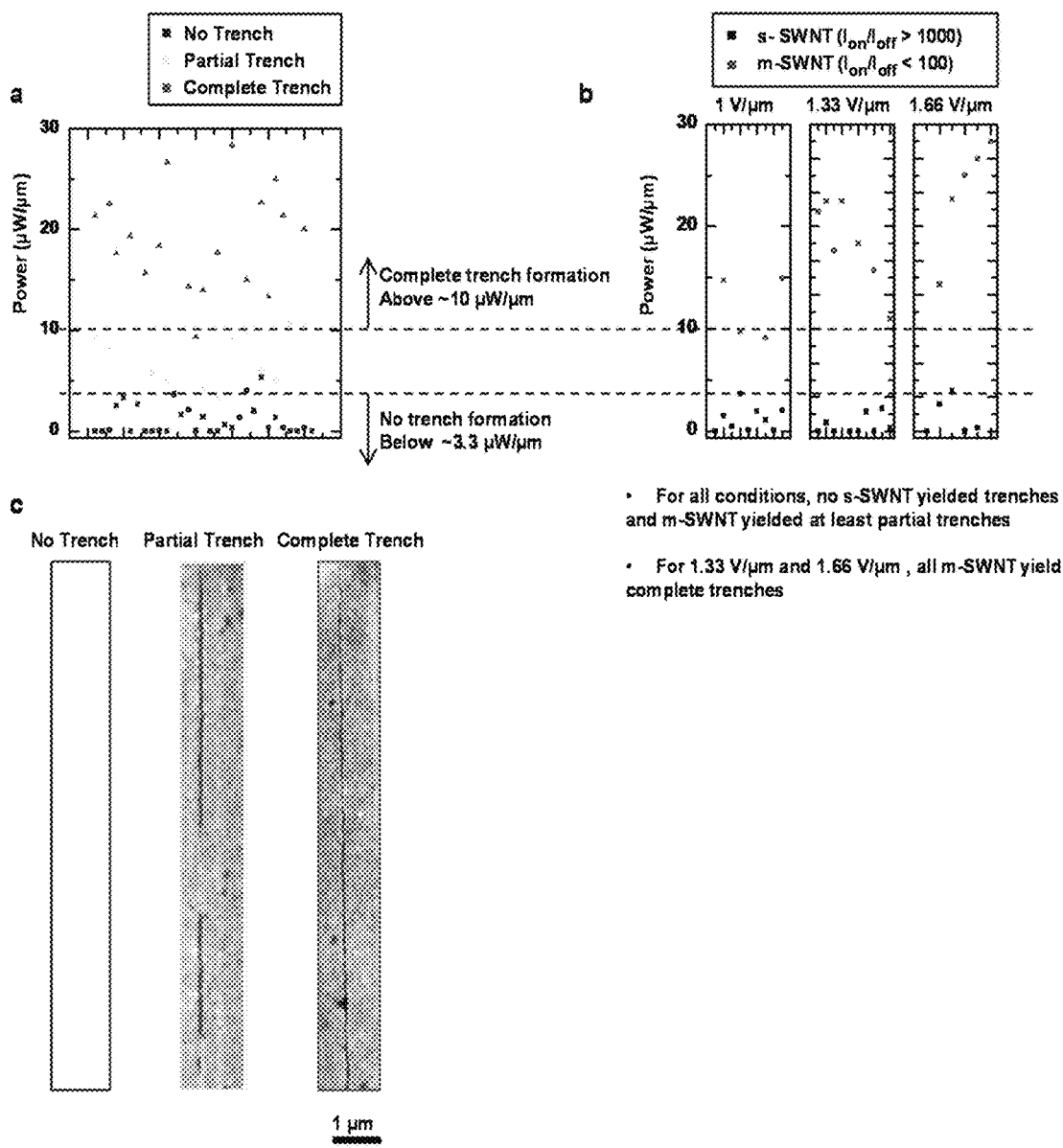
FIG. 7. Critical power for trench formation. Summary of results on experimental investigations of trench formation (5 min, 60° C.) in devices with single or several SWNT, in which an individual SWNT contributed a majority of the current. The findings define the critical power density to form trenches. All experiments were performed with s-SWNT in their "off" state (+20 $V_G$). (a) Scatter plot of device-level power density associated with the experiments. All devices with power density below 3.3 μW/μm show no trenches (blue), all devices with power density above 10 μW/μm show complete trenches along the entirety of their length (red), while those with intermediate powers show trenches along part of their length (yellow). Here, local variations in resistance along the length of the SWNT yield powers sufficient for trench formation in some, but not all regions of the SWNT. (b) The same set of experiments, organized by source-drain bias and SWNT electronic type. Although there is a large variation in the power associated with various SWNT at a given bias condition, for optimized conditions (−1.33 and −1.66 V/μm) all s-SWNT exhibit no trenches, while all m-SWNT exhibit complete trenches along their entire length. (c) Representative AFM images for: no trench (left), partial trench (middle), and complete trench (right) formation.
Figure 9:
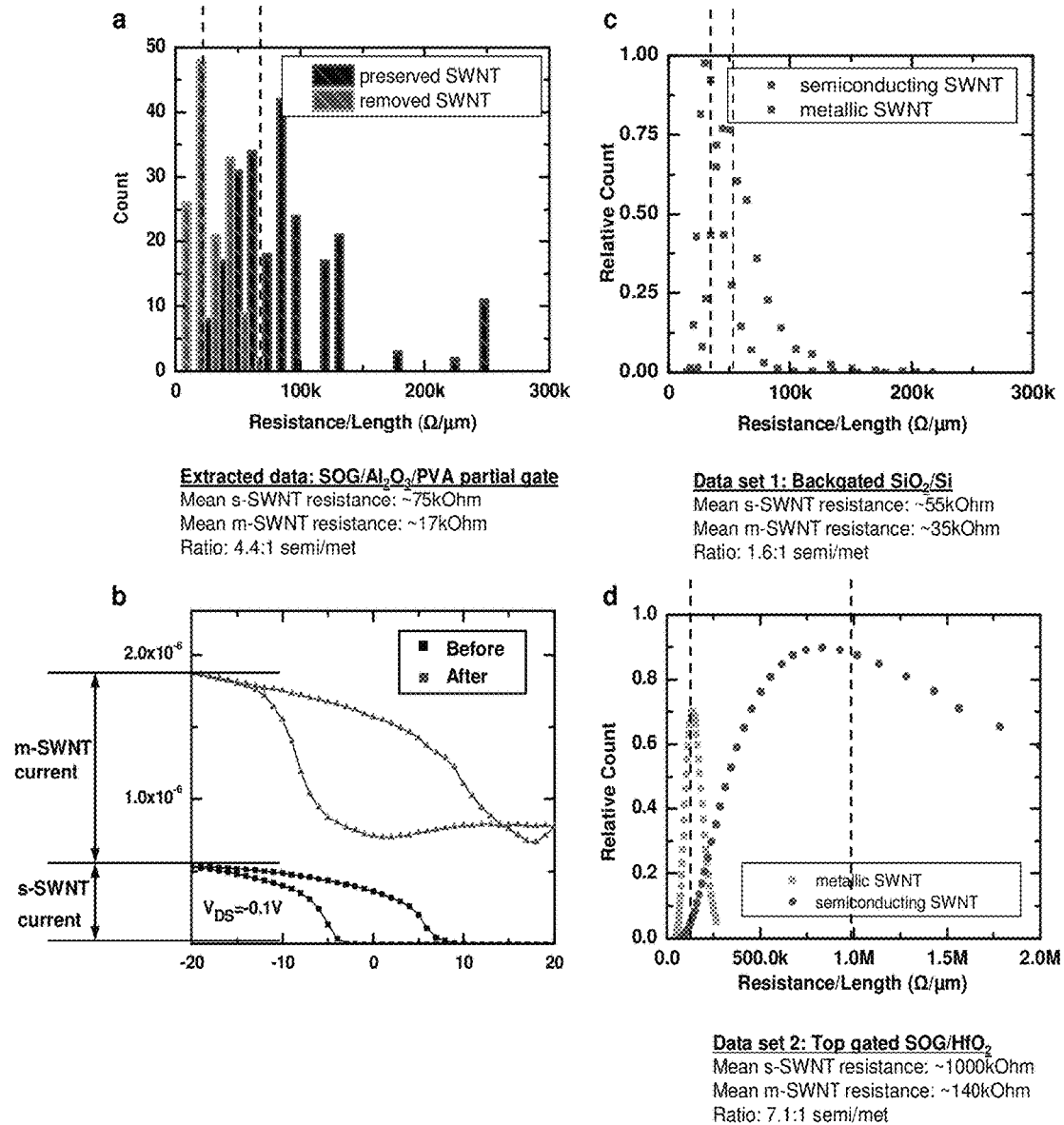
FIG. 9. SWNT resistivity data. (a) Extracted average resistivity for m-SWNTs and s-SWNTs based on sorted small area arrays. Average resistivity for each of 37 devices based on device resistance changes before and after TcEP and the number of SWNTs removed and remaining (based on AFM). (b) Typical I-V for an array before and after TcEP showing the relative conductance attributed to both m-SWNT and s-SWNT. (c,d) Histograms showing distributions of individual SWNT resistivities for two data sets, one based on back-gated devices on SiO₂/Si and the other based on top-gated devices with a gate dielectrica of SOG/HfO₂. Distributions representative of previously published results on arrays of SWNT.
Figure 24:
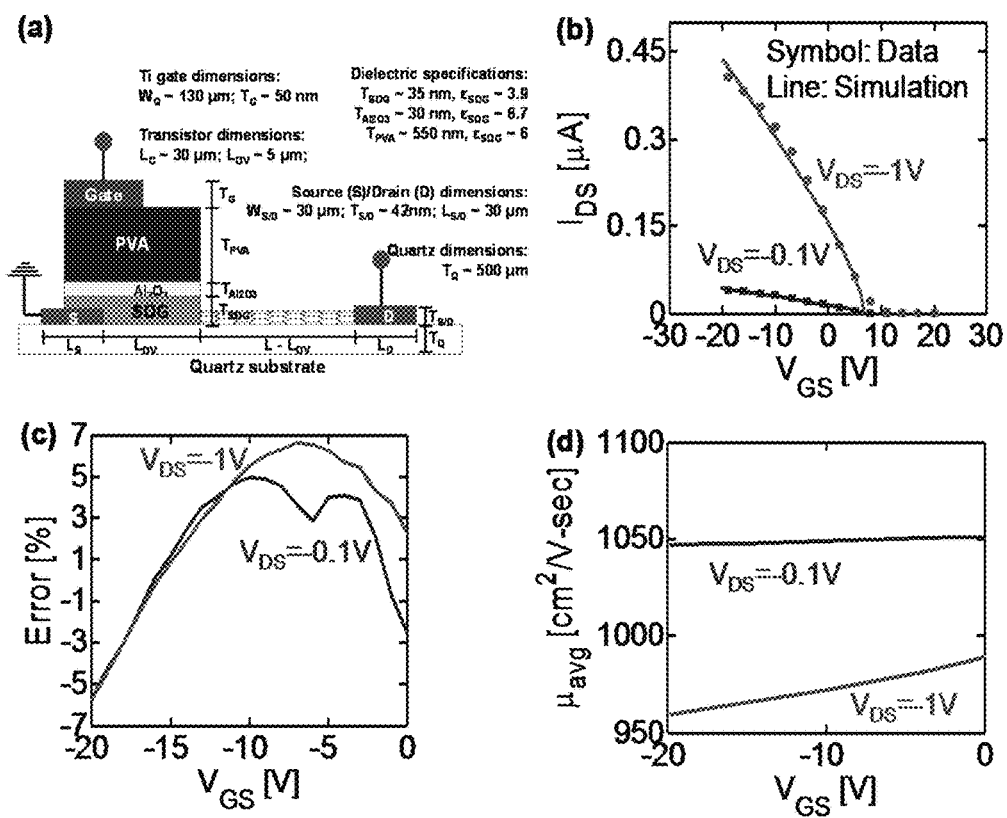
FIG. 24. Modeling results used to extract mobilities from device characteristics. (a) Cross-sectional schematic illustration of a partial gate device consisting of source/drain (Ti/Pd), gate (Ti), and a gate dielectric of PVA/Al$_2$O$_3$/Spin-on-glass (SOG). Values for the width (W), length (L) and thickness (T) of different components of the device are also specified. (b) Measured drain to source current ($I_{DS}$) vs gate to source bias ($V_{GS}$) averaged over ~35 such devices having 200 semiconducting SWNTs (s-SWNTs) at two different drain to source bias ($V_{DS}$). Simulation of the device characteristics by considering the dimensions specified in (a) and using ~1 nm diameter (average value for these nanotubes[26]) s-SWNTs. The results match the measured data. (c) Calculated percentage difference between modeling results and data as a function of $V_{GS}$ shows ±5-7% uncertainty in mobility extraction. (d) The simulation yields an average mobility of ~960-1050 cm$^2$/V-sec at different bias conditions.

Other results suggest that the process also preserves most or all of the s-SWNTs. First, of the 377 SWNTs present initially, 63% (i.e. 238 SWNTs) remain after purification. This outcome is consistent with the expected percentage (~66%) of s-SWNTs in collections of SWNTs grown by chemical vapor deposition[3,38]. Second, among 28 devices where the SWNT type can be determined from electrical behaviors measured before and after purification (i.e. those that incorporate ≤2 SWNTs), all of the m-SWNTs and none of the s-SWNTs show trenches (for optimized conditions; see Supplementary Information, FIG. 7). Third, reductions in $I_{on}$ induced by purification are modest; for the device shown in FIG. 1c the ratio of $I_{on}$ after the process to its value before is $I_{on,a}/I_{on,b}$~25%. The weighted average from all of the devices is $I_{on,a}/I_{on,b}$~30%. These results can be interpreted by examining the dependence of $I_{on,a}/I_{on,b}$ on the percentage of SWNTs removed (FIG. 1e). The trends are consistent with models that assume 100% preservation of s-SWNTs, expected populations of s-SWNTs and m-SWNTs, and ratios of conductances of m-SWNTs to s-SWNTs (in their on state) that are within an experimentally observed range of 6:1 and 2:1 (FIG. 9). Collectively, then, all observations suggest highly selective and efficient purification, in which all m-SWNTs are eliminated, and most or all s-SWNTs are preserved without degradation. Rigorous electrostatic analysis indicates mobilities of ~1000 cm²/Vs for the s-SWNTs (See Supplementary Information for details, FIG. 24), similar to values previously reported from unpurified arrays[3,4].

Experimental and Theoretical Studies of Nanoscale Thermocapillary Flow

Figure 2:
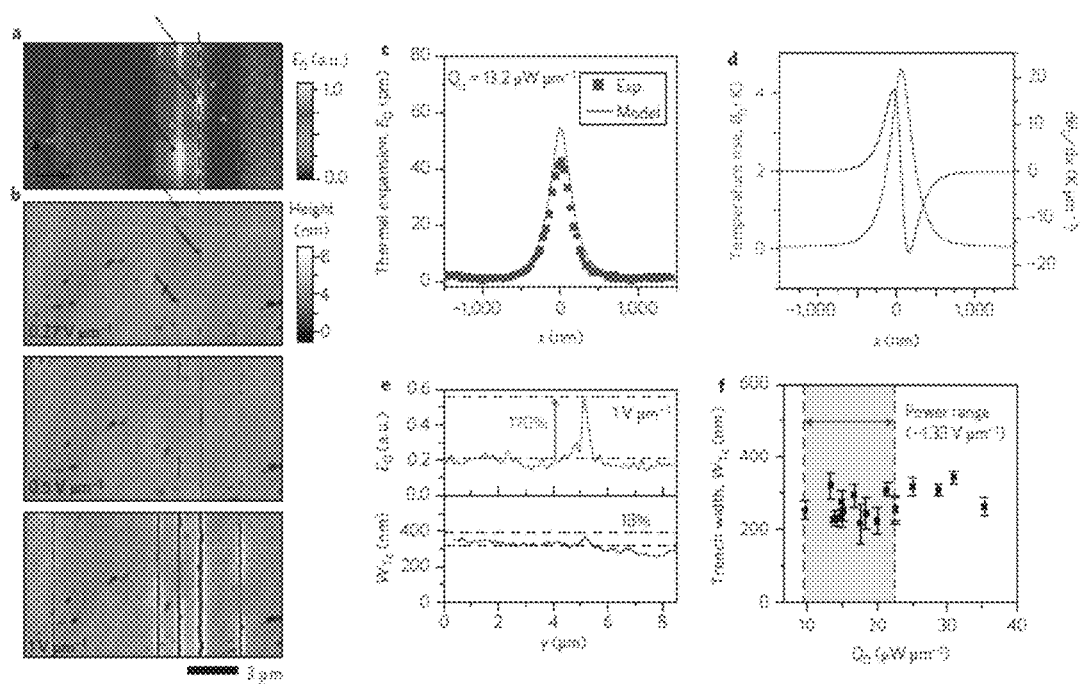
FIG. 2(ii). Nanoscale thermal transport associated with Joule heating in SWNTs leads to thermal gradients that are sufficiently large to drive thermocapillary flows in thin organic coatings. (a) Scanning Joule expansion microscope image of an array of SWNTs in an operating, two terminal device on quartz. The electrodes (separation ~30 µm) are above and below the image, out of the field of view. The coordinates x and y lie perpendicular and parallel, respectively, to the direction of alignment of the SWNTs. (b) Topographical images of the same device shown in the scanning Joule expansion micrograph of (a), coated with a thin (~25 nm) layer of thermocapillary resist, collected after operation at bias conditions of 0.27 (top), 0.5 (middle) and 1.0 V/µm (bottom). Comparison of these images to those collected by scanning Joule expansion microscopy reveals a clear correlation between AC expansion ($E_0$; and, therefore, temperature) and formation of trenches in the thermocapillary resist (DC heating). (c) AC Thermal expansion, $E_0$, induced by Joule heating in an individual SWNT with input power density $Q_0$~13 µW/µm (peak to peak) measured by scanning Joule expansion microscopy (line) as a function of position x, where x=0 is the location of the SWNT, on a $SiO_2$/Si substrate and results of thermomechanical modeling (symbols). (d). Computed AC temperature rise, $\theta_0$, and thermal gradients ($d\theta_0/dx$) at the surface of the thermocapillary resist using experimentally validated models, for the case of the SWNT in (c). The results indicate small increases in temperature for levels of Joule heating that induce trenches in the thermocapillary resist (~3-10 pW/µm). (e) The top graph shows AC thermal expansion (arbitrary units) measured by scanning Joule expansion microscope along the length (y) of the fourth SWNT from the left in the array that appears in (a) and (b). The bottom graph shows the width of the corresponding trench that appears in the thermocapillary resist ($W_{Tc}$ measured at the top of the film) for an applied bias of ~1 V/µm. The results show variations in $W_{Tc}$ that are nearly ten times smaller than those in expansion (and therefore temperature). (f) Measurements of the average $W_{Tc}$ as a function of $Q_0$. The results reveal no systematic dependence on $Q_0$ over this range. The highlighted region corresponds to the values of $Q_0$ associated with optimized conditions for the purification process.

Detailed experimental and theoretical studies reveal quantitative aspects of heat transport and thermocapillary flow. We start by examining the distributions of temperature generated during Joule heating and their role in the behavior of the thermocapillary resist. FIG. 2(ii)a shows a scanning Joule expansion microscope[39,40] image of thermal expansion that results from Joule heating in an array of SWNT, at a drain-source bias condition $V(t)=V_{DS} \cos(2\pi f t)$ with $V_{DS}=5$ V and f=386 kHz. Here, Joule heating with power density $Q(t)=Q_0[1+\cos(4\pi f t)]/2$ yields AC thermal expansion at a frequency of 2f, according to $E(t)=[E_1+E_0 \cos(4\pi f t)]/2$. The components $E_1$ and $E_0$ correspond to DC and AC thermal expansion, respectively. The image signal corresponds to the peak-peak value of the AC expansion, $E_0$. FIG. 2(ii)b shows topographical images of the same array coated with thermocapillary resist after application of several increasing values of $V_{DS}$ (direct current for 5 min; substrate temperature 60° C.). A key observation is that the distributions in expansion, and therefore temperature (FIG. 2a), correspond directly to the geometries of trenches that appear in the thermocapillary resist (FIG. 2b). For instance, trenches progressively form with increasing $V_{DS}$ in an order consistent with the temperatures revealed by scanning Joule expansion microscopy, e.g. trenches at the second and fifth SWNT from the right appear first and last, respectively. Related effects can be observed along an individual SWNT, where trenches nucleate in areas of enhanced temperature ('hot spots'; arrows in FIG. 2a and the top frame of FIG. 2b). These indications establish a clear, although qualitative, connection between temperature and operation of the thermocapillary resist.

Figure 11:
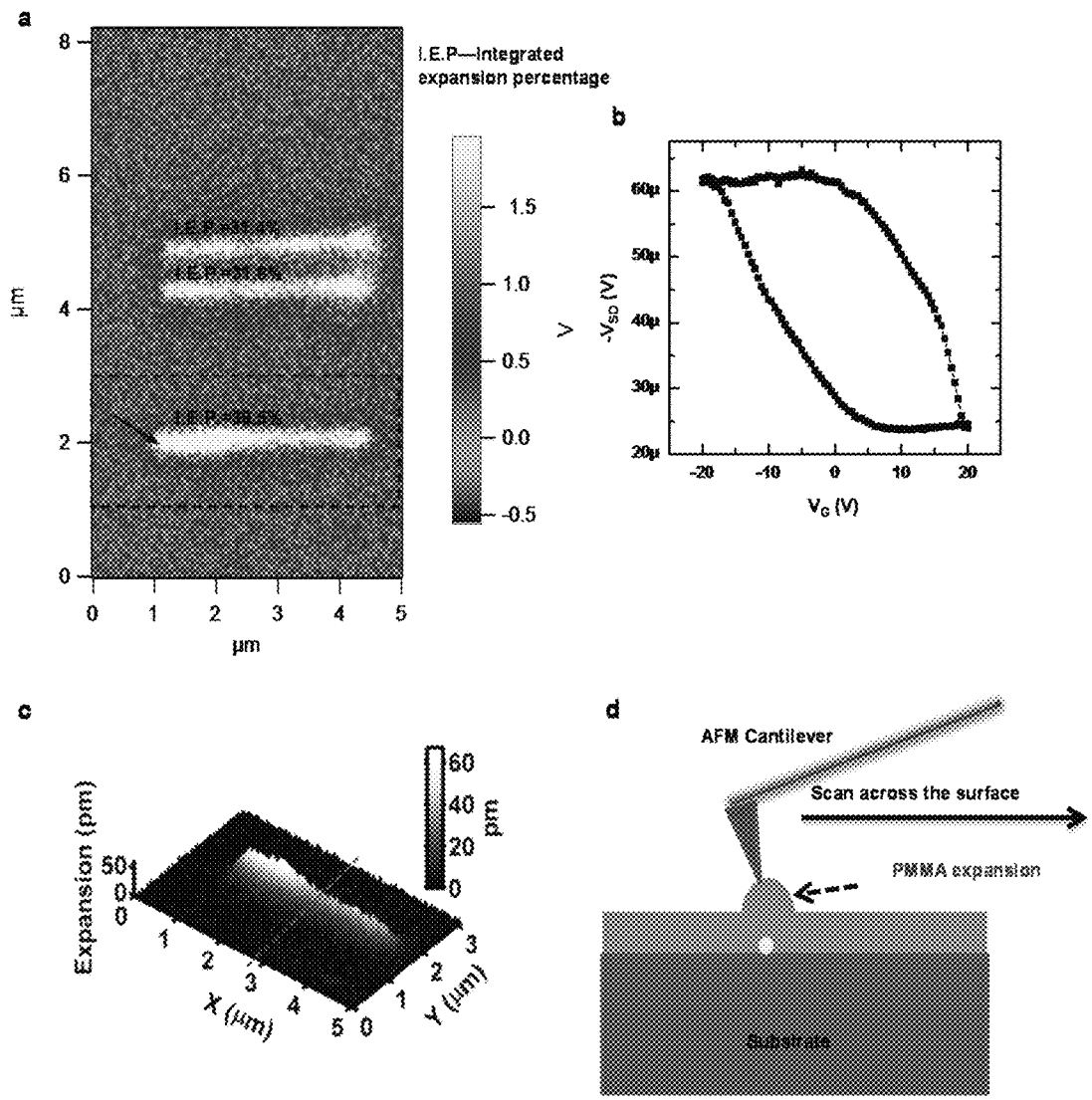
FIG. 11. Summary of SJEM measurements. (a) Full SJEM image for an array of 3 SWNTs. The relative integrated intensity for each SWNT is indicated. This relative intensity is used to calculate the relative proportion of the total device power density associated with each SWNT. (b) Transfer characteristic of a device with an array of 3 SWNTs. (c) SJEM image for a SWNT used for validation of analytical temperature models (FIG. 2c). (d) Schematic illustration of SJEM measurements.
Figure 12:
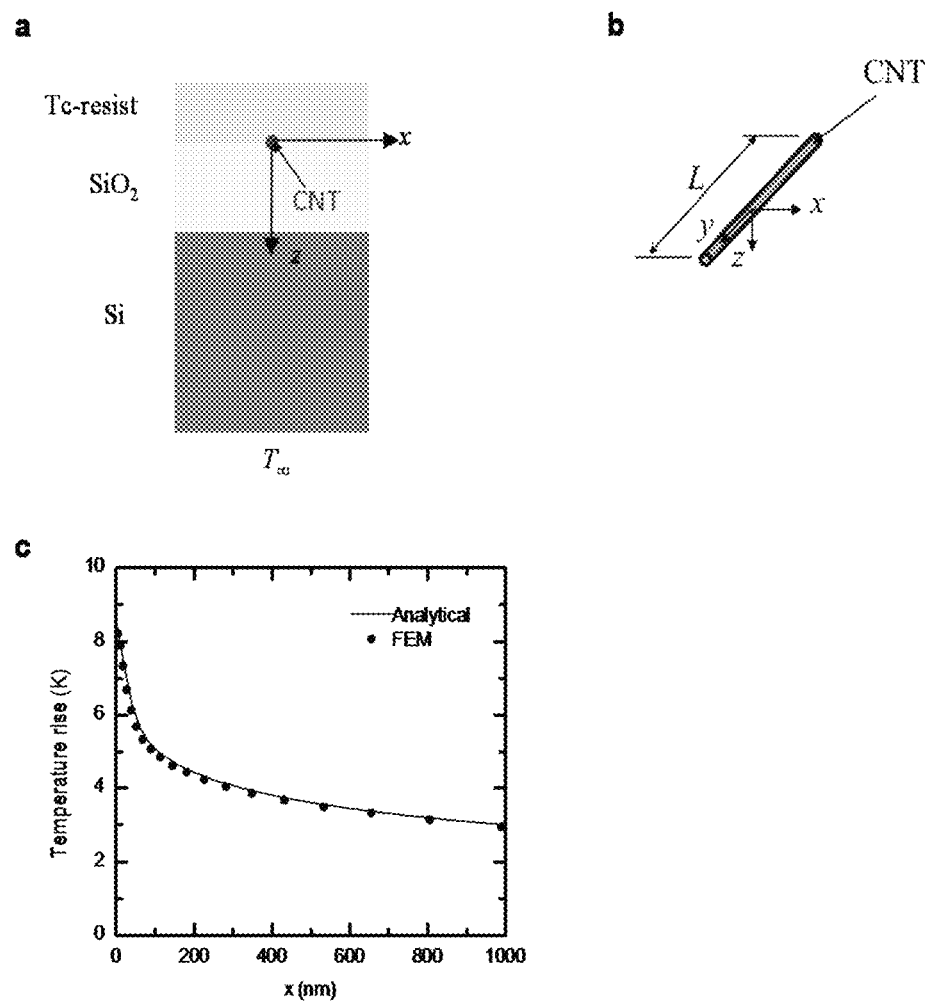
FIG. 12. Thermal modeling geometry. (a) Cross-sectional schematic of the film and substrate geometry associated with thermal modeling, with axes defined. (b) Modeling axes defined relative to the position of the SWNT. (c) Tc-resist surface temperature distribution for the case of a heated SWNT on a quartz substrate (16.6 μW/μm).

The first step towards quantitative understanding is an experimentally validated model for nanoscale heat flow in this system. Raw data from measurements by scanning Joule expansion microscopy indicate relative temperature increases but not their absolute values. FIG. 2(ii)c shows a representative cross-sectional profile of $E_0$ for the case of a SWNT with length ~3.5 μm, along with the corresponding scanning Joule expansion microscopy image (FIG. 11). The power density per unit length is Q(t) with $Q_0$ estimated to be ~13 μW/μm based on the total input power into the device, which includes three SWNTs on an $SiO_2$/Si substrate. Analytical models of temperature distributions that treat the SWNT as line heat source with length L and an input power density, Q(t) can be developed (see Supplementary Information, FIG. 12). Boundary conditions involve continuous temperature and heat flow at all material interfaces except those with the SWNT, negligible heat flow at the top surface and a constant temperature at the base of the substrate. At the SWNT interface, discontinuous heat flow, Q(t), is assumed, as a means to introduce the source of Joule heating. The results, together with materials constants taken from the literature (see Table 1) and analytical treatments of the resulting thermal expansion, yield expansion profiles that have both peak magnitudes ($E_0$~50 pm) and spatial distributions (characteristic widths ~340 nm) consistent with the scanning Joule expansion microscopy results (~40 pm and ~320 nm, respectively), when $Q_0$~13 μW/μm, the estimated experimental value. FIG. 2(ii)d shows the associated AC temperature increases ($\theta_0$) and thermal gradients ($d\theta_0/dx$), where $\theta(t)=[\theta_1+\theta_0 \cos(4\pi f t)]/2$.

TABLE 1

Thermal and Mechanical parameters used in analytical and FE models.

| Materials | Thermal Conductivity (Wm$^{-1}$K$^{-1}$) | Thermal Diffusivity 10$^{-6}$(m$^2$s$^{-1}$) | Coefficient of Thermal Expansion 10$^{-6}$(K$^{-1}$) | Yong's Modulus 10$^9$(Pa) | Poisson Ratio |
|---|---|---|---|---|---|
| Si | 120(ref[5]) | 73 | 2.6(ref[6]) | 165(ref[7]) | 0.28(ref[8]) |
| SiO2 | 1.3(ref[9]) | 0.84(ref[9]) | 0.50(ref[10]) | 64(ref[7]) | 0.17(ref[11]) |
| Quartz | 6.0(ref[12]) | — | — | — | — |
| PMMA | 0.19(ref[13]) | 0.11(ref[14]) | 50(ref[15]) | 3.0(ref[16]) | 0.35(ref[17]) |
| Tc-resist | 0.2(meas) | — | — | — | — |

When applied to the case of DC heating (f=1.0 Hz), and quartz substrates, the same analytical model yields an expression for the rise in temperature of the surface of the thermocapillary resist, $\theta=T-T_\infty$ where $T_\infty$ defines the temperature of the background, $$\theta(x, y) = \frac{1}{2k_s\pi} \int_{-L/2}^{L/2} d\eta \int_0^\infty \frac{Q_0 J_0\left(\xi\sqrt{(\eta-y)^2+x^2}\right)}{\cosh(\xi h_f) + \frac{k_f}{k_s}\sinh(\xi h_f)} d\xi \quad (1)$$

Here, $k_s$ and $k_f$ are the thermal conductivity of the thermocapillary resist and quartz substrate, respectively, and $h_f$ is the thickness of the resist. This solution, which is also consistent with 3D finite element analysis (ABAQUS), suggests small increases in temperature at the SWNTs (~2-5° C.) for power densities needed to achieve trenches. The flows arise from large associated gradients in temperature (~20° C./μm). (See Supplementary Information, FIG. 12). Studies of flow induced with heated tips in an atomic force microscope verify the low temperature operation. (See Supplementary Information, FIG. 16.)

Figure 19:
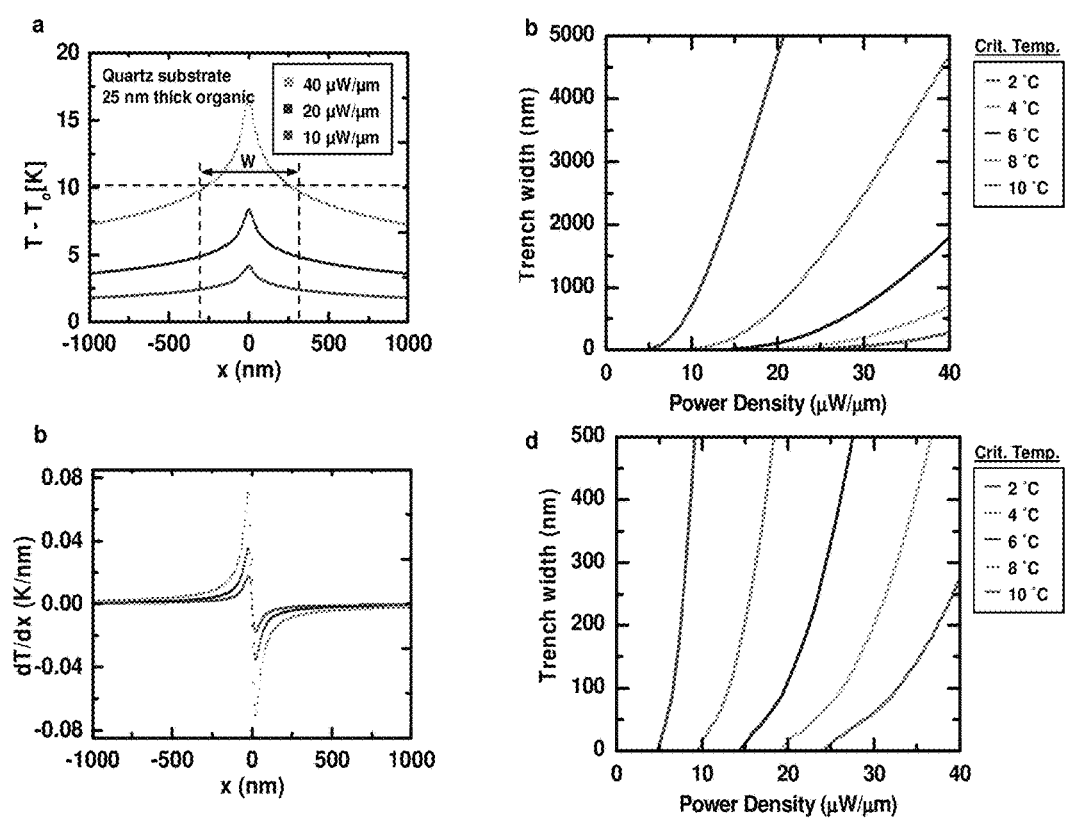
FIG. 19. Theoretical trench width for processes based on critical temperatures. (a,b) Temperature profiles and gradients predicted by analytical thermal models for a variety of powers. Processes such as sublimation or ablation have a critical temperature associated with them such that all material at or above this temperature is removed and all below the critical temperature is preserved. (c,d) Power dependence of predicted trench width associated with processes with critical temperatures ranging from 2-10° C. Processes with higher critical temperature should show similar scaling but with higher power density required to yield trenches (unsuitable for TcEP). This type of scaling is not ideal for TcEP, since at conditions sufficient to yield trenches in the least conductive m-SWNT, the most conductive SWNTs would exhibit very wide trenches (several μm), thereby exposing neighboring SWNTs.

The characteristics of this flow provide several attractive features for present purposes, one of which is immediately evident from inspection of FIG. 2a,b. At large $V_{DS}$ ($V_{DS}/L_{ch}$>1 V/μm), the trenches associated with SWNTs that have pronounced hot spots exhibit uniform widths. Likewise, SWNTs that show vastly different temperatures at a given $V_{DS}$ display similar trench widths at sufficiently large $V_{DS}$ ($V_{DS}/L_{ch}$>1 V/μm). FIG. 2(ii)e presents results for the second SWNT from the right, extracted from FIG. 2a and the bottom frame of FIG. 2b. Clearly, the variations (between the mean value and maximum value) in expansion measured along the length of the SWNT are much larger than those in the trench widths ($W_{Tc}$), as quantified by separations between the raised regions of the thermocapillary resist at the edges of the trench. This physics provides an ability to realize trenches with small, uniform widths even across large-scale arrays that incorporate m-SWNTs with wide ranges of conductances and diameters, and consequently, peak temperatures and thermal gradients. FIG. 2(ii)f shows the average $W_{Tc}$ for a number of different, individual SWNTs as a function of $Q_0$. Similar values occur over ranges of power (~10-40 μW/μm) that exceed those associated with optimized conditions for purification. This behavior is much different than that expected from other thermally driven processes, such as sublimation or ablation, which typically involve abrupt temperature thresholds (FIG. 19).

Figure 3:
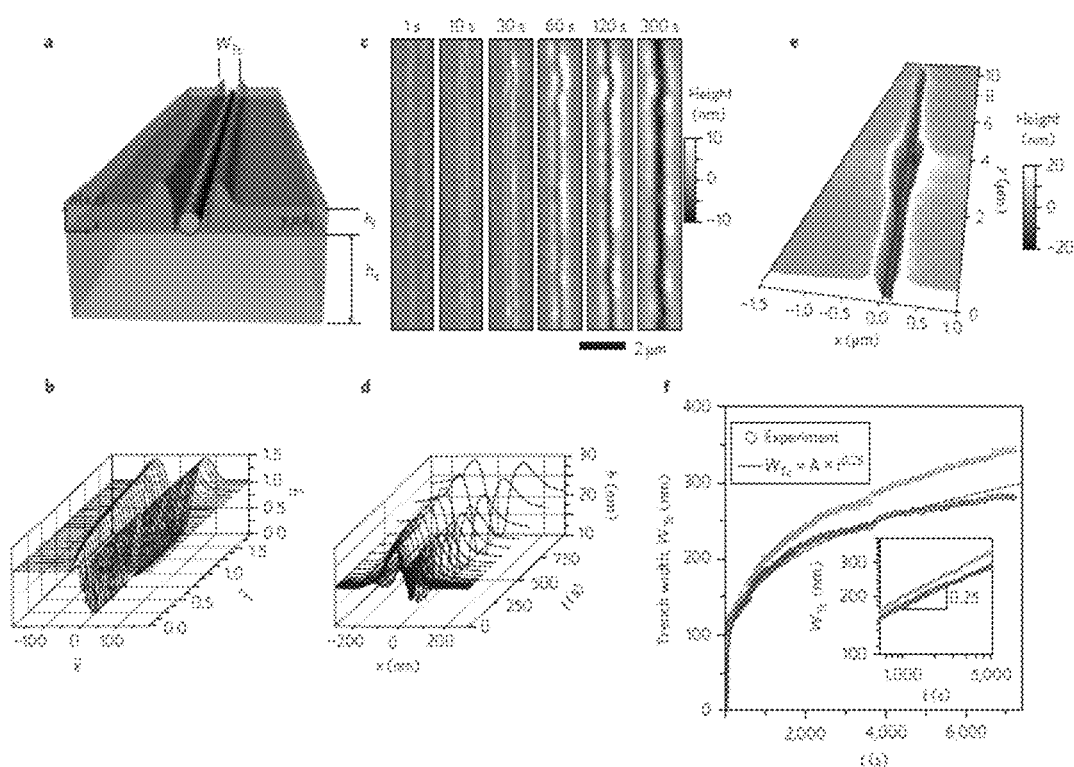
FIG. 3. Experimental and theoretical studies reveal essential aspects of nanoscale thermocapillary flows in thin organic coatings on heated SWNTs. (a) Schematic illustration of the geometry of the system, with key parameters defined. The SWNT, the thermocapillary resist and the substrate are grey, green and blue, respectively. (b) Theoretically calculated normalized surface profiles of the thermocapillary resist ($\bar{h}$), as a function of normalized distance ($\bar{x}$) and time ($\bar{t}$), showing the evolution of the trench geometry with thermocapillary flow. The simulations used polystyrene due to availability of relevant materials parameters in the literature. (c) Atomic force microscope images of a SWNT coated with thermocapillary resist (~25 nm) after Joule heating (0.66 V/µm) for 1, 10, 30, 60, 120 and 300 s, induced by current injection at electrodes that lie outside of the field of view. Thermocapillary flow creates a trench that aligns to the SWNT and grows in width over time. (d) Averaged cross sectional profiles extracted from measurements like those shown in (c). The results compare favorably to the modeling in (b). (e) Atomic force microscope image, rendered in a 3D perspective view collected at a duration of 1800 s. The width in this case is sufficiently large that Atomic force microscope measurements reveal clearly that thermocapillary flow completely and cleanly exposes the SWNT. (f) Widths of trenches measured by atomic force microscopy from the ridges that form at the top surface ($W_{Tc}$) as a function of time of Joule heating in two different SWNT, at a field of 0.66V/µm. Both model and experiment show a power law time dependence with an exponent of 0.25.

The governing equation of motion for thermocapillarity in systems where the dimension along the SWNTs can be considered infinite corresponds to unidirectional flow in which the thickness profile in the thermocapillary resist can be written h(x,t) with $$\frac{\partial \bar{h}}{\partial \bar{t}} + \frac{\partial}{\partial \bar{x}} \left[ \frac{\bar{\tau} \bar{h}^2}{2\bar{\mu}} + \frac{\bar{h}^3}{3\bar{\mu}} \frac{\partial}{\partial \bar{x}} \left( \bar{\gamma} \frac{\partial^2 \bar{h}}{\partial \bar{x}^2} \right) \right] = 0 \quad (2)$$

where $\bar{h}=h/h_f$, $\bar{x}=x/h_f$, $\bar{t}=\gamma_1 Q_0 t/(\mu_0 k_f h_f)/(\mu_0 k_f h_f)$, $\bar{\mu}=\mu/\mu_0$, $\bar{\gamma}=k_f t/(Q_0 \gamma_1)$, $\bar{\theta}=k_f \theta/Q_0$, $\bar{\tau}=\partial \bar{\theta}/\partial \bar{x}$ the thermocapillary stress, μ is viscosity at temperature T, $\mu_0$ is the viscosity at the background temperature $T=T_\infty$, and γ is the surface tension, which often exhibits a linear dependence on temperature (i.e., $\gamma=\gamma_0-\gamma_1 \theta$). FIG. 3a shows the geometry. The appropriate initial condition is $\bar{h}/(\bar{x},\bar{t}=0)=1$. The boundary conditions are, $\bar{h}(\bar{x}=\pm\infty,\bar{t})=1$, and zero pressure, $$\frac{\partial^2 \bar{h}}{\partial \bar{x}^2}(\bar{x}=\pm\infty, \bar{t}) = 0.$$

Figure 14:
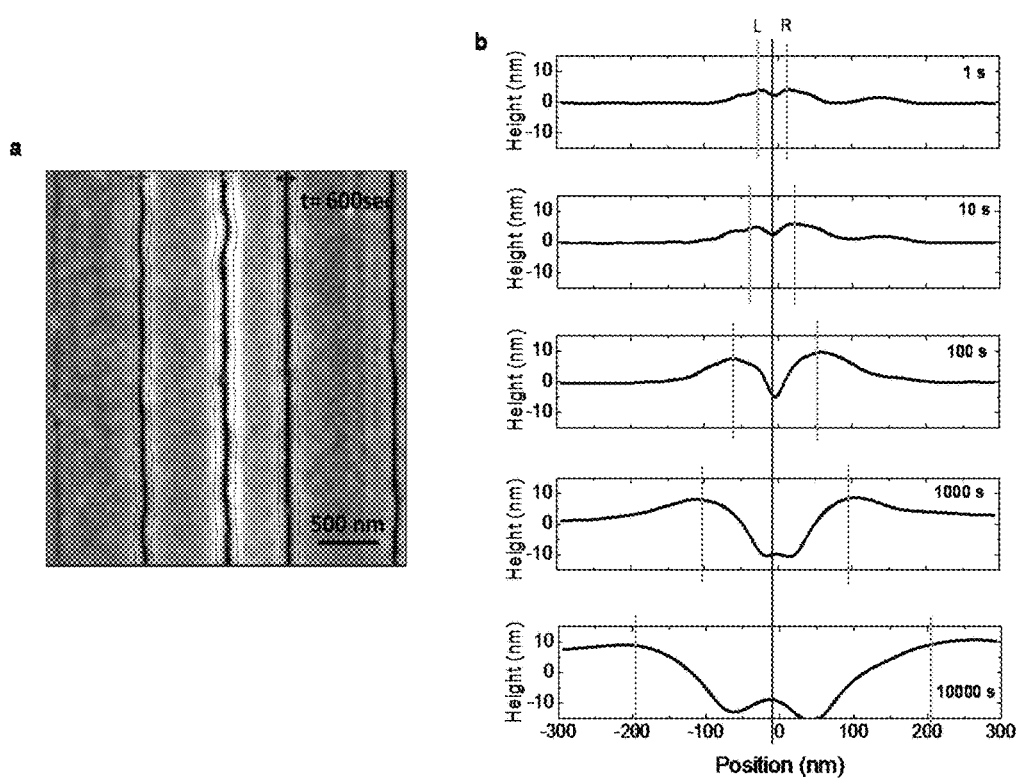
FIG. 14. Details of trench width identification. (a) Representative image of trench formation. Lines showing the position identified as the right and left trench edge. (b) Representative cross-sectional height profiles at various points in trench evolution. For the purposes of establishing reliable methods of consistently identifying trench width that are independent of AFM tip condition and can yield comparison to features easily identified by thermocapillary flow modeling, the trench edges were associated with the peaks of the pileup on the trench edge. As is evident from the cross-section profiles, that width of the trench at the base is substantially narrower than these values. AFM tip artifacts make precise measurement of this inner width difficult.
Figure 15:
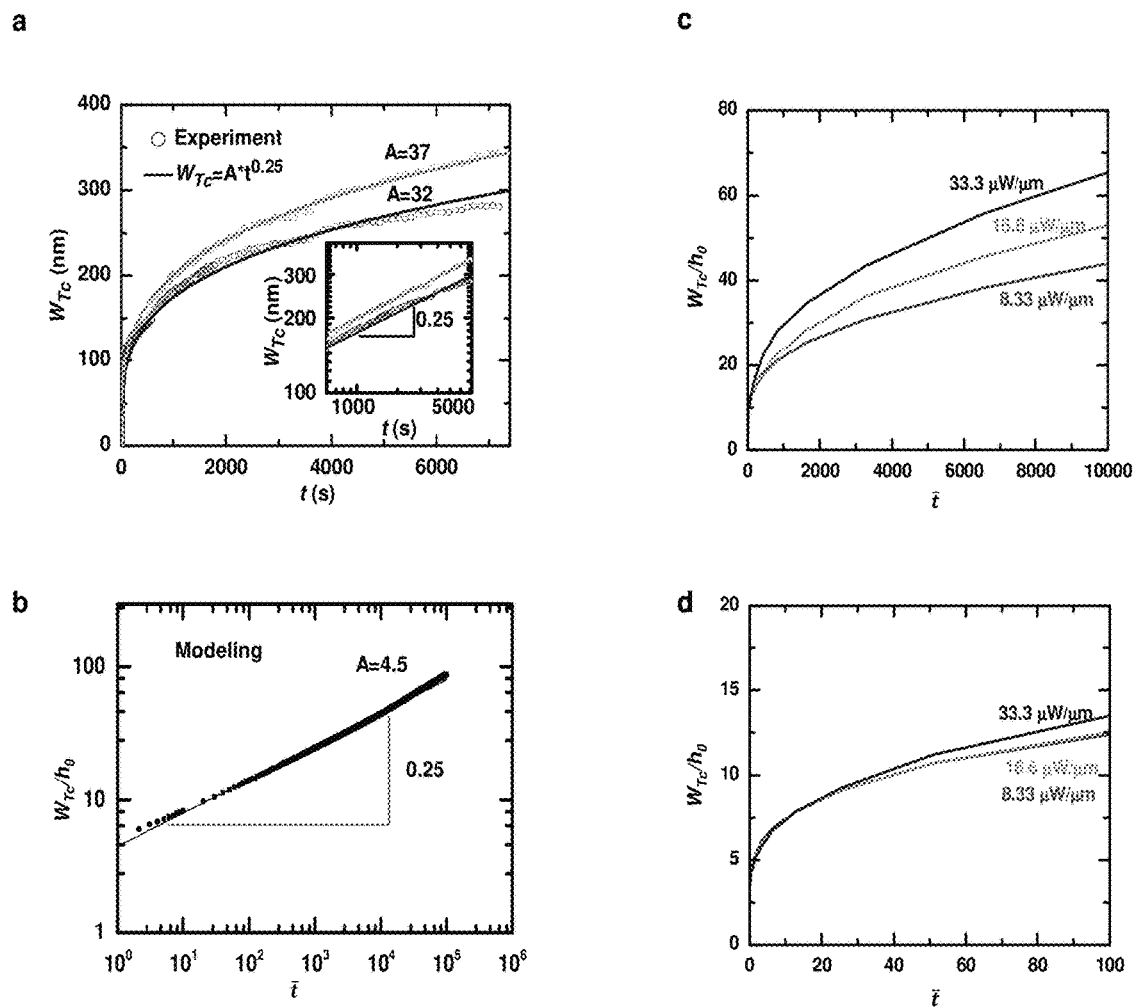
FIG. 15. Time dependence of trench width. (a) Experimental results showing power law time dependence, with $t^{0.25}$ scaling, for the width. Trenches associated with different SWNTs have slightly different prefactors, most likely associated with slight differences in relative power densities. (b) Modeling showing similar $t^{0.25}$ dependence, thus indicating that the model for Tc-flow accurately captures the fundamental scaling of trench formation. (c,d) Time dependence of width for various powers over long and short time scales respectively. For short time scales, where trench widths are comparable to those in TcEP, the width only depends weakly on the power.
Figure 18:
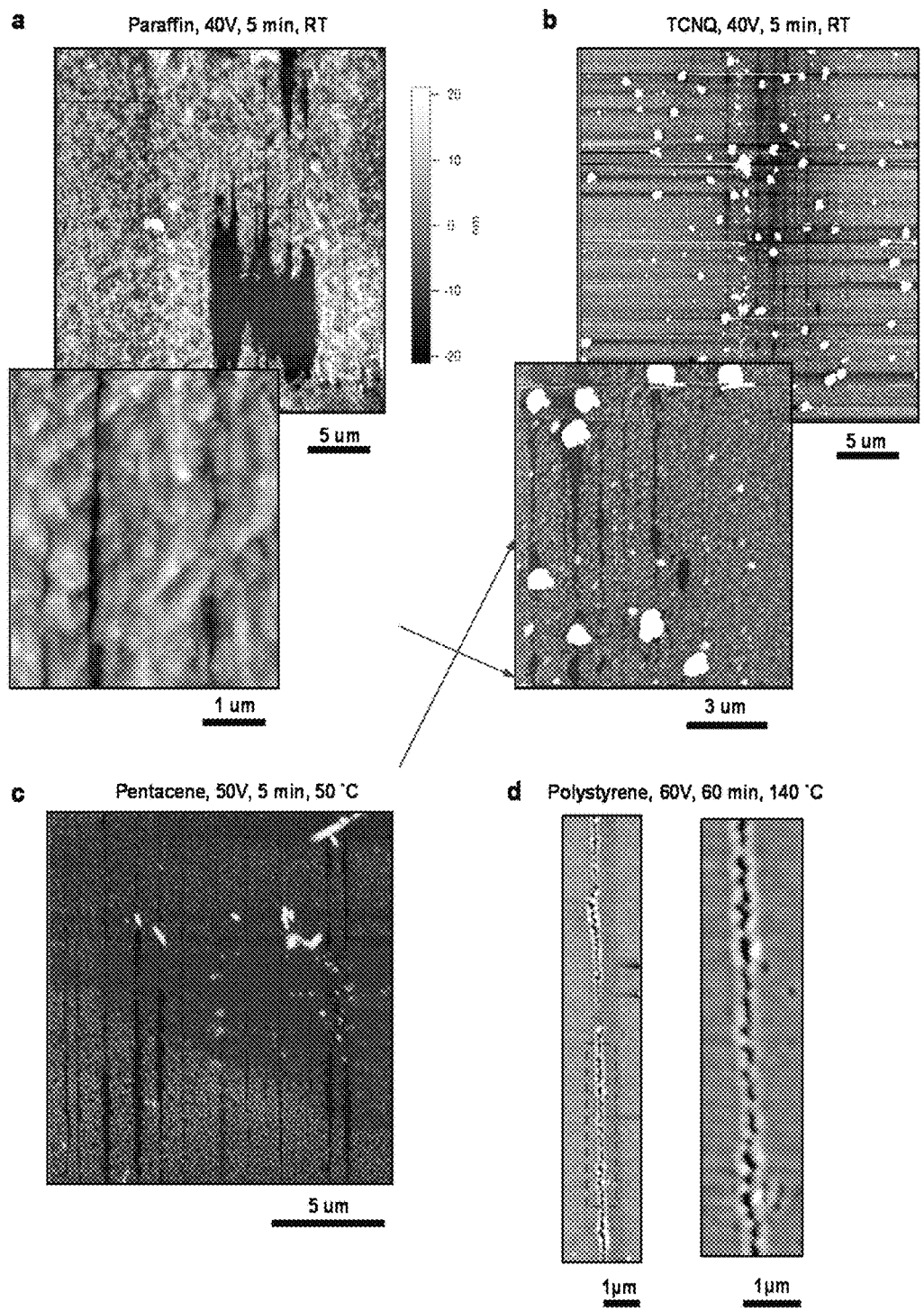
FIG. 18. Behaviors in other candidate materials for Tc-resists. AFM images of trenches formed for (a) paraffin, (b) TCNQ, and (c) pentacene. Some trenches are observed, but with non-uniform widths. For these materials, such behaviors can be attributed to their morphology. Other materials explored, such as polystyrene (d) failed as Tc-resists due to inability to form trenches at sufficiently low powers (likely due to high viscosity or low temperature coefficient of surface tension) and/or insufficient etch resistance.

With Eq. (1) for the temperature, numerical solutions to this system yield $\bar{h}/h/h_f$, based on assumptions that (a) at each point along x, the temperature throughout the thickness of the thermocapillary resist is equal to the temperature at its interface with the substrate and (b) flow in the thermocapillary resist does not change the temperature distributions. FIG. 3b shows results for the case of polystyrene, which exhibits behaviors like the thermocapillary resist (see Supplementary Information, FIG. 18) but has a known temperature dependent surface tension; γ=50.40−0.07388 mJ/m². For this example, $\bar{\mu}=1$, consistent with the small rise in temperature, and $Q_0=16.7$ μW/μm (from experiment). The trenches gradually widen and deepen with time, as the displaced material forms ridges at the edges. Topographical measurements of a representative SWNT coated with thermocapillary resist after Joule heating for various time intervals ($V_{DS}/L_{ch}$~0.7 V/μm, 30° C. background heating), show similar behaviors and profiles (FIG. 3c, d). At longer times, wider trenches result, to the point where SWNTs can be clearly observed at the base (FIG. 3e). Although the specific time durations needed to form complete trenches ($\bar{t}$~1) yield computed values of $W_{Tc}$ that are larger than those observed experimentally, the theory captures the essential time dependence. For example, FIG. 3f shows the measured time dependence of $W_{Tc}$ for two SWNTs, where both roughly follow the expected theoretical behavior, namely $W_{Tc}$~$t^{0.25}$ (see FIGS. 13-15). Another prediction of the theory is that, for a given time t=300 s, the value of $W_{Tc}$ depends only weakly on $Q_0$, over a remarkably large range, i.e. from ~10 μW/μm to ~35 μW/μm (see Supplementary Information, FIG. 15). This finding is consistent with observations discussed in the context of FIG. 2(ii). Finally, besides capturing the underlying physics, these models also suggest that optimal materials properties for thermocapillary resists include large temperature coefficients of surface tension and low viscosities. Furthermore, decreasing the thickness reduces the trench widths. Empirical studies of various materials for thermocapillary resists (see Supplementary Information, FIG. 18) led to the selection of the molecular glass reported here.

Application of the Purification Process

Figure 4:
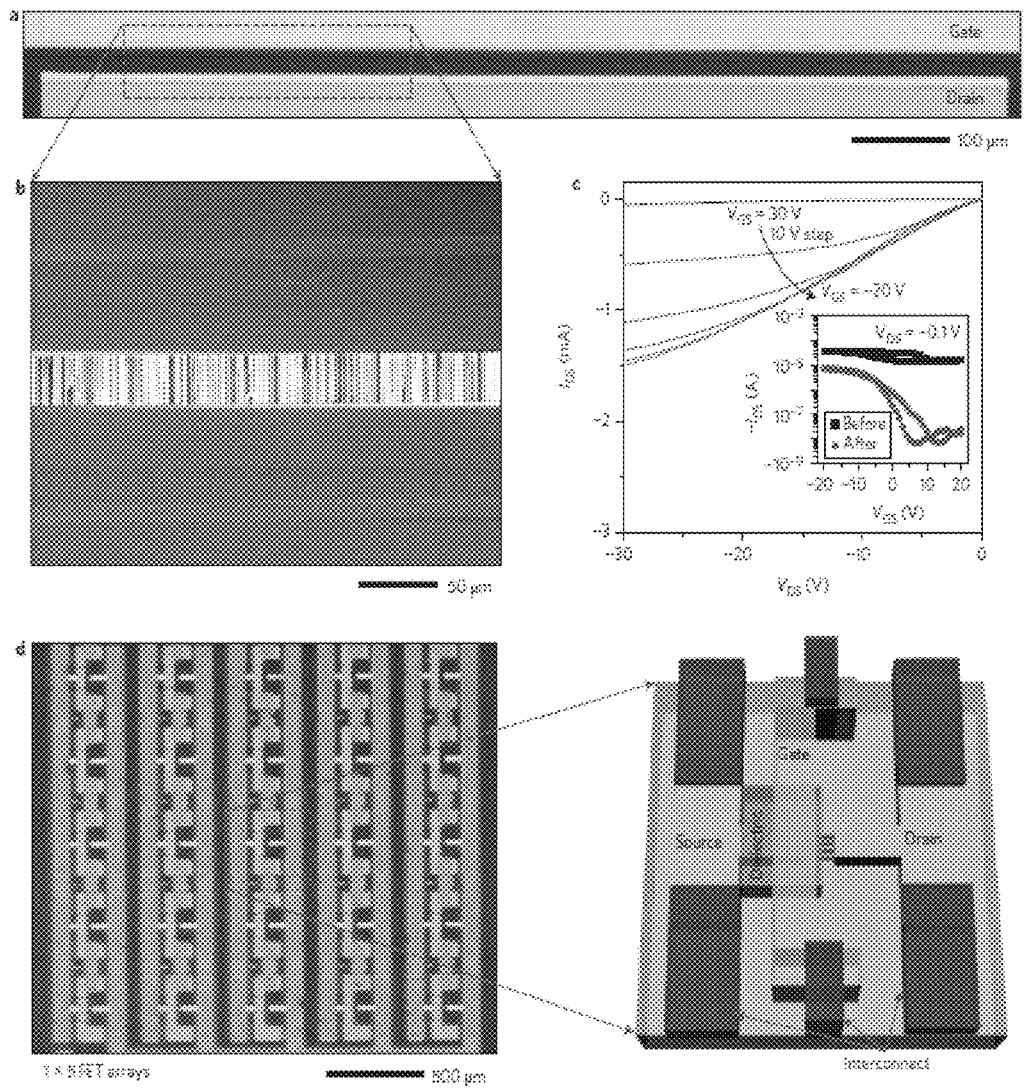
FIG. 4. Thermocapillary effects can be used to achieve purely semiconducting arrays of SWNTs in strategies that scale to large areas. (a) Optical microscope image of a set of electrodes for thermocapillary purification of an array of many hundreds of SWNTs. (b) Scanning electron microscope image of a small region of the structure shown in (a). (c) Transfer characteristics before and after removal of m-SWNTs from the region between the electrodes shown in (a). The results indicate outcomes consistent with observations of small-scale demonstrations, i.e. high on/off ratios ~$1\times10^3$ and modest reductions in on current ($I_{on,\ a}/I_{on,\ b}$~20%). (d) Optical micrograph and schematic illustration of alternative mode for scaled implementation. Here, an interconnected array of 25 sets of electrodes allows purification over a collection of small regions, in a parallel fashion. Associated transfer curves are similar to those shown in (c).
Figure 21:
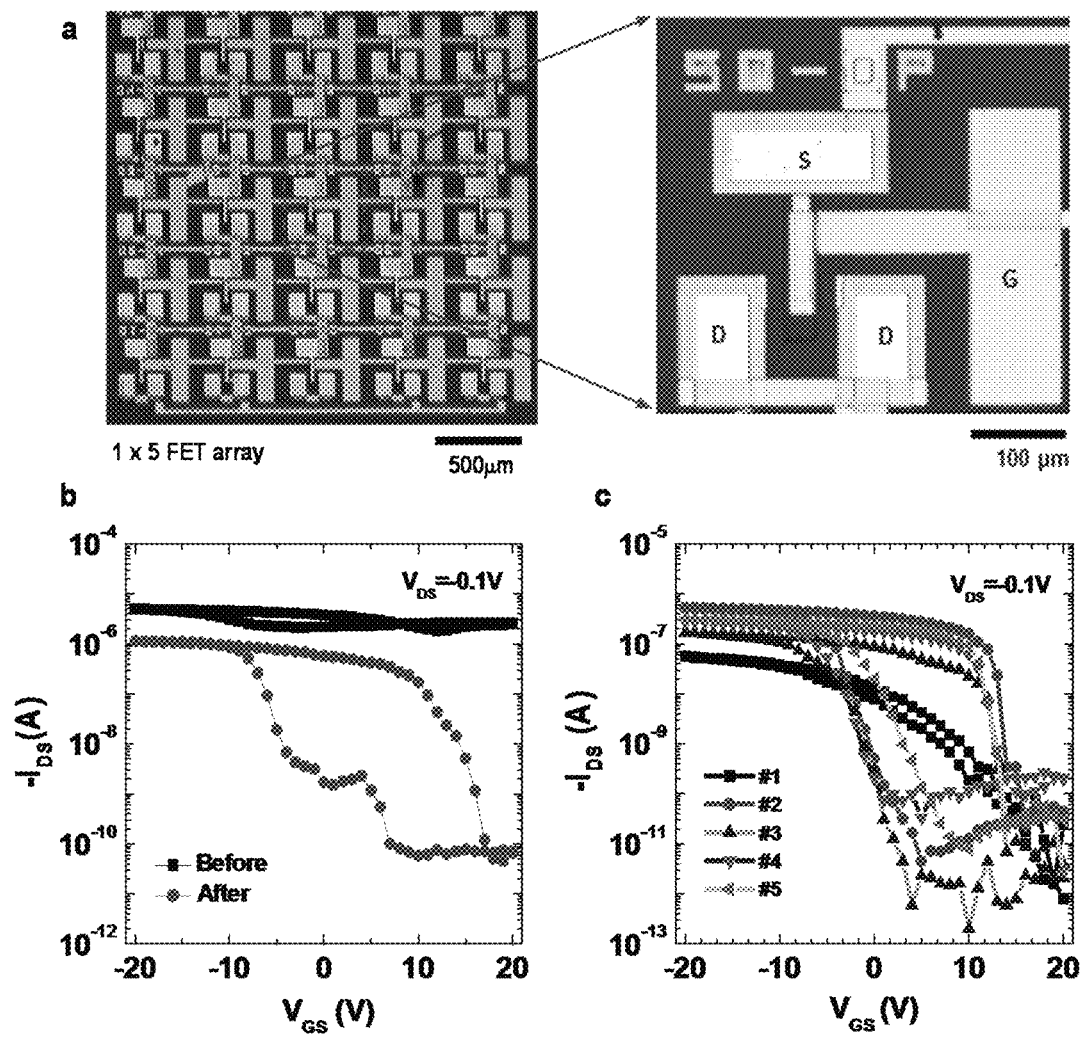
FIG. 21. Details of TcEP in a parallel operational mode. (a) Optical images for a 1×5 array of SWNT arrays and associated electrodes for TcEP, with electrodes connected in parallel (b) transfer characteristics before and after TcEP in parallel and (c) transfer characteristics for disconnected individual arrays following TcEP. All arrays show high on/off ratio following TcEP.
Figure 29:
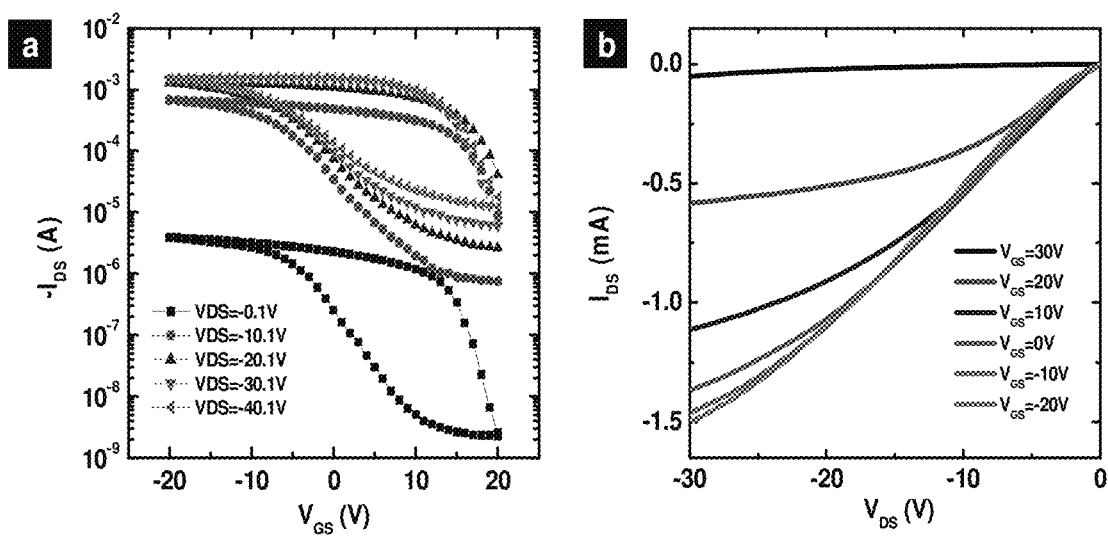
FIG. 29. Full characterization of split gate devices. (a) Transfer characteristics for a device with W/L=1000/30 μm after TcEP, evaluated at various drain bias ($V_{DS}$) conditions (b) output characteristics for this same device. All measurements were performed in a dry N$_2$ environment.
Figure 30:
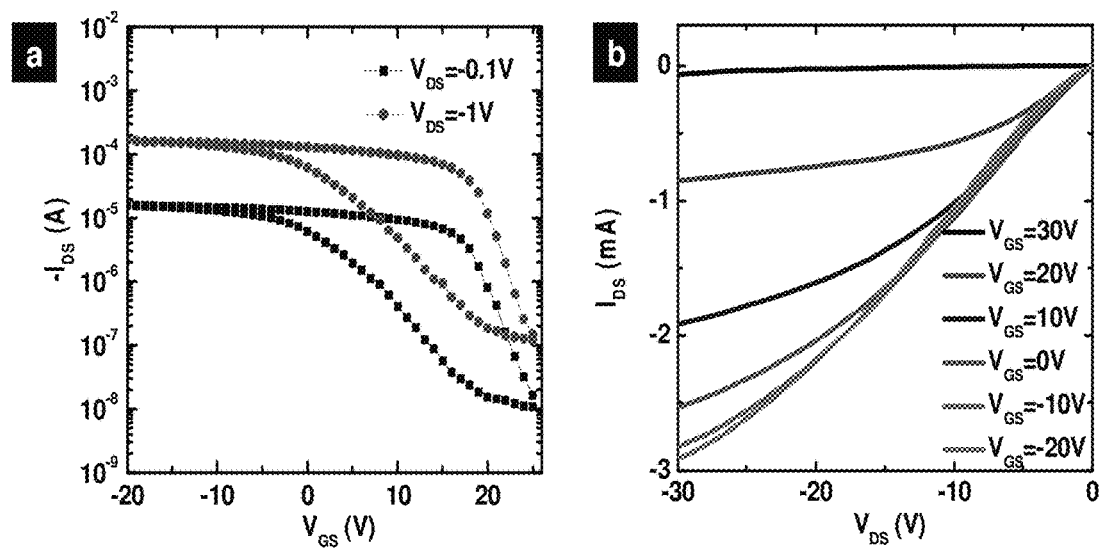
FIG. 30. Full characterization of split gate devices. (a) Transfer characteristics for two interconnected, purified devices to form effective channel dimensions of W/L=2000/30 μm, at low drain bias. (b) Output characteristics from the same structure. All measurements were performed in a dry N$_2$ environment.
Figure 31:
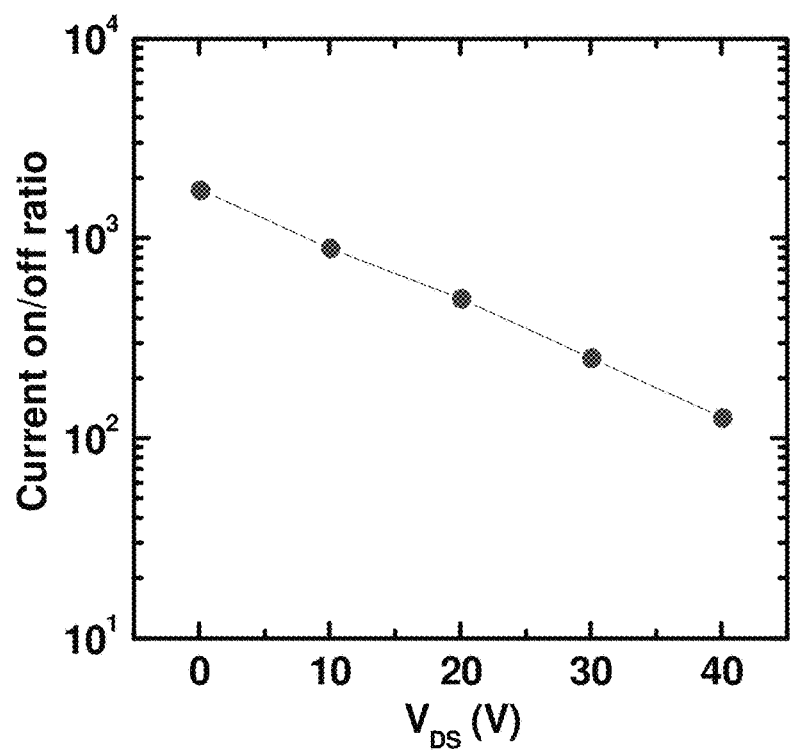
FIG. 31. On/off ratio as a function of drain bias for split gate device. On/off ratio as a function of $V_{DS}$ for a device with W/L=1000/30 μm, described in FIG. 4(c).
Figure 32:
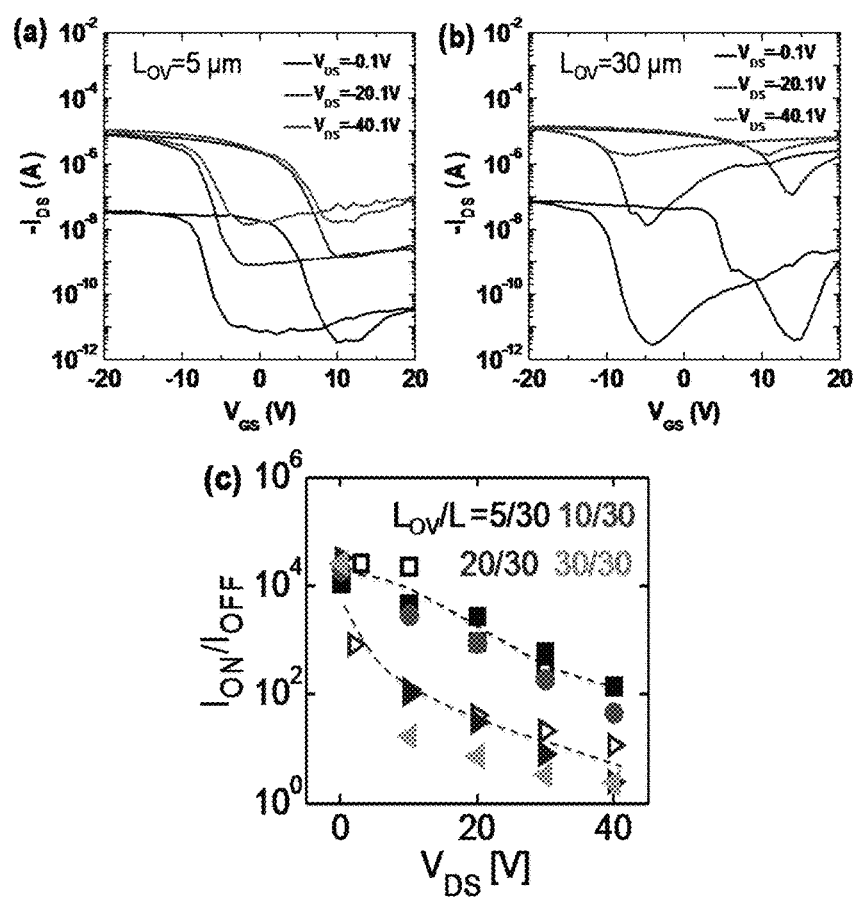
FIG. 32. Simulation and experimental results on trends in on/off ratio with bias condition. (a): Experimental $I_{DS}$-$V_{GS}$ characteristics for different drain bias at (a) $L_{OV}$=5 μm and (b) 30 μm. (c) Experimental (solid symbol) on/off current ratio vs $V_{DS}$ for different $L_{OV}$ follows simulation (open symbols are simulated for $L_{OV}$=5, 20 μm). Dotted lines are guide to eye only.
Figure 33:
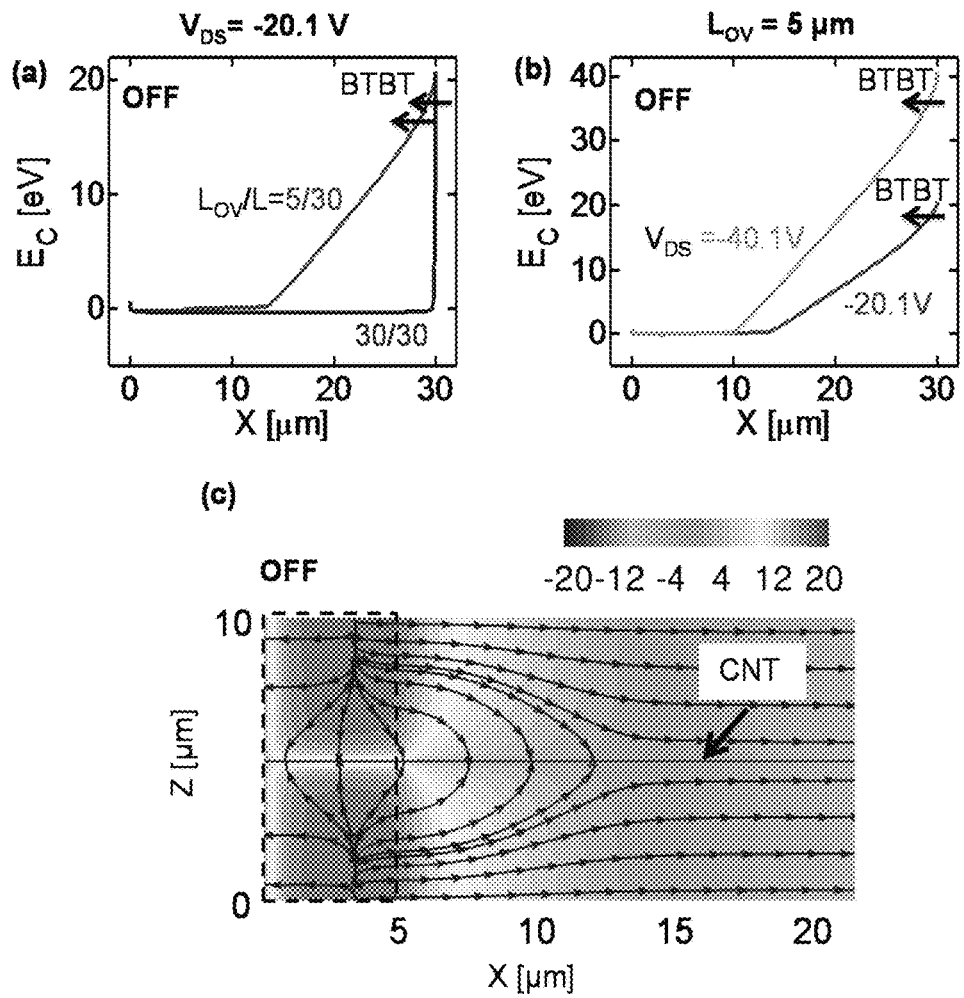
FIG. 33. Conduction band profiles along a d=1.74 nm semiconducting nanotube for different (a) overlap length and (b) drain bias. Regions with higher band bending near the drain end are prone to band-to-band tunneling (BTBT) that increases $I_{DS}$ at $V_{DS}$=20 V and, therefore, calculated on/off ratio (i.e., $I_{DS}@V_{GS}=-20$ V/$I_{DS}@V_{GS}=20$ V. (c) Two-dimensional potential profile (color contours) in off-state along the surface of a quartz wafer (directions X and Z are along and across the nanotube, respectively) containing the nanotube. The nanotube is biased in parallel-gate FET configuration (FIG. S18a) with $L_{OV}/L=5/30$ μm. Electrostatic control of gate extends beyond the gate region and results gradual change in potential along the nanotube and therefore, low BTBT for the partial-gate configuration.

The envisioned use of thermocapillary enabled purification is in a preparatory mode, where it serves as one of the several steps, such as substrate cleaning, SWNT growth, transfer and others that occur before device processing. Such a scheme decouples purification from any detailed consideration in component or circuit layout, and is made possible by the ability to eliminate entirely all of the m-SWNTs. Two approaches can be considered. In the first, one or a small number of electrode structures, each with large lateral extent as illustrated in FIGS. 4a-b, enable elimination of m-SWNTs over significant areas. Here processing occurs on hundreds or thousands of SWNTs at once, using pulsed currents to avoid cumulative heating (see Supplementary Information, FIG. 17). FIG. 4c shows the electrical characteristics of the structure in FIG. 4a before and after purification, where $I_{on, a}/I_{on, b}$ is ~20% and the on/off ratio after the process is ~$1\times10^3$, similar to results achieved on small arrays discussed previously. Current outputs can reach the mA range, as shown in FIG. 4c and FIG. 29. Additional details and examples of outputs up to ~3 mA appear in FIG. 30. FIG. 4d illustrates an alternative approach, in which smaller pairs of interconnected electrodes provide for purification in distributed regions, capable of lithographic alignment at a coarse level to areas of interest in a final application. Effects on $I_{on}$ and $I_{off}$ in this case are in the range of those achieved in other geometries (see Supplementary Information, FIG. 21, Table 2).

TABLE 2

Summary of conductance of 1 × 5 arrays of devices before and after TcEP.

| Array # | $I_{on, b}$ (A) | $I_{on, a}$ (A) | $I_{on}/I_{off}$ ratio | $I_{on, a}/I_{on, b}$ (%) |
|---|---|---|---|---|
| #1 | 4.50E−06 | 1.02E−06 | 1.06E+03 | 22.6 |
| #2 | 5.28E−06 | 1.03E−06 | 6.60E+03 | 19.5 |
| #3 | 4.99E−06 | 1.13E−06 | 2.46E+04 | 22.7 |
| #4 | 7.18E−06 | 1.21E−06 | 9.26E+03 | 16.9 |
| #5 | 1.20E−05 | 1.16E−06 | 4.38E+03 | 9.7 |
| AVG | 6.80E−06 | 1.11E−06 | 9.18E+03 | 18.3 |

The process can be applied to arrays of SWNTs that have both local (FIG. 20) and area averaged (FIG. 17) densities of a few per micron. Improved densities can be realized using transfer techniques.[42-44] Although high densities can be important in electronics, modest or low densities can be useful in sensors and other devices.

Figure 5:
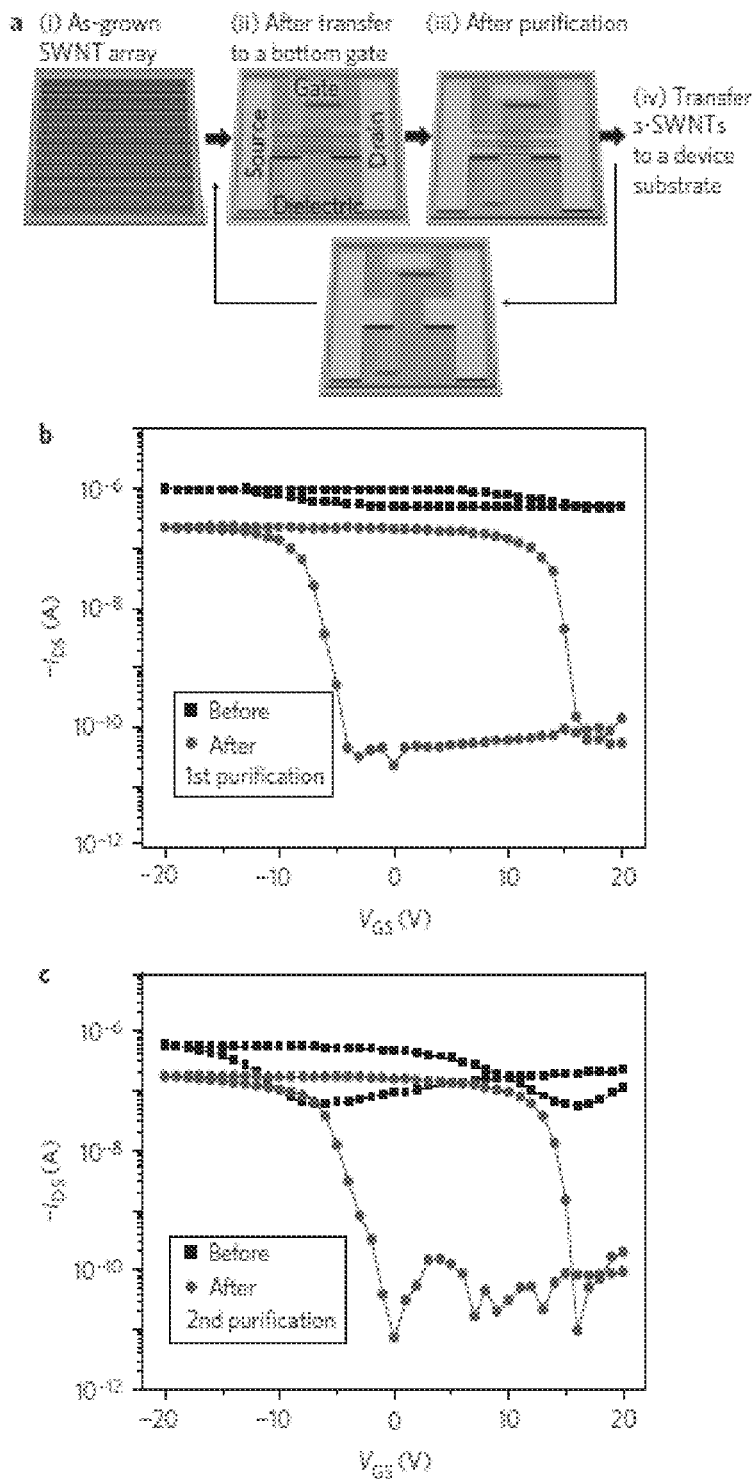
FIG. 5. A re-usable bottom electrode structure reduces the number of processing steps needed for thermocapillary purification. (a) Schematic illustration of two purification processes implemented on different arrays of SWNTs using a single bottom split gate electrode structure (i) As-grown array of aligned SWNTs (ii) bottom electrode after transfer of these SWNTs (gate dielectric: red; source and drain electrodes: gold; gate electrode: gold); (iii) s-SWNTs that remain after purification, (iv) transfer of the s-SWNTs to a device substrate. (b) Transfer characteristics before and after a first purification process with a bottom electrode structure; $I_{on,a}/I_{on,b}$ is 23% and the on/off ratio after purification is ~1×10⁴. (c) Transfer characteristics before and after a second purification process with the same bottom electrode structure; $I_{on,a}/I_{on,b}$ is 30% and the on/off ratio is ~2×10⁴. This reusable structure has W/L=30/30 μm.
Figure 25:
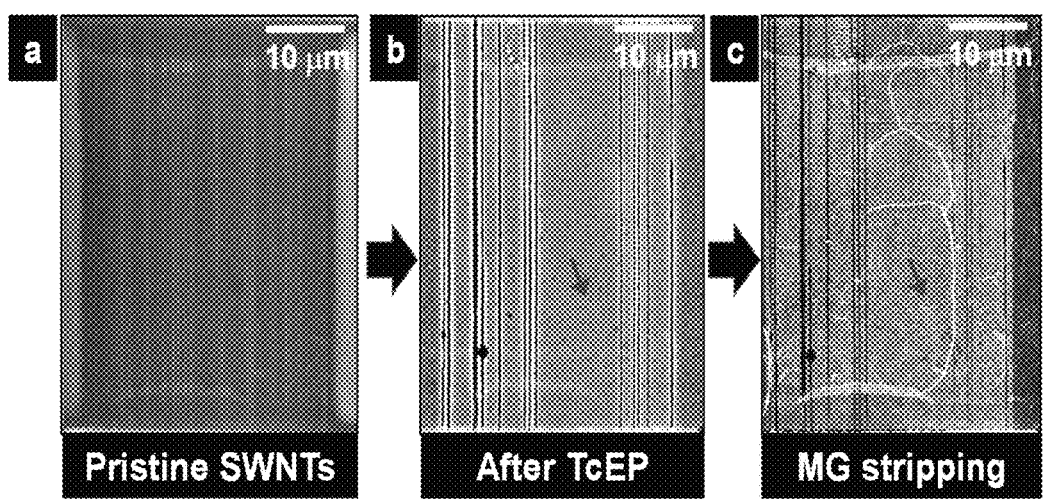
FIG. 25. SEM and AFM images at each stage of the TcEP process, as implemented with a BSGS. (a) SEM image of an as-grown array of SWNTs after transfer onto the BSGS (source and drain electrodes out of the field of view, top and bottom) (b) AFM image after selective trench formation by thermocapillary flow, (c) AFM image after RIE etching and stripping of the Tc resist. The red arrow highlights a pair of s-SWNTs throughout this process. This BSGS has W/L=30/30 μm.
Figure 26:
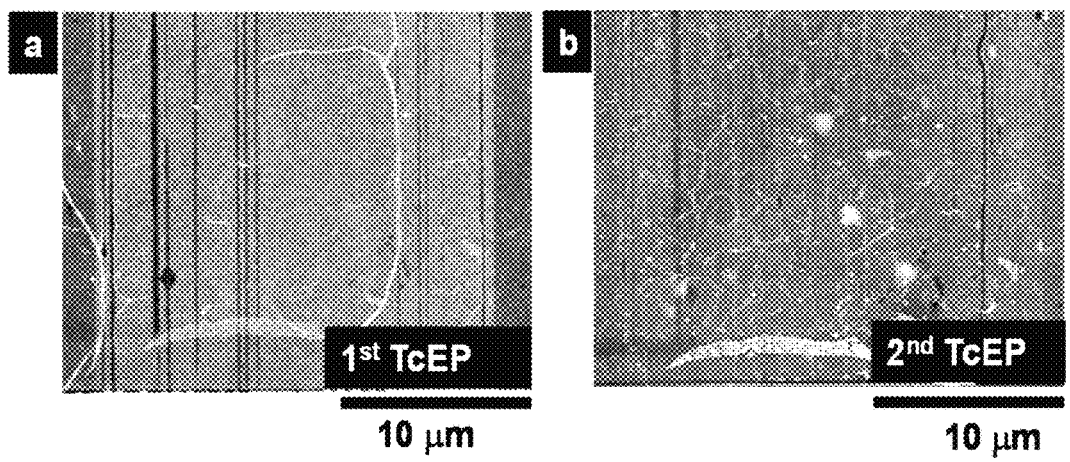
FIG. 26. Demonstration of reusability of the BSGS. (a) AFM image after the first TcEP process, showing regions of selective etching of m-SWNTs (dark) and preserved s-SWNTs (light) (b) AFM image after a second TcEP process with the same BSGS, indicating new etched m-SWNTs and preserved s-SWNTs.

To simplify implementation, a re-usable bottom electrode structure can be exploited to eliminate cycles of processing that would otherwise be necessary for repetitive fabrication of top electrode structures described previously. As shown in FIG. 5a, a single, re-usable substrate provides a fully formed, bottom split gate structure for use in the purification process. Aligned arrays of SWNTs transferred to this substrate using techniques described previously[42-44] can be processed to remove m-SWNTs. The remaining s-SWNTs can then be transferred to a final device substrate. FIG. 5a schematically illustrates two cycles of this process. FIG. 5*b,c* present transfer characteristics of arrays of SWNTs before and after purification, performed with a single back gate structure in two separate cycles of use. Additional details appear in FIGS. 25 and 26.

Figure 6:
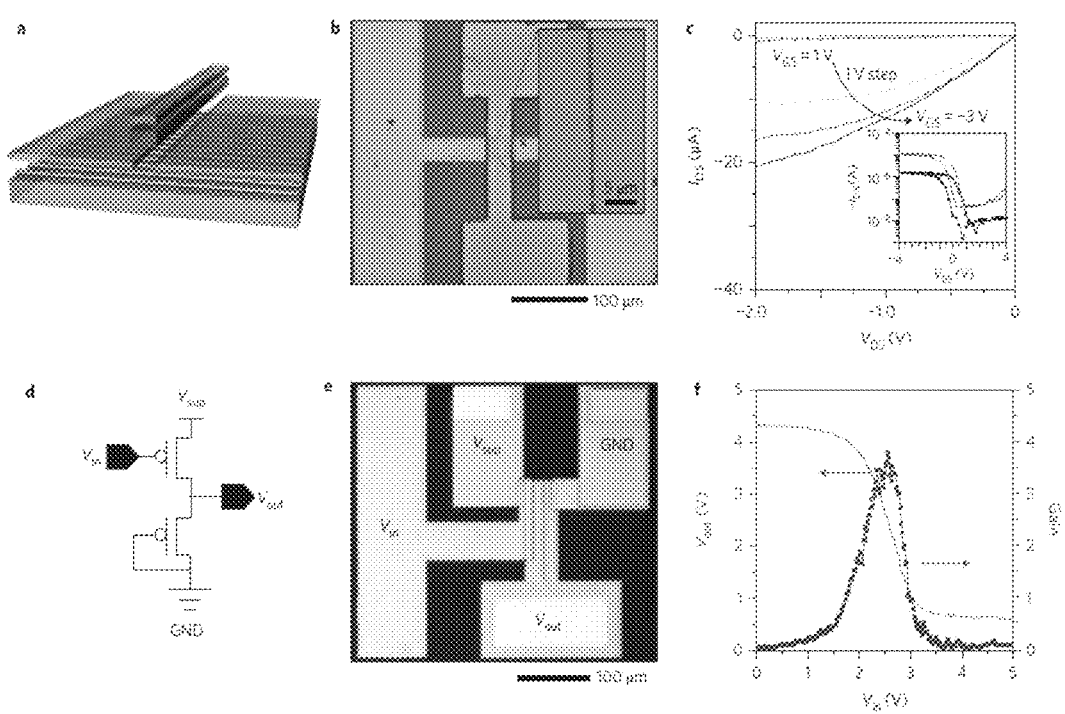
FIG. 6. Purified arrays of s-SWNTs can be used in short channel transistors and logic gates. (a) Schematic illustration of the geometry of a short channel (L~800 nm) transistor that incorporates an array of s-SWNTs formed by the thermocapillary purification process (~10 s-SWNTs). (b) Optical micrograph and SEM image (taken prior to deposition of the gate dielectric) of the device. (c) Output characteristics for gate bias $V_{GS}$=−3, −2, −1, 0, 1 V, over a range of $V_{DS}$=−2 to 0 V. Transfer characteristics appear as an inset for $V_{DS}$=−0.1 V (black) and −1 V (red). (d, e) Circuit diagram and optical micrograph of an inverter formed with two transistors that use arrays of s-SWNTs formed by thermocapillary purification. (f) Voltage transfer characteristics of the inverter.
Figure 22:
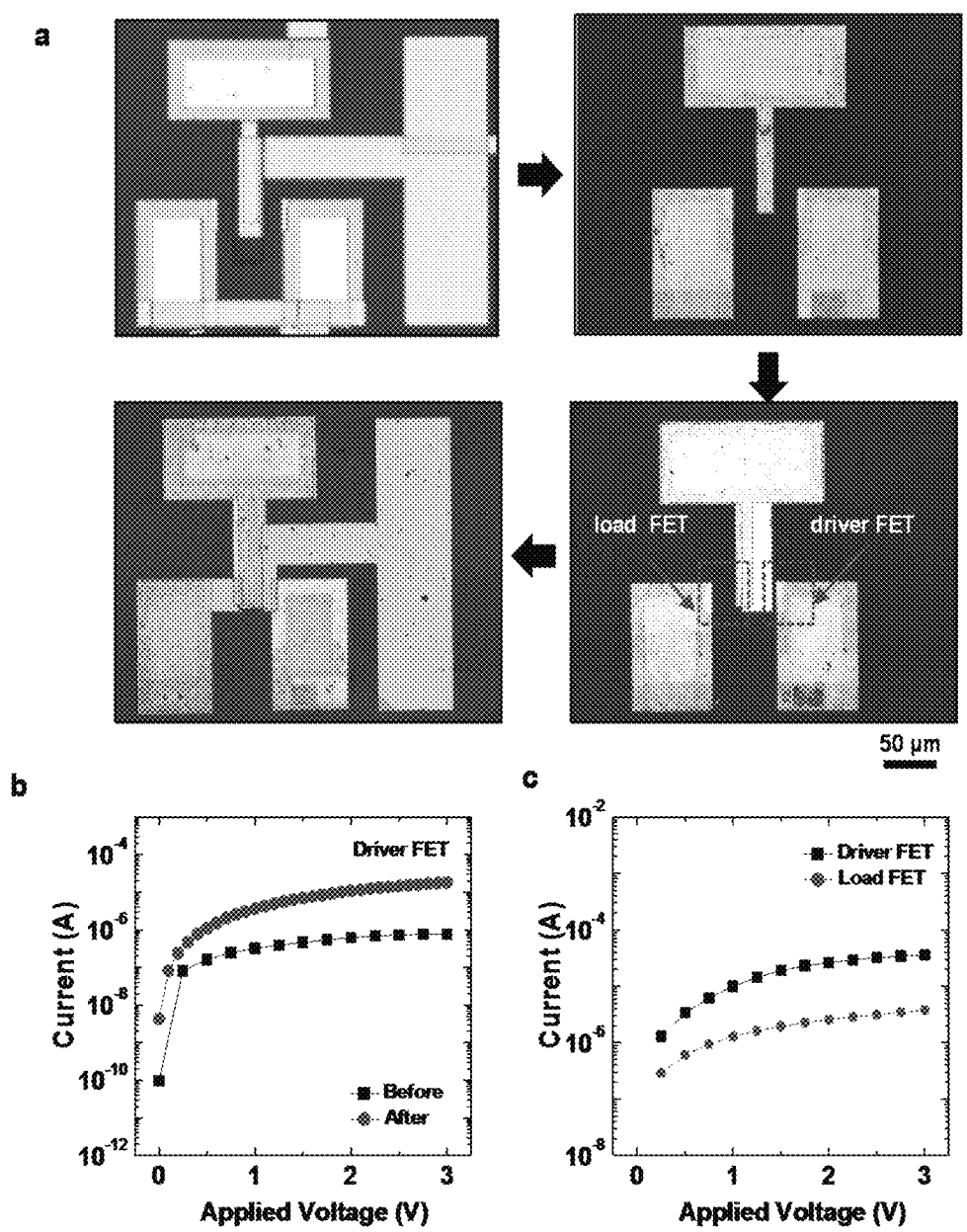
FIG. 22. Details of inverter fabrication (a) Optical micrographs corresponding to process steps for inverter fabrication. TcEP was performed on two arrays in parallel, the gate electrode and dielectric layers were removed, and then new, top-gated TFTs were fabricated with appropriate channel lengths for optimal inverter performance. (b) I-V characteristics of driver FETs associated with electrodes used for TcEP (30 μm channel length) and final device configuration (3.5 μm channel length), respectively. (c) I-V characteristics of driver and load TFTs following inverter fabrication.

Because the purification occurs on entire arrays of SWNTs, the resulting s-SWNTs can be easily integrated into nearly any type of component or circuit layout. Devices with short channel lengths (~800 nm) defined using a near-field phase shift lithography technique[50] provide a demonstration, as shown in FIGS. 6*a,b*. FIG. 6*c* presents electrical properties that are consistent with those of long channel devices when effects of contact resistance are included. The observed hysteresis has known origins that can be minimized using strategies described elsewhere[45-48]. A simple logic gate, consisting of two transistors using arrays of s-SWNTs, provides an additional example of the utility of this process, as illustrated in FIG. 6*d,e*. FIG. 6*f* shows the voltage transfer characteristics and gain associated with this p-type inverter. The peak gain is ~4, consistent with expectation for this design (see Supplementary Information, FIGS. 22-23).

Conclusions

In summary, the purification method introduced here provides scalable and efficient means for converting heterogeneous arrays of SWNTs into those with purely semiconducting character. An important advantage is that the processing steps are fully compatible with fabrication tools used for commercial manufacture of digital electronics and display backplanes.

Methods Summary

Fabricating Top Electrode Structures.

Photolithography, electron beam evaporation (2 nm Ti, 48 nm Pd; AJA) and liftoff defined source and drain electrodes. Reactive ion etching (100 mTorr, 20 sccm $O_2$, 100 W, 30 s; Plasma-Therm) removed SWNTs everywhere except for regions between these electrodes. Prebaking (250° C., 2 hr, in a glove box) a spin cast (4000 rpm, 60 s) solution to a spin-on glass (SOG; Filmtronics; methylsiloxanes 215F, 15:1 diluted in IPA)[45] and then curing the material formed films of SOG (35 nm) uniformly across the substrate. Atomic layer deposition (80° C.; Cambridge NanoTech) created films of $Al_2O_3$ (30 nm) on top of the SOG. Photolithography (AZ 5214) and etching (6:1 BOE for 50 s) removed the SOG/$Al_2O_3$ bilayer from the region between the source/drain electrodes. Prebaking (110° C., 10 min) a spin cast (4000 rpm, 60 s) solution of polyvinyl alcohol (PVA; $M_w$ between 89,000 and 98,000, 99%, hydrolyzed, Sigma-Aldrich; solvent: D.I. water) mixed with photosensitizer (ammonium dichromate, >99.5% at 40:1 by weight[49]) followed by photolithographic patterning and postbaking (110° C., 30 min) defined a layer of PVA (~400 nm) on top of and aligned to the SOG/$Al_2O_3$. Photolithography (AZ 5214), electron beam evaporation (50 nm Ti or Cr), and lift-off defined a gate electrode on top of this dielectric stack.

Thermocapillary Flow and Etching to Remove m-SWNTs.

Thermal evaporation (0.5 Å/s) formed thin layers (25 nm) of the thermocapillary resist (α,α,α'-Tris(4-hydroxyphenyl)-1-ethyl-4-isopropylbenzene; TCI international). Applying a voltage between the source/drain electrodes ($V_{DS}$=−40 to −50 V, corresponding to fields of $V_{DS}/L_{ch}$~1.33-1.66 V/μm) while biasing the source/gate to +20 V under vacuum (~$10^{-4}$ Torr, Lakeshore) and holding the substrate temperature at 60° C., all for ~5 min, yielded trenches in the thermocapillary resist at the locations of the m-SWNTs. Reactive ion etching (10 mTorr, 1 sccm $O_2$, 1 sccm $CF_4$, 75 W, 20 s; Plasma-Therm RIE) eliminated the m-SWNTs exposed in this manner, without affecting the s-SWNTs. Immersion in acetone for 30 min removed the thermocapillary resist, to complete the process.

Scanning Joule Expansion Microscopy.

Devices were wire bonded to a sample holder (Spectrum Semiconductor Materials) to allow contact mode atomic force microscopy (Asylum MFP 3D and Cantilever Asylum # Olympus AC240TS) while applying suitable biases to the electrode structures. A function generator (Agilent 33250A) provided the AC bias and the reference signal for lock-in (Stanford SR844) detection of the amplitude and phase of the signal associated with the thermal expansion. Measurements on quartz were performed with thick layers (~100 nm) of thermocapillary resist deposited on arrays of SWNTs between two electrodes (i.e. two terminal devices, with L=30 μm, W=30 μm). The bias consisted of a sinusoidal voltage with amplitude of 5 V and frequency of 386 kHz. Measurements on $SiO_2$ (200 nm)/Si, used similar two terminal devices, but with spin cast overcoats of poly(methylmethacrylate) (Microchem. 950 A2) with thicknesses of ~120 nm. The bias in such cases consisted of a sinusoidal voltage with amplitude of 3V and frequency of 30 kHz with the substrate electrically grounded.

Studying the Kinetics of Thermocapillary Flow.

Thermal evaporation formed thin layers of thermocapillary resist (~25 nm) on two terminal devices (L=30 μm, W=100 μm) configured for electrical connection while in the atomic force microscope (Asylum research ORCA sample mount). Images collected by fast scanning (~30 s acquisition times) defined the topography of a small region of interest. In between scans, application of electrical biases for durations, of 0.1 s at short times and increasing to 30 min at long times caused the trenches to increase in width by controlled amounts. A total of ~400 scans, corresponding to the device under bias for a total, accumulated time of ~8 hr, revealed the kinetics of trench formation, throughout and well beyond the time of interest.

Fabricating Reusable Bottom Electrode Structures

Photolithography and etching defined gate electrodes (2 nm Cr and 13 nm Pd). A bilayer of silicon nitride (STS 200 nm by plasma enhanced chemical vapor deposition) and SOG (35 nm)[45] served as a gate dielectric. Source and drain electrodes (2 nm Cr and 13 nm Pd) were formed using the same procedures as those for the gate completed the fabrication.

Finite Element Modeling of Heat Flow.

The 3D finite element model for the temperature distributions used eight-node, hexahedral brick elements in a finite element software package (ABAQUS) to discretize the geometry. The SWNT was treated as a volume heat source, with a zero heat flux boundary at the top surface of Tc-resist, and a constant temperature $T_\infty$ at the bottom of the quartz substrate.

Numerical Modeling of Thermocapillary Flows.

The equations of motion represent a pair of coupled partial differential equations $$\frac{\partial \bar{h}_1}{\partial \bar{t}} = \frac{\partial}{\partial \bar{x}}\left(-\frac{\tau \bar{h}_1^2}{2\bar{\mu}} - \frac{\bar{h}_1^3}{3\bar{\mu}}\frac{\partial \gamma}{\partial \bar{x}}\bar{h}_2 - \frac{\bar{h}_1^3 \gamma}{3\bar{\mu}}\frac{\partial \bar{h}_2}{\partial \bar{x}}\right) \text{ and}$$

$$\frac{\partial^2 \bar{h}_1}{\partial \bar{x}^2} - \bar{h}_2 = 0$$

where $\bar{h}_1=\bar{h}$. The boundary conditions are $\bar{h}_1(\bar{x},\bar{t}=0)=1$ $\bar{h}_2(\bar{x},\bar{t}=0)=0$, $\bar{h}_1(\bar{x}=\pm\infty,\bar{t})=1$ and $\bar{h}_2(\bar{x}=\pm\infty,\bar{t})=0$. A Fortran routine (PDE_1D_MG) was used to solve these two partial differential equations directly.

References

1. Franklin, A. D., Lin, A., Wong, H. S. P. & Chen, Z. Current Scaling in Aligned Carbon Nanotube Array Transistors With Local Bottom Gating. *IEEE Electron Dev. Lett.* 31, 644-646 (2010).
2. Zhou, X., Park, J.-Y., Huang, S., Liu, J. & McEuen, P. L. Band Structure, Phonon Scattering, and the Performance Limit of Single-Walled Carbon Nanotube Transistors. *Phys. Rev. Lett.* 95, 146805 (2005).
3. Kang, S. J. et al. High-performance electronics using dense, perfectly aligned arrays of single-walled carbon nanotubes. *Nature Nanotechnol.* 2, 230-236 (2007).
4. Kocabas, C. et al. Radio frequency analog electronics based on carbon nanotube transistors. *Proc. Natl Acad. Sci. USA* 105, 1405-1409 (2008).
5. Nougaret, L. et al. 80 GHz field-effect transistors produced using high purity semiconducting single-walled carbon nanotubes. *Appl. Phys. Lett.* 94, 243505-243503 (2009).
6. Wang, C. et al. Extremely Bendable, High-Performance Integrated Circuits Using Semiconducting Carbon Nanotube Networks for Digital, Analog, and Radio-Frequency Applications. *Nano Lett.* 12, 1527-1533 (2012).
7. Cao, Q. et al. Medium-scale carbon nanotube thin-film integrated circuits on flexible plastic substrates. *Nature* 454, 495-500 (2008).
8. Sun, D.-m. et al. Flexible high-performance carbon nanotube integrated circuits. *Nature Nanotechnol.* 6, 156-161 (2011).
9. Snow, E. S., Perkins, F. K., Houser, E. J., Badescu, S. C. & Reinecke, T. L. Chemical Detection with a Single-Walled Carbon Nanotube Capacitor. *Science* 307, 1942-1945 (2005).
10. Arnold, M. S., Green, A. A., Hulvat, J. F., Stupp, S. I. & Hersam, M. C. Sorting carbon nanotubes by electronic structure using density differentiation. *Nature Nanotechnol.* 1, 60-65 (2006).
11. Green, A. A. & Hersam, M. C. Nearly Single-Chirality Single-Walled Carbon Nanotubes Produced via Orthogonal Iterative Density Gradient Ultracentrifugation. *Adv. Mater.* 23, 2185-2190 (2011).
12. Zheng, M. & Semke, E. D. Enrichment of Single Chirality Carbon Nanotubes. *J. Am. Chem. Soc.* 129, 6084-6085 (2007).
13. Liu, H., Nishide, D., Tanaka, T. & Kataura, H. Large-scale single-chirality separation of single-wall carbon nanotubes by simple gel chromatography. *Nature Commun.* 2, 1-8 (2011)
14. Wu, J. et al. Short channel field-effect transistors from highly enriched semiconducting carbon nanotubes. *Nano Research* 5, 388-394 (2012).
15. Krupke, R., Hennrich, F., Löhneysen, H. v. & Kappes, M. M. Separation of Metallic from Semiconducting Single-Walled Carbon Nanotubes. *Science* 301, 344-347 (2003).
16. Tu, X., Manohar, S., Jagota, A. & Zheng, M. DNA sequence motifs for structure-specific recognition and separation of carbon nanotubes. *Nature* 460, 250-253 (2009).
17. Li, X. et al. Langmuir-Blodgett Assembly of Densely Aligned Single-Walled Carbon Nanotubes from Bulk Materials. *J. Am. Chem. Soc.* 129, 4890-4891 (2007).
18. Engel, M. et al. Thin Film Nanotube Transistors Based on Self-Assembled, Aligned, Semiconducting Carbon Nanotube Arrays. *ACS Nano* 2, 2445-2452 (2008).
19. LeMieux, M. C. et al. Self-Sorted, Aligned Nanotube Networks for Thin-Film Transistors. *Science* 321, 101-104 (2008).
20. Wang, C., Ryu, K., Badmaev, A., Zhang, J. & Zhou, C. Metal Contact Engineering and Registration-Free Fabrication of Complementary Metal-Oxide Semiconductor Integrated Circuits Using Aligned Carbon Nanotubes. *ACS Nano* 5, 1147-1153 (2011).
21. Patil, N. et al. Wafer-Scale Growth and Transfer of Aligned Single-Walled Carbon Nanotubes. *IEEE Trans. Nanotech.* 8, 498-504 (2009).
22. Zhou, W., Rutherglen, C. & Burke, P. Wafer scale synthesis of dense aligned arrays of single-walled carbon nanotubes. *Nano Research* 1, 158-165 (2008).
23. Kocabas, C., Kang, S. J., Ozel, T., Shim, M. & Rogers, J. A. Improved Synthesis of Aligned Arrays of Single-Walled Carbon Nanotubes and Their Implementation in Thin Film Type Transistors†. *J. Phys. Chem. C* 111, 17879-17886 (2007).
24. Huang, H., Maruyama, R., Noda, K., Kajiura, H. & Kadono, K. Preferential Destruction of Metallic Single-Walled Carbon Nanotubes by Laser Irradiation. *J. Phys. Chem. B* 110, 7316-7320 (2006).
25. Collins, P. G., Arnold, M. S. & Avouris, P. Engineering Carbon Nanotubes and Nanotube Circuits Using Electrical Breakdown. *Science* 292, 706-709 (2001).
26. Balasubramanian, K., Sordan, R., Burghard, M. & Kern, K. A Selective Electrochemical Approach to Carbon Nanotube Field-Effect Transistors. *Nano Lett.* 4, 827-830 (2004).
27. Banerjee, S. & Wong, S. S. Demonstration of Diameter-Selective Reactivity in the Sidewall Ozonation of SWNTs by Resonance Raman Spectroscopy. *Nano Lett.* 4, 1445-1450 (2004).
28. Hu, H. et al. Sidewall Functionalization of Single-Walled Carbon Nanotubes by Addition of Dichlorocarbene. *J. Am. Chem. Soc.* 125, 14893-14900 (2003).
29. Pop, E. The role of electrical and thermal contact resistance for Joule breakdown of single-wall carbon nanotubes. *Nanotechnology* 19, 295202 (2008).
30. Javey, A. et al. High-Field Quasiballistic Transport in Short Carbon Nanotubes. *Phy. Rev. Lett.* 92, 106804 (2004).
31. Xiao, J. et al. Alignment Controlled Growth of Single-Walled Carbon Nanotubes on Quartz Substrates. *Nano Lett.* 9, 4311-4319 (2009).
32. Liao, A., Zhao, Y. & Pop, E. Avalanche-Induced Current Enhancement in Semiconducting Carbon Nanotubes. *Phy. Rev. Lett.* 101, 256804 (2008).
33. Ryu, K. et al. CMOS-Analogous Wafer-Scale Nanotube-on-Insulator Approach for Submicrometer Devices and Integrated Circuits Using Aligned Nanotubes. *Nano Lett.* 9, 189-197 (2008).
34. Liao, A. et al. Thermal dissipation and variability in electrical breakdown of carbon nanotube devices. *Phy. Rev. B* 82, 205406 (2010).
35. Davis, S. H. Thermocapillary Instabilities. *Annual Review Fluid Mechanics* 19, 403-435 (1987).
36. Dai, J. et al. Molecular Glass Resists for High-Resolution Patterning. *Chem. Mat.* 18, 3404-3411(2006).
37. Islam, A. E. et al. Effect of variations in diameter and density on the statistics of aligned array carbon-nanotube field effect transistors. *J. Appl. Phys.* 111, 054511-054517 (2012).

38. Saito, R., Dresselhaus, G. & Dresselhaus, M. S. *Physical Properties of Carbon Nanotubes*. (World Scientific).
39. Varesi, J. & Majumdar, A. Scanning Joule expansion microscopy at nanometer scales. *App. Phys. Lett.* 72, 37-39(1998).
40. Grosse, K. L., Bae, M.-H., Lian, F., Pop, E. & King, W. P. Nanoscale Joule heating, Peltier cooling and current crowding at graphene-metal contacts. *Nature Nanotechnol.* 6, 287-290 (2011).
41. Wulf, M., Michel, S., Jenschke, W., Uhlmann, P. & Grundke, K. A new method for the simultaneous determination of surface tension and density of polymer melts. *Phy. Chem. Chemical Phys.* 1, 3899-3903 (1999).
42. Shulaker, M. et al. Linear Increases in Carbon Nanotube Density Through Multiple Transfer Technique. *Nano Lett.* 11, 1881-1886 (2011).
43. Kang, S. J. et al. Printed Multilayer Superstructures of Aligned Single-Walled Carbon Nanotubes for Electronic Applications *Nano Lett.* 7, 3343-3348 (2007).
44. Wang, C. et al. Synthesis and device applications of high-density aligned carbon nanotubes using low-pressure chemical vapor deposition and stacked multiple transfer *Nano Research* 3, 831-842 (2010).
45. Jin, S. H. et al. Sources of Hysteresis in Carbon Nanotube Field-Effect Transistors and Their Elimination Via Methylsiloxane Encapsulants and Optimized Growth Procedures. *Adv. Func. Mat.* 22, 2276-2284 (2012).
46. Kim, W et al. Hysteresis Caused by Water Molecules in Carbon Nanotube Field-Effect Transistors. *Nano Lett.* 3, 193-198 (2003).
47. Hur, S.-H. et al. Organic Nanodielectrics for Low Voltage Carbon Nanotube Thin Film Transistors and Complementary Logic Gates. *J. Am. Chem. Soc.* 127, 13808-13809 (2005).
48. Weitz, R. T. et al. High-Performance Carbon Nanotube Field Effect Transistors with a Thin Gate Dielectric Based on a Self-Assembled Monolayer. *Nano Lett.* 7, 22-27 (2007).
49. Jin, S. H. et al. Pentacene OTFTs with PVA Gate Insulators on a Flexible Substrate. *J. Kor. Phy. Soc.* 44, 181 (2004).
50. Maria, J., Malyarchuk, V., White, J. & Rogers, J. A. Experimental and computational studies of phase shift lithography with binary elastomeric masks. *J. Vac. Sci. & Technol. B: Microelectronics and Nanometer Structures* 24, 828-835, (2006).

Supplementary Information

Individual SWNT Thermocapillary Trench Experiments.

Thermocapillary flows in thermocapillary resists (Tc-resists) were studied (5 min, 60° C. background heating) using devices that incorporate single or several SWNTs. Devices were fabricated in geometries to ensure that only 1 or 2 SWNTs were present in the channel, as confirmed by AFM. In the case of single SWNT devices, the electronic type could be determined directly from the electrical properties (on/off ratio>100, s-SWNT; on/off ratio<100, m-SWNT). For devices with 2 SWNTs that exhibited high on/off ratio, both SWNTs must be s-SWNTs. For similar devices with low on/off ratio before thermocapillary enabled purification (TcEP) and high on/off ratio after TcEP, one SWNT must be a m-SWNT and the other a s-SWNT. Devices with two m-SWNTs were not used for these experiments. Biases were applied to increase the resistance of the s-SWNTs (i.e. their "off" state, at +20 $V_{GS}$), resulting in relatively low (high) current levels for all s-SWNTs (m-SWNTs). As a result, all 2 SWNT devices fell into one of two cases: their currents were dominated by a single m-SWNT or they contained two s-SWNTs. For the second case, one s-SWNT is likely to dominate, but at worst, the s-SWNTs have roughly equal current levels in which case the data served as an upper limit for the actual current and could be as little as half that level. The large number of devices that were studied and the observation that most s-SWNTs showed current levels more than ten times below the threshold for trench formation suggest that assumptions concerning relative current distributions in s-SWNTs are unlikely to affect the broad conclusions. The thresholds were accurately defined by devices with just one SWNT. We performed systematic studies of trenches formed under a range of input powers for single s-SWNTs and single m-SWNTs. A range of outcomes for input powers between 0.1-30 µW/µm (SWNT length=30 µm) were observed by AFM (FIG. 7a). For all experiments, powers below 3.3 µW/µm led to no trenches. For powers between 3.3-10 µW/µm most devices exhibited trenches, but only partly along the lengths of the SWNTs. For all experiments with powers greater than 10 µW/µm, trenches with widths $W_{Tc}$~250-300 nm, were observed along the entire lengths of the SWNTs. This analysis provides information on threshold powers for trench formation, which, via analytical modeling, can be correlated to peak temperatures of ~2-5° C. By sorting these same results by input field and SWNT electronic type (FIG. 7b), optimized conditions can be established. At fields below the optimal range, the heating is insufficient to yield trenches along the entire lengths of all of the m-SWNTs; at higher fields, the most conductive s-SWNTs begin to show partial trench formation. However, for optimized conditions, all s-SWNTs yielded no trenches, while all m-SWNTs yield complete trenches, as required for proper operation of TcEP.

Deposition Conditions for the Tc-Resist and its Properties.

FIG. 8a shows the chemical structure of the Tc-resist. The material was deposited via thermal evaporation. FIG. 8b shows AFM images of a film deposited on a $SiO_2$/Si substrate. The surface roughness is comparable to that of the underlying substrate, i.e. 2-3 Å. Experiments that involved heated substrates (quartz or $SiO_2$/Si) with thin coatings of Tc-resist (~25 nm thickness) showed an onset of dewetting between 80-120° C., depending on substrate hydrophobicity. Clean, hydrophilic surfaces yielded higher dewetting temperatures. In vacuum (~1×10$^{-4}$ torr), sublimation began at ~100° C., as determined by experiments using lithographically patterned, calibrated resistive heaters of Pt (lengths ~1-3 mm, widths ~6-10 µm). Differential Scanning calorimetry (dry nitrogen) yielded a specific heat of ~1.5 J/C/cm$^3$ (FIG. 8c, $T_m$=225° C., $T_g$=95° C., $T_{rc}$=155° C.). Time resolved, picosecond pump-probe experiments based on thermoreflectance[1] using relatively thick films (300 nm, FIG. 8d) yielded thermal conductivities of ~0.2 W/m/K, similar to most organic thin films. Furthermore, similar experiments with relatively thin films (~25, ~50, ~75 nm), suggest that the thermal interface resistance between quartz and the Tc-resist is ~50-150 MW/m$^2$/K.

Single SWNT Conductance Statistics.

The large number of SWNTs studied by TcEP on devices with small arrays of SWNTs provided statistics on the process. For each array, the number of SWNTs and the values of $I_{on, b}$ and $I_{on, a}$ (shown for a typical device, FIG. 9b) together with an assumption that all of the removed SWNTs are m-SWNTs and all of the remaining SWNTs are s-SWNTs, yields estimates for the average conductance of these two types of SWNTs, for each device. FIG. 9a shows a histogram of the conductances of individual SWNTs determined in this way. (We note that a device with 3 s-SWNTs and an average conductance of 50 k$\Omega$/μm is counted 3 times.) The mean conductances for m-SWNTs and s-SWNTs (in their on state) are 17 k$\Omega$/μm and 75 k$\Omega$/μm, respectively. These distributions are in the range of those reported for single SWNTs studied previously[2]; with values of 35 k$\Omega$/μm (m-SWNTs) and 55 k$\Omega$/μm (s-SWNTs) for backgated devices (FIG. 9c)[2]; and 140 k$\Omega$/μm (m-SWNTs) and 1000 k$\Omega$/μm (s-SWNTs) for top gated devices[2]. Using the experimentally observed ratios of numbers of m-SWNTs to s-SWNTs, and a ratio of mean conductances of ~4:1, the assumption that TcEP preserves all s-SWNT is consistent with observations.

Partial Gate Device Properties.

The electrode geometries used for TcEP involved a partial gate structure shown schematically in FIG. 1a. This configuration results in reduced gate-drain fields, which minimize Schottky barrier tunneling, band-to-band tunneling and avalanche phenomena[3]. The operation avoids ambipolar conduction at the bias conditions needed for TcEP (characterization at conditions consistent with TcEP, 60° C. background heating, ~1×10$^4$ torr). These effects are clearly observed in transfer characteristics for devices based on an individual s-SWNT in partial gate (FIG. 10a) and full gate (FIG. 10b) layouts. Here, the same SWNT, same pair of source-drain electrodes, and dielectric were used for both devices. The only difference is the length of gate extension into the channel. Both configurations exhibit ideal device behavior at low bias ($V_{DS}$=−0.1 V). At high bias ($V_{DS}$<−10 V, L=30 μm), however, the full gate device shows pronounced ambipolar conduction, unlike the partial gate case. FIG. 9c illustrates the effect of source-drain bias and gate overlap ($L_{ov}$) on on/off ratio, where all measurements were performed on the same SWNT. The device with 5 μm gate overlap (i.e. the configuration used for TcEP) exhibits on/off ratios 2-3 orders of magnitude higher than the device with full overlap ($L_{ov}$=30 μm). FIG. 10d shows the ability of the partial gate configuration to maintain current levels several orders of magnitude lower than that of the full gate configuration, even for long bias durations ("off" state, $V_{DS}$=−40V, $V_{GS}$=+20V, 5 min, consistent with TcEP experiments).

Scanning Joule Expansion Microscopy.

FIG. 11a shows a scanning Joule expansion microscope (SJEM) image[4] of an array of SWNTs (two terminal device, SiO$_2$ (200 nm)/Si substrate) covered with a 120 nm thick film of PMMA, collected at the condition of V(t)=$V_{DS}$ cos (2πft) with $V_{DS}$=3 V and f=30 kHz and $V_{GS}$=0 V. FIG. 11a shows the integrated expansion percentage (I.E.P.). To determine this quantity, we first located the maximum expansion along each measured cross-section perpendicular to the length of the SWNT. Next, we integrated these values along each SWNT, to get the integrated expansion (I.E.). The I.E.P. is the ratio of the I.E. to the sum of the I.E. for all three SWNTs, times 100%. Since the maximum expansion is proportional to the input power, the I.E.P. can be used to estimate the power input for each SWNT, from the measured total power into the device. FIG. 11c shows a 3D rendering of the SJEM signal for the SWNT associated with FIG. 2b. FIG. 11d shows a schematic of the SJEM measurement.

Computed Temperature Distributions Associated with Joule Heating in Individual SWNTs.

In this section, we describe procedures for determining the temperature distribution resulting from a SWNT embedded in a film of PMMA on SiO$_2$/Si substrate with power dissipation at the SWNT for an AC applied voltage. The temperature rise at the surface of the Tc-resist can be obtained by considering first the analytical solution for a disk heat source with radius $r_0$ at the interface between the Tc-resist and the SiO$_2$. Here, a cylindrical coordinate system is set such that the origin is coincident with the center of the heat source as shown in FIG. 12a,b. The heat transfer governing equation temperature in cylindrical coordinate is $$\frac{\partial^2 T}{\partial r^2} + \frac{1}{r}\frac{\partial T}{\partial r} + \frac{\partial^2 T}{\partial z^2} - \alpha \frac{\partial T}{\partial t} = 0 \tag{1}$$

where $$\alpha = \frac{k}{c\rho}$$

is thermal diffusivity, k is thermal conductivity, ρ is density, and c is specific heat capacity. The subscripts 0, 1 and 2 denote Tc-resist, SiO$_2$ and Si, respectively. Setting θ=T−$T_\infty$, where $T_\infty$ is the remote temperature, the above equation is equivalent to $$\frac{\partial^2 \theta}{\partial r^2} + \frac{1}{r}\frac{\partial \theta}{\partial r} + \frac{\partial^2 \theta}{\partial z^2} = \alpha \frac{\partial \theta}{\partial t} \tag{2}$$

The boundary conditions are $$z=-h_0 \text{(top surface)} \tag{1}$$

$$-k_0 \frac{\partial \theta}{\partial z}\bigg|_{z=-h_0} = 0 \tag{3}$$

$$z=0 \tag{2}$$

$$\theta_{0^+} = \theta_{0^-}, \tag{4}$$

$$-k_0 \frac{\partial \theta}{\partial z}\bigg|_{z=0^-} = \begin{cases} Q_1 & 0 \le r \le r_0 \\ Q_{c1} & r_0 < r < +\infty \end{cases},$$

$$-k_1 \frac{\partial \theta}{\partial z}\bigg|_{z=0^+} = \begin{cases} Q_2 & 0 \le r \le r_0 \\ Q_{c1} & r_0 < r < +\infty \end{cases}$$

where $Q_1$ and $Q_2$ satisfy $$-Q_1 + Q_2 = \frac{P}{\pi r_0^2},$$

P is the total power of the disk.

$$z=h_1 \tag{3}$$

$$\theta_{h_1^+} = \theta_{h_1^-} \text{ and } -k_1 \frac{\partial \theta}{\partial z}\bigg|_{z=h_1} = -k_2 \frac{\partial \theta}{\partial z}\bigg|_{z=h_1} \tag{5}$$

$$z=h_1+h_2 \sim \infty \tag{4}$$

$$\theta_{h_1+h_2}=0 \tag{6}$$

For a voltage V(t)=$V_0$ cos(ωt) with angular frequency ω=2πf, the Joule heating has angular frequency 2ω. The total power of the disk can then be obtained as $P(t)=P_0[1+\cos(2\omega t)]/2$, which yields a constant temperature rise (DC component) due to $P_0/2$ and a time oscillating temperature rise (AC component) due to $P_0 \cos(2\omega t)/2$. It should be noted that the DC component of temperature rise can be easily obtained by setting $\omega=0$ in the solution of AC component.

The time oscillating temperature rise (AC component) has the same frequency as the power density, i.e. $\theta(r,z,t)=\theta(r,z)\exp(2\omega t i)$. Therefore, we have $$\frac{\partial^2 \theta}{\partial r^2} + \frac{1}{r}\frac{\partial \theta}{\partial r} + \frac{\partial^2 \theta}{\partial z^2} - q^2 \theta = 0 \quad (7)$$

where $$q^2 = \frac{2\omega i}{\alpha}$$

and $\theta=\theta(r,z)$.

Equation (7) can be solved via the Hankel transform, for which the following transform pair of the first kind is applicable, $$\varphi(r,z) = \int_0^\infty \overline{\varphi}(\xi,z) J_0(\xi r) \xi d\xi$$

$$\overline{\varphi}(\xi,z) = \int_0^\infty \varphi(r,z) J_0(\xi r) r dr \quad (8)$$

where $\varphi(r,z)$ is the original function, $\overline{\varphi}(\xi,z)$ is the transform, and $J_0$ is the $0^{th}$ order Bessel function of the first kind. Equation (7) then becomes $$\frac{d^2 \overline{\theta}}{dz^2} - (\xi^2 + q^2)\overline{\theta} = 0 \quad (9)$$

Solving the above equation gives $$\overline{\theta} = A \exp(z\sqrt{\xi^2+q^2}) + B \exp(-z\sqrt{\xi^2+q^2}) \quad (10)$$

where A and B are two unknown functions to be determined according to boundary and continuity conditions. The temperature rise is then obtained by $$\theta = \int_0^\infty (Ae^{-z} + Be^{\overline{z}}) J_0(\xi r) \xi d\xi \quad (11)$$

Therefore, the temperature rise in Hankel space at each layer is obtained as

Tc-resist: $\overline{\theta}_0(\xi,z) = A_0 \exp(z\sqrt{\xi^2+q_0^2}) + B_0 \exp(-z\sqrt{\xi^2+q^2})$ SiO$_2$ layer: $\overline{\theta}_1(\xi,z) = A_1 \exp(z\sqrt{\xi^2+q_1^2}) + B_1 \exp(-z\sqrt{\xi^2+q_1^2})$ Si layer: $\overline{\theta}_2(\xi,z) = A_2 \exp(z\sqrt{\xi^2+q_2^2}) + B_2 \exp(-z\sqrt{\xi^2+q_2^2})$ With BCs (3)-(6) in Hankel space, we can obtain the temperature at each layer. For example, $A_0$ and $B_0$ are given by $$A_0 = \frac{\kappa+1}{(1-\kappa)\left[1+\exp\left(-2h_0\sqrt{\xi^2+q_0^2}\right)\right] + (\kappa+1)\frac{k_0\sqrt{\xi^2+q_0^2}}{k_0\sqrt{\xi^2+q_1^2}}\left[1-\exp\left(-2h_0\sqrt{\xi^2+q_0^2}\right)\right]} \quad (12)$$

$$\frac{P_0}{k_1 \pi \xi \sqrt{\xi^2+q_1^2}} \frac{J_1(\xi r_0)}{2r_0}$$

$$B_0 = A_0 \exp\left(-2h_0 \sqrt{\xi^2+q_0^2}\right)$$

where $\kappa = \dfrac{1 - \dfrac{k_2}{k_1}\dfrac{\sqrt{\xi^2+q_2^2}}{\sqrt{\xi^2+q_1^2}}}{1 + \dfrac{k_2}{k_1}\dfrac{\sqrt{\xi^2+q_2^2}}{\sqrt{\xi^2+q_1^2}}} \exp\left(-2h_1\sqrt{\xi^2+q_1^2}\right)$ The temperature rise due to the disk heat source can be obtained by Eq. (11). For example, the temperature rise in the Tc-resist is obtained as $$\theta(r,z) = \int_0^{+\infty} A_0 [\exp(z\sqrt{\xi^2+q_0^2}) + \exp(-z\sqrt{\xi^2+q_0^2}) - 2h_0 \sqrt{\xi^2+q_0^2})] \cdot J_0(\xi r) \xi d\xi \quad (13)$$

The surface temperature rise of the Tc-resist is then obtained by setting $z=-h_0$ as $$\theta(r) = \int_0^{+\infty} 2A_0 \exp(-h_0\sqrt{\xi^2+q_0^2}) \cdot J_0(\xi r) \xi d\xi \quad (14)$$

As $r_0 \to 0$, we obtain the temperature rise due to a point heat source as $$\theta_P(r) = \quad (15)$$

$$\frac{1}{4k_1\pi} \int_0^{+\infty} \frac{(\kappa+1) J_0(\xi r) \xi}{(1-\kappa)\cosh\left(h_0\sqrt{\xi^2+q_0^2}\right) + (\kappa+1)\dfrac{k_0\sqrt{\xi^2+q_0^2}}{k_1\sqrt{\xi^2+q_1^2}} \sinh\left(h_0\sqrt{\xi^2+q_0^2}\right)} \cdot \frac{P_0}{\sqrt{\xi^2+q_1^2}} d\xi$$

For a point heat source at $(0,\eta,0)$ with heat generation $P_0 = Q \cdot d\eta$ and $Q_0$ as the power density, the integration of Eq. (15) with $r = \sqrt{(\eta-y)^2 + x^2}$ gives the temperature rise at point (x, y) due to a line heat source as $$\theta(x, y) = \frac{1}{4k_1\pi} \quad (16)$$

$$\int_{-L/2}^{L/2} d\eta \int_0^{+\infty} \frac{(\kappa+1) J_0\left(\xi\sqrt{(\eta-y)^2+x^2}\right)\xi}{(1-\kappa)\cosh\left(h_0\sqrt{\xi^2+q_0^2}\right) + (\kappa+1)\dfrac{k_0\sqrt{\xi^2+q_0^2}}{k_1\sqrt{\xi^2+q_1^2}}\sinh\left(h_0\sqrt{\xi^2+q_0^2}\right)} \cdot \frac{Q_0}{\sqrt{\xi^2+q_1^2}} d\xi$$

It should be noted that Eq. (16) gives the magnitude of time oscillating temperature rise, i.e., $\theta_0$ in the main text is equal to $2\theta(x,y)$. The total surface temperature rise can be obtained as $\theta(x,y,t)=\theta(x,y)|_{\omega=0} + \theta(x,y)\cos(4\pi ft) = [\theta_0 + \theta_0 \cos(4\pi ft)]/2$ due to a line heat source with power density $Q(t)=Q_0[1+\cos(2\omega t)]/2$.

Here, boundary conditions involve continuous temperature and heat flow at all material interfaces except those with the SWNT, negligible heat flow at the top surface and a constant temperature at the base of the substrate. For the SWNT interface, discontinuous heat flow, is assumed, as a means to introduce the Joule heat source. The results, together with materials constants taken from the literature (see Table 1) and analytical treatments of the resulting thermal expansion, yield expansion profiles that have both peak magnitudes ($E_0 \sim 50$ pm) and spatial distributions (characteristic widths ~340 nm) that are remarkably consistent with the SJEM results (~40 pm and ~320 nm, respectively), when $Q_0 \sim 13$ μW/μm, the estimated experimental value.

Computed Thermal Expansion at the Surface of a Thin Film Coating on a Heated SWNT on a Substrate.

Under the assumptions of (1) plane strain in y direction since the length of SWNT (~30 μm) is much larger than its radius and (2) plane stress in z direction since the film is very thin (~25 nm), the peak-peak value of AC surface thermal expansion (i.e., the out-of-plane displacement) of the Tc-resist can be obtained as $$E_0 = \frac{1+v_0}{1-v_0}\beta_0 h_0 \theta(x, y = -h_0) \tag{17}$$

where $v_0$ and $\beta_0$ are the Poisson's ratio and coefficient of thermal expansion of the PMMA, respectively.

Computed Temperature Distribution for a System Consisting of a SWNT Undergoing Joule Heating with a Constant Bias, on a Quartz Substrate Coated with Tc-Resist.

Setting $k_2=k_1=k_s$, $k_0=k_f$, $h_0=h_f$ and $\omega=0$, Eq. (16) gives the surface temperature of Tc-resist for Tc-resist/quartz under DC voltage as $$\theta(x, y) = \frac{1}{2k_s\pi}\int_{-L/2}^{L/2}d\eta\int_0^\infty \frac{Q_0 J_0(\xi\sqrt{(\eta-y)^2+x^2})}{\cosh(\xi h_f) + \frac{k_f}{k_s}\sinh(\xi h_f)}d\xi \tag{18}$$

where $k_f$ and $k_s$ are the thermal conductivity of Tc-resist and quartz, respectively and $h_f$ is the thickness of Tc-resist.

A 3D finite element model was established to study the temperature distribution in the system and validate the analytical model. Eight-node, hexahedral brick elements in the finite element software ABAQUS are used to discretize the geometry. A volume heat source was applied on the SWNT. The zero heat flux boundary was applied at the top surface of the Tc-resist, and a constant temperature $T_\infty$ is applied at the bottom of the quartz substrate. The finite element simulations agree well with analytical modeling as shown in FIG. 12c for the surface temperature of the Tc-resist with $k_0=0.2$ W/m/K, $k_f=6$ W/m/K, $Q_0=16.7$ μW/μm and L=30 μm.

Effects of Thermal Interface Resistance.

The models above do not consider the effect of thermal interface resistance, which can in some cases affect the resulting temperature distributions. For the case of AC heating for relatively thick films (~250 nm) for PMMA, the interface resistance has negligible effect (for ~100 MW/m$^2$/K for the SiO$_2$/PMMA interface, the result is a relatively small increase in peak temperature rise, ~1%). For the case of thinner films of Tc-resist (~25 nm) with DC heating, the surface temperature rise incorporating interface resistance can be obtained using Hankel transform as $$\theta(x, y) = \tag{19}$$

$$\frac{1}{k_f\pi}\int_{-L/2}^{L/2}d\eta\int_0^\infty \frac{Q_0 e^{-\xi h_f}\left(1+\frac{k_s\xi}{\zeta}\right)J_0(\xi\sqrt{(\eta-y)^2+x^2})}{-\left(1+\frac{k_s\xi}{\zeta}-\frac{k_s}{k_f}\right)e^{-2\xi h_f}+\left(1+\frac{k_s\xi}{\zeta}+\frac{k_s}{k_f}\right)}d\xi$$

where $\zeta$ is the thermal interface conductance. As $\zeta$ approaches to infinity, Equation (19) denigrates to Eq. (18). For ~100 MW/m$^2$/K for the Tc-resist/quartz interface, the result shows a ~40% increase in peak temperature rise. However, this rise is not significant enough to affect any of the major conclusions associated with this study. Namely, that at the powers used to induce trenches by Tc-flow, temperature rises are small. Similarly, the qualitative aspects and scaling laws associated with the Tc-flow modeling are unaffected by these minor corrections.

Modeling of Thermocapillary Flow in TcEP.

The viscous flow of Tc-resist is essentially unidirectional and the evolution of film thickness h(x,t) can be obtained from a lubrication equation $$\frac{\partial h}{\partial t} + \frac{\partial}{\partial x}\left[\frac{\tau h^2}{2\mu} + \frac{h^3}{3\mu}\frac{\partial}{\partial x}\left(\gamma\frac{\partial^2 h}{\partial x^2}\right)\right] = 0. \tag{20}$$

where $\gamma$ is the surface tension, which usually linearly depends on the temperature rise (i.e., $\gamma=\gamma_0-\gamma_1\theta$), $$\tau = \frac{\partial\gamma}{\partial T}\frac{\partial T}{\partial x}$$

is the thermocapillary stress with $T=T_\infty+\theta$, and μ is viscosity. By introducing the following non-dimensional terms $\bar{h}=h/h_f$, $\bar{x}=x/h_f$, $\bar{t}=\gamma_1 Q_0 t/(\mu_0 k_f h_f^2)$, $\bar{\mu}=\mu/\mu_0$, $\bar{\gamma}=k_f h_f \gamma/(Q_0\gamma_1)$, $\bar{\tau}=\partial\bar{\theta}/\partial\bar{x}$ and $\bar{\theta}=k_f h_f \theta/Q_0$, Eq. (20) can be written in non-dimensional form as $$\frac{\partial\bar{h}}{\partial\bar{t}} + \frac{\partial}{\partial\bar{x}}\left[\frac{\bar{\tau}\bar{h}^2}{2\bar{\mu}} + \frac{\bar{h}^3}{3\bar{\mu}}\frac{\partial}{\partial\bar{x}}\left(\bar{\gamma}\frac{\partial^2\bar{h}}{\partial\bar{x}^2}\right)\right] = 0. \tag{21}$$

The Fortran solver PDE_1D_MG can be used to solve for $\bar{h}$.

Experimental and Theoretical Time Dependence of Trench Evolution in TcEP.

Figure 13:
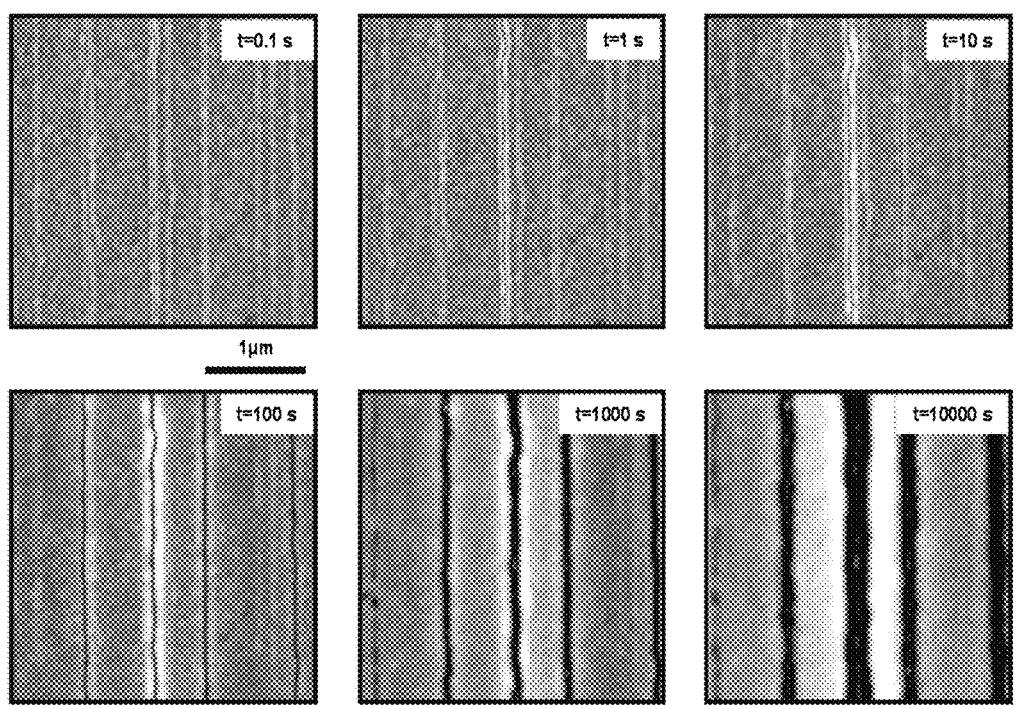
FIG. 13. Time dependent trench formation study. 3×3 μm AFM images associated with in-situ measurement of trench formation. Brief intervals of bias were applied and the associated topography was measured (30 s scans) in between each interval. These images are associated with various total accumulated bias durations as trenches evolve.

The time dependence of trench evolution was studied for a small area (3×3 μm) within an array of SWNTs by collecting a sequence of AFM images (~30 s), for different durations of applied bias ($V_{DS}$=0.66 V/μm, L=30 μm, 30° C. background heating). During imaging no bias was applied, thereby leaving the trenches in fixed geometries for the duration of the measurement. In between images, biases were applied, driving trench formation for controlled durations (durations varied depending on accumulated duration ranging from 0.1 s for very short accumulated duration, <10 s, to 30 min for very long accumulated duration, 6-8 hrs). The total time of trench formation was taken to be the sum of the durations for all preceding experiments. FIG. 13 shows representative images at various points in the evolution of trenches (FIG. 3c shows cropped images associated with the second trench from the left). At relatively short durations, trenches were shallow (<1 nm deep) and characterized by slight ridges in the Tc-resist on each side of the SWNT, over time evolving into fully formed trenches, which grow and eventually (hours) began to interact with trenches from adjacent SWNTs, limiting further growth. Data associated with analysis of time dependence was restricted to durations where trenches were isolated from one another (<2 hr). For the purposes of establishing reliable measures of trench evolution, the trench width, $W_{Tc}$, was defined as the width between the peak of the pile-up on either side of the trench (actual minimum widths, evaluated at the base of the Tc-resist, were much narrower). Analysis to determine the left and right side of the trench was performed in MATLAB, and involved identifying the first location to the left and right side of the trench where the slope fell below a certain threshold, $5 \times 10^{-11}$. FIG. 14a shows an AFM image for t=600 s with the identified left and right sides of the trench highlighted for the three central trenches. FIG. 14b shows cross-sectional profiles associated with the central trench at various points in the trench evolution and the identified left and right positions. FIGS. 3f and 15a show the resulting experimentally extracted $W_{Tc}$. Smaller trenches ($W_{Tc}$<150 nm, associated with t<10 min), were less distinct, and identifying the left and right positions was more difficult. While values of $W_{Tc}$ were roughly accurate, there was significantly more error at shorter times than longer times. The short time values were not used for power law fitting (FIG. 15a). Power law fitting was performed in data ranges where the standard deviation was <10% of $W_{Tc}$. (For data outside of this range, standard deviation was $W_{Tc}$~20-50% of $W_{Tc}$). The data fit well to a power law with exponent 0.25 (The value for the constant of proportionality, A, are shown). FIG. 15b shows the predicted $W_{Tc}$ based on modeled trench profiles (peaks in $\bar{h}(\bar{x},\bar{t})$, which also fit well to a power law with exponent of 0.25 (The parameter A depends on various Tc-resist properties, several of which are unknown). FIGS. 15c,d show the predicted $W_{Tc}$ for power densities varying from 8.3-33.3 µW/µm for long durations and for durations that yield trench widths associated with those typical for TcEP. (Comparison to model can be difficult given the uncertainty in materials properties for the Tc-resist. Because $\bar{t}$ is normalized with respect to µ and γ, which are unknown, it is not possible to compare directly to t. Nevertheless, the computed $W_{Tc}$ is only normalized by $h_0$, so it is meaningful to compare modeled $\bar{t}$ to ranges of experimental t that yield trenches of similar size to those measured experimentally). For long times, $W_{Tc}$ varies with power density. At durations associated with experimental conditions, however, almost no variation is predicted. This relative insensitivity to power is consistent with experimental observation (FIG. 2e,f), where only ~20% variations in $W_{Tc}$ are typically observed. Such variations likely result from local changes in film viscosity associated with heating, or other effects not explicitly included in the model.

In addition, besides capturing the underlying physics, these models also establish a set of guidelines for the selection of optimal materials for Tc-resists, i.e. large temperature coefficients of surface tension and low viscosities yield narrow trenches within reasonable experimental times. Furthermore, decreasing the thickness reduces the trench widths. Empirical studies of various materials for Tc-resists (see FIG. 18) led to the selection of the molecular glass reported here.

Thermocapillary Flows in Tc-Resist, Studied by Heated AFM Tips with Integrated Temperature Sensors.

Figure 16:
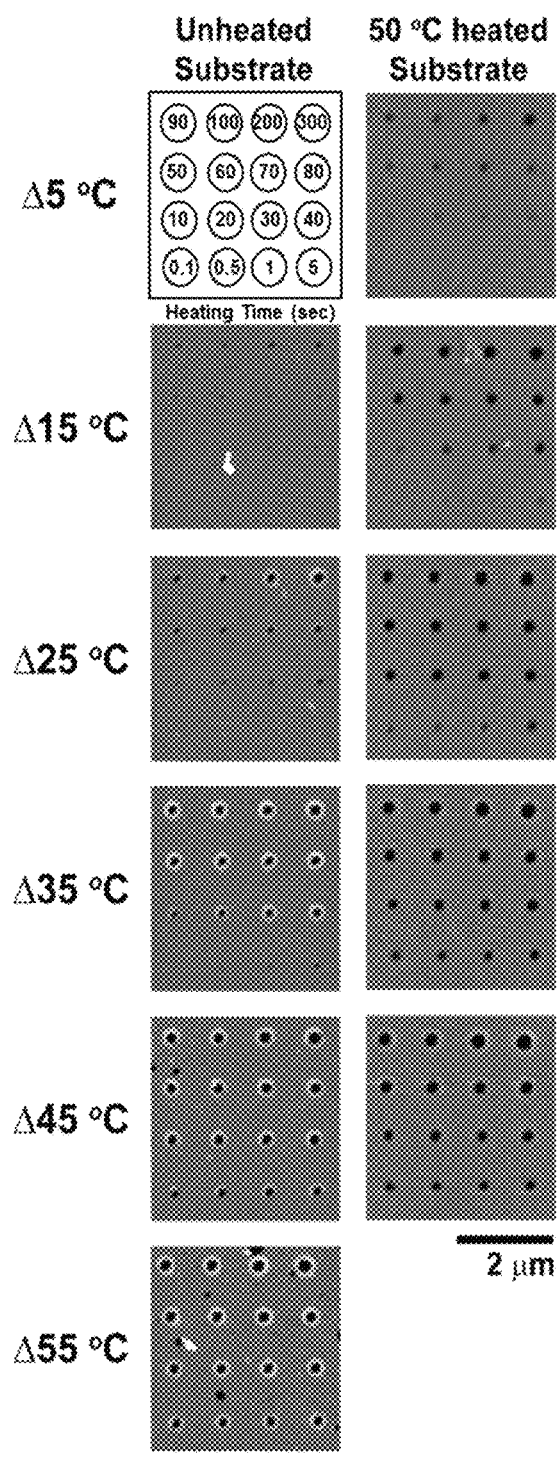
FIG. 16. Thermocapillary flows in Tc-resist studied with calibrated, heated AFM tips. AFM images of a series of arrays of dots patterned in films of Tc-resist, created by contact of heated AFM tips for a variety of temperature differences (tip to substrate) and contact durations (indicated in first frame) at both room temperature and 60° C. General behavior is consistent with that observed for SWNT Joule heating. In particular, features form in the Tc-resist even at low temperature rises. Feature sizes increase with time.

Heated atomic force microscope (AFM) tips with known temperatures contacted with the Tc-resist layer for various times, and with various applied powers, allow study of the effects of thermocapillary flow in a nanoscale system where temperature and other parameters are controlled (and known) more accurately than the case for SWNTs. The heated tip (radius<100 nm) was fabricated from doped single crystal silicon, and is capable of reaching temperatures of 1000° C. with a temperature calibration to within 5° C. for this entire range.[18] Previous studies of viscous mass flow from a heated tip to a substrate revealed thermocapillarity to be an important driver of flow[19]. FIG. 16 shows Tc-resist layer deformation induced by tip heating for tip-substrate temperature differences between 5-45° C. and dwell times between 0.1-300 s on both an unheated Tc-resist layer and a Tc-resist layer heated to 50° C. The tip dwelled on the surface with tip forces below 20 nN and did not deform the surface when unheated. The results show that significant material flows radially away from the heated tip for Tc-resist layer temperatures far below the sublimation temperature, consistent with thermocapillary stresses induced by the temperature gradient around the tip.

Pulsed Heating in TcEP for Large Scale Arrays of SWNTs.

Figure 17:
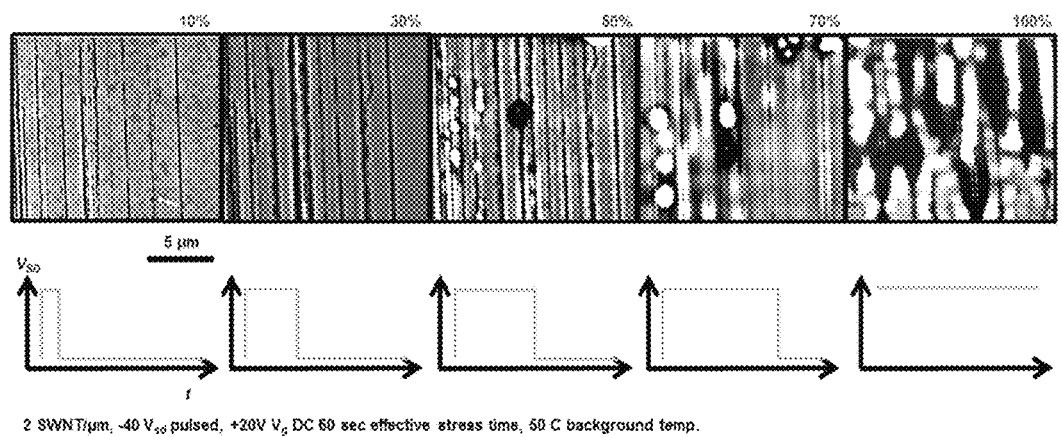
FIG. 17. Pulsed biases for forming trenches in large and/or high density arrays of SWNTs. AFM trenches formed in Tc-resist for an array with 2-3 SWNT/μm associated with pulsed heating with increasing duty cycle ($V_{DS}$=−40V peak amplitude, period=10 μs, duration=1-10 μs, $V_{GS}$=+20V DC, 60 sec total stress duration, 50° C. background heating). For 10% duty cycle clearly defined trenches are observed. As the duty cycle increases, trenches become less clearly defined and flow is observed that does not correlate to the underlying SWNT positions. This result from delocalized heating associated with parallel operation in many SWNT. Pulsed heating aids in localizing the flows needed for proper operation in TcEP.

For arrays that contain large numbers of SWNTs (either at high densities or over large areas) the coupled heating of many SWNT leads to bulk, and sometimes large, increases in temperature. These effects can yield thermocapillary flow on larger length scales and in ways that are difficult to confine to the positions of the SWNTs (FIG. 17). Pulsed bias conditions (~1-10 µs) can avoid these cumulative effects, to yield localized heating and thereby preserve well-behaved trenches even with large arrays of SWNTs and/or relatively high densities (up to 3 SWNT/µm studied here). FIG. 17, shows the resulting trenches for a localized region within a large area high density array (30 µm×1 mm, 2-3 SWNT/µm) for increasing duty cycles (10 to 100%) with a fixed pulse duration (10 µs). These data clearly show the gradual transition from narrow, well defined trenches associated with individual SWNTs to uncontrolled flow not correlated to SWNTs. For optimized application of pulsed TcEP (large area, high density arrays), 1-3 µs pulses (40V) were applied with 10 µs pulse periods.

Tc-Resist Material Selection.

There are numerous characteristics that are critical for an effective Tc-resist material. Basic requirements are that the material can be easily deposited in thin film configurations, where vacuum deposition is preferable to spin coating, since it easily yields uniform film thickness even in regions near the partial gate electrode structures, where substrate topography is highly nonuniform. The films must afford good coverage and adhesion to both the SWNT and the quartz substrate, and at the same time be sufficiently impermeable to $O_2/CF_4$ plasma to act as an effective etch resist. The unique chemistry of the Tc-resist material studied here combines hydroxyl and phenyl moieties which provide compatibility with both SWNT and oxide substrates. It is critical for films to exist in an amorphous phase, to avoid spatial nonuniformities in thermal properties (thermal conductivity, k), viscous flow properties (temperature coefficient of surface tension, $γ_1$, and viscosity, µ) and thickness that can be associated with crystalline grains. FIG. 18a,b,c shows AFM associated with trench formation experiments with arrays of SWNTs and Tc-resists consisting of thin films of paraffin, TCNQ, and pentacene (similar results were achieved for TCTA and F4-TCNQ). All of these materials show features that roughly correlate to underlying SWNT heaters, but showed massive variations in resulting trenches over the area of the film. Films of TAZ and anthracene (deposited at −80° C.) yielded amorphous films, but, over the time scales associated with experiments and characterization, exhibited spontaneous crystallization. Other materials, such as polystyrene ($M_w$=288,000, FIG. S12d) or Alq3 provided high quality amorphous films, but significantly higher power densities (and/or higher background heating, $T_\infty$>140° C.) were required to yield trenches. (In the case of Alq3, crystallization occurred at lower temperatures than those required for trenches to be observed, in reasonable experimental time scales). These power densities (or background heating) lead to bias requirements and/or operating conditions in which non-ideal device behaviors (e.g. non-negligible current through the s-SWNTs) limit the selectivity of the TcEP process. Models of thermocapillary flow suggest that such behaviors are due to either low temperature coefficients of surface tension or high viscosities. While both parameters play an important role in the flow (and $\gamma_1$ also plays a role in the trench profile), most materials exhibit $\gamma_1$ between ~0.05 and ~0.15 mJ/m²/° C., while viscosities can vary by many orders of magnitude. It is likely, then, that viscosity is the most significant parameter that determines whether materials yield trenches in experimentally practical time scales and with low power levels, without significant background heating. While the Tc-resist demonstrated here meets all of these criteria, advances could be obtained through the development of materials with similar properties but also with the ability for use at smaller thicknesses (e.g. 5-10 nm, rather than 25 nm). Reductions in thickness enable decreases in $W_{Tc}$ (linearly with $h_f$) which, in turn, could allow application to arrays of SWNTs with high densities.

Processes Defined by Critical Temperatures.

The unique scaling (particularly power invariance) associated with thermocapillary flow is critical to the success of TcEP, because it allows uniform trenches in arrays of SWNT that incorporate significant variations in power densities among the various SWNTs. Although it is possible to envision approaches like TcEP but which rely on processes such as sublimation or ablation, their robust operation is limited by the existence of a critical temperature, $T_C$. In such cases, at temperatures below $T_C$, the resist will remain, while at temperatures above $T_C$, the film will be removed. Thermal models can provide key insights into the scaling of this type of process. FIG. 19a,b show temperature profiles and thermal gradients for a range of power densities similar to those measured experimentally. Both peak power and peak gradient scale linearly with power. A width associated with a process that relies on a critical temperature, $W_C$, can be determined (FIG. 19a). FIGS. 19c,d show the predicted scaling for processes associated with critical temperatures of 2-10° C. It reveals that these processes yield no trench until a certain power density is reached. Afterward, the width increases dramatically with increasing power, to widths that would expose other SWNT in arrays of densities>0.1 SWNT/μm. This type of scaling is incompatible with desired operation. For higher $T_C$ the range of powers that yield practical trench widths (several hundred nm) becomes larger. Here, the required power density to initiate trenches grows dramatically, which is also highly undesirable.

Effects of Trench Formation in Neighboring SWNTs.

Figure 20:
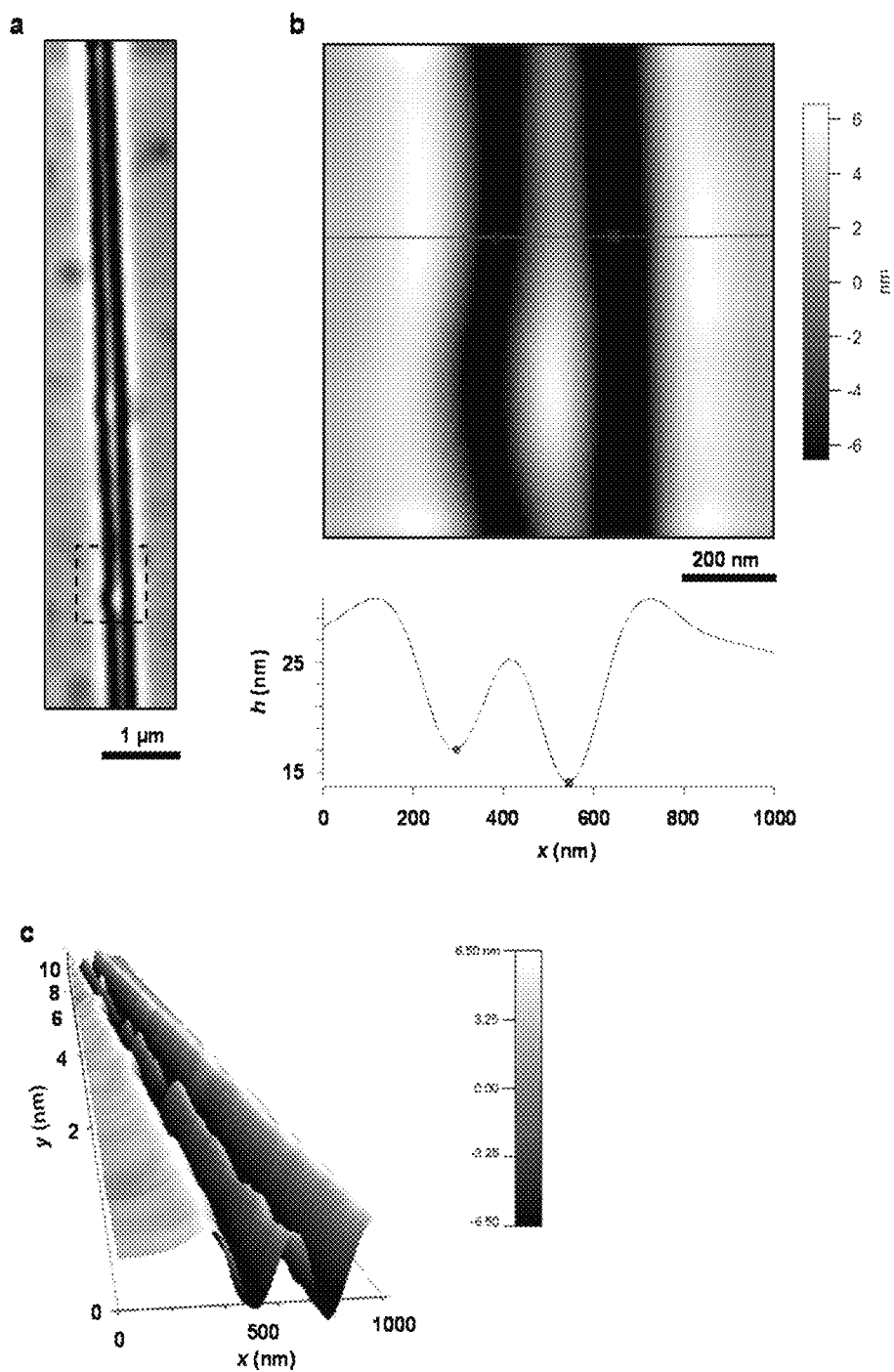
FIG. 20. Trenches in cases with neighboring SWNTs. (a), (b) AFM images associated with two distinct trenches that form from heating in neighboring SWNTs. Despite their close proximity (250 nm) two distinct trenches form along the lengths of the SWNTs (~10 μm), as in (b). (c) A topographical representation of the trenches.

For very high SWNT densities, non-ideal behavior in TcEP can occur if a trench associated with an m-SWNT exposes an s-SWNT in close proximity. The trench width provides an indicator for the density at which this type of behavior can be expected. In particular, for an array of SWNTs with regular spacing, the maximum density is defined roughly by the average trench width (trench width measured at the base of the Tc-resist ~100 nm, where $W_{Tc}$ is ~250 nm). We note, however, that thermocapillary flow can be altered as neighboring trenches approach one another. At long times the pileup from two adjacent trenches coalesces, creating a narrow strip of Tc-resist in between them. It is unclear from the simple models here, which apply to isolated SWNT, how close the SWNTs can be before their trenches merge. As a result, the minimum spacing between trenches where Tc-resist remains in between them provides the best indicator of the maximum density that can be accommodated in TcEP, as implemented here. AFM measurements of trench formation in arrays with locally high densities suggest that neighboring trenches can be as close as 250 nm while still showing well-defined Tc-resist in between. FIG. 20 shows an AFM, cross-sectional height profile, and associated 3D renderings of such trenches. Here, isolated trenches are observed along the entire lengths of the trenches (~8 μm).

Interconnected Arrays of SWNT for Large Area TcEP.

For applications where the collections of devices in a target application are known roughly, then it is practical to perform TcEP in local patches, as part of an interconnected array of electrodes. FIG. 21a shows five 1×5 sets of SWNT processed by TcEP in this manner. FIGS. 21b,c show the transfer characteristics for one of the arrays before and after TcEP and the characteristics for all five devices after TcEP. Table 2 summarizes the results for all five arrays. For each array, after removing interconnects (lithography and etching), all of the devices (25 total) showed high on/off ratios (>1×10³). This result demonstrates the effectiveness of performing TcEP over large areas using this type of interconnection scheme.

Inverter Fabrication and Load Line Analysis.

Figure 23:
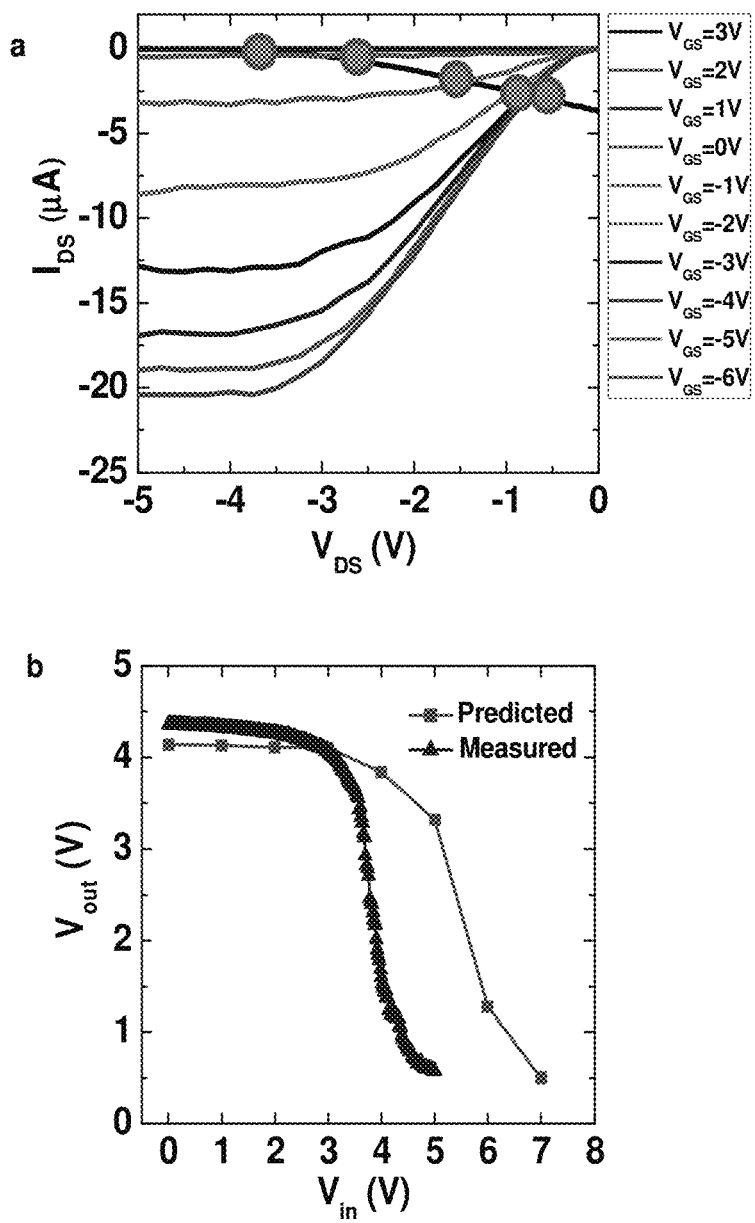
FIG. 23. Inverter fabricated using arrays processed by TcEP. (a) load line analysis for the inverter and (b) voltage transfer characteristics measured and predicted from load line analysis.

A p-type inverter was fabricated from two devices based on arrays treated by TcEP. FIG. 22a shows optical micrographs associated with this process. Here, a common source electrode is used to perform TcEP on two arrays with interconnected drain electrodes. Following TcEP, the gate and dielectric layers were removed. For one transistor (the load TFT), the associated source and drain electrodes for TcEP served as electrodes for the final device. For the other (the driver TFT) the source electrode was extended to yield a reduced channel length (~3.5 μm). Finally, new dielectric (SOG/HfO₂, 35/20 nm) and top gate (Ti, 70 nm) structures were defined, to complete the fabrication. The current level for the driver TFT increased roughly linearly with the reduction in channel length from 30 μm to 3.5 μm (expected ratio ~8.5, measured ratio ~9.5). This yielded for a current ratio between driver and load TFTs of ~10. FIG. 22b,c shows the electrical properties of the driver and load TFTs. The measured voltage transfer curve (VTC) is consistent with that predicted from load line analysis (FIG. 23). Some variation between the measured and predicted VTC curves results from hysteresis in the load and driver TFTs. The measured voltage gain (~4) is near expectation based on conventional diode-load inverter circuit design equation (~3, $A_V=g_m/g_{m\_load}=(L_{load}/L_{driver})^{0.5})^{20}$.

In addition, this demonstration hints that the TcEP scheme can be important for short channel devices and their circuit demonstrations. In particular short channel devices, such as the one shown in FIG. 6c, would difficult or impossible to fabricate reliably using a traditional method to eliminate the role of m-SWNTs, such as electrical breakdown, for two reasons: (1) heat sinking at the electrode contacts[29] progressively drives required powers to levels that reduce selectivity and leads to biases that can cause electrical breakdown in the necessarily thin gate dielectrics and (2) arrays of SWNT processed by breakdown in large device geometries lead to small discontinuities[34] in the m-SWNTs at positions that cannot be aligned, in determinate fashion, with the channels of subsequently fabricated devices.

Modeling of Electrical Properties of SWNTs in Partial Gate Configurations, after TcEP.

To determine the mobility of s-SWNTs following TcEP, the transfer characteristics from the devices comprising ~200 s-SWNTs with similar operating voltages were averaged and used as the basis of fitting to simulation results. In particular, self-consistent solutions to the Poisson and drift-diffusion equations[21] were used to simulate a partial gate SWNT field effect transistors (PG-FET) with 1 nm diameter (average diameter expected for populations grown by this technique[2]) s-SWNT as channel. Dimensions and other parameters are based on experiments and shown in FIG. 24a. Solution of the three-dimensional Poisson equation captures the effect of contact dimensions on the electrostatics of PG-FETs; whereas solution of the drift-diffusion equation describes one-dimensional carrier transport along the s-SWNT. In addition to using analytical expressions for mobility and carrier densities, simulation also considers acceptor doping to capture the influence of (oxygen and water induced) negatively charged interface defects.

FIG. 24b shows measured and simulated drain to source current ($I_{DS}$) vs. gate voltage ($V_G$) characteristics of the PG-FET at different source-drain bias ($V_{DS}$) for the averaged s-SWNT response. The simulation shows good agreement with the values measured under similar bias conditions. (Measured values represent average characteristics for ~30 PG-FETs with ~200 s-SWNTs). As shown in FIG. 24c, the percentage difference between experiment and simulation, defined as $(I_{DS\_exp} - I_{DS\_sim})/I_{DS\_exp} \times 100\%$ from $V_{GS} \sim 0$ V (i.e., the voltage where transconductance, $g_m = dI_{DS}/dV_{GS}$, is maximum) to $V_{GS} = -20$ V, is within ±5-7%. The variation reflects the uncertainty of device parameters used in the simulation. The average mobility throughout the devices, averaged over the quasi-Fermi level variation[22], i.e., $$\mu_{avg}(V_{DS}, V_{GS}) = \frac{\int_0^L \mu(x) \left| \frac{dQ_{Fp}}{dx} \right| dx}{\int_0^L \left| \frac{dQ_{Fp}}{dx} \right| dx} \quad (22)$$

is summarized in FIG. 24d. We find that $\mu_{avg} \sim 960$-1050 cm$^2$/V-sec. Variation of mobility with $V_{GS}$ and $V_{DS}$ follows the classical trend, i.e., decreases with both higher $|V_{GS}|$[22,23] and higher $|V_{DS}|$[22]. Such reduction of mobility at higher $V_{GS}$ is routinely observed in s-SWNT's mobility measurements[23,24] and is related to the increase of average electric field along the SWNT (considered in simulation) and also to the non-parabolicity in SWNTs' band-structure[25] (ignored in simulation). The effect of contact resistance (~28 kΩ) is observed to have negligible effect in extracted mobility for these long-channel length PG-FETs.

In addition, the average mobility (Eq. (22)) was extracted based on the following mobility equation (Eq. (23)). Mobility at position x, $\mu(x)$, along the nanotube is calculated using[22,23,25]

$$\mu(x) = \frac{\mu_{peak}}{1 + \mu_{peak} \left| \frac{dQ_{Fp}}{dx} \right| / v_s} \quad (23)$$

where $\mu_{peak}$ is the peak mobility, V is the potential at x, $v_s$ is the saturation velocity. This position dependent mobility (Eq. (23)) is later used for calculating average mobility ($\mu_{avg}$) at a particular $V_{GS}$, $V_{DS}$ using[22].

SEM and AFM images at each stage of the TcEP process, as Implemented with a Back Split Gate Structure (BSGS).

As a simplified version of TcEP, we demonstrated the feasibility of a re-usable electrode/gate structure, to eliminate cycles of processing that would otherwise be necessary for repetitive fabrication of top split gate structures used in the original scheme.

FIG. 25a shows an AFM image of the channel region of the BSGS (bottom split gate structure) immediately after transfer of an array of SWNTs. The AFM image in FIG. 25b shows selective formation of trenches for the entire channel length of 30 μm, by thermocapillary flow in an overlying layer of Tc-resist. The bias conditions to initiate this flow were similar to those for the corresponding top gate geometry, i.e, $V_{DS}=-40V$, $V_{GS}=20V$ for 5 min at 60° C. in vacuum (1×10$^{-4}$ torr). After dry etching to remove m-SWNTs, the Tc-resist is removed with acetone. The resulting channel appears in FIG. 25c. The red arrow highlights a pair of s-SWNTs throughout this process. This BSGS has W/L=30/30 μm.

Demonstration of Re-Use of a BSGS.

To demonstrate reusability, a BSGS was used for a 1$^{st}$ TcEP cycle and then cleaned by O$_2$ plasma treatment (200 mTorr, O$_2$ 20 SCCM, 100 W, 20 min, Plasma-Therm RIE). New, as-grown arrays of SWNTs were then transferred to the same BSGS using PVA/thermal tape. After a 2$^{nd}$ TcEP process, we observed expected operation, as shown in FIG. 26b. The behavior of the BSGS in this second cycle was the same as for the first. The successful multiple operation was confirmed by electrical measurements before and after TcEP for each of the two arrays of SWNTs, as summarized in FIG. 5 b, c.

Off-State Stability of Operation in Top Split Gate Structures.

Figure 27:
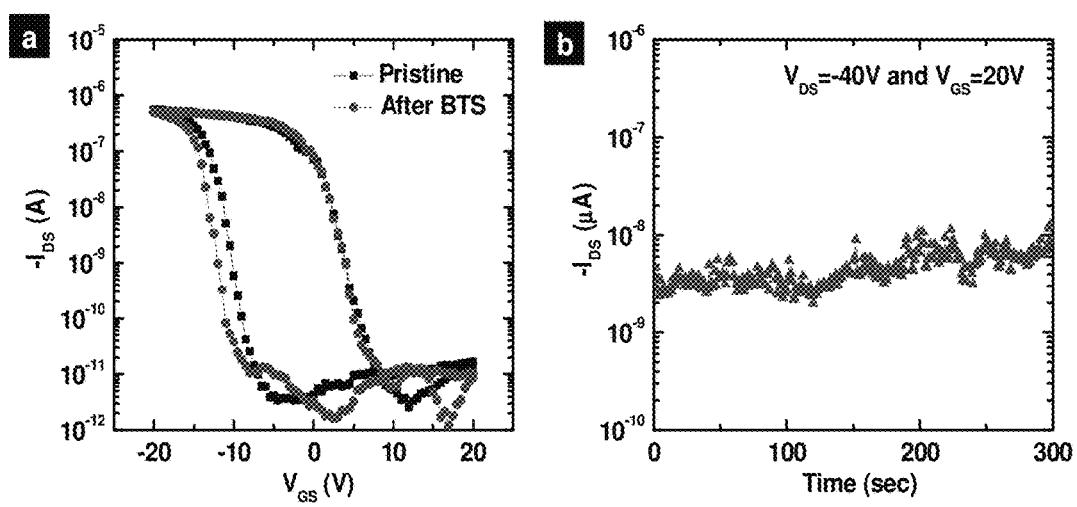
FIG. 27. Off state stability for top split gate structures. (a) Transfer characteristics before and after application of bias stress in the off-state, i.e, $V_{DS}$=−40V and $V_{GS}$=20V for 5 min and (b) off-state current as a function of time during this test. All characterization was performed under vacuum (1×10$^{-4}$ torr) at a substrate temperature of 60° C.

For the purpose of selective metallic nanotube removal by TcEP process, current stability in the 'off state' condition (i.e. large negative gate biases) for the s-SWNTs is particularly important. To verify this stability, we measured current outputs in devices with several s-SWNT tubes at conditions corresponding to those used to induce thermocapillary flow (i.e, $V_{GS}=20V$, $V_{DS}=-40V$, $T_{sub}=60°$ C., 1×10$^{-4}$ torr). FIG. 27(b) shows that the current remains less than several nA throughout the experiment.

Off-State Stability of Operation in Top Split Gate Structures.

Figure 28:
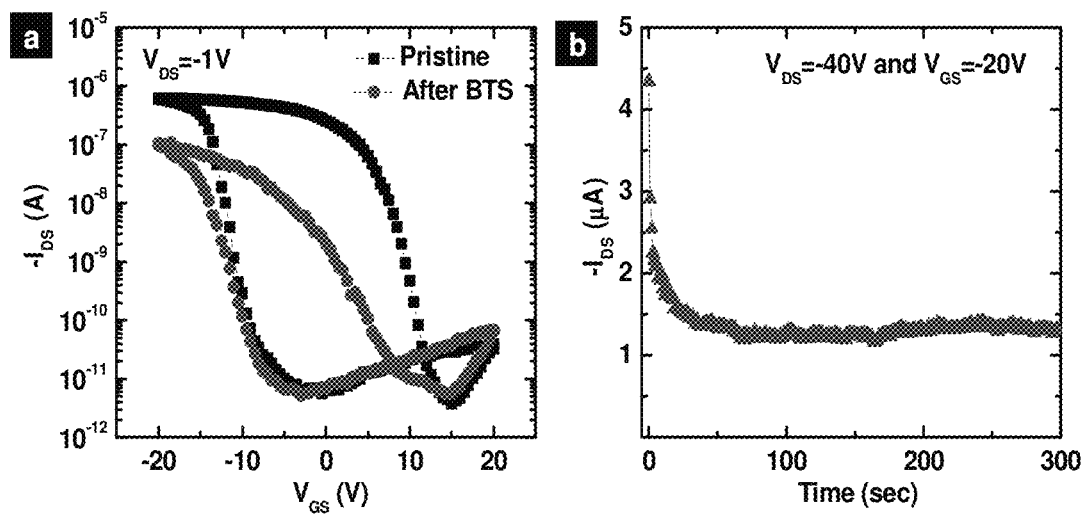
FIG. 28. On-state stability of operation in top split gate structures (a) Transfer characteristics before and after application of bias stress in the on-state, i.e, $V_{DS}$=−40V and $V_{GS}$=−20V for 5 min and (b) on-state current as a function of time during this test. All characterization was performed under vacuum (1×10$^{-4}$ torr) at a substrate temperature of 60° C.

To evaluate on-state stability, we measured current output in the device of FIG. 28 at bias condition ($V_{GS}=-20V$ and $V_{DS}-40V$) for 5 min in vacuum (1×10$^{-4}$ torr). The results of FIG. 28 indicate that the current in the on-state shows some variation in the first few tens of seconds, likely due to filling of charge traps near the SWNTs and in the gate dielectric, and then remains constant.

Full Characterization of Split Gate Devices with W/L (=1000/30 μm or 2000/30 μm) after TcEP.

For devices with large widths (W/L=1000/30 μm), I-V characteristics after TcEP reveal the maximum achievable current levels, as well as any variations in device switching behavior at high drain biases. In particular, we measured the device of FIG. 4(c), for which W/L=1000/30 μm, at drain biases up to $V_{DS}=-40.1$ V. Here, FIG. 29b indicates that the maximum output current which can be extracted is ~1.5 mA. To further verify the width scalability of devices with purified arrays of s-SWNTs, we connected two devices with the same physical dimensions (W/L=1000/30 μm) to create an effective dimension of W/L=2000/30 μm, with current outputs of ~3 mA as shown in FIG. 30b. These results correspond to the simultaneous operation of at least several hundred s-SWNTs. All characterization was performed in dry $N_2$ ambient.

On/Off Ratio as a Function of Drain Bias in Split Gate Devices with Large Widths.

The on/off ratios of devices shown in FIG. 4(a), (b), diminish somewhat at the most extreme bias conditions, due to effects that arise from band bending near the drain and associated band-to-band tunneling (FIGS. 32 and 33), but remains close to 100.

Electrostatic Behavior Associated with Operation at High Bias Voltage.

Figure 10:
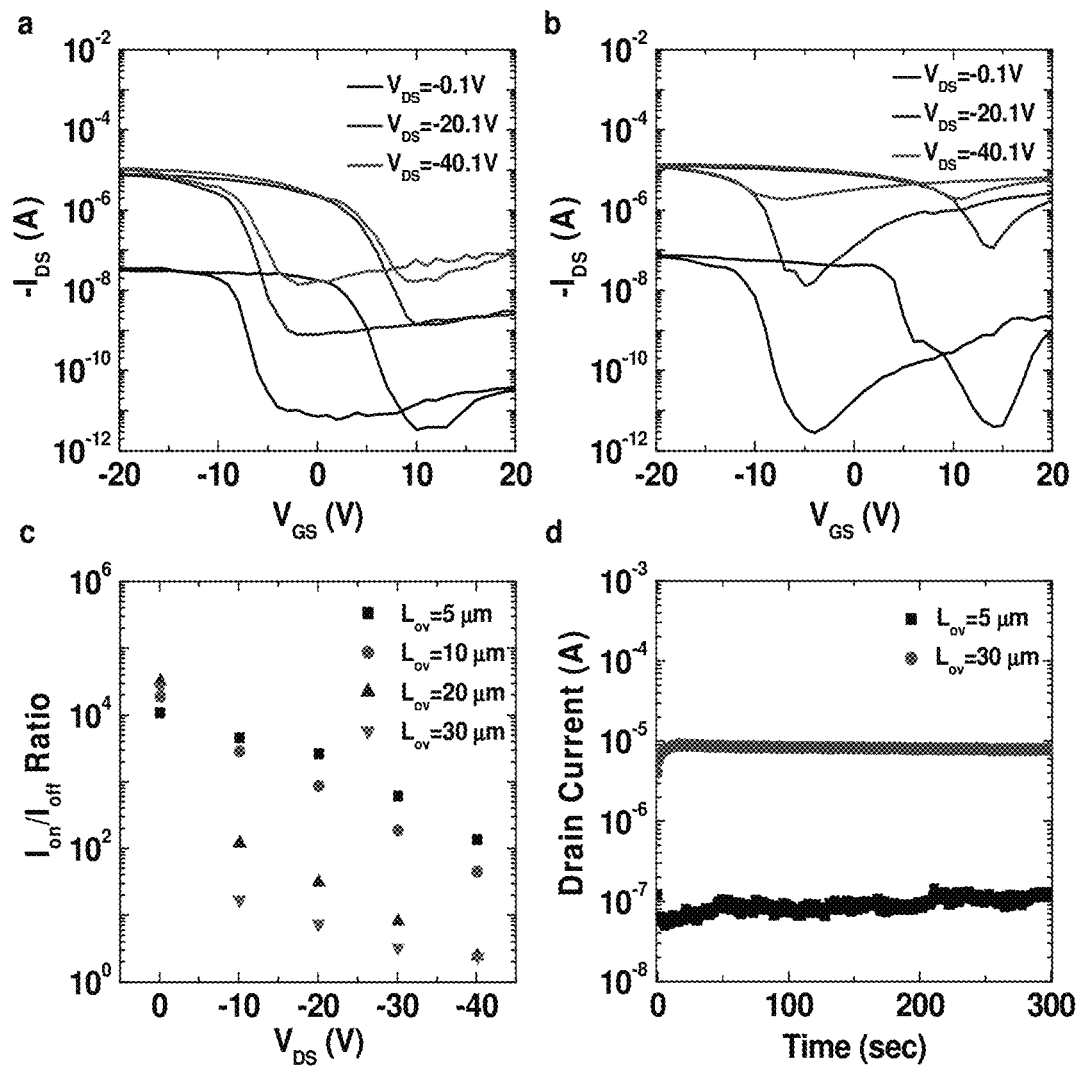
FIG. 10. Effect of partial gate transistor geometry. Electrical characterization of an individual SWNT device with varying gate overlap. Transfer characteristics for different drain voltages ($V_{DS}$=−0.1, −20, −40 V) for the case of (a) partial gate and (b) full gate configurations. (c) $I_{on}/I_{off}$ dependence on gate overlap ($L_{ov}$) ranging from 5 to 30 μm and (d) drain current associated with devices held in their off state ($V_{GS}$=+20 V, $V_{DS}$=−40V) for extended durations, for partial gate and full covered configurations.

The values of on/off ratio (i.e., $I_{DS}@V_{GS}=-20$ V/$I_{DS}@V_{GS}=20$ V) in FIG. 10 and FIG. 6(c) suggest the existence of small bandgap (large diameter) semiconducting CNTs after metallic CNT removal. FIG. 10 is measured for a device that has a single semiconducting nanotube as a channel. Simulation of $I_{DS}$–$V_{GS}$ for this device is consistent with a diameter of 1.74 nm (directly estimated by analysis of Raman spectra) for the SWNT and matches the on/off ratio measured by varying overlap length ($L_{OV}$) and $V_{DS}$ (FIG. 32c). Low on/off ratio for the full-gate device configuration ($L_{OV}=L$; FIG. 32b) is due to larger band bending near the drain end of the nanotube (FIG. 33a) that induces band-to-band tunneling (BTBT)[22] and high $I_{DS}$ at $V_{GS}=20$ V. Band bending near the drain end is relaxed due to the extension of electrostatic gate control in the overlap region (FIG. 33c) and, therefore, BTBT and $I_{DS}$ at $V_{GS}=20$ V is lower and on/off ratio is higher for the same nanotube in the partial-gate configuration ($L_{OV}<L$; FIG. 32a). For all $L_{OV}$ values, band bending (FIG. 33a) and BTBT increases at larger $|V_{DS}|$, therefore, reduces the on/off ratio (FIG. 32c).

Forming Horizontally Aligned Arrays of SWNTs.

Photolithography (AZ 5214 positive photoresist), electron beam evaporation (0.6 nm Fe; AJA), and subsequent liftoff defined regions of catalyst in the geometry of strips oriented perpendicular to the preferred growth direction on ST-cut quartz substrates (Hoffman). Annealing in air at 950° C. for 1 hr at the pressure (1 atm)(quartz tube furnace with ~1 inch outer diameter), cooling the furnace, purging it with hydrogen (300 sccm) at the pressure (1 atm), and then heating to 925° C. with ramping rate of 50° C./min prepared the iron catalyst for chemical vapor deposition. Introduction of growth gases (20 sccm $H_2$, 20 sccm Ar, bubbled through ethanol (T=0° C.) at 925° C. for 20 min yielded well aligned arrays of SWNTs.

Fabricating Devices that Incorporate a Single SWNT.

The fabrication procedures followed those described above. The use of arrays of SWNT grown at low density (0.1-0.2 SWNT/μm), and subsequently etched in patterns that removed all of the SWNTs except those in narrow strips (~3 μm widths) yielded devices with small numbers of SWNTs. Electrical and AFM analyses identified a subset of such devices that incorporated only a single SWNT bridging the source and drain electrodes.

Removing the Gate Electrode and Dielectric.

Following TcEP, the purified SWNTs (i.e. consisting only of s-SWNTs) were protected by a patterned layer of photoresist (AZ 5214) prior to removal of the gate metal (for Ti, Transene, Inc; titanium etchant TFTN; for Cr, Transene, Inc; chrome mask ethant-CE-5M 9). Wet etching ($H_2SO_4$: $H_2O_2$=2:1, 60° C., 5~10 s) removed the crosslinked PVA. Etching in buffered hydrofluoric acid (BOE 6:1, 30 s) removed the SOG/$Al_2O_3$ bilayer. Stripping the photoresist completed the process.

Fabricating Short Channel Devices.

Following removal of the partial gate transistor structure, phase shift lithography[27], electron beam evaporation (2 nm Ti, 25 nm Pd), and lift-off (facilitated by brief ultrasonication, ~1 min) defined a narrow gap separating new source and drain electrodes on a purified array of s-SWNTs. PDMS stamps for phase shift lithography were cast and molded (Dow Corning, Sylgard) from a Si master, fabricated by photolithography (AZ 5214) and Bosch etching (etch/passivation, cycle time: 5 sec/5 sec, RIE power: 20 W/0 W, 35 sccm $SF_6$, 110 sccm $C_4F_8$, for constant ICP power of 600 W, etch rate: 1 μm/80 s) in $SF_6$ to a depth of ~1 μm. Following liftoff, the dimensions of source and drain electrodes were further defined by photolithography (AZ 5214) and a combination of wet and dry chemical etching (Transene Pd etchant, 50 sec, followed by RIE, 40 sccm $CF_4$, 1.2 sccm $O_2$, 150 W, 30 sec; Plasma-Therm). Gate dielectric layer (~30 nm) of $HfO_2$ was deposited by electron-beam evaporation followed by atomic-layer deposition of $HfO_2$(10 nm). Photolithography (AZ 2070), and sputtering (70 nm Ti, 150 W, 3 mTorr Ar; AJA International), followed by lift-off defined gate electrodes, to complete the devices.

Fabricating Inverters.

First, TcEP yielded two purified arrays of s-SWNTs. Photolithography (AZ 5214), electron beam evaporation (2 nm Ti, 48 nm Pd) and lift-off then patterned source and drain electrodes for the driver transistor (L=3.5 μm, W=30 μm). The electrodes associated with the TcEP processes were used for the load transistor (L=30 μm, W=30 μm). Previously described procedures[28] yielded SOG/$HfO_2$ (35 nm/20 nm) dielectrics for both transistors. Photolithography (AZ 5214), electron beam evaporation (100 nm Ti) and lift-off defined the gate electrodes.

References

1. Paddock, C. A. & Eesley, G. L. Transient thermoreflectance from thin metal films. *J. Appl. Phys.* 60, 285-290 (1986).
2. Islam, A. E. et al. Effect of variations in diameter and density on the statistics of aligned array carbon-nanotube field effect transistors. *J. Appl. Phys.* 111, 054511-054517 (2012).
3. Liao, A., Zhao, Y. & Pop, E. Avalanche-Induced Current Enhancement in Semiconducting Carbon Nanotubes. *Phy. Rev. Lett.* 101, 256804 (2008).
4. Xie, X. et al. Quantitative Thermal Imaging of Single-Walled Carbon Nanotube Devices by Scanning Joule Expansion Microscopy, *ACS Nano* 6, 10267-10275 (2012).
5. Liu, W. J., Etessam-Yazdani, K., Hussin, R. & Asheghi, M. Modeling and data for thermal conductivity of ultrathin single-crystal SOI layers at high temperature. *IEEE Trans. Electron Dev.* 53, 1868-1876 (2006).
6. Okada, Y. & Tokumaru, Y. Precise Determination of Lattice-Parameter and Thermal-Expansion Coefficient of Silicon between 300-K and 1500-K. *J. Appl. Phys.* 56, 314-320 (1984).
7. Tada, H. et al. Thermal expansion coefficient of polycrystalline silicon and silicon dioxide thin films at high temperatures. *J. Appl. Phys.* 87, 4189-4193 (2000).
8. Wortman, J. J. & Evans, R. A. Youngs Modulus Shear Modulus and Poissons Ratio in Silicon and Germanium. *J. Appl. Phys.* 36, 153-& (1965).
9. Ju, Y. S. & Goodson, K. E. Process-dependent thermal transport properties of silicon-dioxide films deposited using low-pressure chemical vapor deposition. *J. Appl. Phys.* 85, 7130-7134 (1999).

10. Blech, I. & Cohen, U. Effects of Humidity on Stress in Thin Silicon Dioxide Films. *J. Appl. Phys.* 53, 4202-4207 (1982).
11. Kim, M. T. Influence of substrates on the elastic reaction of films for the microindentation tests. *Thin Solid Films* 283, 12-16 (1996).
12. Beck, A. E., Darbha, D. M. & Schloessin, H. H. Lattice conductivities of single-crystal and polycrystalline materials at mantle pressures and temperatures. *Phys. of the Earth and Planetary Interiors* 17, 35-53 (1978).
13. Assael, M. J., Botsios, S., Gialou, K. & Metaxa, I. N. Thermal conductivity of polymethyl methacrylate (PMMA) and borosilicate crown glass BK7. *Int. J. Thermophys.* 26, 1595-1605 (2005).
14. Tsutsumi, N. & Kiyotsukuri, T. Measurement of Thermal-Diffusivity for Polymer Film by Flash Radiometry. *Appl. Phys. Lett* 52, 442-444 (1988).
15. Chou, S. Y. & Krauss, P. R. Imprint lithography with sub-10 nm feature size and high throughput. *Microelectron Eng.* 35, 237-240 (1997).
16. Ishiyama, C. & Higo, Y. Effects of humidity on Young's modulus in poly(methyl methacrylate). *J. Polym. Sci. Pol. Phys.* 40, 460-465 (2002).
17. Wu, W. L., Vanzanten, J. H. & Orts, W. J. Film Thickness Dependent Thermal-Expansion in Ultrathin Poly(Methyl Methacrylate) Films on Silicon. *Macromolecules* 28, 771-774 (1995).
18. Lee, J. et al. Electrical, thermal, and mechanical characterization of silicon microcantilever heaters. *J. Microelectromech. Syst.* 15, 1644-1655 (2006).
19. Felts, J. R., Somnath, S., Ewoldt, R. H. & King, W. P. Nanometer-scale flow of molten polyethylene from a heated atomic force microscope tip. *Nanotechnology* 23, 215301 (2012).
20. Wang, C., Zhang, J. & Zhou, C. Macroelectronic Integrated Circuits Using High-Performance Separated Carbon Nanotube Thin-Film Transistors. *ACS Nano* 4, 7123-7132 (2010).
21. Xie, X. et al. Electroluminescence in Aligned Arrays of Single-Wall Carbon Nanotubes with Asymmetric Contacts. *ACS Nano* 6, 7981-7988 (2012).
22. Lundstrom, M., Fundamentals of Carrier Transport. (Cambridge University Press, 2000), p. 235.
23. Zhou, X., Park, J.-Y., Huang, S., Liu, J. & McEuen, P. L. Band Structure, Phonon Scattering, and the Performance Limit of Single-Walled Carbon Nanotube Transistors. *Phy. Rev. Lett.* 95, 146805 (2005).
24. Yang, Z., Liao, A. & Pop, E. Multiband Mobility in Semiconducting Carbon Nanotubes. *IEEE Electron Dev. Lett.* 30, 1078 (2009).
25. Perebeinos, V., Tersoff, J. & Avouris, P. Mobility in Semiconducting Carbon Nanotubes at Finite Carrier Density. *Nano Lett.* 6, 205-208 (2006).
26. Islam, A. E.; Du, F.; Ho, X.; Jin, S. H.; Dunham, S., Effect of variations in diameter and density on the statistics of aligned array carbon-nanotube field effect transistors. *J. Appl. Phys.* 111, 054511 (2012).
27. Maria, J., Malyarchuk, V., White, J. & Rogers, J. A. Experimental and computational studies of phase shift lithography with binary elastomeric masks. *J. Vac. Sci. & Technol. B: Microelectronics and Nanometer Structures* 24, 828-835, (2006).
28. Jin, S. H. et al. Sources of Hysteresis in Carbon Nanotube Field-Effect Transistors and Their Elimination Via Methylsiloxane Encapsulants and Optimized Growth Procedures. *Adv. Func. Mat.* 22, 2276-2284 (2012).

EXAMPLE 2

Aligned single walled carbon nanotubes (SWNTs) are well suited for applications in high dynamic range RF electronics, low-noise linear amplifiers, mixed-signal devices and sensors. During CVD growth of aligned tube arrays both metallic and semiconducting tubes naturally grow at a statistical ratio of 1:3. Many electronic device applications require arrays of purely semiconducting SWNTs. The presence of metallic nanotubes degrades the device electronic properties, impeding high performance. In the example above, we introduced nanoscale thermocapillary flow (NTF) processing in thermal resists for complete, selective removal of metallic SWNTs from CVD arrays. Here, we explore three distinct purification paths with a focus on complete process development, modeling and scalability. Microwave initiated NTF, laser initiated NTF, and direct laser ablation were assessed in detail. We have shown while all the techniques offer promise, microwave excitation is the most promising and can provide an efficient, highly scalable path for selective heating of metallic tubes via NTF enabling highly selective removal of the metallic tubes (99.999%). To build on this, we also suggest "scale-up" of direct microwave heating of m-SWNTs to initiate thermo-capillary enabled purification (TcEP) to enable purification of aligned 3 inch SWNT wafers.

Figure 34:
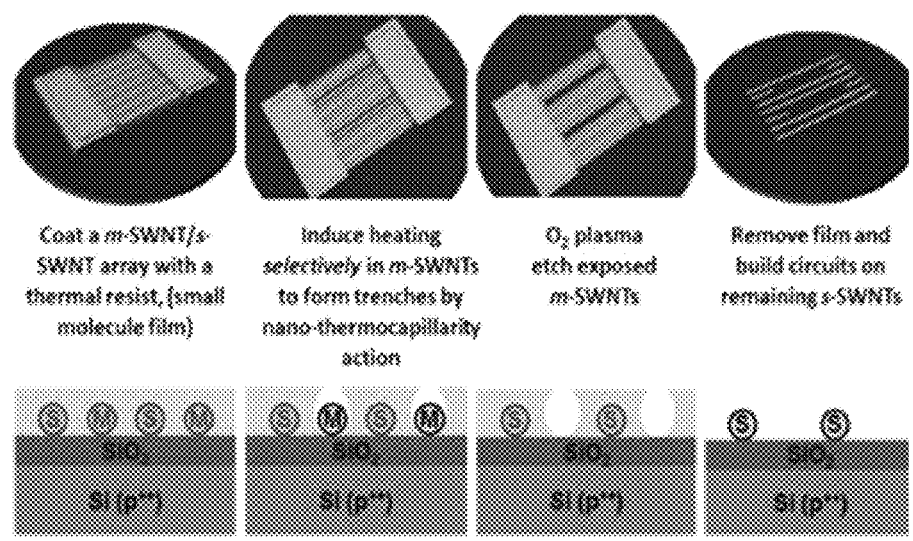
FIG. 34. Schematic showing exemplary purification process involving thermocapillary flow.

We report completion of the exploration and development of three techniques for the selective elimination of metallic SWNTs from aligned nanotube substrates. FIG. 34 shows the general technical results based on the initial program objectives. As noted, the primary project goal was to identify a scalable technology which would enable selective elimination of metallic SWNTs. Three removal strategies were explored. Microwave initiated thermocapallary enabled purification (TcEP), laser initiated TcEP, and direct laser ablation, were studied in detail both experimentally and theoretically to assess the technical feasibility and scale-up potential of each. Results indicate that all of the techniques offer some level of selectivity enabling elimination of metallic tubes from the nanotube die. Importantly, the key finding of the program was that the microwave approach, due in part to our ability to use metal-semiconductor interactions to manipulate properties of the tubes during processing, shows in essence, perfect selectivity, i.e., complete removal of metallic nanotubes with no semiconducting nanotubes damaged or destroyed. This suggests it as the best scalable choice for full wafer processing. In this example we detail all three approaches, summarizing the experimental designs and findings, and accessing the purified die either spectroscopically or via the fabrication of transistors.

CNT transistors are an important technology area and have demonstrated an ability to provide highly linear, high performance device operation at low drive voltages. Technology development is enabled using single walled carbon nanotubes (SWNTs), an extremely powerful and versatile class of nanomaterials with a wide array of intriguing electrical properties [1]. They are being explored as the base paradigm for a wide range of device applications ranging from high performance RF electronics to flexible electronics [2]. As an electronics platform, SWNT transistors are being pursued for applications that include low-noise linear amplifiers and mixers where low power and high spurious-free dynamic range are very important. Aligned submonolayer films of SWNTs, grown by CVD represent the most promising materials platform for the applications under consideration. While there have been many demonstrations of impressive single tube devices, arrays, i.e., multi-tube structures (array transistors), are needed for the technology to mature. Key to the advance of high performance applications is the availability of ordered dense films of semiconducting material, with high purity (>99.9% s-SWNT[6]), at the wafer scale. Among all needs essential for this technology evolution; nanotube electrical purification has been the key challenge. There have been several attempts to develop controlled growth CVD conditions to achieve populations with enhanced s-SWNT content [7]. While conceptually these approaches could be ideal, to date, the achieved purity is rather limited, (current best practice >5% m-SWNTs remain), and is often not reproducible. The differences in the electronic characteristics of nanotubes are driven by very subtle changes in "structure" making "pure" direct growth extremely unlikely. Clearly a purification strategy that starts with highly aligned CVD based materials would have distinct advantages. Post growth purification has also been difficult. One strategy involves exploiting subtle differences in surface chemistry within SWNTs of different chirality in solution. Using chromatography or ultracentrifugation, the tubes are purified to generate the required semiconducting populations [8]. In addition, surface chemical methods and/or electrophoresis are utilized to sort suspended tubes as they are deposited onto a substrate. While extremely pure populations of SWNTs can be achieved in this manner, high purity requires multiple iterations due to the wide range of chiralities and diameters present in the starting population. While this approach can achieve electronic purity, generating parallel, aligned arrays of SWNTs is still problematic. While several approaches attempt to achieve post purification alignment, they are difficult and are generally non-scalable. Recently we developed a path to purification for CVD grown aligned materials based on utilization of a thermal resist which serves as an etch barrier for semiconducting tubes during processing. The demonstrated process uses nanoscale thermocapillary flows (NTF) in thin film organic thermal resists as a processing strategy for complete, highly efficient and selective removal of metallic SWNTs from aligned arrays of SWNTs grown on quartz substrates. The low temperatures involved and the ease of integration with current micro/nanofabrication tools inherent with this process suggests it can serve as a robust technique for nanotube die purification. While thermocapillary enhanced purification (TcEP) was initially developed using selective joule heating of the m-SWNTs, detailed experimental and theoretical study has now shown that we can use other mechanisms to generate the selective heating needed to drive the underlying thermophysical phenomena. In this example, we show that laser irradiation and microwave excitation, in a coupled waveguide geometry, can lead to efficient, selective removal of metallic tubes via NTF. Moreover we have explored direct ablation of metallic nanotubes. After a thorough analysis and comparison we have concluded that microwave initiation is an optimal purification approach enabling 100% purity. We detail the system physics leading to this purification advance and show the performance of the resulting transistor arrays. We also define a path to "scale" microwave NTF methods for wafer scale manufacture. The approach is consistent with current manufacturing paradigm best practices and wafer processing protocols.

The electronic properties of single walled carbon nanotubes (SWNTs) make them uniquely suited for diverse applications in high dynamic range RF electronics, sensors and other device technologies. To realize the benefit of SWNT electronics, "scalable" process options consistent with manufacturing best practices are needed. In electronics, the program has emphasized large-scale carbon nanotube (CNT)-based memory, CNT-based logic devices, and CNT field-effect transistors with a goal of developing processes that are completely compatible with operations in a standard silicon foundry. Most high performance applications, require ordered dense films with high purity (>99% s-SWNT [6]) populations. Nanotube electrical purification is one of the fundamental barriers to technology development. This effort has removed the purification issue from the list of process needs.

Figure 35:
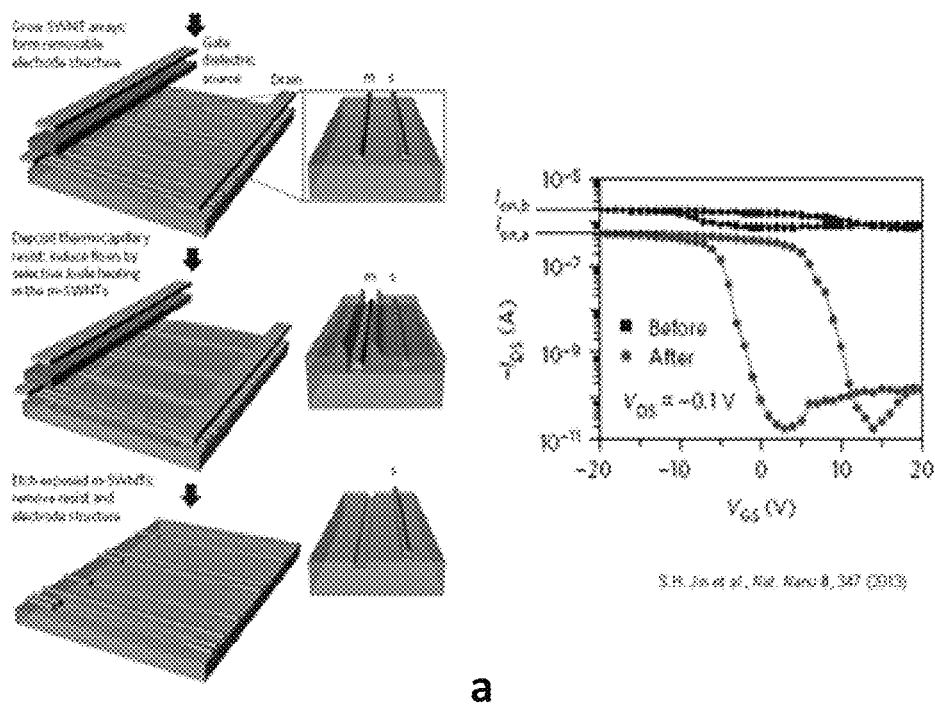
FIG. 35. (a) Schematic of thermocapillary based purification process; (b) Scalability questions. Split gate structure need poses a barrier to wafer scale deployment. Clearly an e-field exposure based approach would provide scalability.
Figure 35:
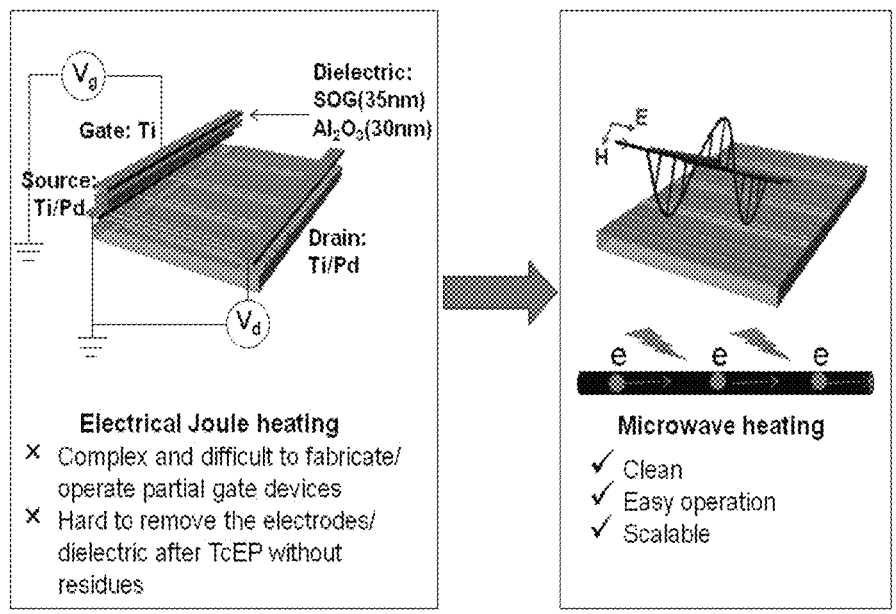

As described above we utilized our innovative nano thermocapilary approach as a base development platform. A basic description of the joule heating based TcEP process is illustrated in FIG. 35 (left). Currently, 1) aligned arrays of SWNTs are fitted with removable electrodes to enable selective heating. 2) A thermal resist material is then deposited on the array and a bias current is applied to the array structure resulting in joule heating in the metallic tubes. Thermocapillary action induces the formation of an opening, i.e., a trench above the metallic tubes. This in essence, de-protects the metallic tubes allowing them to be selectively and exclusively removed in a simple $O_2$ etch process, completely compatable with conventional processing. Obviously, the impact on device performance is dramatic. The transfer curve on the right of FIG. 35 illustrates the increase on device on/off ratio. SWNT transistors with on/off ratios in excess of $10^5$ have been fabricated. Shown is a typical $I_{ON}/I_{OFF}$ curve before and after m-SWNT removal. It is important to note that no damage to semiconductor SWNTs is observed using the TcEP process.

While this technique shows great promise, the direct joule heating approach as the NTF driver may face scalability challenges. For example, the addition of a partial gate structure to enable joule heating is a complex multistep process. FIG. 35b shows one simplified process example. Here a simple electromagnetic field is used to selectively heat the metallic tubes. Our work shows that differences in the electromagnetic absorptive properties of metallic and semiconducting tubes can be exploited for initiation leading to simplified purification. We developed, tested, and modeled, these alternative processes for initiating the selective NTF needed for purification. Feasibility and demonstration of CVD array purification has been achieved using both microwave and laser initiation, moreover direct laser ablation was explored. The work shows that the microwave technique is superior and has the most obvious path to manufacture, yet both options hold great promise. More generally the primary program deliverables are as follows:

1. Both laser and microwave initiated TcEP processes were shown feasible and scalable, moreover they were demonstrated to produce CNT transistor arrays with device performance at or exceeding the program targets.
2. For the microwave process, the "contact case" proved to be the best option for scale-up.
3. Direct laser ablation was shown feasible.
4. We developed models of the processes developed.
5. We defined first generation resist specifications and a media model.

Figure 36:
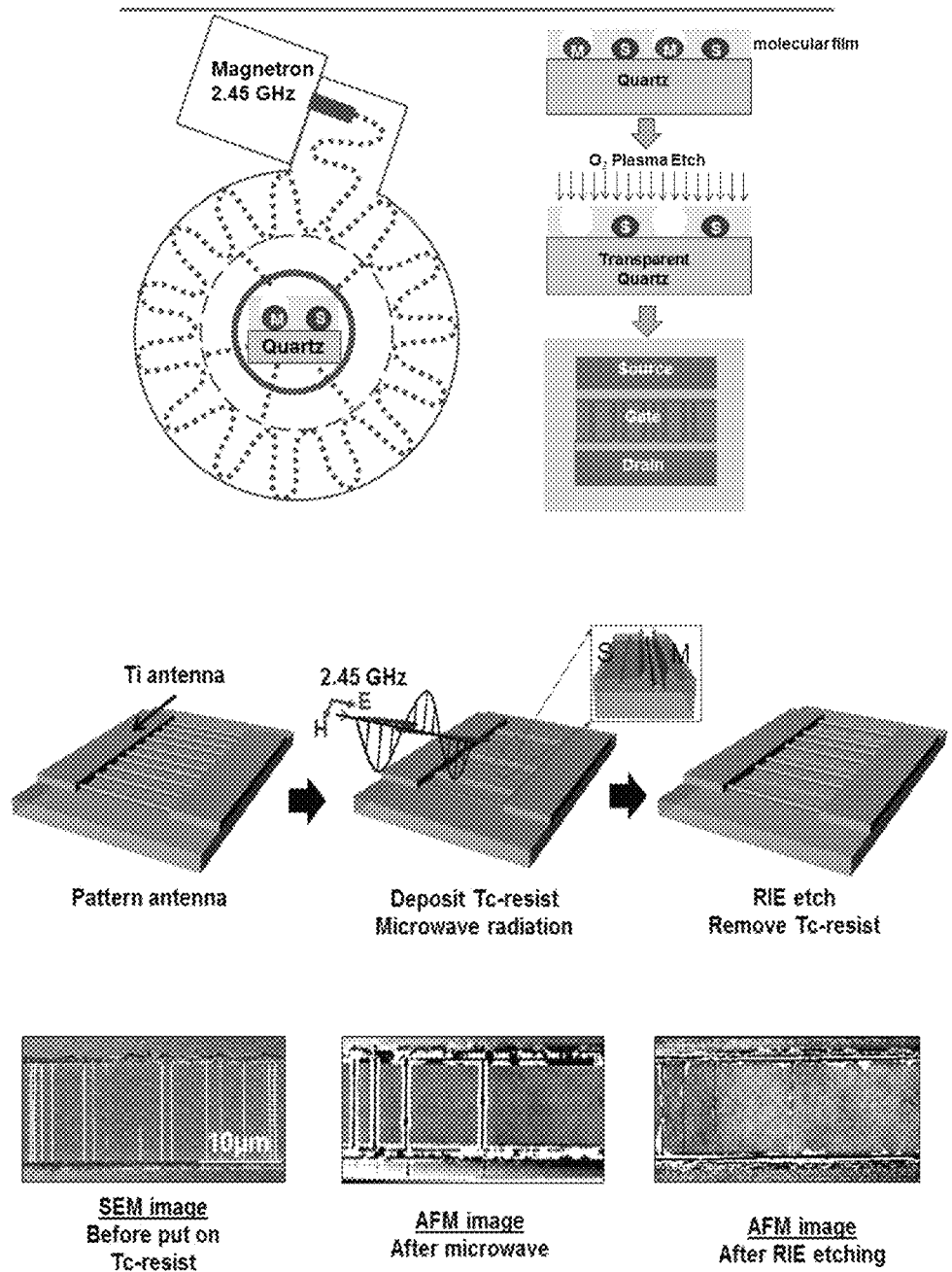
FIG. 36. NTF process driven by microwave irradiation.
Figure 37:
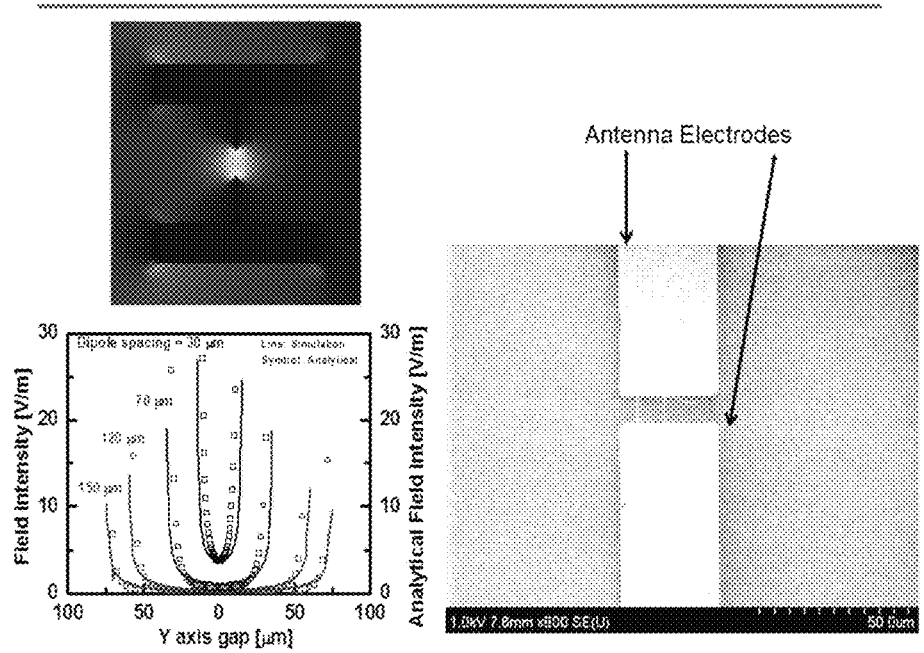
FIG. 37. Microwave antenna structure.

Microwave Initiated TcEP:

We developed the use of microwave initiation of the TcEP through to the fabrication of single CNT transistors and array devices. FIG. 36 shows the current microwave processing path. The thermal resist coated, aligned tube samples are mounted in a single mode microwave reactor and exposed at a fixed time and power. The radiation initiates the NTF de-wetting process with trenches opening above the metallic tubes which are subsequently removed using a $O_2$ plasma etch. The current process uses dipole antenna structures deposited onto the nanotube substrates to enhance the microwave field intensity at the tube positions, (FIG. 37). This feature allows for optimization of the NTF process at reasonable reactor powers. FIG. 37 shows a SEM image of the antenna structure with the SWNTs in the gap (right). An image of the microwave field distribution and a plot of the field intensity vs antenna gap width is also shown, (left, top). This gap can be tuned for process efficiency (left, bottom).

Figure 38:
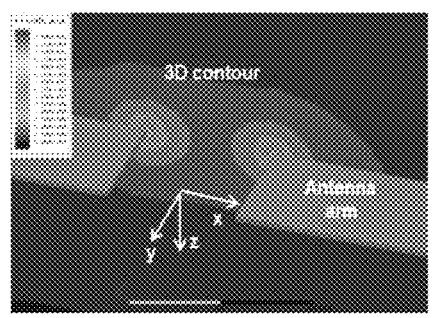
FIG. 38. Two developed microwave irradiation geometries.
Figure 38:
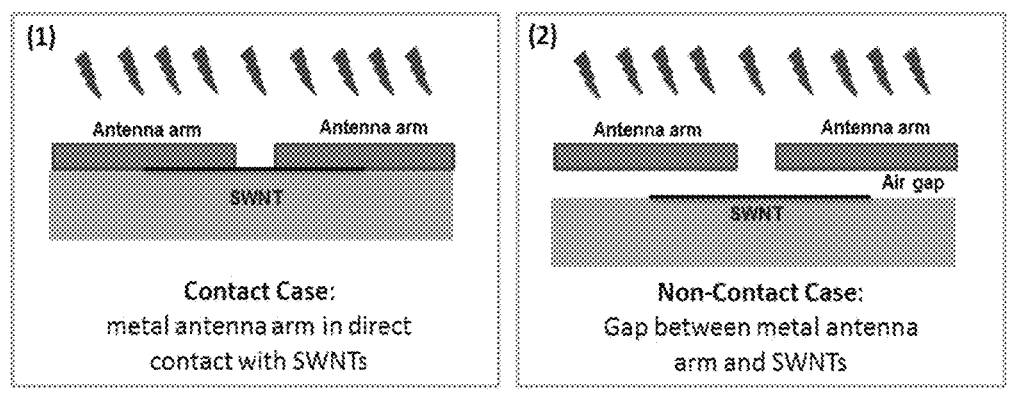
Figure 39:
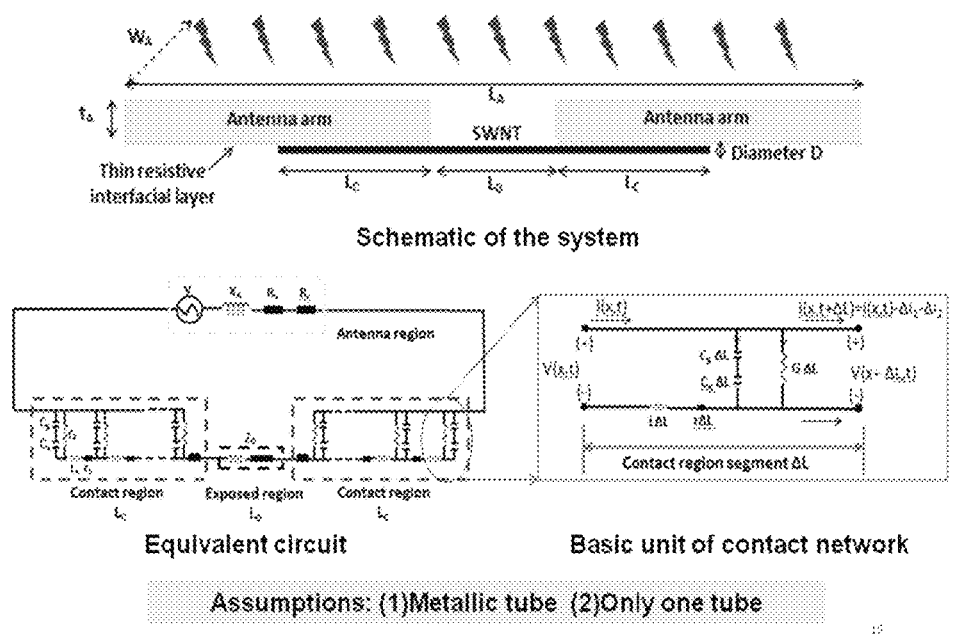
FIG. 39. Current Equivalent Circuit model.

Model of Microwave Initiated NTF:

To support the experimental work we have in addition developed a comprehensive picture for the microwave initiation geometries explored. The two common geometrical variations of the microwave process that have been developed are shown in FIG. 38. They simply differ in how the microwave antenna engages the die. In the first configuration, (scheme 1), the electrodes are deposited directly on the tube substrate. This "contact case" geometry has consistently produced the lowest processing power thresholds, has resulted in the highest performing transistors, and has given us the largest processing window. All the devices, (both single and multi-tube), show high on/off current ratios, ($10^3$-$10^4$ or greater). The second geometry shown in FIG. 38, (scheme 2), is the "non contact" case. While this technique has proven to be more versatile, it clearly requires more microwave power. The implementation of this approach would allow the antenna structures to be removed. We have developed an equivalent circuit model to quantify these geometries. The base model is illustrated in FIG. 39. The schematic shows the combined geometries; the contact mode is of course the limit that D>0. The contact network shows the circuit with all the relevant parameters. Clearly the model has some very specific implications. 1) In both cases we are defining a heating process where metallic tube heating is driven by a microwave induced current. Importantly, the nature of the effective contacts, i.e., the metal/semiconductor (MS) interface to the tubes becomes increasingly important.

Figure 40:
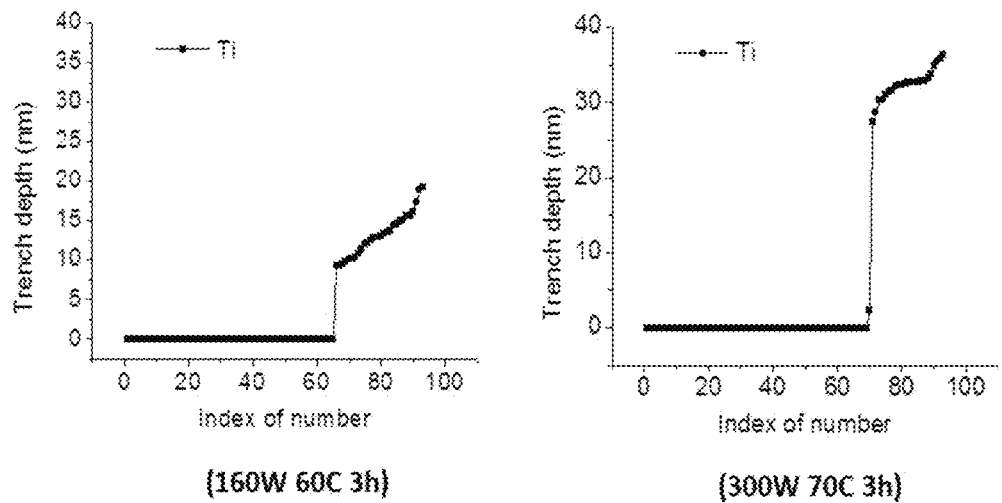
FIG. 40. Metal electrode performance.
Figure 40:
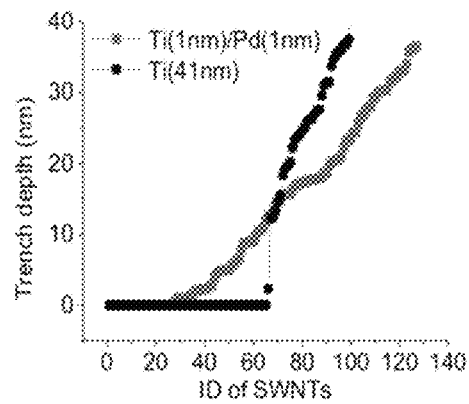

First, turning our focus fully to the contact case (FIG. 39, scheme 1). We focus here first for two reasons; 1) The contact case has shown the most success and 2) Adding antenna electrodes to a conventional die layout is not prohibitive. The contact case as stated above is the best, first, process scale-up path. FIG. 40 (top), shows the selectivity of the contact case, (Ti antenna). The selectivity cure shown indexes every tube on an exposed die and simply measures the trench depth at that location. A sharp step indicates high selectivity. In the ideal case the fraction of tubes forming "deep" trenches should be ~33% consistent with expected growth statistics. Shallow trench formation is the hallmark of heating either semi-metallic or "doped" semiconducting tubes. FIG. 40 (bottom) illustrates the difference between antenna using Ti (41 nm) and those predominately Pd (40 nm), (Ti (1 nm)) is used here as a very thin adhesion layer). It should be noted that trenches need to be of order 15-20 nm to "de-protect" via reactive ion etch. Titanium shows some of the best results, but selectivity is sufficiently high using many metallic contact materials tested. FIG. 40 is a summary of the Ti contact results. Important to note is; a) the sharp distinction, i.e., you either get trenches or no trenches in Ti. Moreover, b) additional power appears to just deepens the trenches formed but does not change the selectivity, Important here is for Ti, shallow trenches are not detected.

Figure 41:
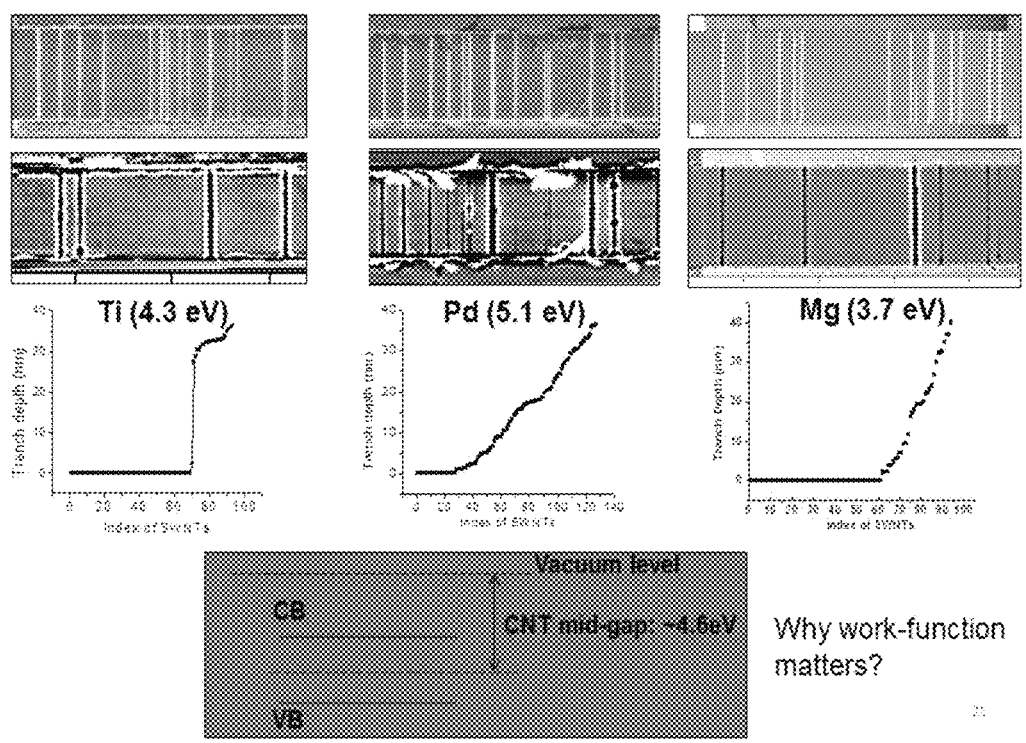
FIG. 41. Selectivity as a function of metal type.
Figure 42:
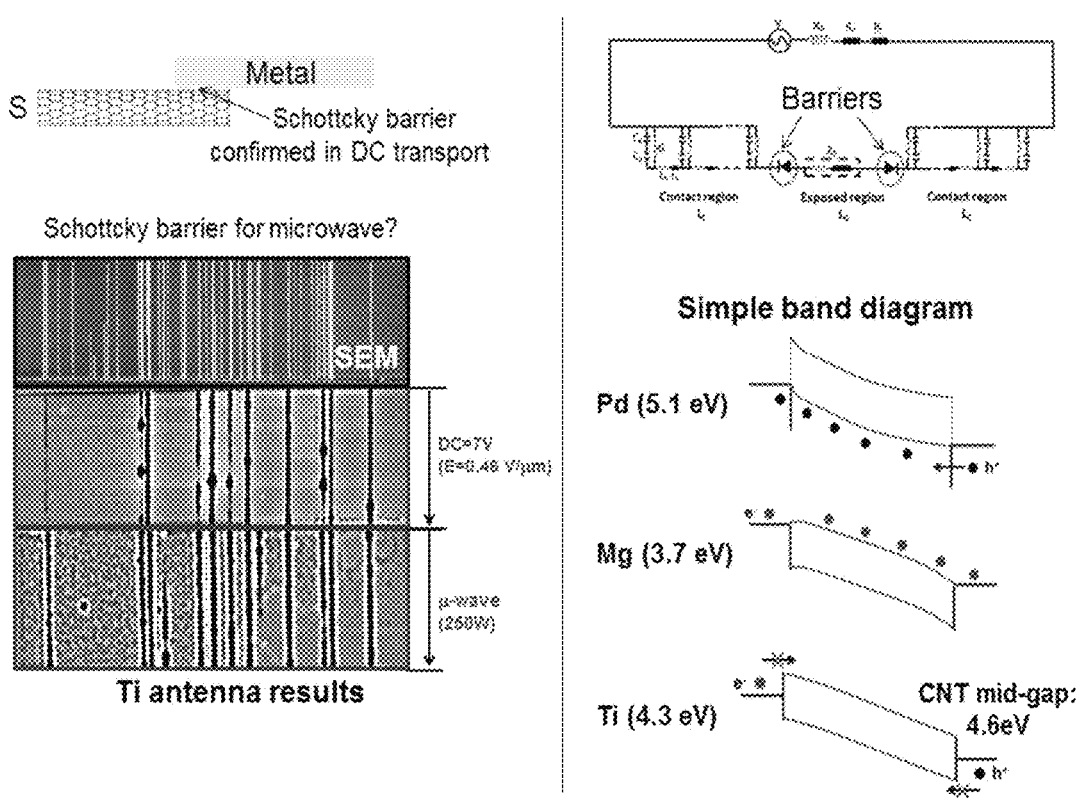
FIG. 42. Transport barrier picture.
Figure 43:
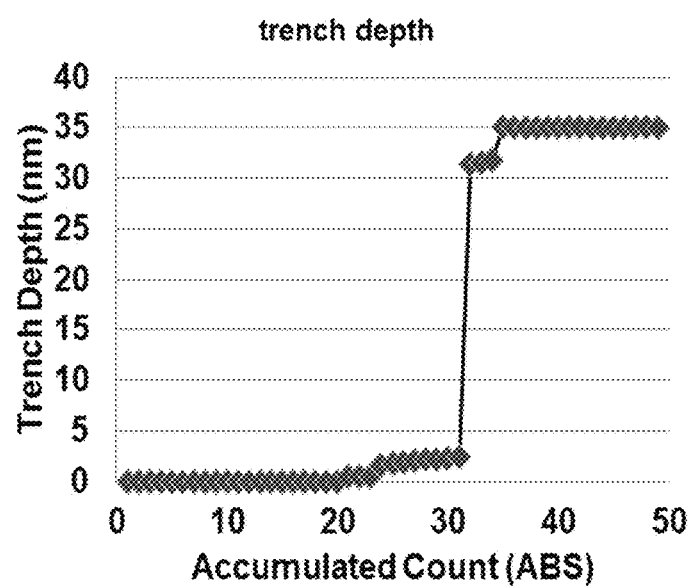
FIG. 43. Selectivity with Mo contacts.
Figure 44:
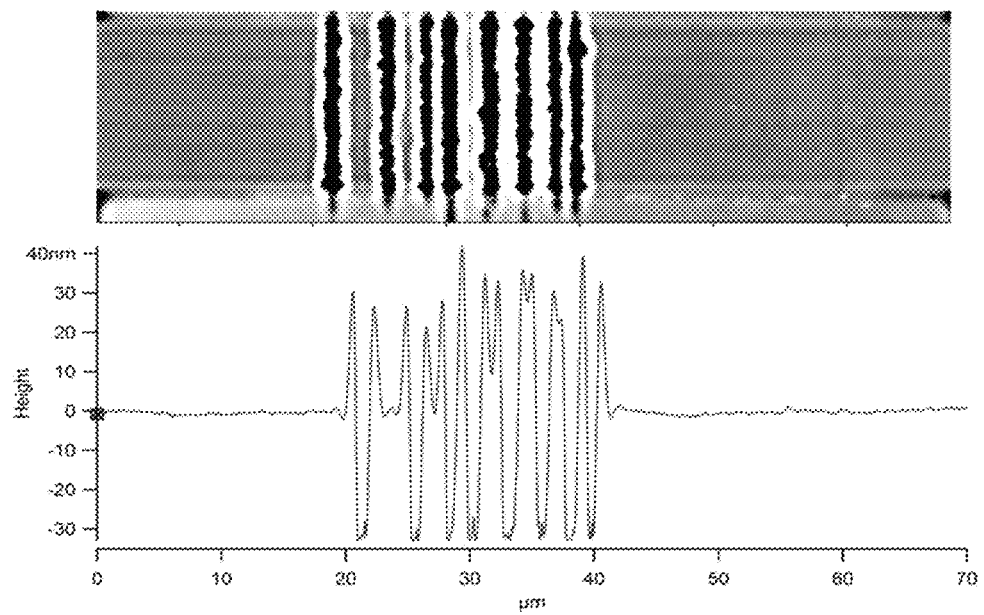
FIG. 44. Deep trench formation in Mo. Clearly we "bottom out" the trenches suggesting we can lower power of processing time (bottom).
Figure 44:
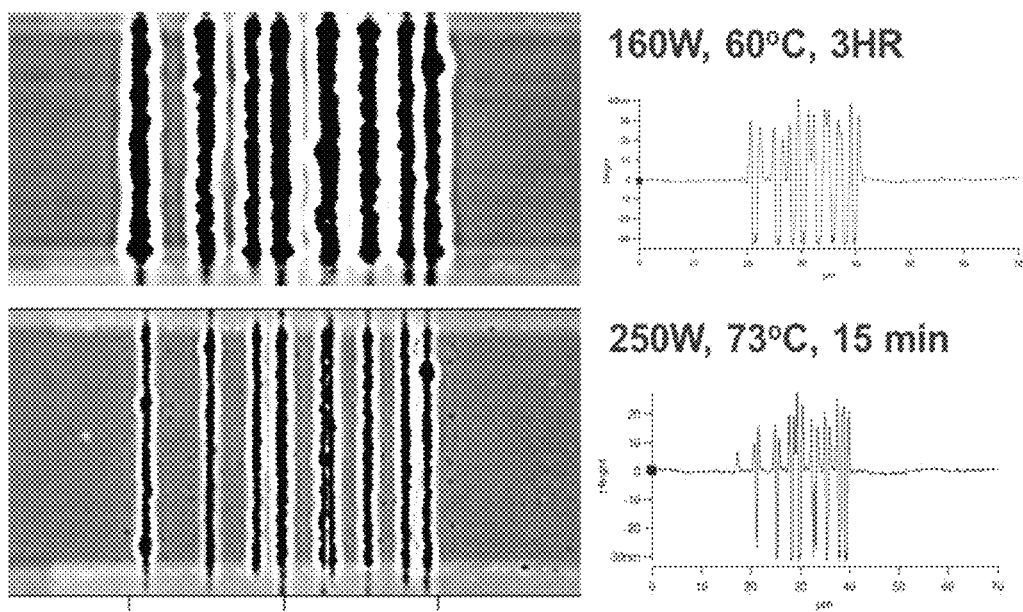

For example in the Pd case (FIG. 40, bottom), 300 W exposure results is some semiconducting tubes starting to form modest, shallow trenches continuously, ranging from 2-15 nm in depth, (as illustrated by the curvature in the red curve of FIG. 40). This is not seen in Ti at identical processing conditions, (black curve). As noted, the use of Ti seems to have taken the semi-metallic or doped semiconducting nanotubes "out of play". This is an extremely important finding which greatly solidifies the scalability and precision of this process. Suggested is an important dependence of the antenna metal work function on the selectivity of the TcEP process. FIG. 41 shows the results for 3 metals with varying work functions. (Note: samples were studied using Pd (5.1 eV), Ti (~4.33 eV), Mo (4.36 eV), Al (4.06), and Mg (3.7 eV) as the electrode materials. All early samples were Ti (1 nm)/Pd (40 nm) work function ~5.0 eV.) The data shows the effect is clearly not due to work function only. FIG. 42 (left) indicates that something more subtle is in play. Here Mg electrodes are used, lowering the work function by more than 500 meV beyond Ti. Interestingly, we again derive a range of trench depths detected indicating that our selectivity is diminished. Ti, which has the most distinct selectivity, has its work function near the mid-gap of the semiconducting nanotubes. The relationship of the work function of the metal relative to the electron affinity of the tubes makes it a source of electrons for hole-doped semiconducting tubes and a sink for electrons in semi-metallic tubes. In fact the effect suggests the all tubes have been rendered either metallic or semiconducting with intrinsic properties buy the MS junction formed. From a device physics perspective; It is clear that changing the metal contact work function would modify the Schottky barrier present, changing the current/carrier dynamics. The view of this effect suggested by the model is shown in FIG. 42 (right). (Important here is, exploitation of this effect will also improve joule heating initiated TcEP.) FIG. 42 (left) shows trenches formed on the same sample, (the resist was deposited twice), where we have simply applied a low DC bias directly to the Ti antenna electrodes. Our model suggests that a work function of 4.3 eV results in barriers for both hole and electron transport (FIG. 42), resulting in all non-metallic SWNTs behaving as intrinsic materials. We have in essence eliminated semi-metallic behaving tubes. While we are still exploring the details of the mechanism, all needed process protocols have been explored from metal deposition optimization to μ-wave processing conditions. We have fully explored the work function space, (with Mg being the lowest), and also tested metals with a similar work function but with a difference in conductivity (Mo). Ti or Mo appear to be optimal choices. Mo, which has a work function nearly identical to Ti, was also used. As seen in FIG. 43 its selectivity curve results are similar to Ti (but you can clearly see the formation of very shallow trenches (sub 5 nm) in the thermal resist above some semi-metallic/semiconducting tubes.) FIG. 44 offers the clear explanation of this effect. We have not lost selectivity; the conductivity increase achieved with Mo lowers our needed excitation power. (Mo has a conductivity a factor of 8 higher than Ti.) Here again we form a distinct step function in the formation of full trenches at 250 W operation, but with only 15 minutes of irradiation. The increase in contact conductivity gives us a greater coupling of the microwave field to the nanotubes by making the contacts "better" antennas. This improvement greatly widens the operational window for the process. We are now optimizing the Mo deposition and general process and are processing transistors. In addition we are now pattering inter-digitated electrode structures to allow larger area irradiation. With these improvements we clearly establish microwave initiated TcEP as an efficient purification option.

Figure 45:
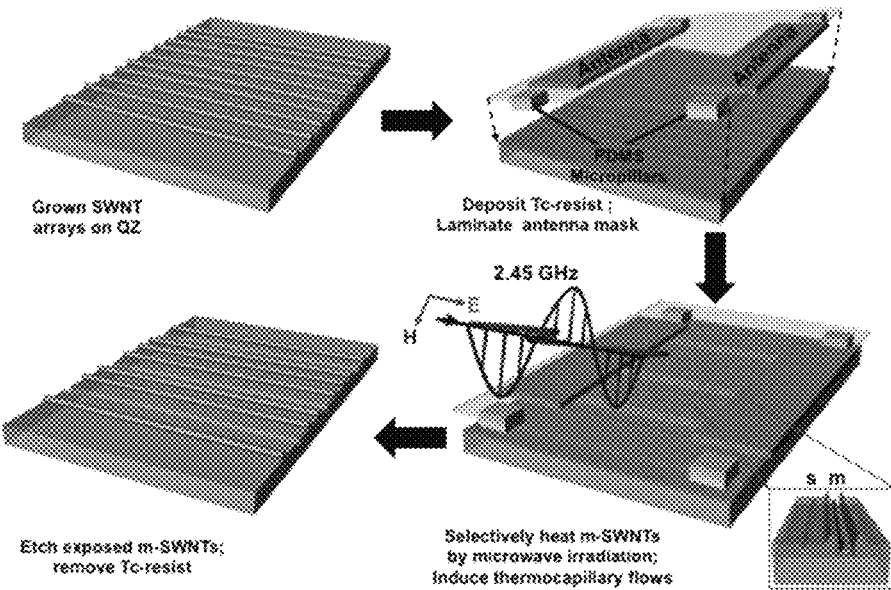
FIG. 45. Process flow for non-contact microwave case.
Figure 46:
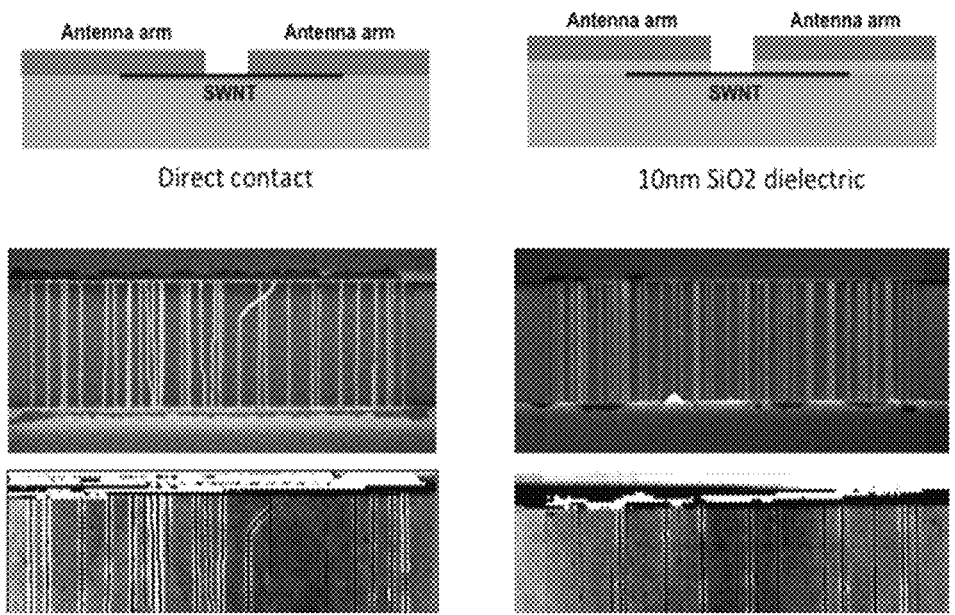
FIG. 46. NTF process driven by microwave irradiation: contact case vs. non-contact case.

Next, we will describe the results from the non-contact case. FIG. 45 shows the basic flow of the process. This approach enables processing of substrates without adding "permanent" antenna electrodes. As stated above, this approach requires more power from the microwave reactor but may offer more in device design flexibility. FIG. 46 shows a direct comparison between the contact and non-contact cases. Here, we have used 10 nm of $SiO_2$ as the spacer layer. In this experiment Ti/Pd electrodes are used for both, with identical exposure conditions. Deep trenches are formed in both cases. The non-contact structure does have a few shallow features, consistent with the need for higher exposure power. This is a limiting case, (i.e., minimizing d).

Figure 47:
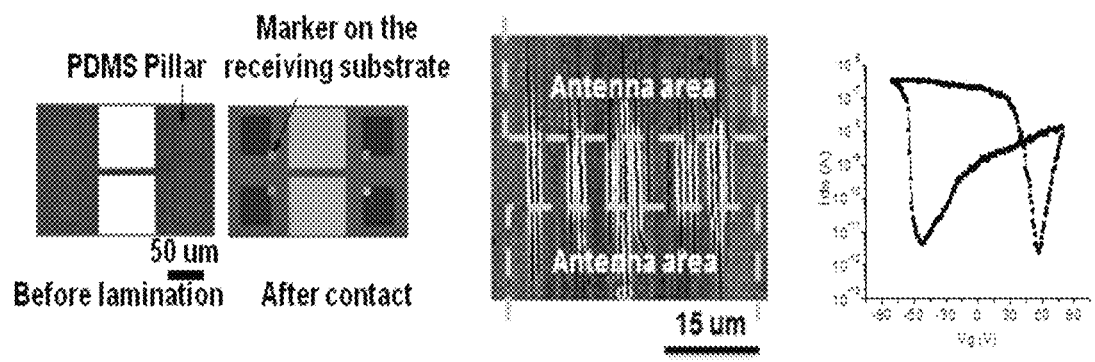
FIG. 47. Structure of removable antenna structure.
Figure 48:
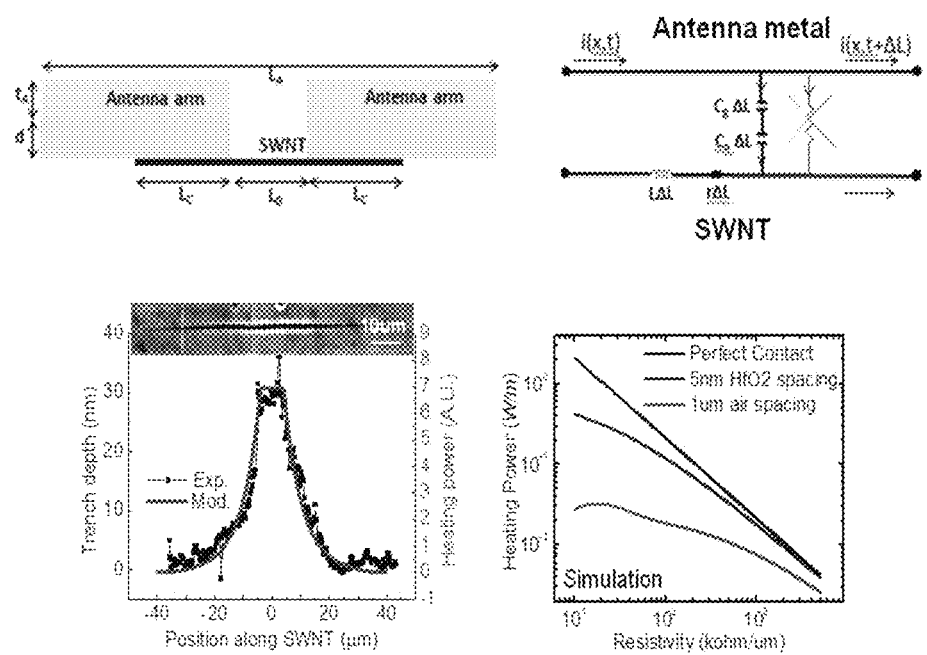
FIG. 48. Model for the non-contact microwave case.
Figure 49:
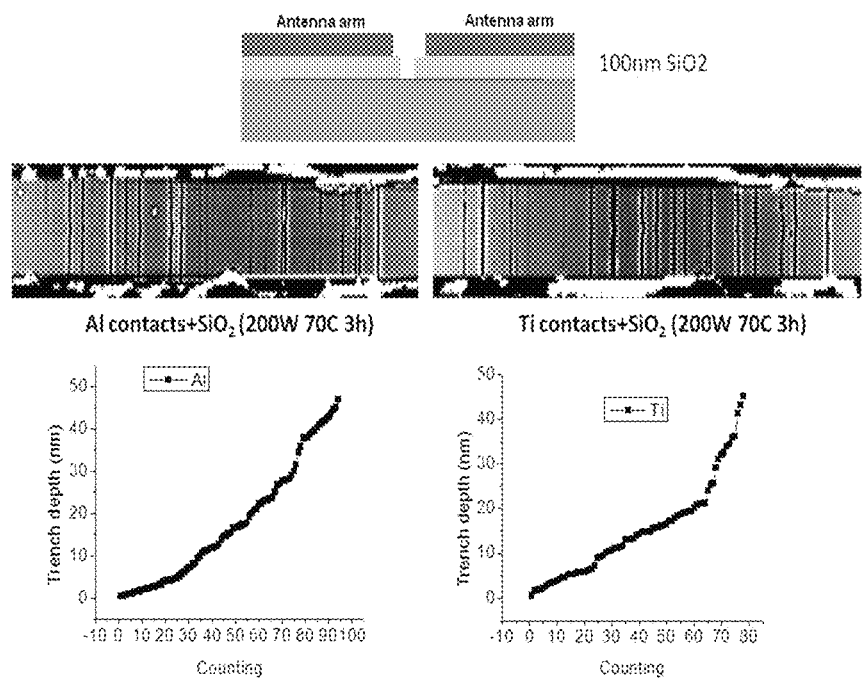
FIG. 49. Work function dependence; non-contact case.

In practice a process similar to lamination is used. As shown in FIG. 47, the antenna mask is applied to the die using PDMS pillars as spacers (left image). The d in this case ranges from 500 nm-1 μm. The exposure results are shown in the micrographs. We use markers on the nanotube die to align the laminate antenna to the substrate. The middle image shows the result of a processed array die. The transfer function for a typical array transistor using this process is shown at the far right. Just as in the contact case, array transistor device performance far exceeds the program goals. The model for the non-contact case is shown in FIG. 48. As shown (bottom left), the model fits our observed trench profiles. The difference in mechanism here from the contact case is the heating current is generated from capacitive coupling of the microwave field to the metallic nanotubes. Importantly we see the same work function dependence observed as in the contact case (FIG. 49), suggesting optimization can be driven by contact case results.

Figure 50:
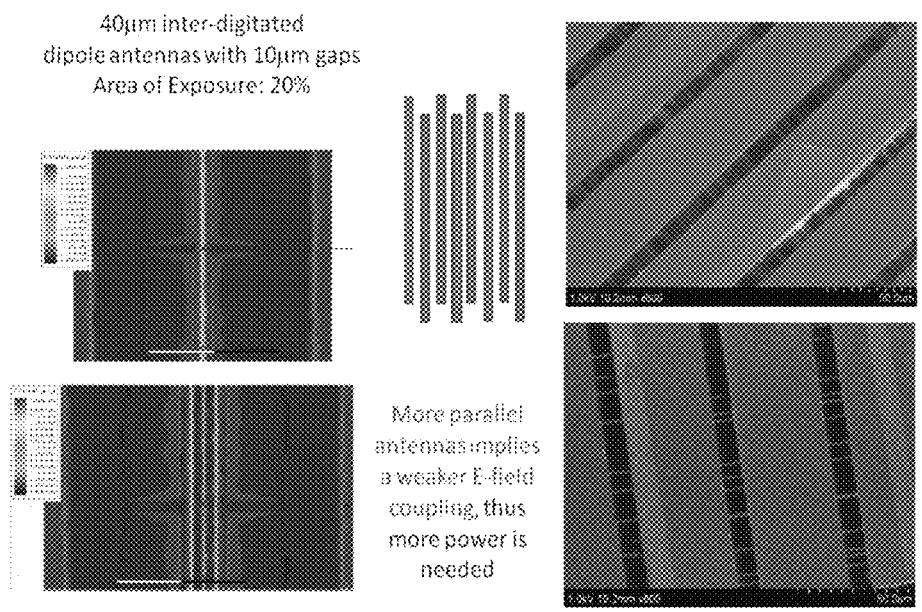
FIG. 50. Antenna array strategy to achieve large area irradiation.
Figure 51:
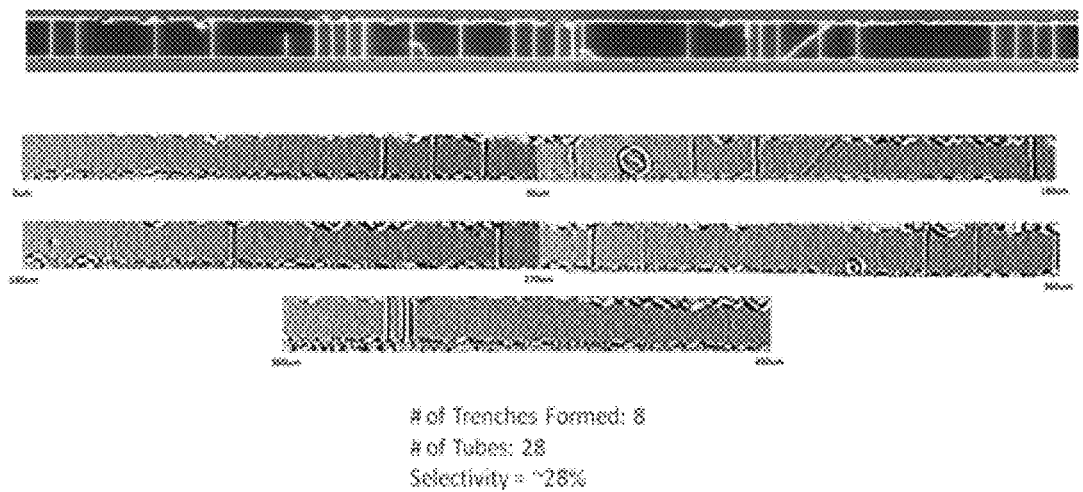
FIG. 51. Trenched generated via an antenna array.

Finally we illustrate the path to larger processed area. To enable large area irradiation we have utilized inter-digitated structures for the coupling antennas. FIG. 50 shows an example of a structure used. Shown is a simple electrode structure with 40 micron legs and 10 micron gaps. The structure acts as a series of coupled microwave transmission lines, with the spatial field pattern amplitude and phase dependent on the size and spacing of the whole structure. The SEM image on the right shows the structure deposited on a nanotube die. The tubes can easily be imaged in the gaps. FIG. 51 shows typical trenches formed with this basic structure. The top image is a SEM of one of the typical gap positions. Below are atomic force images of gap sections. (The scan range on the AFM is limited to about 90 microns.) The statistics of the trenches formed is consistent with that expected, (~33% trench formation). Other interdigitated designs can be used and the metal used may be modified to control the e-field pattern and overall power. To fully optimize this approach in a processing environment one must design the lithography mask structure for the RF device envisioned, integrating the antenna design into the device layout footprint.

Figure 52:
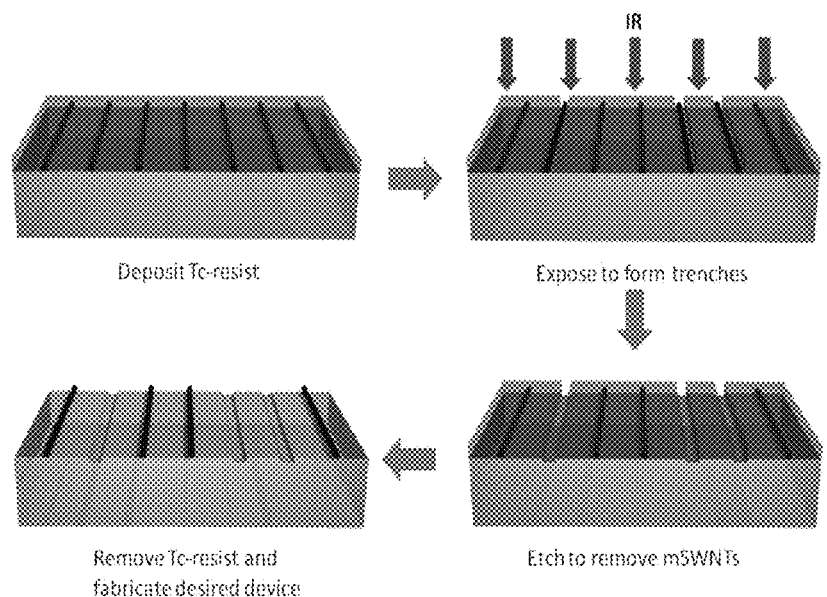
FIG. 52. Process flow Laser initiated heating of metallic nanotubes.
Figure 53:
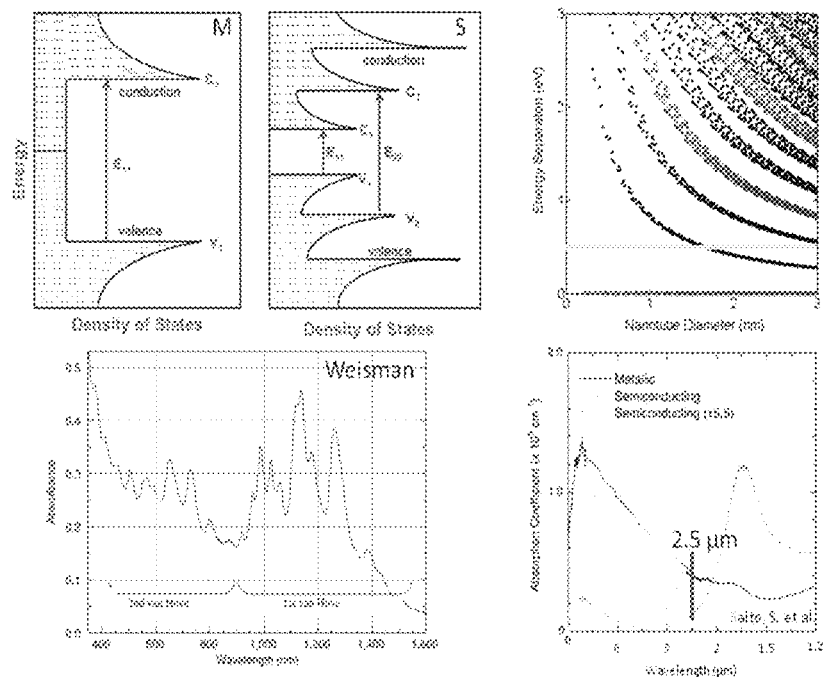
FIG. 53. Absorption properties of SWNT.
Figure 54:
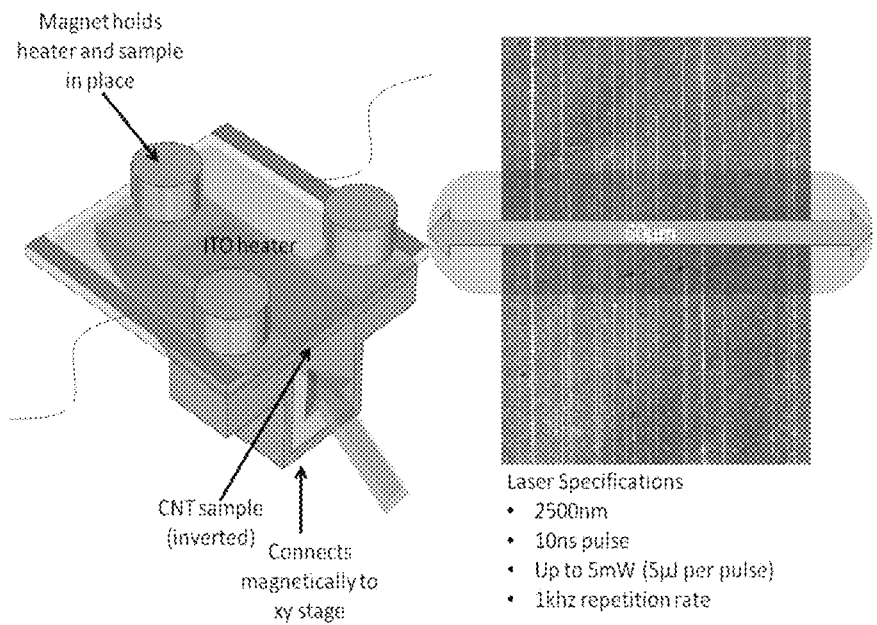
FIG. 54. Laser baser exposure set-up. Diffraction limited excitation beam is raster scanner over the nanotubes.
Figure 55:
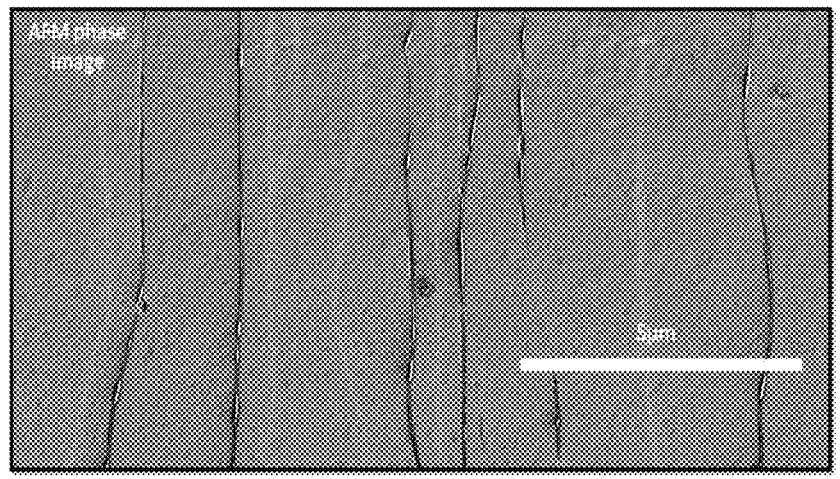
FIG. 55. AFM imager of laser irradiated substrate. Trenches are observed.
Figure 56:
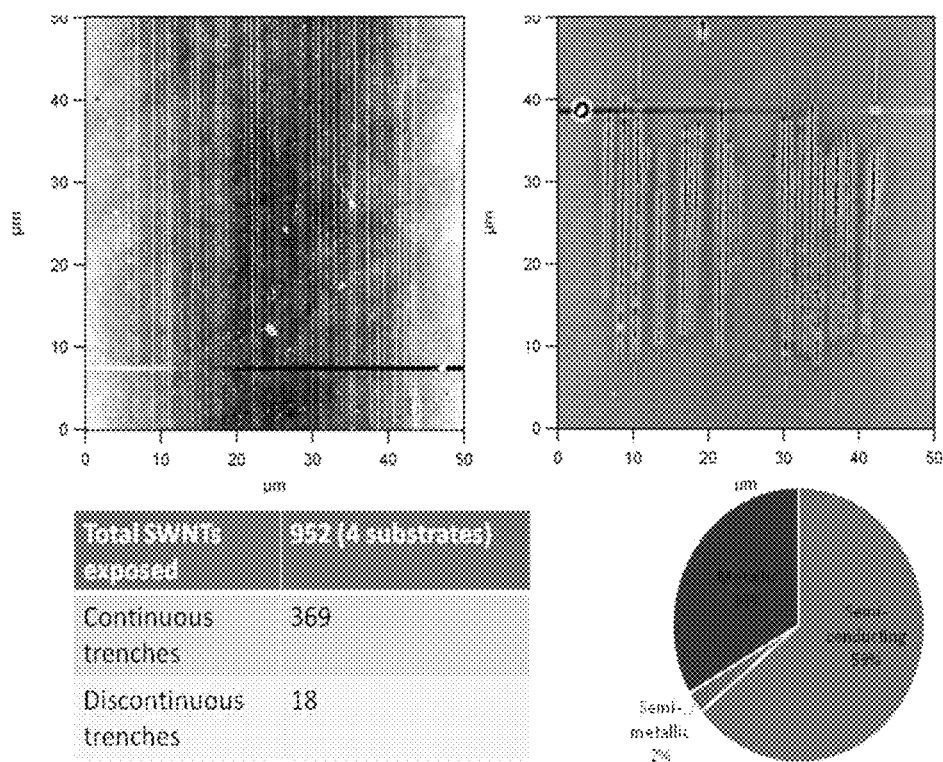
FIG. 56. A series of laser irradiated samples. Selectivity is statically consistent but was additionally confirmed via Raman analysis.
Figure 57:
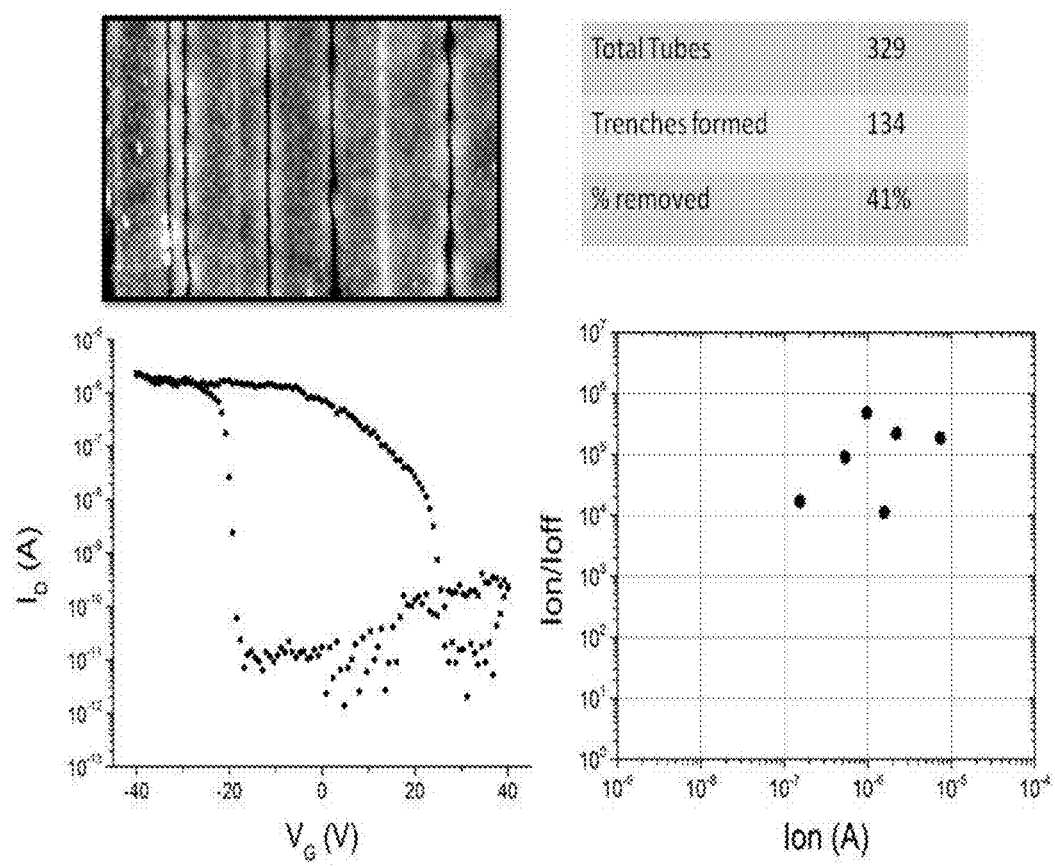
FIG. 57. Transfer characteristics of devices.
Figure 58:
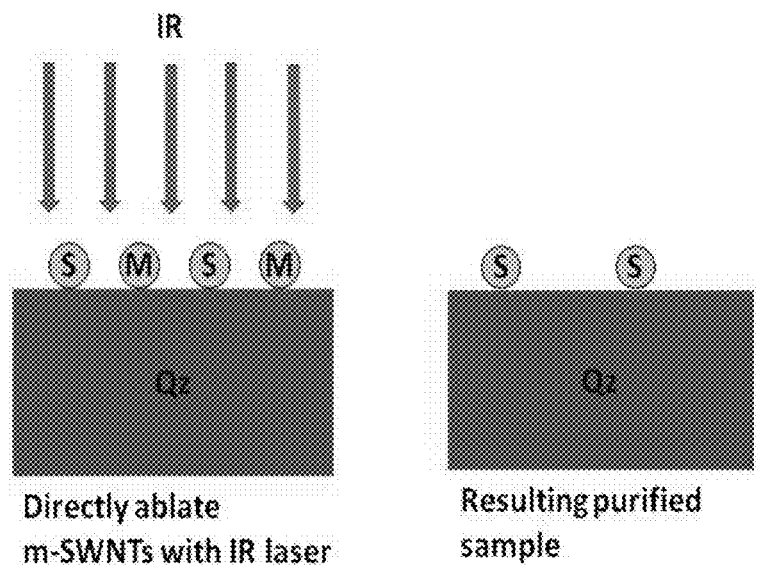
FIG. 58. Process flow of direct laser ablation of metallic nanotubes.

Laser Initiated TcEP:

We have also completed a full assessment of laser initiated purification. The basic process schematic is shown in FIG. 52. Here as in the microwave case we are utilizing differences in absorption in metallic and semiconducting tubes to selectively heat and initiate the nanocapillary flow in the resist. The spectral behavior of SWNTs in the region of interest is shown in FIG. 53. Shown is the density of states for both types of nanotubes along with the absorption spectra, (bottom). The bottom right plot shows the spectra on an expanded scale. In the wavelength range from 2-6 microns the semiconducting tube absorption is minimized relative to their metallic counterparts. We chose to operate at 2.5 microns because it was a point where the difference is large and the resist absorption is still very low. The exposure set-up is shown in FIG. 54. Here the nanotube die was exposed in an inverted geometry with the laser beam raster scanned along the die surface. The image on the right shows the exposure area with the exposure conditions described. The laser was focused to a diffraction limited spot and scanned to a length of 60 microns. (The absorption is ~0.01 for a layer of nanotubes at current densities, (~1 tube/micron)). FIG. 55 shows an AFM of an exposed die, as expected we form trenches above the metallic nanotubes, (verified using scanning Raman micro-spectroscopy). Statistical data on a number of nanotube die are shown in FIG. 56. Here more than 950 nanotubes have been irradiated with more than 360 continuous trenches formed. Again the number of trenches is consistent with that expected for the number of metallic tubes likely exposed. FIG. 57 shows a typical transfer function for fully processed transistors from the die. Again we obtain devices which operate well beyond the program target. Fully optimized, IR irradiation could be a viable processing option. One clear drawback is the selectivity. Thus far while small in number, we do generate trenches among a few semi-metallic and doped semiconducting tubes. These tubes of course are lost upon etching. It may be possible to treat substrates to mitigate this issue.

Figure 59:
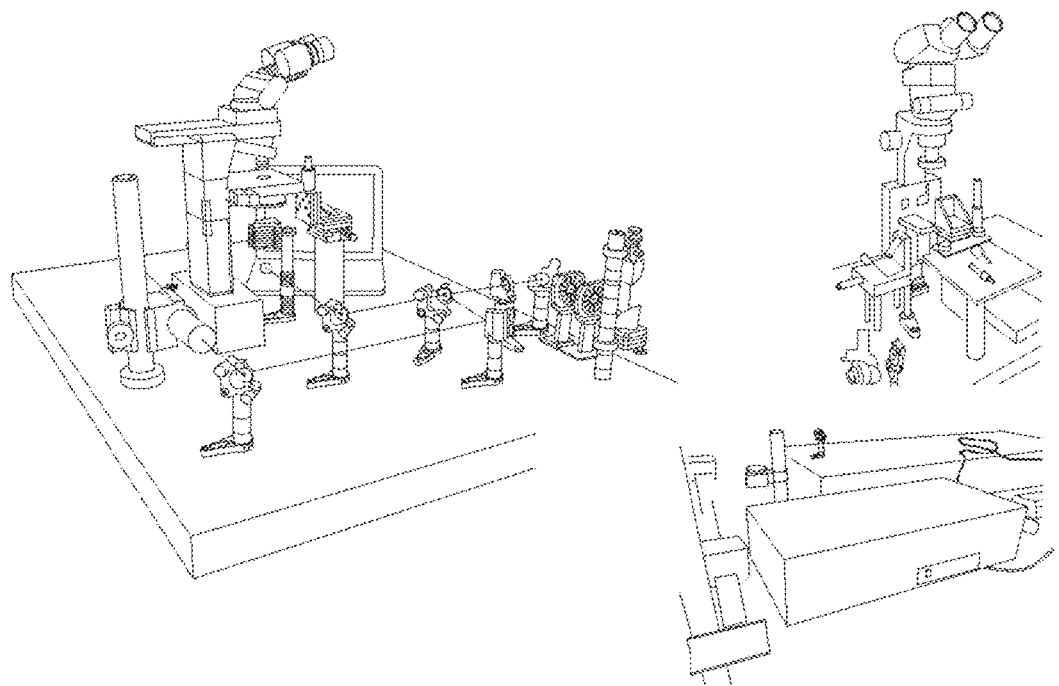
FIG. 59. In-situ ablation apparatus.
Figure 60:
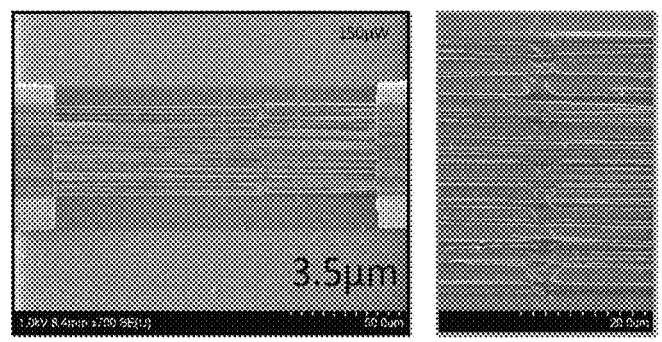
FIG. 60. SEM of ablated die area.
Figure 61:
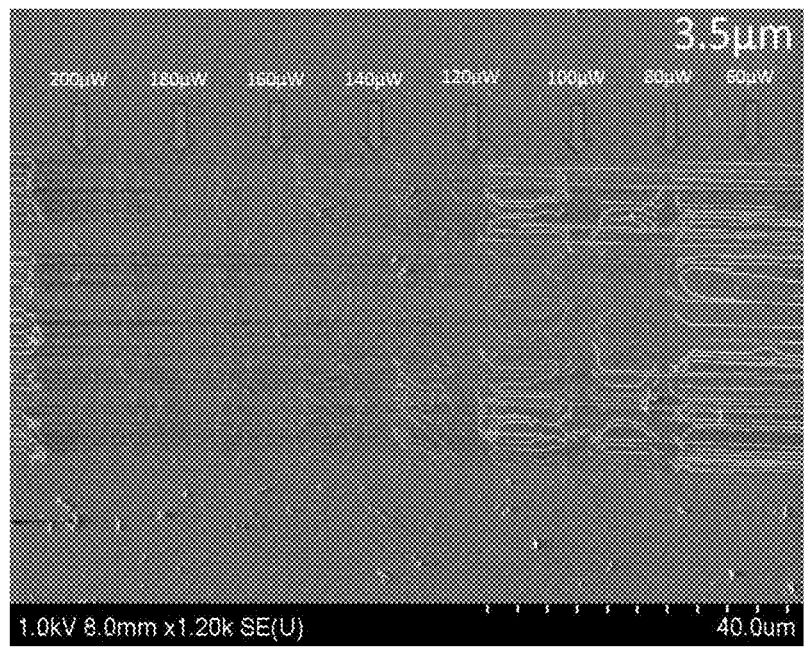
FIG. 61. Ablation power/wavelength dependence.
Figure 61:
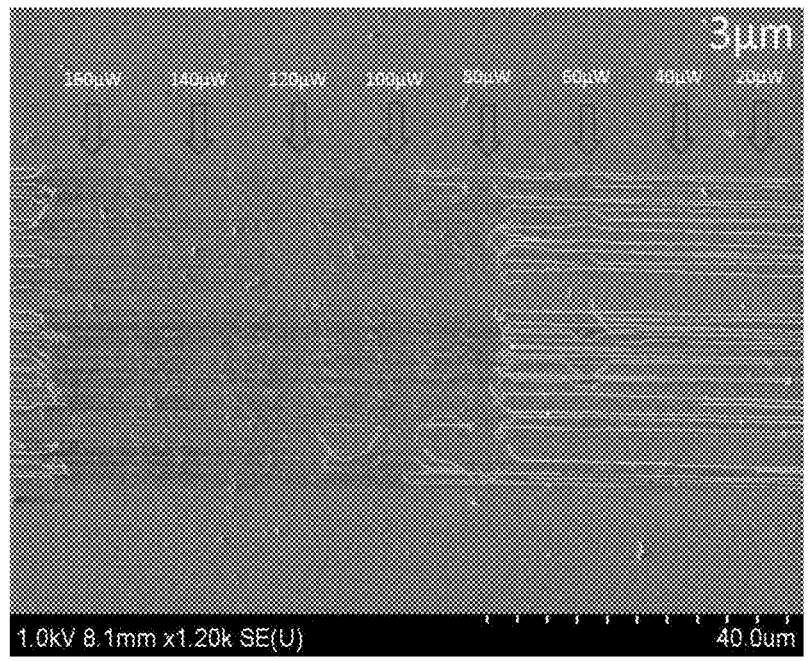
Figure 62:
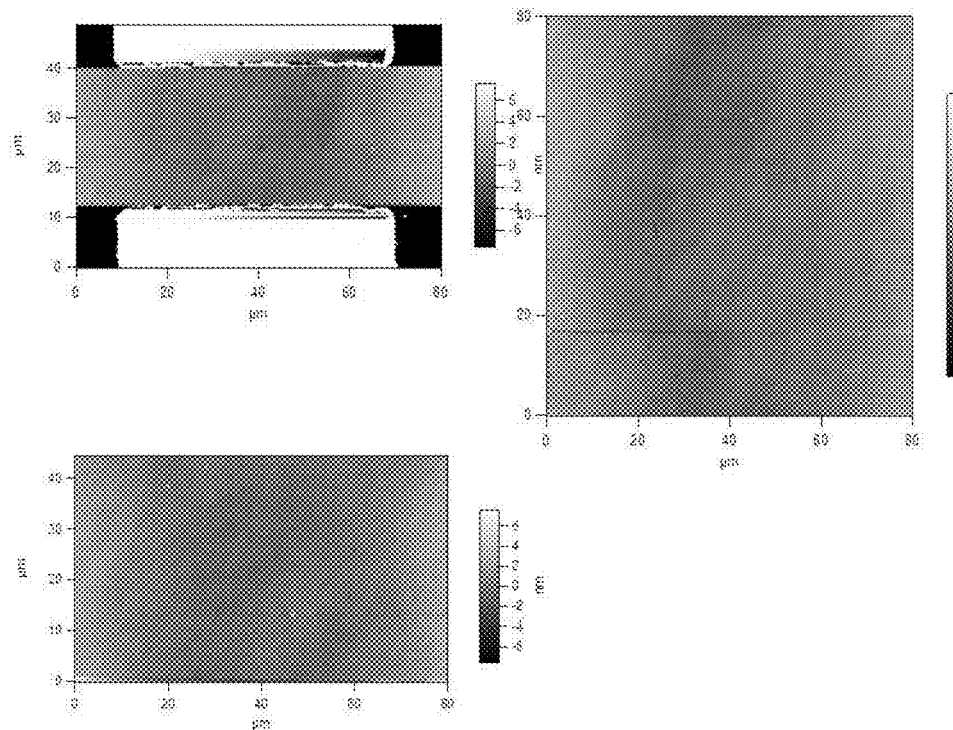
FIG. 62. AFM topography of CW irradiated TcEP substrate. There is no trench formation indicated even at full power.

Laser Ablation: Direct Purification Via Ablation:

We explored and quantified the use of direct laser ablation of metallic nanotubes as a viable strategy. A platform based on a high peak power, near and far IR capability was developed (FIG. 59). The kHz repetition rate parametric amplifier system fitted with a difference frequency generator enabled exposure wavelength options ranging from 1-20 microns at high peak power. The optical layout of the laser exposure set-up was later modified to allow both pulsed and CW excitation. A nearly 1 Watt QCL (quantum cascade laser) developed by Daylight Photonics was used to explore the power scaling of the process. The system was retrofitted with an alignment and inspection microscope to enable precision alignment and in-situ characterization. The system was built with automated substrate motion control and laser power control to enable precision mapping. (These features led to the initial demonstration of selective laser ablation.) Moreover this system allowed us to explore the power and wavelength dependence of the process in detail. FIG. 60 shows an SEM image of an ablated array. Clearly some of the individual tubes are destroyed while others remain intact. (Note: at very high power, "all" tubes ablate.) FIG. 61 shows a direct power mapping of the ablation process at two different IR wavelengths, (3 μm and 3.5 μm). Here fluencies range from 10's to 100's of μWatts with near diffraction limited focus. Interestingly here the higher energy, i.e., shorter wavelength excitation seems to have a better ablation range, albeit with a higher threshold power. The extent of selectivity of the ablation mechanism is modest. While there is a clear range, i.e., a likely processing window, it seems factors other than simply electronic behavior impact the required power and the window is narrow. To probe this we attempted ablation with CW (continuous wave) exposure. Under all CW exposure geometries, no ablation was observed. We also attempted CW IR initiation of Tc flow to see if there was sufficient energy from CW sources to heat metallic tubes at all. (FIG. 62 illustrates the results using CW excitation driven TcEP.) Again very little heating occurred. This led us to detail the power question. Our early work suggests that to initiate TcEP via Joule heating requires of order 10 μW/μm to drive the process. Power calculations suggest that our CW flux, may be nearly 2 orders of magnitude lower in absorbed peak power. For our pulsed laser cases our energies are comparable to, or greater than used in joule heating. More importantly, it appears that to initiate ablation we are at 30-50 µW/µm, comparable to the joule heating limit. If high peak power is required, as the driver for the observed physics, the temperature jump experienced by the nanotubes, optically, may be much larger than we expected relative to the joule heating initiated process. This indicates the basic mechanism may be very different in these absorptive approaches. As noted, at this point, the ratio of ablated/un-ablated tubes suggests while we can find a range where we are likely selectively destroying metallic tubes, the selectivity window is modest.

Figure 63:
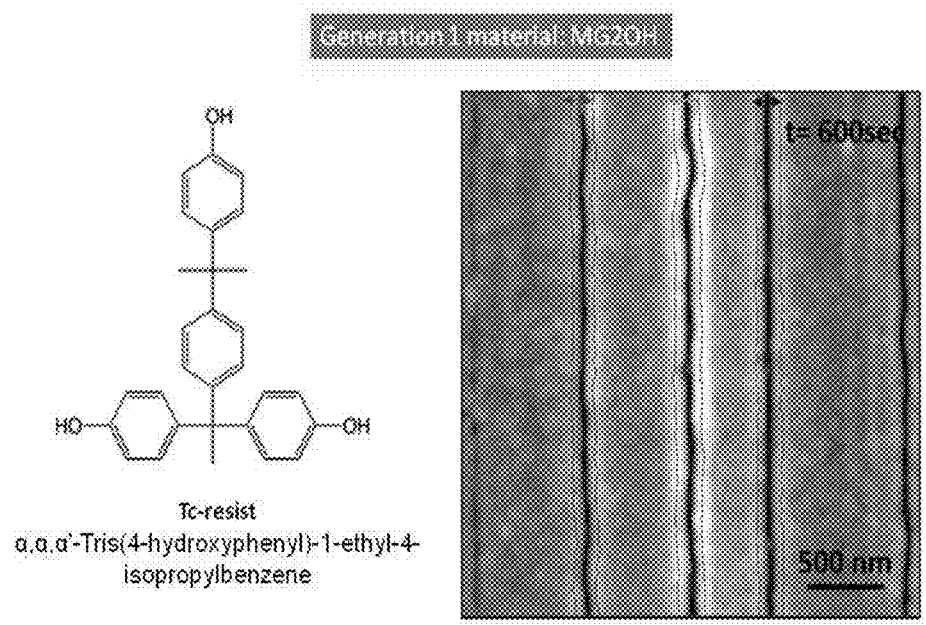
FIG. 63. MG2OH our first generation TcEP resist.
Figure 64:
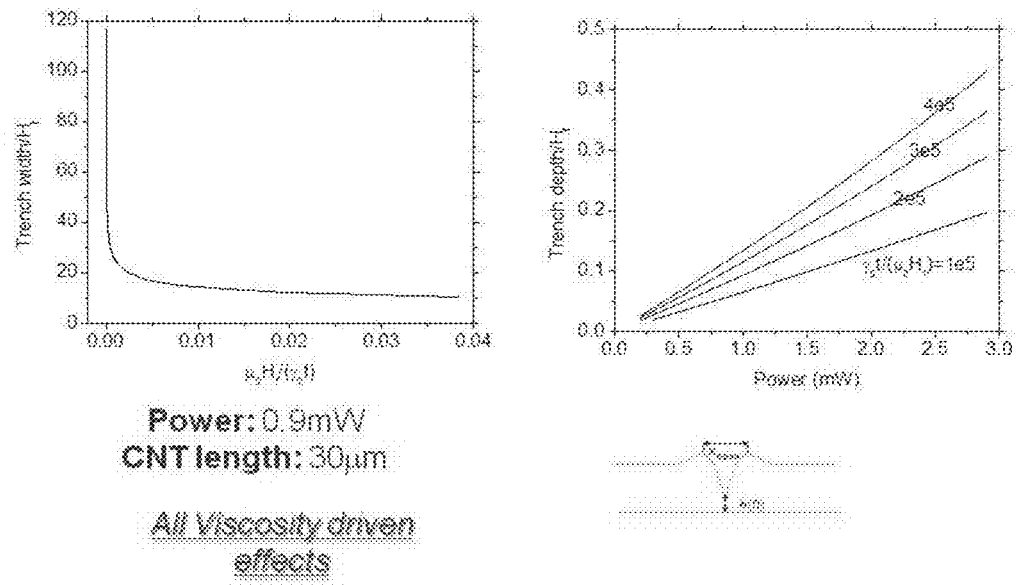
FIG. 64. Model derived dependence of trench properties on viscoelastic parameters and heating power.
Figure 64:
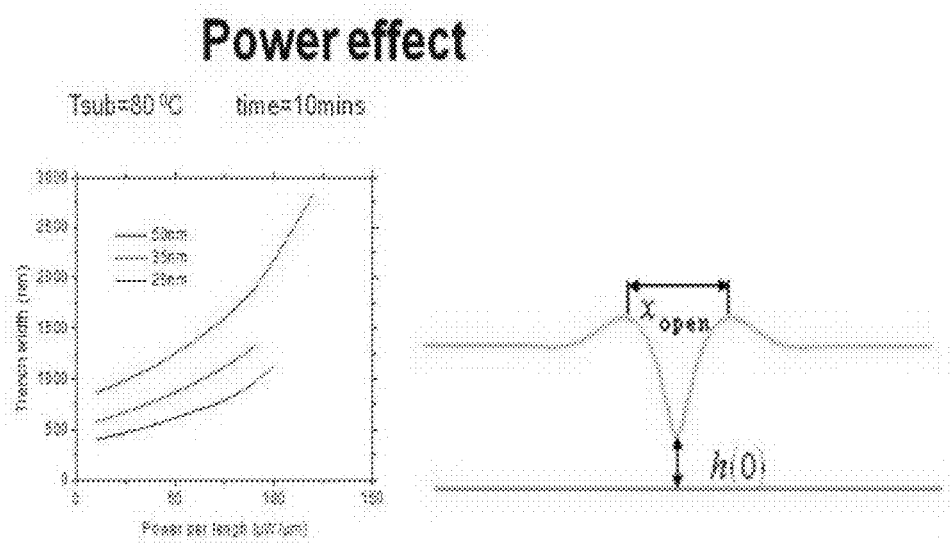
Figure 65:
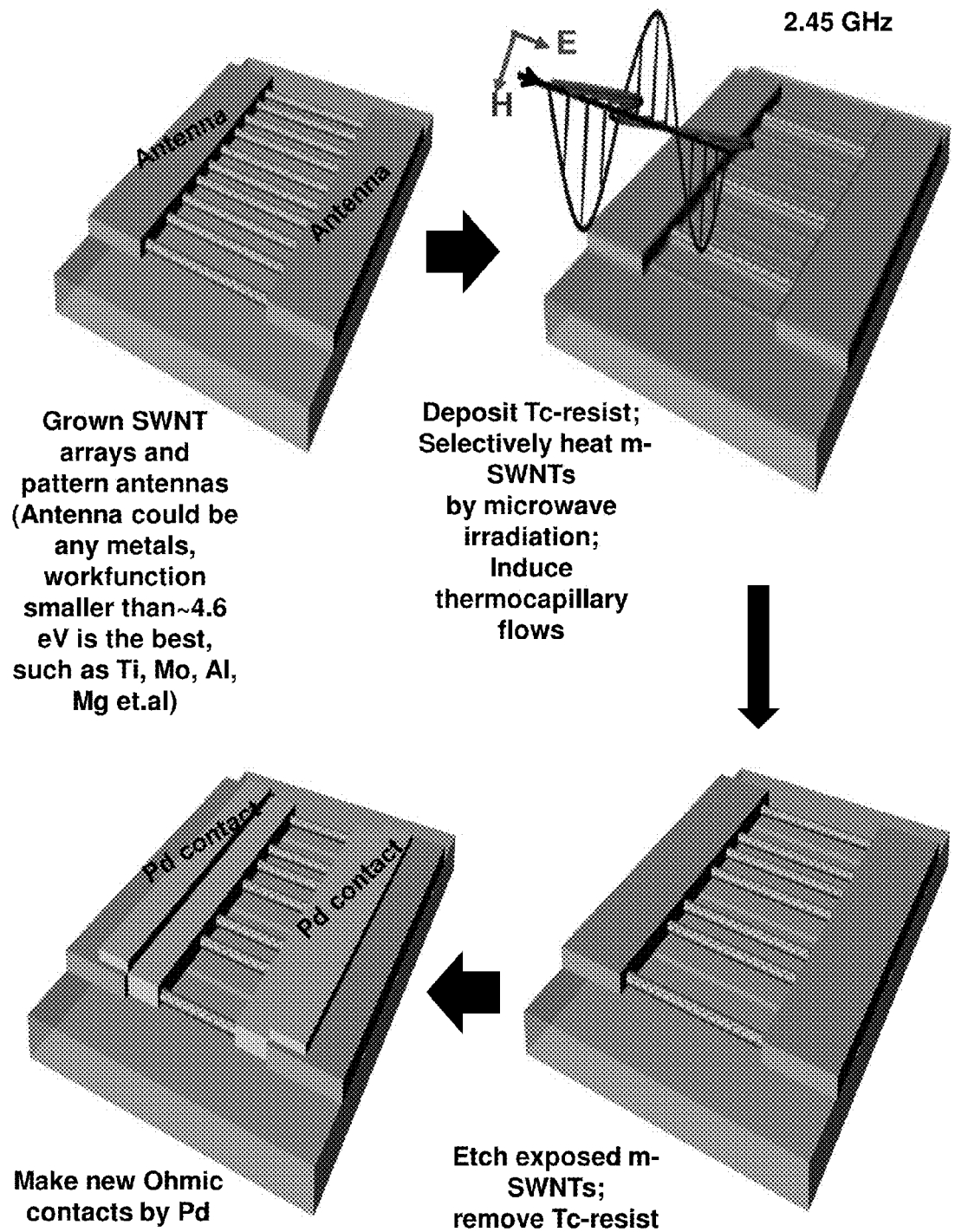
FIG. 65. Process flow for removing metallic SWNTs via a microwave contact approach.
Figure 66:
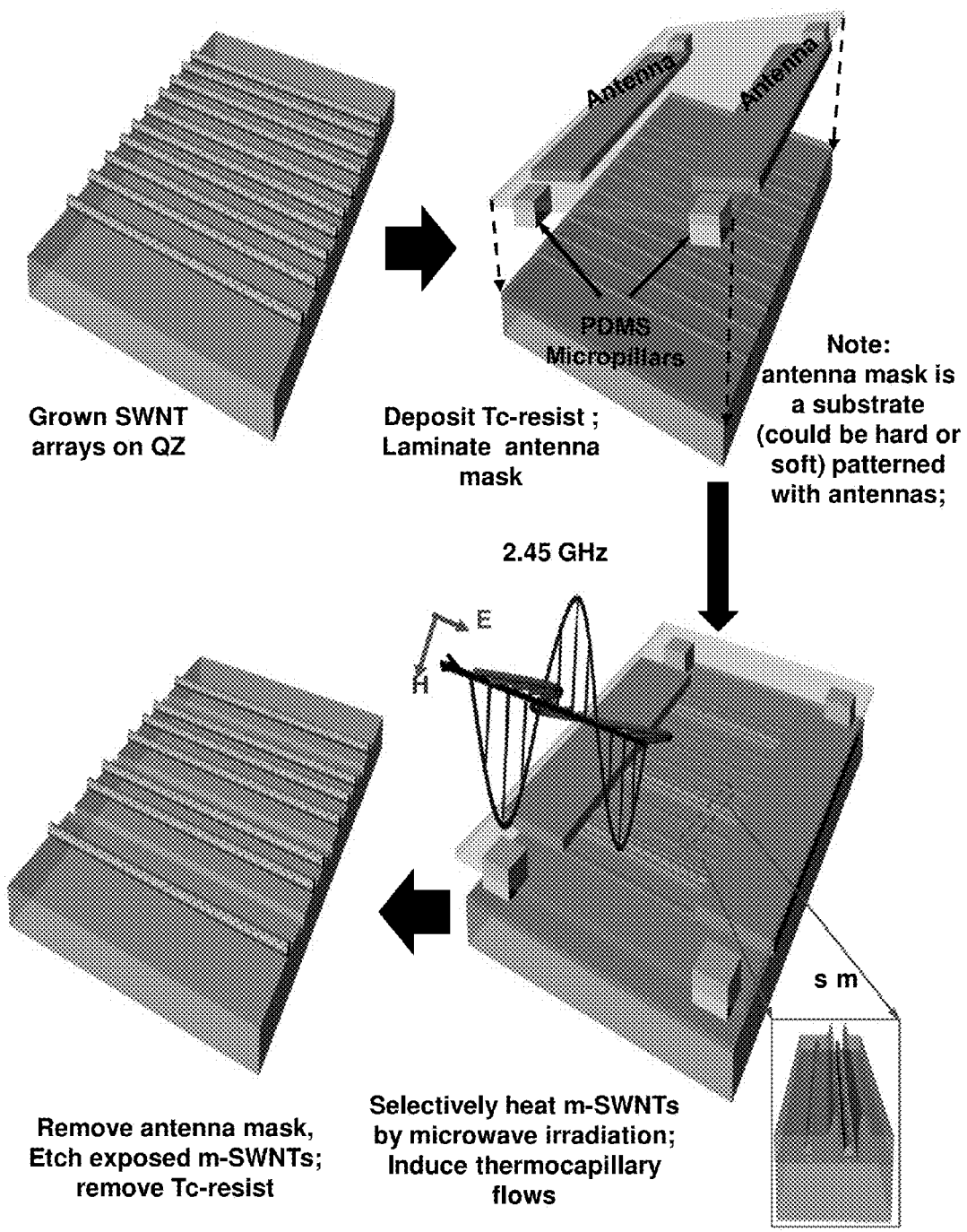
FIG. 66. Process flow for removing metallic SWNTs via a microwave noncontact approach.
Figure 67:
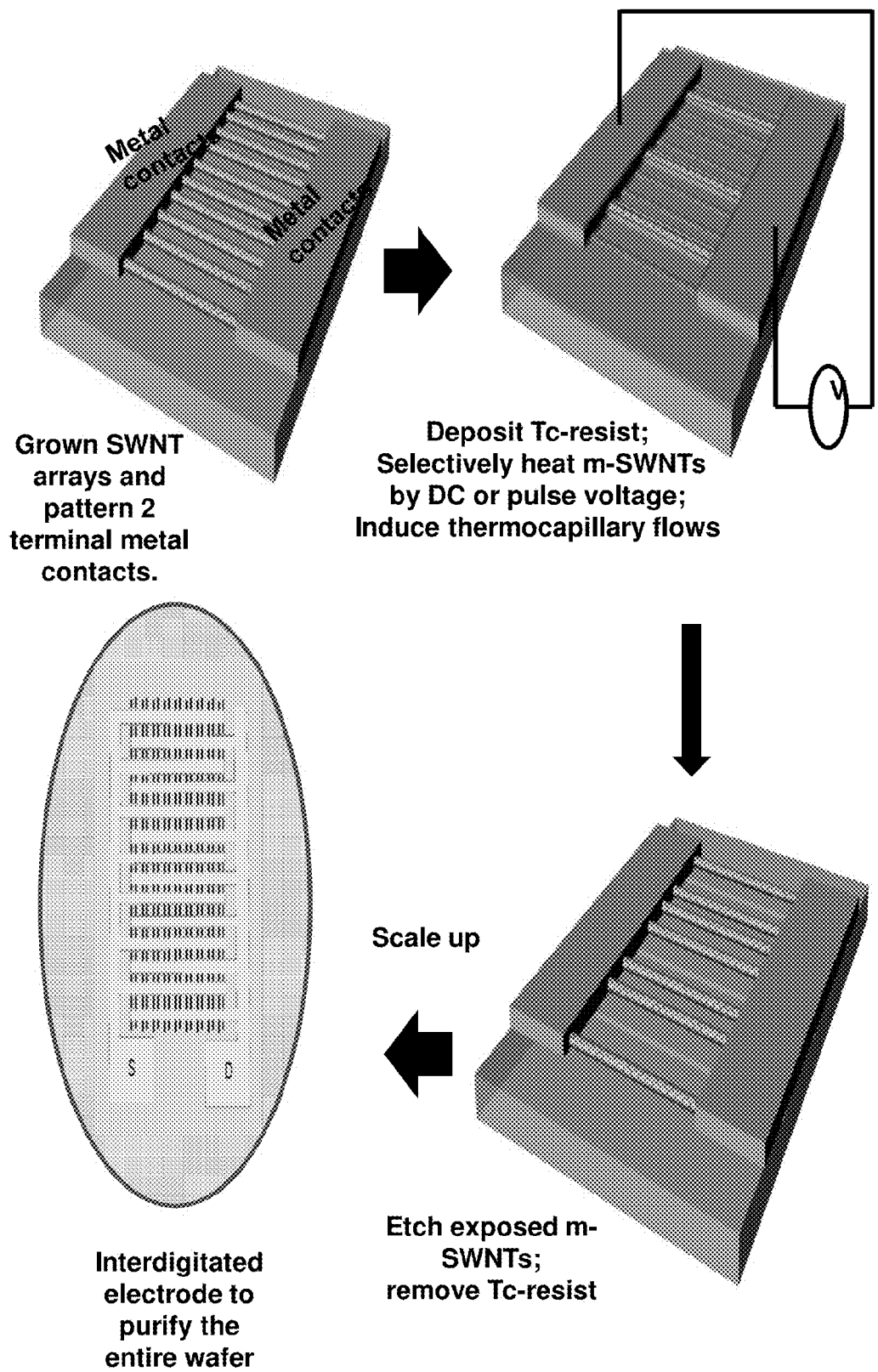
FIG. 67. Process flow for removing metallic SWNTs via a 2-terminal Joule heating approach.

Assessment of TcEP Resist:

Finally we explored issues relevant to the development of advanced resist materials for TcEP. The focus was to both develop a full predictive model of resist performance and to define a guide for the development of next generation materials. The current resist is shown in FIG. 63. Shown is the molecular structure for MG2OH, α,α,α'-Tris(4-hydroxyphenyl)-1-ethyl-4-isopropylbenzene, with its typical trench formation performance (right). We developed a model which captured all the relevant materials physics. The dependence of trench width on materials parameters such as viscosity and other thin film properties was detailed. The primary findings suggest that to fully optimize the resist there are two interrelated issues that need to be addressed and improved. First is the limiting width of the trenches formed. Here the density of tube die which can be purified with this method will be determined by the width of full trenches. Currently deep trenches range from 100-500 nm. At current CVD grown wafer densities (1-2 tubes/micron), this is sufficient. As we move to wafers at 5-10 tubes/micron, deep trenches need to be narrower. The path to narrower trenches is simply to apply thinner resist layers, but this leads to the second issue. A thinner resist layer leads to weaker etch protection. If our path to higher density performance is to use thinner layers, we need to improve substantially the etch resistance of our resist. For example, adding ring structure to the MG2OH framework or using Si containing materials could be a solution but care must be taken to keep proper viscoelastic properties. We have identified several classes of materials, such as low molecular weight polymers, including but not limited to (polystyrene) PS and (polymehtylmethacrylate) PMMA, which offer promise. By controlling molecular weight we control film viscosity and therefore thermocapillary kinetics.

We have shown that we can purify SWNT die to yield ~100% semiconducting nanotubes using TcEP initiated by microwave and laser irradiation. We have shown that these die can be processed into high performance transistors. We have shown that the developed techniques, especially microwave initiation has paths to scale-up which will enable processing of full wafers. We note we have already begun the process of integrating and transferring this technology to a number of nanotube electronics efforts nationwide. Much of the momentum in SWNT device research has been stifled by the inability of device processers to purify nanotubes. This work removes this barrier.

References

[1] Rutherglen, C., Jain, D., and Burke, P., *Nature Nanotechnology* (4), pg. 811, (2009); Cao, Q. and Rogers, J. *Advanced Materials*, (21) pg. 29 (2009)

[2] S. J. Kang, C. Kocabas, T. Ozel, M. Shim, N. Pimparkar, M. A. Alam, S. V. Rotkin and J. A. Rogers, "High-performance Electronics Using Dense, Perfectly Aligned Arrays of Single-Walled Carbon Nanotubes," *Nature Nanotechnology* 2, 230-236 (2007).

[3] C. Kocabas, S. Dunham, Q. Cao, K. Cimino, X. Ho, H.-S. Kim, D. Dawson, J. Payne, M. Stuenkel, H. Zhang, T. Banks, M. Feng, S. V. Rotkin and J. A. Rogers, "High-Frequency Performance of Submicrometer Transistors That Use Aligned Arrays of Single-Walled Carbon Nanotubes," *Nano Lett* 9(5), 1937-1943 (2009).

[4] A. A. Pesetski, J. E. Baumgardner, S. V. Krishnaswamy, H. Zhang, J. D. Adam, C. Kocabas, T. Banks and J. A. Rogers, "A 500 MHz Carbon Nanotube Transistor Oscillator," *Applied Physics Letters* 93, 123506 (2008).

[5] C. Kocabas, H.-S. Kim, T. Banks, J. A. Rogers, A. A. Pesetski, J. E. Baumgardner, S. V. Krishnaswamy and H. Zhang, "Radio Frequency Analog Electronics Based on Carbon Nanotube Transistors," *Proceedings of the National Academy of Sciences USA* 105(5), 1405-1409 (2008).

[6] Lan, Y., Wang, Y., and Ren, Z. F., *Advances in Physics; volume* 60(4), pg. 533, (2011)

[7] Ding, L. et al. *Nano Letters* 9, 800-805, doi:10.1021/nl803496s (2009); Zhou, C. et al. *ACS Nano*, ArticleASAP

[8] Arnold, M. S., Green, A. A., Hulvat, J. F., Stupp, S. I. & Hersam, M. C., *Nature Nanotechnology* (1), pg. 60 (2006)

EXAMPLE 3

Laser IR Based Approaches to Induce Thermocapillary Flow

Figure 68:
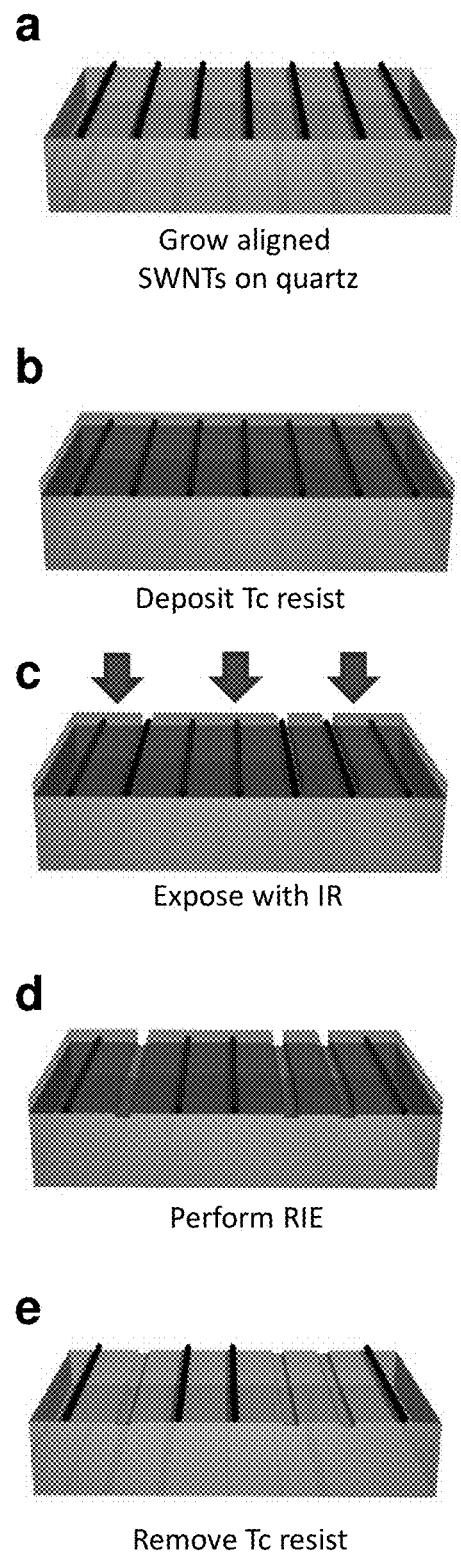
FIG. 68. Schematic of the IR-based TcEP process: (a) aligned SWNTs are grown on quartz, (b) a Tc resist is deposited on the SWNTs, (c) IR radiation is applied to induce thermocapillary flow, (d) reactive ion etching removes exposed SWNTs, (e) the Tc is removed.

A schematic of the IR-based TcEP process is presented in FIG. 68. SWNTs were grown via CVD on ST-cut quartz. A 25 nm amorphous film of α,α,α'-Tris(4-hydroxyphenyl)-1-ethyl-4-isopropylbenzene, a small organic molecule, is deposited onto the substrate. This material, hereinafter referred to as the thermocapillary (Tc) resist, was chosen for its thermal properties, resistance to RIE, as well as its ability to form a uniform and continuous ultrathin film on SWNTs and quartz. In addition, the detailed mechanisms behind thermocapillary flow of this material have been thoroughly explored in previous publications. Background heating of 65° C. was uniformly applied to the substrate, decreasing the viscosity of the Tc resist and promoting thermocapillary flow. The SWNTs were exposed using a λ=2500 nm pulsed infrared laser with a pulse duration of 10 ns and repetition rate of 1 kHz focused to a 5 µm beam spot size. The beam was rastered back-and-forth over a distance of 60 µm orthogonally with respect to the direction of the aligned SWNTs at a rate of 0.4 µm/s. Selective IR absorption caused heating in the m-SWNTs, inducing thermocapillary flow of the Tc resist and forming trenches. RIE was used to etch m-SWNTs exposed after trench formation and the Tc resist was removed using organic solvents.

Figure 69:
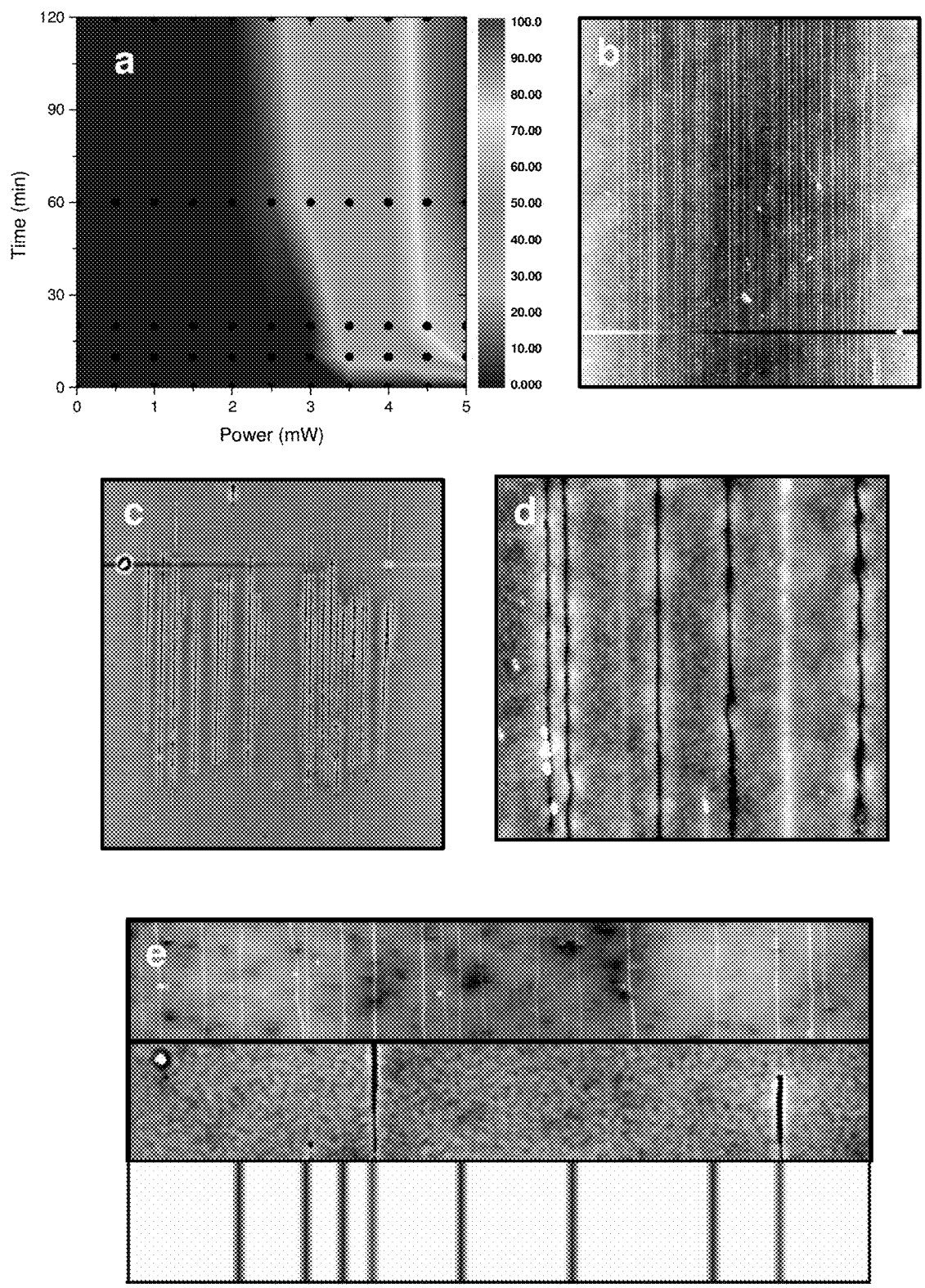
FIG. 69. Variation of laser power and rastering time for optimization of exposure dose and selectivity. (a) Percentage of SWNTs that yielded trenches with respect to these two parameters. (b) AFM topography image of an isolated patch of aligned SWNTs on quartz patterned using photolithography and oxygen plasma etching. (c) The device of (b) after Tc resist deposition and laser exposure at the optimized condition. (d) Higher magnification AFM scan of an exposed substrate. (e) AFM images of a substrate before processing (top) and after Tc resist deposition and exposure (middle) correspond perfectly with its Raman spectra (bottom). (f) I-V measurements conducted before and after exposure for a representative device. Histograms of $I_{DS}$ at $V_{DS}=2$ V among 22 devices (g) before and (h) after exposure.
Figure 69:
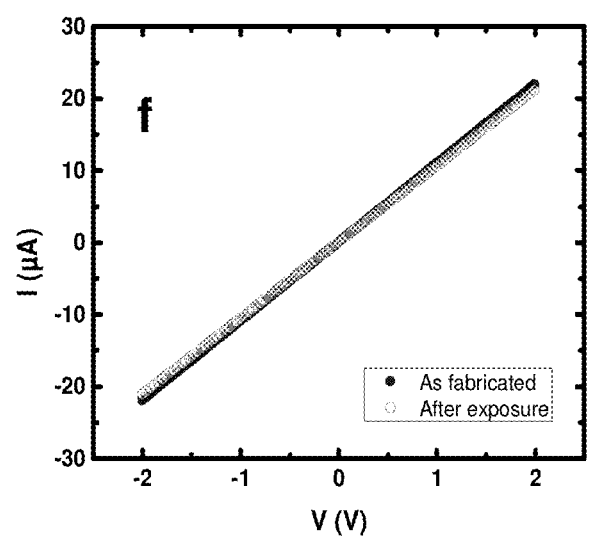
Figure 69:
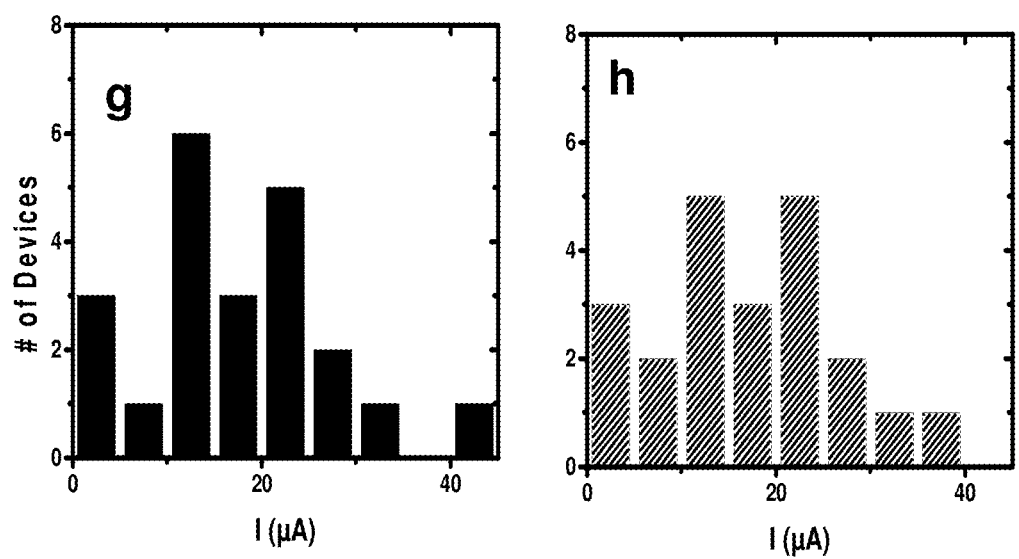

Laser power and rastering time was varied to optimize exposure dose and thereby selectivity. FIG. 69a shows the percentage of SWNTs that yielded trenches with respect to these two parameters. There are three distinct regions; Blue represents little to no trench formation, green shows 40-60% trench formation, and red indicates trenches formed by nearly all SWNTs. These are abrupt transitions between these regions, suggesting the presence of three distinct, stable conditions. In the blue region, heating is not sufficient for any trench formation. In the green region, m-SWNTs are heated to sufficient temperatures to allow for trench formation. In the red region, s-SWNTs also form trenches. Exposures in which the beam is rastered for 20 minutes or longer have little effect on selectivity. Trenches may become deeper or wider, but few new trenches form again suggesting stable, but phenomenologically distinct states. An optimal exposure condition of 3.5 mW laser power rastered for 120 minutes were chosen for all subsequent experiments.

FIG. 69b shows an AFM topography image of an isolated patch of aligned SWNTs on quartz patterned using photolithography and oxygen plasma etching. This patterning facilitates ease of counting. FIG. 69c shows the same device after Tc resist deposition and laser exposure at the optimized condition. Trenches have been formed by some, but not all SWNTs, indicating selectivity. Trenches formed are approximately 20 nm deep and 100 nm wide. Variation in trench length arises due to Gaussian power distribution of the laser beam profile and differences in absorption coefficient among species of m-SWNTs. FIG. 69d shows a higher magnification AFM scan of an exposed substrate, from which we can observe continuous and highly selective trench formation. Several SWNTs, presumably m-SWNTs, form continuous trenches in the exposed area while the remaining s-SWNTs do not exhibit any such trench formation. The variation in trench width along each SWNT can be attributed to the presence of small defects or kinks.

Raman spectroscopy was conducted to determine diameter and electronic type of SWNTs. Aligned arrays of SWNTs were grown on R-plane cut sapphire via CVD. Using sapphire substrates allows for direct assessment of SWNT diameter using the radial breathing mode (RBM) peaks, which are usually obscured by vibrational modes in quartz. In FIG. 69e, AFM images of a substrate before processing (top) and after Tc resist deposition and exposure (middle) correspond perfectly with its Raman spectra (bottom). Red and blue lines correspond to RBM signals from m-SWNTs and s-SWNTs, respectively. Raman signals from 39 individual SWNTs were acquired, 11 from m-SWNTs, and 28 from s-SWNTs. All 11 m-SWNTs yielded complete trenches while only 2 s-SWNTs yielded trenches, indicating excellent selective heating of m-SWNTs. Trenches formed by s-SWNTs could be caused by bundling with m-SWNTs, small band gap s-SWNTs, or heavily doped s-SWNTs.

Two-terminal devices were used to monitor device degradation during the laser exposure process. I-V measurements conducted before and after exposure for a representative device are shown in FIG. 69f. Current retention for this particular device was 95.4%. Histograms of $I_{DS}$ at $V_{DS}$=2 V among 22 devices before and after exposure are shown in FIGS. 69g and 69h, respectively. Average current retention was 97.9%.

Figure 70:
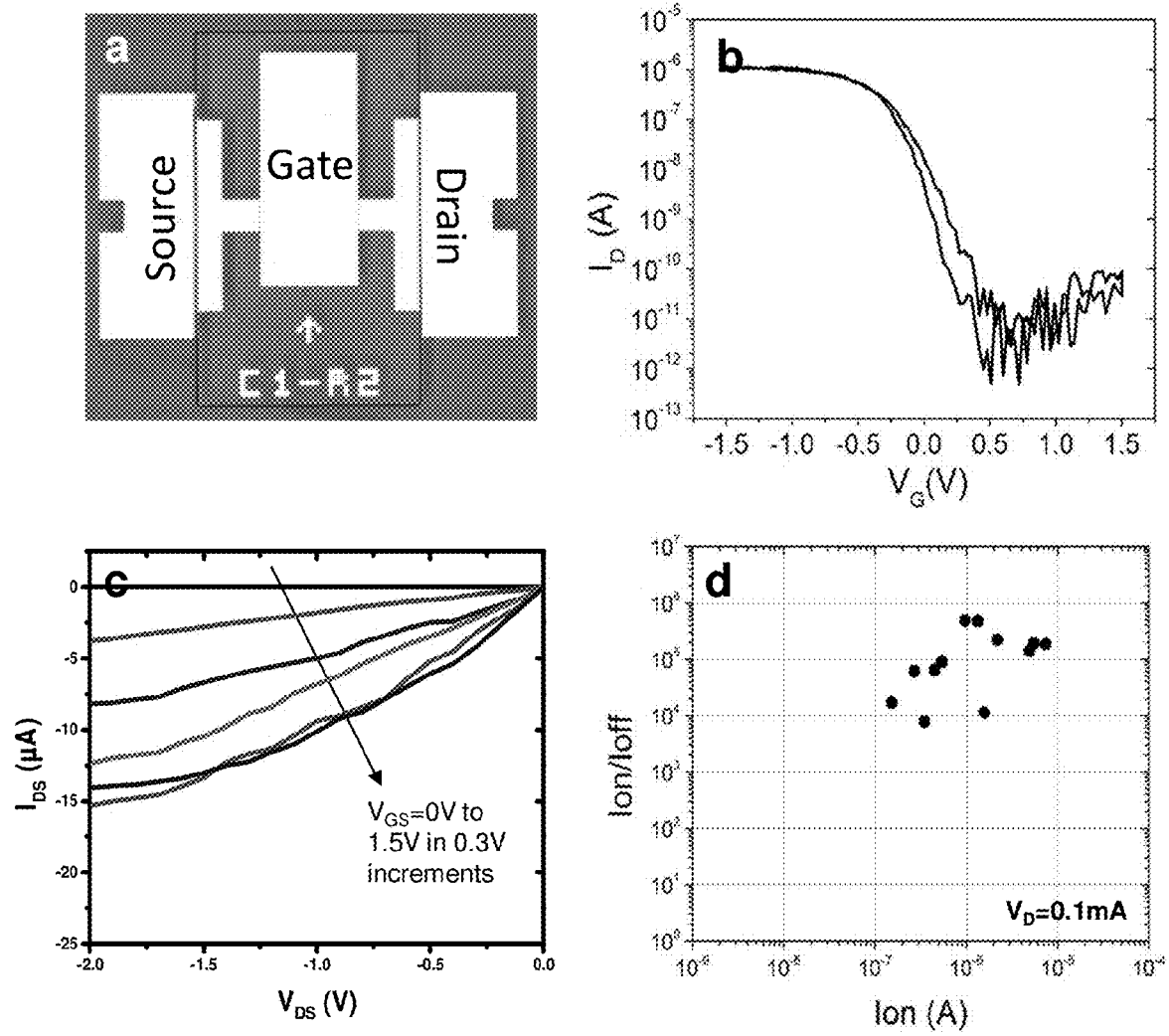
FIG. 70. (a) An optical microscopy image of a thin film transistor integrating purified s-SWNTs after IR-based TcEP processing. Transfer (b) and output (c) characteristics of a representative device. (d) On/off ratio as a function of $V_D$ for the device.

Thin film transistors integrating purified s-SWNTs after IR-based TcEP processing were fabricated. An optical microscopy image of the device is shown in FIG. 70a. Device dimensions are as follows: $L_C$=200 nm and $W_C$=40 µm. Representative transfer and output characteristics of a representative device are shown in FIGS. 70b and 70c respectively. $I_{ON}/I_{OFF}$ ratio>$10^5$ indicates complete removal of m-SWNTs. Switch ratios of 12 devices are plotted vs. the on-state currents. $I_{ON}/I_{OFF}$ of no less than $10^4$ are measured and some devices exhibit switching ratios of nearly $10^6$.

EXAMPLE 4

Figure 71:
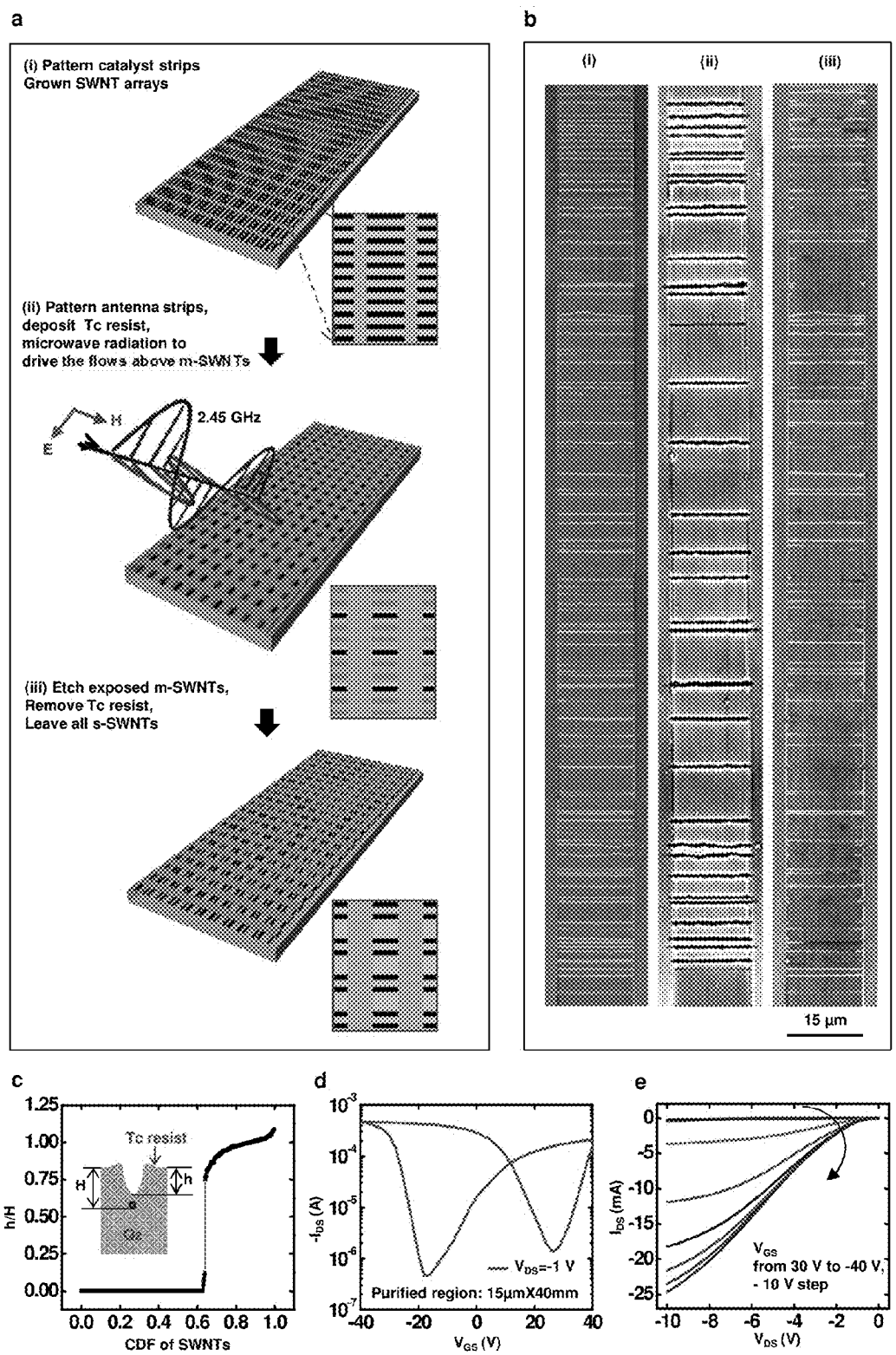
FIG. 71. Process and outcomes of the microwave-based purification of large-area arrays of aligned SWNTs. (a) Schematic illustration of the process. Patterning well defined strips of Fe catalysts and the following CVD growth yield aligned SWNTs which consists both metallic and semiconducting types. A second patterning defines the microstrip antennas (typically Ti) all over the substrate which serve as means to selectively transfer the microwave radiation energy into m-SWNTs. The resulting heating induces the local flow of a thermo-evaporated thin layer (~40 nm) of thermocapillary resist (Tc-resist) and opens trenches above the m-SWNTs. Reactive ion etching (RIE) subsequently etch away the exposed m-SWNTs while leaving arrays of s-SWNTs under the Tc-resist intact. (b) SEM and AFM images correspond to each step in the schematics, showing the mixtures of SWNTs before the purification, the trench formations on m-SWNTs and the s-SWNTs after the purification. (c) Statistics of the normalized trench depths h/H for more than 500 tubes, arranged in an ascending manner (x axis is the accumulated fraction of the SWNTs), showing that ~36% of the SWNTs creates trenches deep enough to etch away. This statistics matches that ~⅓ of the SWNTs are metallic types. Inset represents the schematics of the geometry for extracting the trench depth, with key parameters defined. The SWNT, the Tc-resist and the substrate are grey, green and blue, respectively. (d) (e) Transfer curve and output characteristics for 40 transistors built with large-areas (~40 mm in total width) of SWNTs after the purification. The transistors utilize the Ti microstrip antenna as the source and drain contacts, and achieve an on/off ratio ~$10^3$, and large output current ~25 mA.

Purification of Aligned Arrays of Single-Walled Carbon Nanotubes Via Microwave Induced Thermocapillary Flows FIG. 71 shows processes and outcomes of the microwave-based purification of large-area arrays of aligned SWNTs. (a) Schematic illustration of the process. Patterning well defined strips of Fe catalysts followed by CVD growth yields aligned SWNTs which consist of both metallic and semiconducting types. A second patterning defines the microstrip antennas (typically Ti) over the substrate which serve as means to selectively transfer the microwave radiation energy into m-SWNTs. The resulting heating induces the local flow of a thermo-evaporated thin layer (~40 nm) of thermocapillary resist (Tc-resist) and opens trenches above the m-SWNTs. Reactive ion etching (RIE) subsequently etches away the exposed m-SWNTs while leaving arrays of s-SWNTs under the Tc-resist intact. (b) SEM and AFM images correspond to each step in the schematics, showing the mixtures of SWNTs before the purification, the trench formations on m-SWNTs and the s-SWNTs after the purification. (c) Statistics of the normalized trench depths h/H for more than 500 tubes, arranged in an ascending manner (x axis is the accumulated fraction of the SWNTs), showing that ~36% of the SWNTs create trenches deep enough to etch away. This statistic matches that ~⅓ of the SWNTs being metallic types. Inset represents the schematics of the geometry for extracting the trench depth, with key parameters defined. The SWNT, the Tc-resist and the substrate are grey, green and blue, respectively. (d), (e) Transfer curve and output characteristics for 40 transistors built with large-areas (~40 mm in total width) of SWNTs after the purification. The transistors utilize the Ti microstrip antenna as the source and drain contacts, and achieve an on/off ratio ~$10^3$, and large output current ~25 mA.

Figure 72:
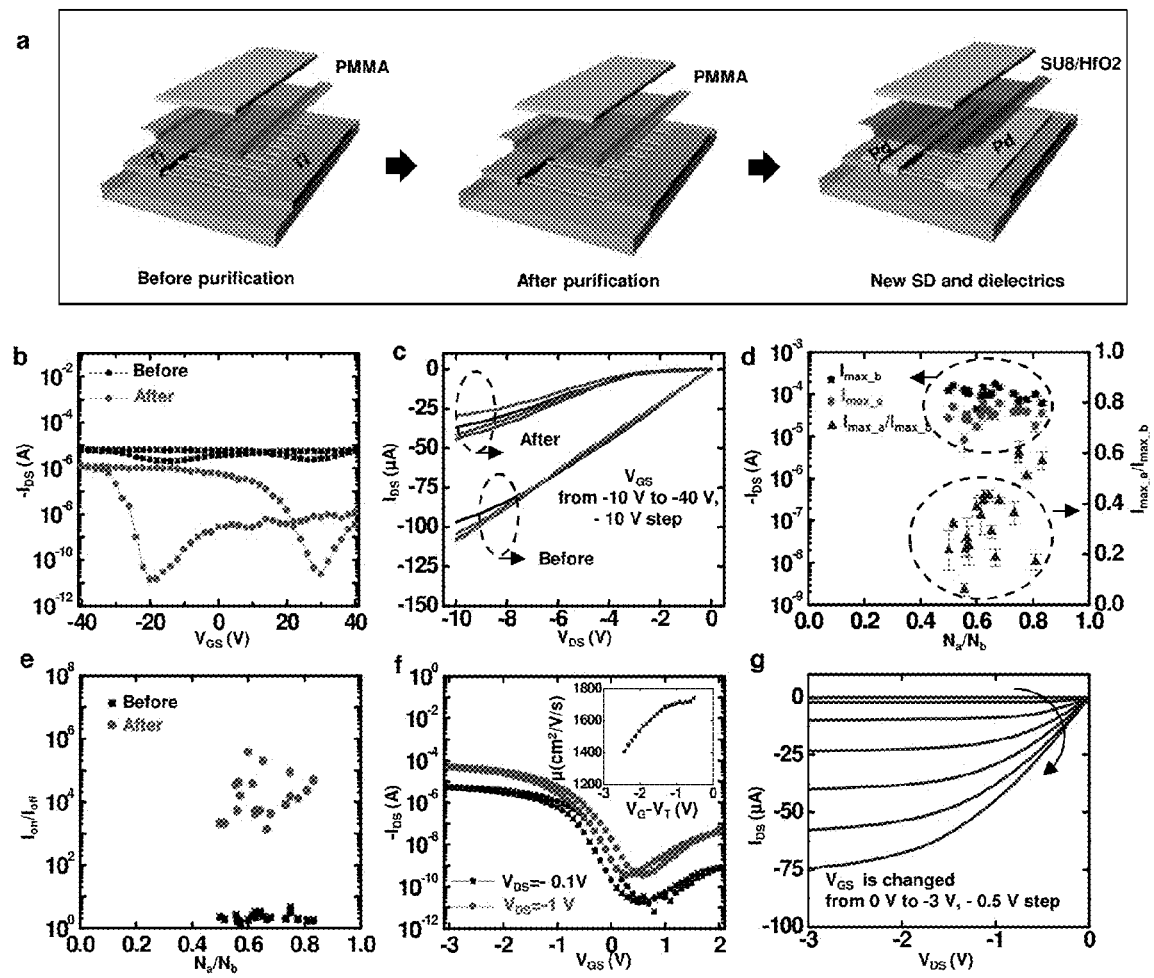
FIG. 72. The effectiveness of the microwave-based purification process. (a) Schematic illustration of various steps to verify the effectiveness of the purification process. Fabrication and measurements of transistors built on small arrays of SWNTs (number of SWNTs from 10 to 25) before and after the purification facilitates the direct comparisons. The source and drain of the transistor also serve as the antenna for the purification. The PMMA dielectrics make the top-gate easily remove by acetone after the characterizations. Patterning new Ohmic contacts by Pd afterwards, and depositing SU8 (20 nm)/HfO2 (5 nm) as new dielectric lead to transistors with low operational voltage and low hysteresis. (b)(c) Typical transfer curve and output characteristics (near the on state region) for a transistor before and after the purification. The on-off ratio increases from ~3 to ~8.5×10$^4$, and the maximum output current retains ~40% after the purification. (d) The maximum output current before and after (I$_{max\_b}$ and I$_{max\_a}$, respectively) purification, as a function of the ratio (N$_a$/N$_b$) of the number of SWNTs after purification respect to the one before purification. I$_{max\_b}$/I$_{max\_a}$ ranges from 0.1 to 0.6, increasing with the rise of N$_a$/N$_b$, which suggests that the s-SWNTs are well protected. (e) Statistics of the on-off ratios of the transistors based on the SWNTs, before (black square) and after (red dot) the purification, respectively. The I$_{on}$/I$_{off}$ increases from <10 to 1×10$^3$~10$^6$, agreeing with the removal of all the m-SWNTs. (f) (g) Typical transfer curve and output characteristics of a transistor built on a small array of purified SWNTs (15 SWNTs), by using Pd as new contacts and SU8 (50 nm)/HfO2 (5 nm) as dielectrics. The low hysteresis feature facilitates the extraction of the device mobility, which is ~1600 cm$^2$/V/s as shown in the insert graph.

FIG. 72 shows the effectiveness of the microwave-based purification process. (a) Schematic illustration of various steps to verify the effectiveness of the purification process. Fabrication and measurements of transistors built on small arrays of SWNTs (number of SWNTs from 10 to 25) before and after the purification facilitates the direct comparisons. The source and drain of the transistor also serve as the antenna for the purification. The PMMA dielectrics make the top-gate easily removeable by acetone after the characterizations. Patterning new Ohmic contacts by Pd afterwards, and depositing SU8(20 nm)/HfO$_2$(5 nm) as new dielectric lead to transistors with low operational voltage and low hysteresis. (b)(c) Typical transfer curve and output characteristics (near the on state region) for a transistor before and after the purification. The on-off ratio increases from ~3 to ~8.5×$10^4$, and the maximum output current retains ~40% after the purification. (d) The maximum output current before and after ($I_{max\_b}$ and $I_{max\_a}$, respectively) purification, as a function of the ratio ($N_a/N_b$) of the number of SWNTs after purification with respect to the one before purification. $I_{max\_b}/I_{max\_a}$ ranges from 0.1 to 0.6, increasing with the rise of $N_a/N_b$, which suggests that the s-SWNTs are well protected. (e) Statistics of the on-off ratios of the transistors based on the SWNTs, before (black square) and after (red dot) the purification, respectively. The $I_{on}/I_{off}$ increases from <10 to 1×$10^3$~$10^6$, agreeing with the removal of all the m-SWNTs. (f) (g) Typical transfer curve and output characteristics of a transistor built on a small array of purified SWNTs (15 SWNTs), by using Pd as new contacts and SU8(50 nm)/HfO$_2$(5 nm) as dielectrics. The low hysteresis feature facilitates the extraction of the device mobility, which is ~1600 cm$^2$/V/s as shown in the insert graph.

Figure 73:
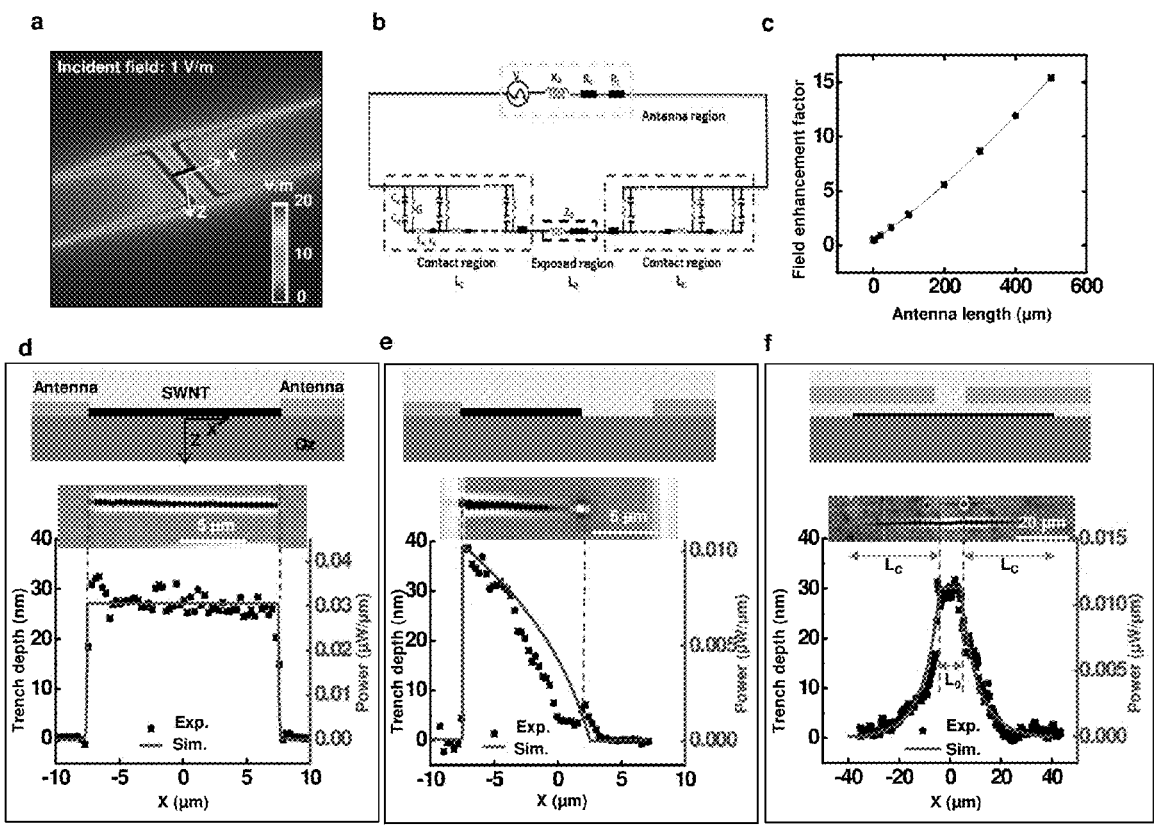
FIG. 73. Coupling between the microwave field, microstrip antenna and SWNTs, and the heating mechanism. (a) 3D FEM-simulation results of the electrical field distribution around the microdipole antenna. The incident microwave is assumed to be a TEM mode, propagating perpendicular to the antenna plane (Z axis), and with electrical field polarized along the length of the antenna (X axis). The simulation indicates the enhancement of the microwave field in the gap between the two antenna arms. (b) An equivalent circuit model for the antenna and SWNT structure. The antenna is treated as a voltage source with resistance of R$_o$+R$_r$ and inductance of X$_A$. The SWNT is assumed to be a metallic type, with a resistivity of r$_s$ and inductance of L$_k$ per unit length. Within the contact length L$_c$, strong coupling exist between the antenna and the SWNT, through a series of capacitance C$_g$ (geometric capacitance) and C$_q$ (quantum capacitance), and a shunt conductance G. In the exposed region between the two antenna arms (L$_0$), the coupling between the antenna and the SWNT is neglected for simplicity. (c) FEM Simulated field enhancement respect to the length of the antenna, indicating an approximately linear relationship within the length of interests. (d) Schematic illustration and AFM topography image of the case where the SWNT is in contact with both side of the antenna arms. The plot below shows the trench depth profile along the length of the SWNT extracted from the AFM image (black square) and the heating profile calculated from the circuit model (red curve). The heating as well as the trench depth is relatively constant along the SWNT. (e) Schematic illustration and AFM topography image of the case where the SWNT is in contact with one side of the antenna arms. The extracted trench depth (black square) decreases starting from the left contact, all the way to the end of the SWNT, where the trench eventually diminishes. This trend can be well captured by the FEM simulation of the heating profile (red curve), by using the resistivity of the SWNT as the only fitting parameter. (f) Schematic illustration and AFM topography image of the case where the SWNT is separated from the antenna by an air gap with a constant distance ~1.1 um. The trench not only exists in between the two antenna arms, but also extends underneath the antenna. The trench profile can be well matched by the calculated heating profile from the circuit model, by using the resistance of the SWNT as the only fitting parameter.

FIG. 73 shows coupling between the microwave field, microstrip antenna and SWNTs, and the heating mechanism. (a) 3D FEM-simulation results of the electrical field distribution around the microdipole antenna. The incident microwave is assumed to be a TEM mode, propagating perpendicular to the antenna plane (Z axis), and with electrical field polarized along the length of the antenna (X axis). The simulation indicates the enhancement of the microwave field in the gap between the two antenna arms. (b) An equivalent circuit model for the antenna and SWNT structure. The antenna is treated as a voltage source with resistance of $R_o+R_r$ and inductance of $X_A$. The SWNT is assumed to be a metallic type, with a resistivity of $r_s$ and inductance of $L_k$ per unit length. Within the contact length $L_c$, strong coupling exists between the antenna and the SWNT, through a series of capacitance $C_g$ (geometric capacitance) and $C_q$ (quantum capacitance), and a shunt conductance G. In the exposed region between the two antenna arms ($L_0$), the coupling between the antenna and the SWNT is neglected for simplicity. (c) FEM simulated field enhancement with respect to the length of the antenna, indicating an approximately linear relationship within the length of interest. (d) Schematic illustration and AFM topography image of the case where the SWNT is in contact with both sides of the antenna arms. The plot below shows the trench depth profile along the length of the SWNT extracted from the AFM image (black square) and the heating profile calculated from the circuit model (red curve). The heating as well as the trench depth is relatively constant along the SWNT. (e) Schematic illustration and AFM topography image of the case where the SWNT is in contact with one side of the antenna arms. The extracted trench depth (black square) decreases starting from the left contact, all the way to the end of the SWNT, where the trench eventually diminishes. This trend can be well captured by the FEM simulation of the heating profile (red curve), by using the resistivity of the SWNT as the only fitting parameter. (f) Schematic illustration and AFM topography image of the case where the SWNT is separated from the antenna by an air gap with a constant distance of ~1.1 um. The trench not only exists in between the two antenna arms, but also extends underneath the antenna. The trench profile can be well matched by the calculated heating profile from the circuit model, by using the resistance of the SWNT as the only fitting parameter.

Figure 74:
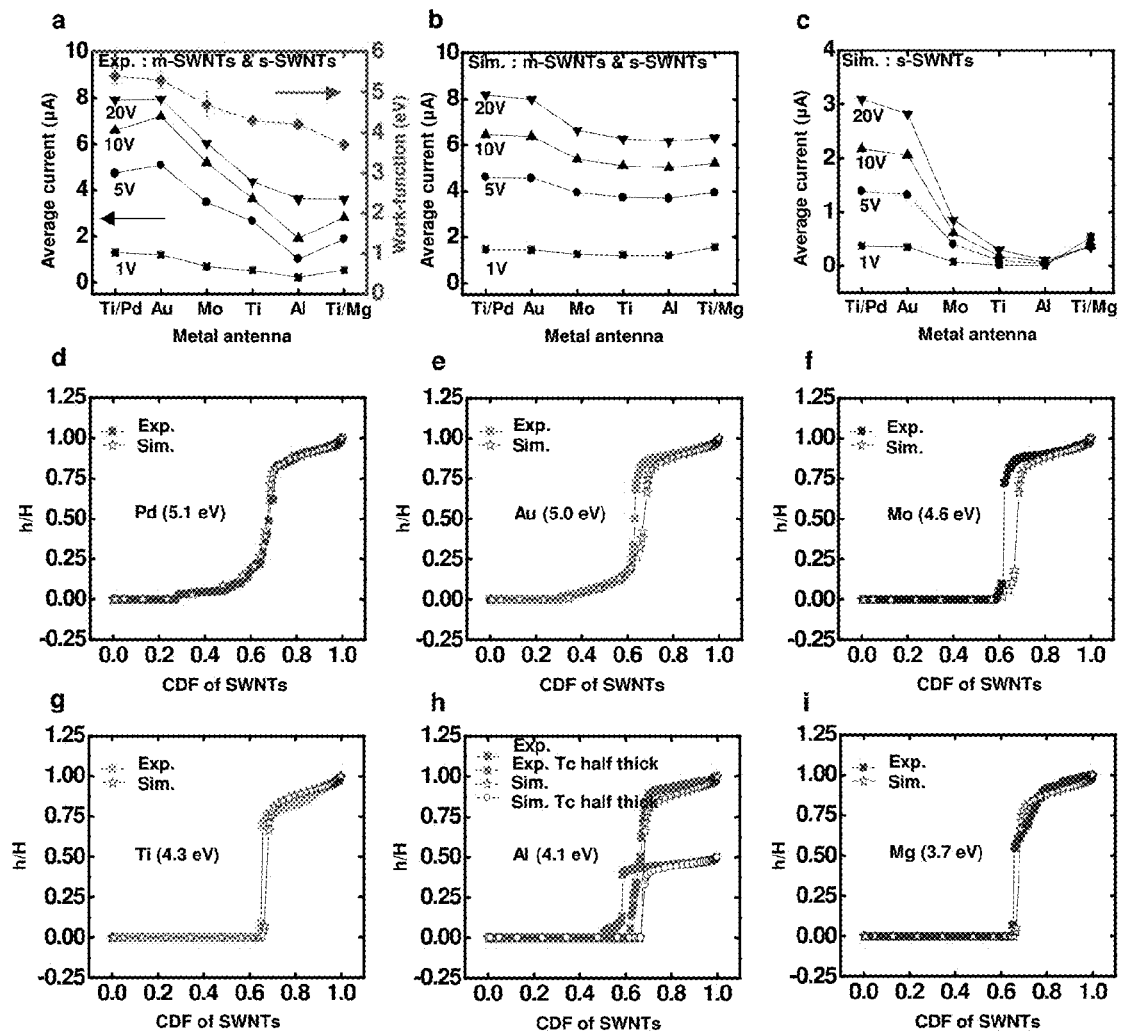
FIG. 74. Different metals as the antennas. (a) Average current per tube at 1V, 5V, 10V and 20V, for different metals serving as the antennas. The DC voltage is applied across the dipole antenna bridged by small arrays of SWNTs for the measurements. Data of each metal type averages the results from more than 100 of SWNTs. The average current decreases as the work-function of the metal decreases. (b)(c) Transport simulation of the average current per tube for different contacts. The simulation averages the current from SWNTs with different diameters (distribution taken from literature from the same group). For (b), it assumes that ⅓ of the SWNTs are metallic and the others are semiconducting. (c) is the results from only s-SWNT. The general trend matches with the experimental observations. As the work-function of the contacts decreases, the current in the s-SWNTs decreases, which is a result of the formation of Schottky barrier at the contact region for s-SWNTs. The slight increase of the current for Mg contact is due to band to band tuning effect. (d)-(i) Experimental (square) and simulated (curve) statistics of the normalized trench depths for different metals as the antennas during the microwave process, (d) Pd, (e) Au, (f) Mo, (g) Ti, (h) Al, (i) Mg. The T$_c$ film thickness (~40 nm) and microwave conditions (250 W 73 C 3 h) are the same for all metal types. For metals with relative high work-function like Pd and Au, both the m-SWNTs and s-SWNTs create trenches (h>0); while for metals with low work-function like Mo, Ti, Mg, a distinct gap in the statistics separate the m-SWNTs from the s-SWNTs. The Al antenna results in a continuous distribution of the trench depth, and the gap appears when the thickness of the film decreases to ~20 nm. This suggests insufficient heating for the m-SWNTs, which is probably due to the poor wettability of Al to the SWNTs. The simulations match with the experimental results quite well, verifying that the Schottky barrier plays the key role for selectively heating the m-SWNT by using metals with low work-function as the antennas.

FIG. 74 shows different metals as the antennas. (a) Average current per tube at 1V, 5V, 10V and 20V, for different metals serving as the antennas. The DC voltage is applied across the dipole antenna bridged by small arrays of SWNTs for the measurements. Data of each metal type averages the results from more than 100 SWNTs. The average current decreases as the work-function of the metal decreases. (b)(c) Transport simulation of the average current per tube for different contacts. The simulation averages the current from SWNTs with different diameters (distribution taken from literature from the same group). For (b), it assumes that ⅓ of the SWNTs are metallic and the others are semiconducting. (c) shows the results from only s-SWNTs. The general trend matches with the experimental observations. As the work-function of the contacts decreases, the current in the s-SWNTs decreases, which is a result of the formation of a Schottky barrier at the contact region for s-SWNTs. The slight increase of the current for the Mg contact is due to a band to band tuning effect. (d)-(i) Experimental (square) and simulated (curve) statistics of the normalized trench depths for different metals as the antennas during the microwave process, (d) Pd, (e) Au, (f) Mo, (g) Ti, (h) Al, (i) Mg. The $T_c$ film thickness (~40 nm) and microwave conditions (250 W 73 C 3 h) are the same for all metal types. For metals with relatively high work-functions like Pd and Au, both the m-SWNTs and s-SWNTs create trenches (h>0); while for metals with low work-functions like Mo, Ti, Mg, a distinct gap in the statistics separate the m-SWNTs from the s-SWNTs. The Al antenna results in a continuous distribution of the trench depth, and the gap appears when the thickness of the film decreases to ~20 nm. This suggests insufficient heating for the m-SWNTs, which is probably due to the poor wettability of Al to the SWNTs. The simulations match with the experimental results quite well, verifying that the Schottky barrier plays the key role for selectively heating the m-SWNT by using metals with low work-functions as the antennas.

Figure 75:
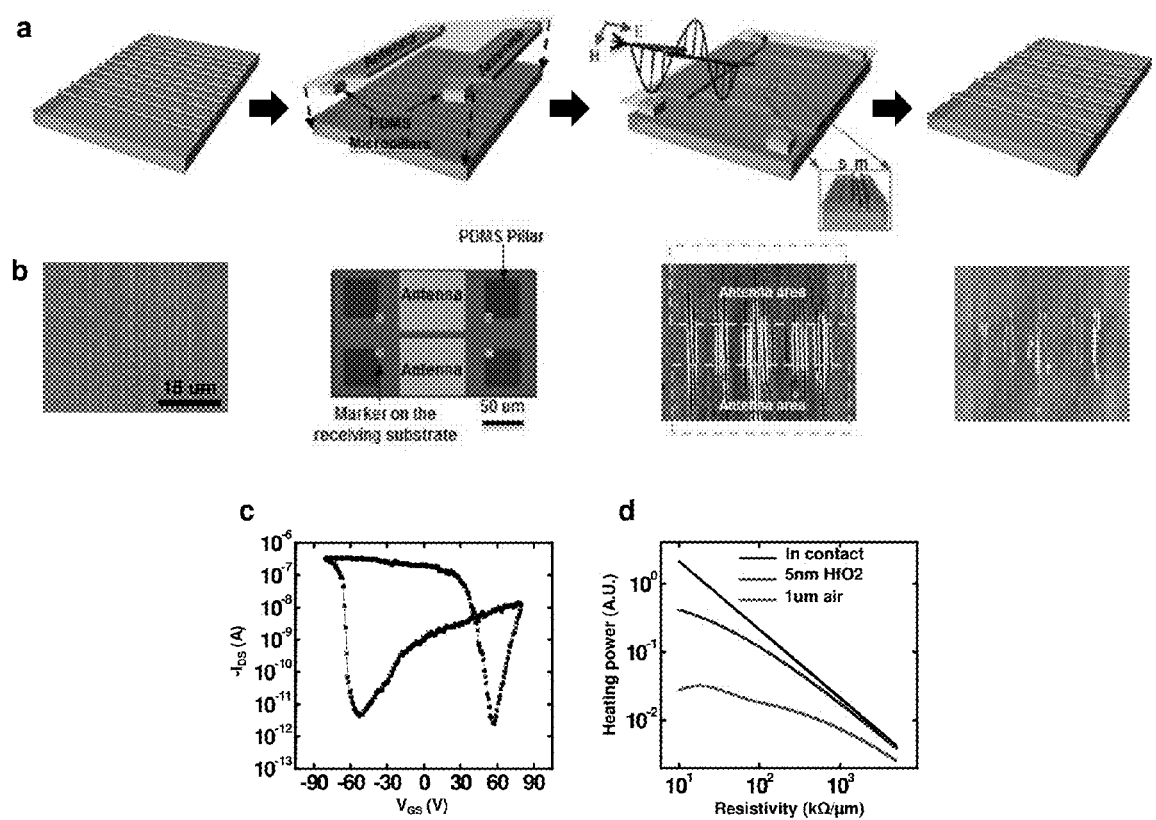
FIG. 75. Microwave purification based on the removable antennas. (a) Schematic illustration of the purification process based on the removable antennas. Patterning the antenna on a substrate and molding PDMS micropillars forms the antenna mask. Laminating the antenna mask to the quartz substrates with SWNTs results in sufficient heating to create deep trenches above the m-SWNTs during the microwave process. The micropillars hold the antenna mask and substrate together, with a constant distance in between. After the microwave process, the antenna mask can be easily peeled off, leaving SWNTs without any metal contacts. (b) Images correspond to each step shown in the schematics: SEM image of the SWNTs before the purification; optical image of the antenna mask after contacting the quartz substrate; AFM topography image of the trench formation and SEM image after the etching and washing away the T$_c$ resist. (c) Transfer curve of a typical transistor based on the purified arrays via the removable antenna scheme. (d) Simulation of the heating power respect to the resistivity of the SWNTs for different cases. Decreasing the distance, and increasing the dielectric constant of the materials between the antenna and the SWNT can increase their capacitive coupling, resulting in a higher heating level.

FIG. 75 shows microwave purification based on removable antennas. (a) Schematic illustration of the purification process based on removable antennas. Patterning the antenna on a substrate and molding PDMS micropillars forms the antenna mask. Laminating the antenna mask to the quartz substrates with SWNTs results in sufficient heating to create deep trenches above the m-SWNTs during the microwave process. The micropillars hold the antenna mask and substrate together, with a constant distance in between. After the microwave process, the antenna mask can be easily peeled off, leaving SWNTs without any metal contacts. (b) Images correspond to each step shown in the schematics: SEM image of the SWNTs before the purification; optical image of the antenna mask after contacting the quartz substrate; AFM topography image of the trench formation and SEM image after the etching and washing away the $T_c$ resist. (c) Transfer curve of a typical transistor based on the purified arrays via the removable antenna scheme. (d) Simulation of the heating power with respect to the resistivity of the SWNTs for different cases. Decreasing the distance, and increasing the dielectric constant of the materials between the antenna and the SWNTs can increase their capacitive coupling, resulting in a higher heating level.

EXAMPLE 5

Selective Removal of Metallic SWNTs Via 2-Terminal Joule Heating Induced Thermocapillary Flows Through selectively inducing Joule heating on m-SWNTs, the 2-terminal (2T) probing method provides another simple way for driving the thermocapillary flows for purification.

Figure 76:
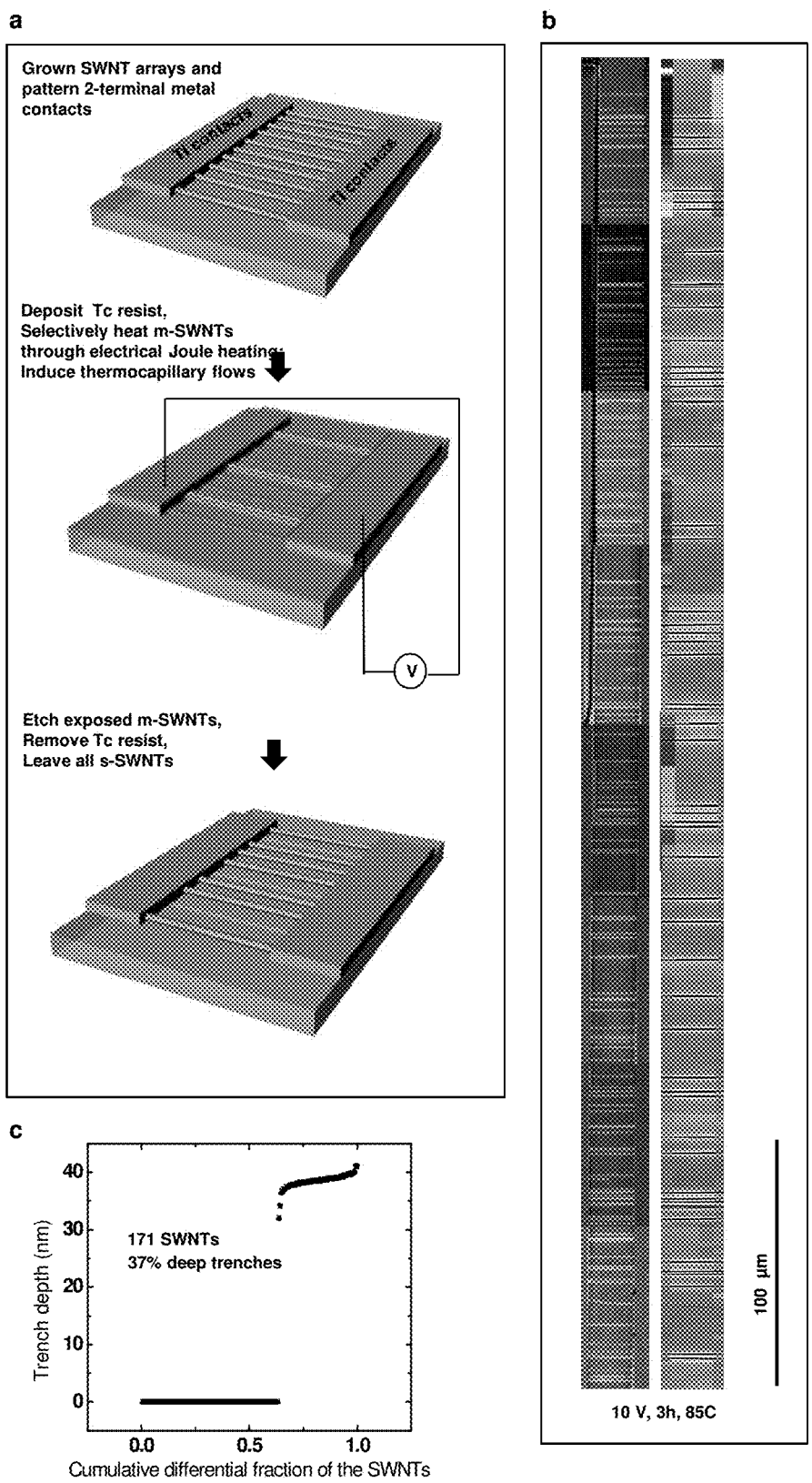
FIG. 76.

FIG. 76a shows a schematic illustration of this process. To do the purification, the SWNTs are first grown on the quartz substrate, followed by patterning strips of metal contacts on the SWNTs. Metals with relatively low work-functions with respect to the middle gap energy of the SWNTs, as well as good wettability to the SWNTs are typically good choices for the contacts. After the deposition of the thermocapillary resist ($T_c$ resist), a DC voltage is applied across the metal contacts, which selectively induces Joule heating on the m-SWNTs, causing the flows of the $T_c$ resist to open trenches above the m-SWNTs. Reactive ion etching is then used to etch away the exposed m-SWNTs, leaving the s-SWNTs well protected by the $T_c$ resist. FIG. 76b shows the SEM image of a pristine array of SWNTs and the corresponding AFM topography image of the induced trenches. Such well-defined, uniform trenches along the SWNTs are the key for the successful removal. Statistics of the trench depth associated with each SWNT in a device with total 171 SWNTs are shown in FIG. 76c. The depths are arranged in an ascending manner (x axis is the accumulated differential fraction of the SWNTs), showing that ~37% of the SWNTs create trenches deep enough to etch away. This statistic matches ~⅓ of the SWNTs being metallic types.

Figure 77:
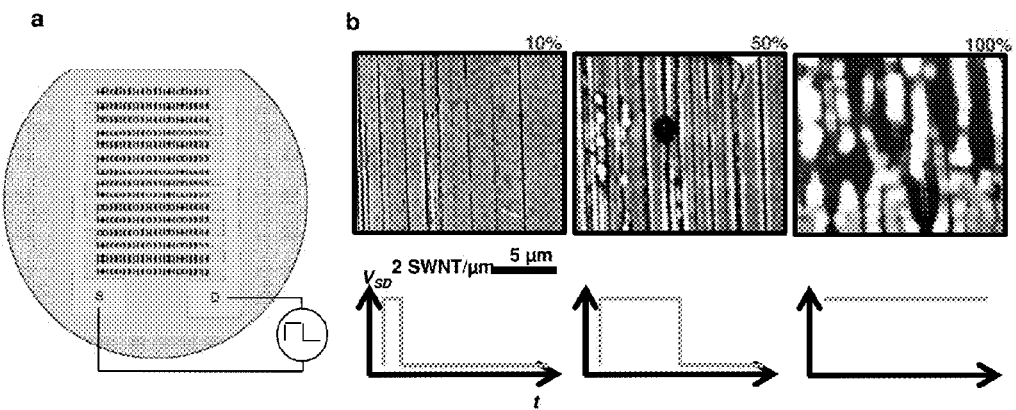
FIG. 77. Pulsed biases for forming trenches in large and/or high density arrays of SWNTs. (a) Interdigitated electrode structure. (b) AFM trenches formed in Tc-resist for an array with 2-3 SWNT/μm associated with pulsed heating with increasing duty cycle ($V_{DS}$=−40V peak amplitude, period=10 μs, duration=1-10 μs, $V_{GS}$=+20V DC, 60 sec total stress duration, 50° C. background heating). For 10% duty cycle clearly defined trenches are observed. As the duty cycle increases, trenches become less clearly defined and flow is observed that does not correlate to the underlying SWNT positions. This results from delocalized heating associated with parallel operation in many SWNT. Pulsed heating aids in localizing the flows needed for proper operation in TcEP.

FIG. 77a is the scheme to scale up the 2T probing method for the wafer scale purification. Here, interdigitated electrodes are patterned over the wafer. Those electrodes are linked together, resulting in electrical paths on the entire wafer. Since the thermocapillary flow is very sensitive to the temperature, it is important to control well the substrate temperature. However, when a wafer of SWNTs simultaneously run through current (especially when the density of the SWNTs is high>1 SWNT/μm), a substantial amount of Joule heating energy will cause the temperature rise, which may eventually result in dewetting of the Tc resist. Therefore, pulse operational mode for the voltage source needs to apply in order to get better thermal management, as shown in the image of FIG. 77b (Sunhun, Simon, Nature Nanotechnology, 2013).

Pulsed Biases for Forming Trenches in Large and/or High Density Arrays of SWNTs.

AFM trenches formed in Tc-resist for an array with 2-3 SWNT/μm associated with pulsed heating with increasing duty cycle ($V_{DS}=-40V$ peak amplitude, period=10 μs, duration=1-10 μs, $V_{GS}=+20V$ DC, 60 sec total stress duration, 50° C. background heating). For 10% duty cycle clearly defined trenches are observed. As the duty cycle increases, trenches become less clearly defined and flow is observed that does not correlate to the underlying SWNT positions. This results from delocalized heating associated with parallel operation in many SWNTs. Pulsed heating aids in localizing the flows needed for proper operation in TcEP.

Figure 78:
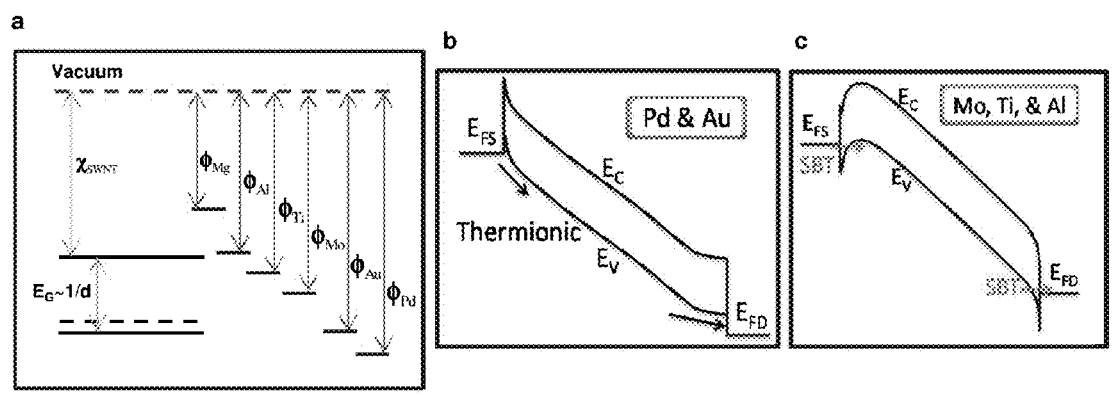
FIG. 78. To qualitatively explain the selectivity of the 2T probe method, FIG. 78a draws out the work-function of different types of metals, respect to the valence and conduction band of the SWNT. S-SWNTs are usually found to be P type, therefore metals with low work-function can form Schottky barriers to them, which will block the current flow (FIG. 78c). On the other hand, the metals with relative high work-function can form Ohmic contact with the s-SWNTs, which enables the current flow (FIG. 78b).

Finally, to qualitatively explain the selectivity of the 2T probe method, FIG. 78a draws out the work-function of different types of metals, with respect to the valence and conduction band of the SWNT. S-SWNTs are usually found to be P type, therefore metals with low work-functions can form Schottky barriers to them, which will block the current flow (FIG. 78c). On the other hand, the metals with relatively high work-functions can form Ohmic contact with the s-SWNTs, which enables the current flow (FIG. 78b).

EXAMPLE 6

Fundamental Effects in Nanoscale Thermocapillary Flow

When implemented on the nanoscale, material flows driven by gradients in temperature, sometimes known as thermocapillary flows, can be exploited for various purposes, including nanopatterning, device fabrication, and purification of arrays of single walled carbon nanotubes (SWNTs). Systematic experimental and theoretical studies on thermocapillary flow in thin polymer films driven by heating in individual metallic SWNTs, over a range of conditions and molecular weights reveal the underlying physics of this process. The findings suggest that the zero-shear viscosity is a critical parameter that dominates the dependence on substrate temperature and heating power. The experimentally validated analytical models in this study allow assessment of sensitivity to other parameters, such as the temperature coefficient of surface tension, the thermal interface conductance, and the characteristic length scale of the heated zone.

Recent reports highlight the ability to use nanoscale, thermally driven processes of pattern formation for applications in ultralow power phase-change memory[1], nanolithography[2-4], purification of aligned arrays of SWNTs[5] and others. In these examples, self-aligned structures in thin film coatings form as a result of local increases in temperature induced at the positions of Si or metal nanowires[2-4] or metallic SWNTs (m-SWNTs)[1,5]. Some of these phenomena are reported to involve physical evaporation and/or chemical change in the films. In one case, data indicates a process of physical mass transport, or flow, that depends on temperature, gradients in temperature and physical/chemical properties of the film and substrate support. Such flows can occur in organic small molecule or polymer films at peak temperatures of just a few degrees, for sources of heat that have nanoscale dimensions. In one application, films coated onto aligned arrays of SWNTs undergo flow only at regions of selective current injection, and Joule heating, at the m-SWNT. This process creates openings that allow removal of the m-SWNTs by gas phase etching, in a manner that leaves the semiconducting SWNTs unaltered. A full understanding of this process is necessary for further optimization and use of this physics, not only in purification of SWNT arrays, but in nanolithography, device fabrication and other areas as well. Here, we report systematic experimental and theoretical studies that highlight, directly and indirectly, the essential aspects of nanoscale thermocapillary flows in films of polystyrene (PS), driven by Joule heating[1,5] in individual single walled carbon nanotubes (SWNTs). Quantitative agreement between experiment and theory establishes use of the models reported here for predictive assessment of the thermocapillary flow process. One key conclusion is that the viscosity[6,7] is a critical parameter that largely defines the influence of substrate temperature and rates of Joule heating on this process.

Figure 79:
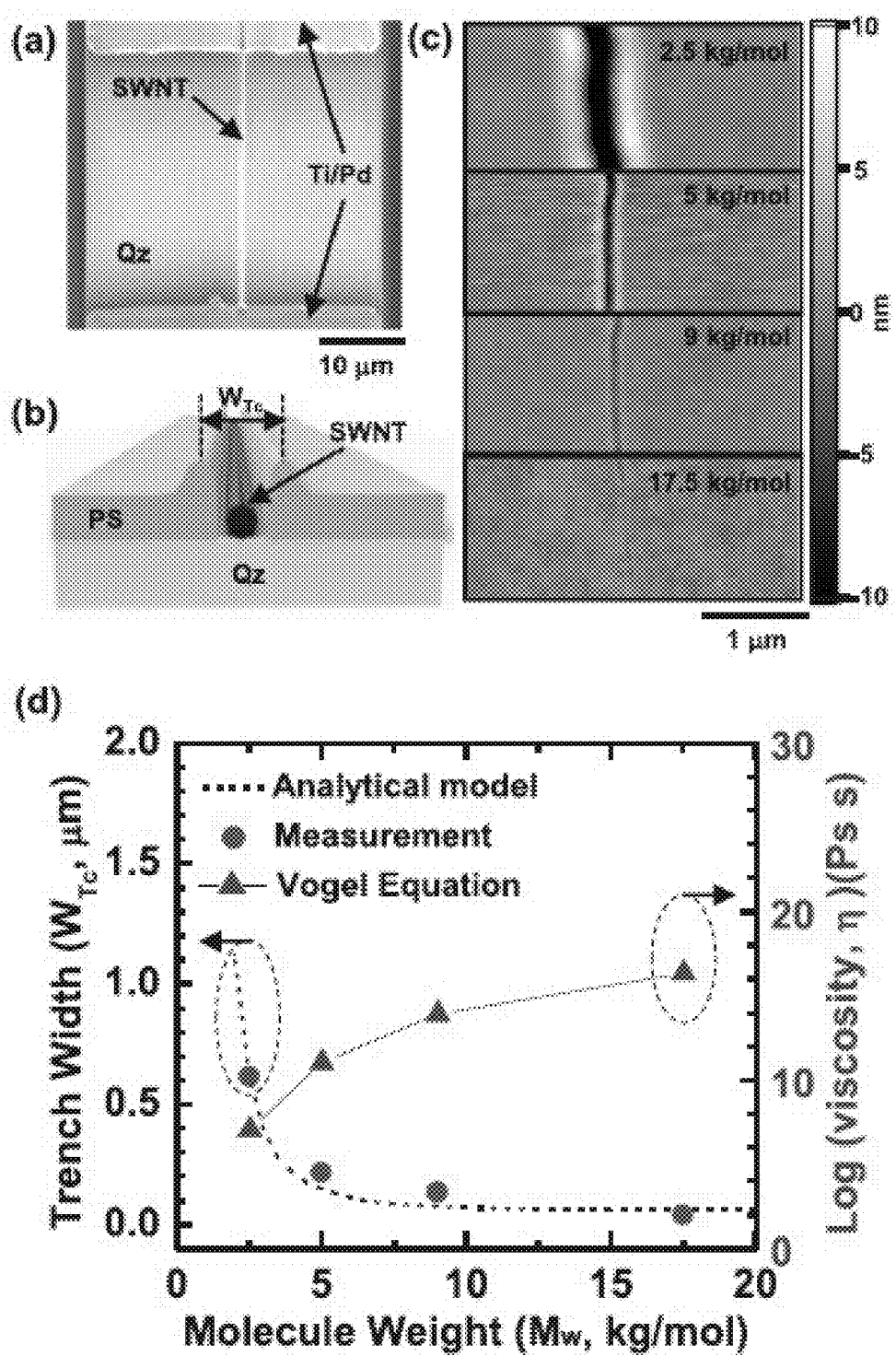
FIG. 79. (a) SEM image of an individual metallic SWNT with a pair of electrode contacts of Ti/Pd on a quartz (Qz) substrate, (b) schematic illustration showing the SWNT (grey), the Qz substrate (blue), and a layer of PS (gold) after nanoscale thermocapillary flow induced by Joule heating in the SWNT. The parameter $W_{Tc}$ defines the width of the trench that forms. (c) AFM images of films of PS with molecule weights ($M_w$) ranging from 2.5 kg/mol to 17.5 kg/mol after inducing nanoscale thermocapillary flows by Joule heating in an underlying SWNT (power dissipation Q0~30 μW/μm) at a substrate temperature, $T_0$=353 K. (d) Dependence of $W_{Tc}$ on $M_w$ of PS (red circles). Also plotted is the zero-shear viscosity, η of PS determined by the Vogel equation (blue triangles). The dashed line corresponds to $W_{Tc}$ computed using an analytical model for nanoscale thermocapillary flow.

FIG. 79(a) provides a scanning electron microscope (SEM) image of an individual SWNT with a pair of metal electrode contacts. For studies reported here, ST-quartz wafers serve as substrates, with Ti/Pd (=²/₄₀ nm) as contacts, separated by 30 μm.[5,8] For such devices formed with m-SWNTs, the voltage drops primarily along the length of the m-SWNTs, rather than at the contacts[8]. Spin casting thin films of PS on top of such devices and then applying a DC bias across the electrodes initiates nanoscale thermocapillary flow along the length of the heated m-SWNT, driven by the temperature dependent surface tension in the film, as described subsequently. FIG. 79(b) shows a typical trench that forms as a result. The trench width ($W_{Tc}$) is defined as the distance between the ridges that form in the PS on either side of the m-SWNT[5]. Studies involve PS (Sigma Aldrich, Inc) with $M_w$ between 2.5 kg/mol to 30 kg/mol, dissolved in toluene to form a 0.8 wt % solution that is passed through a PVDF membrane filter with nominal pore size of 0.2 μm (Whatman) to remove any particulates or polymer aggregates. Typical film thicknesses are $t_{PS}$=30 nm±3 nm. Thermocapillary flow occurs on a temperature-controlled substrate ($T_o$=353 K) in a vacuum chamber (Lake Shore Cryotronics, Inc.) at a base pressure of ~1×10⁻⁴ torr. The process involves applying a DC bias for 10 minutes while monitoring the current with a parameter analyzer (Agilent 4155C). An atomic force microscope (AFM; Asylum MFP 3D, tapping mode) yields images of the patterns of PS induced by thermocapillary flow. Soaking the sample in toluene, drying under a stream of nitrogen, and then baking on a hotplate (110° C. for 10 minutes) allows its re-use in multiple experiments.

FIG. 79(c) shows a collection of AFM images of trenches that form under identical overall conditions (i.e. average power dissipation per unit length of the SWNT, $Q_o$~30 μW/μm, substrate temperature $T_o$=353 K and base pressure ~1×10⁻⁴ torr for 10 min) using PS with $M_w$ from 17.5 kg/mol to 2.5 kg/mol. The results show that $W_{Tc}$ increases significantly with decreasing $M_w$, as summarized by the red symbols in FIG. 79d. The physics of this process is essentially unidirectional, such t) that the evolution of film thickness h(x,t) can be approximated by the one dimensional lubrication equation[5], $$\frac{\partial h}{\partial t} + \frac{\partial}{\partial x}\left[\frac{\tau h^2}{2\eta} + \frac{h^3}{3\eta}\frac{\partial}{\partial x}\left(\gamma \frac{\partial^2 h}{\partial x^2}\right)\right] = 0 \quad (1)$$

with the initial condition $h(x,t=0)=h_0$, where $h_0$ is the initial film thickness, and the boundary conditions $h(x=\pm\infty,t)=h_0$ and $\partial^2 h/\partial x^2$ $(x=\pm\infty,t)=0$ (zero pressure). Here, $\gamma$ is the surface tension, which usually depends linearly on the surface temperature T of film [i.e., $\gamma=\gamma_0-\gamma_1(T-273)$] where $\gamma_0$ is the surface tension at 273K and $\gamma_1$ is the temperature coefficient of surface tension, $$\tau = \frac{\partial \gamma}{\partial T}\frac{\partial T}{\partial x}$$

is the thermocapillary stress, and $\eta$ is the film viscosity. For polystyrene, $\gamma_0$ and $\gamma_1$ are taken as $47.4\times10^{-3}$ N/m and $0.078\times10^{-3}$ N/(mK)[9], respectively, for all PS materials examined since $\gamma_0$ and $\gamma_1$ depend only slightly on $M_w$ (less than 5% change for $\gamma_0$ and 20% change for $\gamma_1$ with $M_w$ between 2 kg/mol to 30 kg/mol)[9]. The model suggests that low viscosity facilitates physical mass transport induced by spatial variations in surface tension due to temperature gradients created by Joule heating in the m-SWNT. The zero-shear viscosity, $\eta$, can be connected to $M_w$ via the Vogel equation[7], $$\eta = Ae^{\frac{B}{\alpha_f(T-T_\infty)}},$$

where A is the structure factor, $B/\alpha_f$ is a constant[7], and $T_\infty$ is the Vogel temperature, respectively. Literature[7] suggests that, $B/\alpha_f=(1620\pm50)$ K, $A=1.925\times10^{-8}$ $M_w^{1.25}$ Pa·sec, and $T_\infty=321.4-8.3\times10^4 M_w^{-1}$ K, both with $M_w$ in g/mol. We use $B/\alpha_f=1640$ K, chosen within the range defined by the literature, but with a specific value that leads to agreement between experiment and theory for the trench width (~0.62 μm) at $T_0=353$K, $Q_0=30$ μW/μm and $M_w=2.5$ kg/mol after 10 minutes of heating. Calculated viscosities from the Vogel equation appear as blue symbols in FIG. 79d.

The temperature distribution for Eq. (1) can be approximated by the surface temperature[5] of the film calculated as a result of heating of the m-SWNT, which can be written $$T(x) = \qquad (2)$$
$$\frac{1}{k_f\pi}\int_{-L/2}^{L/2} du \int_0^\infty \frac{Q_0 e^{-\xi h_0}\left(1+\frac{k_s\xi}{\zeta}\right)J_0(\xi\sqrt{u^2+x^2})}{-\left(1+\frac{k_s\xi}{\zeta}-\frac{k_s}{k_f}\right)e^{-2\xi h_0}+\left(1+\frac{k_s\xi}{\zeta}+\frac{k_s}{k_f}\right)}d\xi + T_0$$

where $k_s$ and $k_f$ are the thermal conductivity of PS and quartz, respectively, L is the length of the SWNT, C is the interface thermal conductance between PS and quartz, and $J_0$ is the $0^{th}$ order Bessel function of the first kind. Here, $h_0=30$ nm, $k_f^{10}=0.15$ Wm$^{-1}$K$^{-1}$ and $k_s^{11}=6$ Wm$^{-1}$K$^{-1}$. Compared with that for the case of $\zeta=\infty$, the computed peak temperatures at the surface of the PS are only ~35% higher for $\zeta=10^8$ W/(m$^2$K) and ~5% higher for $10^9$ W/(m$^2$K), which are sufficiently small that they do not affect any of the major conclusions associated with this study. Therefore, all calculations in this example correspond to the temperature with; $\zeta=\infty$, i.e., $$T(x) = \frac{1}{2k_s\pi}\int_{-L/2}^{L/2} du \int_0^\infty \frac{Q_0 J_0(\xi\sqrt{u^2+x^2})}{\cosh(\xi h_0)+\frac{k_f}{k_s}\sinh(\xi h_0)}d\xi + T_0, \quad (3)$$

Equation (1) is equivalent to a pair of coupled partial differential equations $$\frac{\partial h_1}{\partial t} = \frac{\partial}{\partial x}\left(-\frac{\tau h_1^2}{2\eta} - \frac{h_1^3}{3\eta}\frac{\partial \gamma}{\partial x}h_2 - \frac{h_1^3 \gamma}{3\eta}\frac{\partial h_2}{\partial x}\right) \text{ and } \frac{\partial^2 h_1}{\partial x^2} - h_2 = 0$$

with $h_1=h$, initial conditions $h_1(x,t=0)=1$ and $h_2(x,t=0)=0$, and boundary conditions $h_1(x=\pm\infty,t)=1$ and $h_2(x=\pm\infty,t)=0$. The Fortran solver PDE_1D_MG can be used to evaluated these equations (i.e., $h_1$ and $h_2$), to yield the evolution of the film thickness h(x,t). The dashed line in FIG. 79(d) shows the computed value of $W_{Tc}$ for parameters equivalent to experiment: 10 minutes of heating at $T_0=353$ K and $Q_0=30$ μW/μm. The results agree remarkably well with experiment. The scaling trends arise mainly from variations in A, which yields a power law dependence of $\eta$ on $M_w$($\propto M_w$ 1.25)[7].

Figure 80:
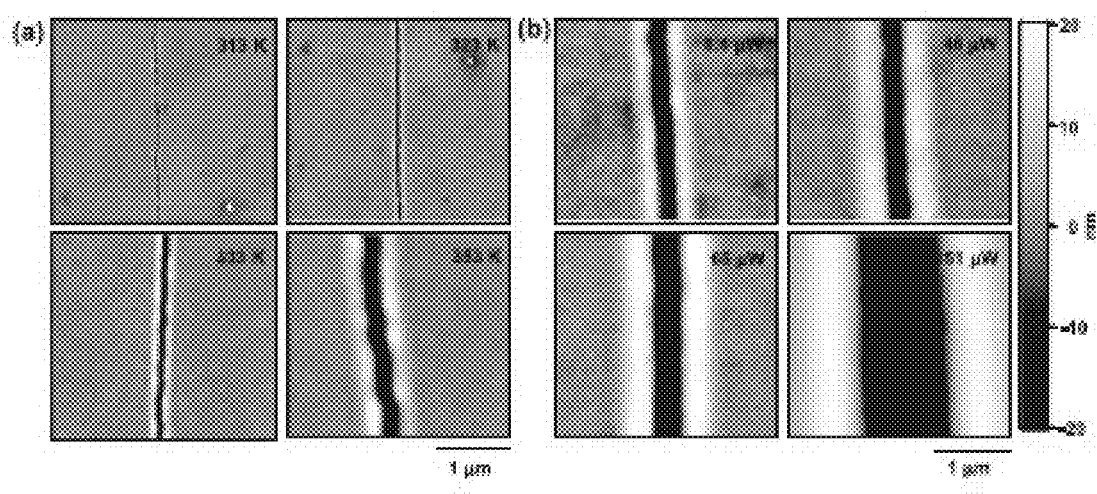
FIG. 80. (a) AFM images after nanoscale thermocapillary flow in a film of PS (Mw=2.5 kg/mol) induced by Joule heating of an underlying SNWT at a power per unit length of 30 μW/μ m, for substrate temperatures between 313 K to 353 K. (b) AFM images after nanoscale thermocapillary flow in a film of PS ($M_w$=2.5 kg/mol) induced by Joule heating of an underlying SNWT at powers per unit length of between 8.4 μW/μm to 214 μW/μm, at a substrate temperature (353 K).
Figure 81:
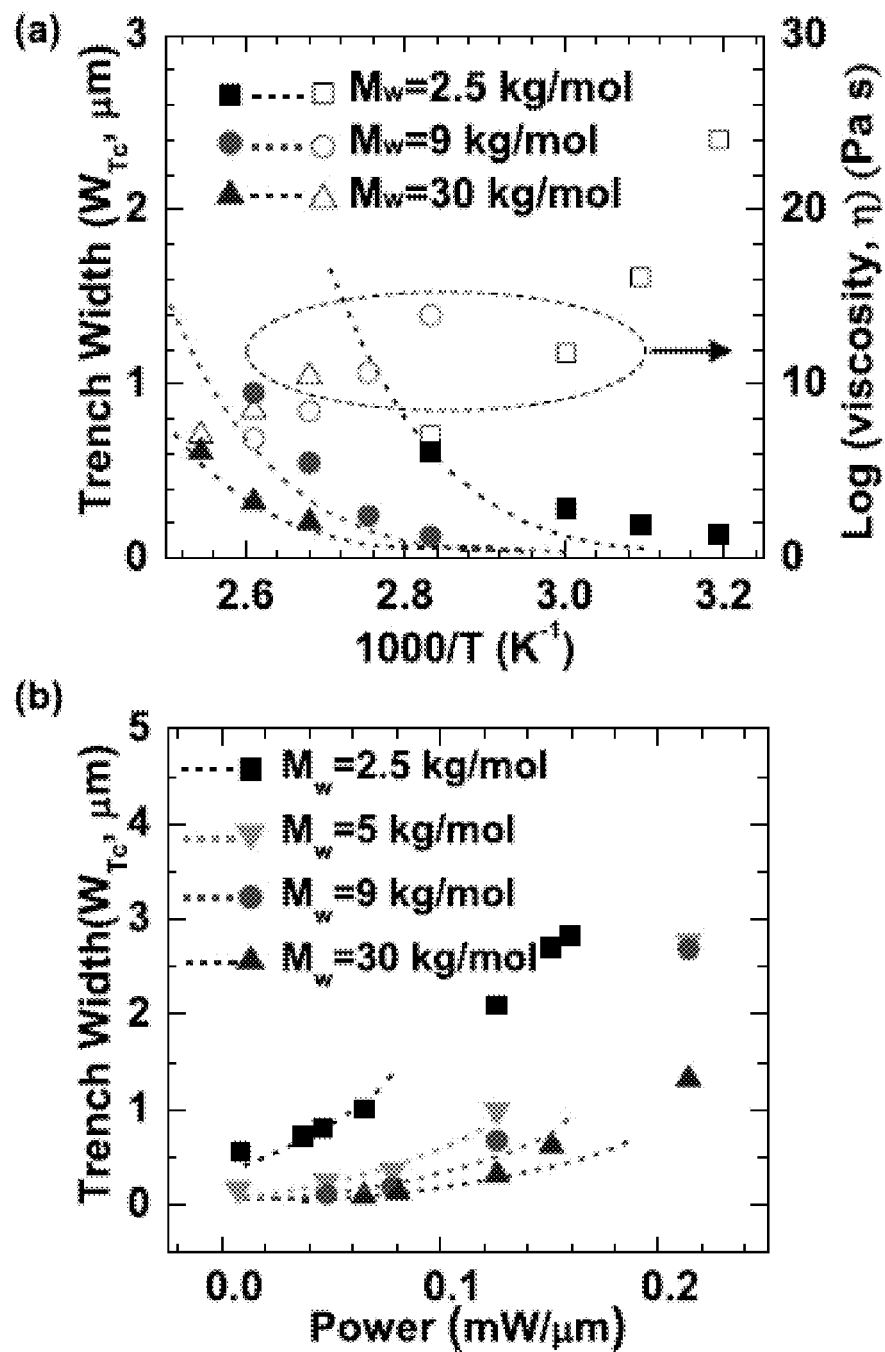
FIG. 81. (a) Trench width ($W_{Tc}$) and zero-shear viscosity (η) of polystyrene as a function of substrate temperature ($T_0$) between 313 K to 393 K, for PS films with different Mw (2.5, 9 and 30 kg/mol). The solid symbols and dashed lines correspond to measured and computed values for $W_{Tc}$. The open symbols correspond to values of η computed using the Vogel equation. (b) $W_{Tc}$ as a function of power per unit length dissipated in the SWNT ($Q_0$) from 8.4 μW/μm to 214 μW/μm for PS films with different $M_w$ (2.5, 5, 9 and 30 kg/mol). The solid symbols and dashed lines correspond to measured and computed values for $W_{Tc}$.

The values of $T_0$ and $Q_0$ are also important. FIG. 80(a) shows AFM images of results of thermocapillary flow in PS with $M_w=2.5$ kg/mol and $Q_0=30$ μW/μm for 10 min, with $T_0$ between 313 K to 353 K. The results show that $W_{Tc}$ increases dramatically with increases in $T_0$. FIG. 80(b) shows effects of changing $Q_0$ from 8.4 to 151 μW/μm for $T_0=353$ K and PS with $M_w=2.5$ kg/mol at $T_0=353$ K. Clearly, as with $T_0$, $W_{Tc}$ depends strongly on $Q_0$. FIG. 81(a) summarizes a set of results similar to those of FIG. 80(a). The Arrhenius type scaling arises from the temperature dependence of $\eta$, as confirmed from results computed with Eqs (1) and (2). Likewise, FIG. 81(b) shows a collection of measurements like those of FIG. 80(b), which reveal scaling with $Q_0$. The trench width is nicely replicated with analytical solution without any fitting, thereby providing further indication that $\eta$ is, to within experimental uncertainties, entirely responsible for the observed variations. We note that the calculations cease to be valid above a critical value h(x=0,t)=0.

In summary, the results presented here indicate that effects of temperature, power dissipation and molecular weight on nanoscale thermocapillary flow all arise primarily from associated variations in viscosity. The sensitivity to the temperature coefficient of surface tension ($\gamma_1$), the thermal interface conductance ($\xi$) are comparatively small, for values of these parameters that lie within ranges reported in the literature[7,9]. For the conditions examined here, the maximum temperature gradient $(dT/dx)_{max}$, for a given $Q_0$, shows little dependence on the width of the heat source for values ranging from those corresponding to a SWNT (i.e. ~1 nm) to ~100 nm diameter range; at 1 μm, the gradient is reduced by nearly an order of magnitude. These and other insights can be developed from an examination of the physics implied by the experimentally validated models reported here. In particular, engineering design rules for control of flows associated with this type of thermally induced pattern formation can be defined. The immediate relevance is to recently described, low temperature approaches for purifying arrays of SWNTs, but can be extended to other areas in nanopatterning and device fabrication where such effects could be useful.

References
1. F. Xiong, M.-H. Bae, Y. Dai, A. D. Liao, A. Behnam, E. A. Carrion, S. Hong, D. Ielmini, and E. Pop, *Nano Lett.* 13, 464 (2013).
2. I. Park, Z. Li, A. P. Pisano, and R. S. Williams, *Nano Lett.* 7, 3106 (2007).
3. H. Zhang, C.-L Wong, Y. Hao, R. Wang, X. Liu, F. Stellacci, and J. T. L. Thong, *Nanoscale* 2, 2302 (2010).
4. C. Y. Jin, Z. Li, R. S. Williams, K.-C. Lee, and I. Park, *Nano Lett.* 11, 4818 (2011).
5. S. H. Jin, S. N. Dunham, J. Song, X. Xie, J. Kim, C. Lu, A. Islam, F. Du, J. Kim, J. Felts, Y. Li, F. Xiong, M. A. Wahab, M. Menon, E. Cho, K. L. Gross, D. J. Lee, H. U. Chung, E. Pop, M. A. Alam, W. P. King, Y. Huang, J. A. Rogers, *Nature Nanotech.* 8, 347 (2013).
6. G. B. McKenna, G. Hadziioannou, P. Lutz, G. Hild, C. Strazielle, C. Straupe, P. Rempp, and A. J. Kovacs, *Macromolecules* 20, 498 (1987).
7. J.-C. Majeste, J.-P. Montfort, A. Allal, G. Marin, *Rheol Acta* 37, 486 (1998).
8. M. A. Wahab, S. H. Jin, A. E. Islam, J. Kim, J. Kim, W.-H. Yeo, D. J. Lee, H. U. hung, J. A. Rogers, and M. A. Alam, *ACS Nano* 7, 1299 (2013).
9. J. C. Moreira, N. R. Demarquette, *Journal of Appl. Polymer Sci.* 82, 1909 (2001).
10. P. Ferkl, R. Pokorny, M. Bobak, J. Kosek, *Chemical Eng. Sci.* 97, 50 (2013).
11. A. E. Beck, D. M. Darbha and H. H. Schloessin, *Phys. Earth and Planet. Interiors* 17, 35 (1978).

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

U.S. Pat. No. 8,367,035, Issued Feb. 5, 2013, entitled "Methods of Making Spatially Aligned Nanotubes and Nanotube Arrays" relates generally to methods for making substantially longitudinally aligned arrays of carbon nanotubes and is hereby incorporated by reference in its entirety.

The following references relate generally to methods of synthesizing and purifying carbon nanotubes, and each is hereby incorporated by reference in its entirety: (1) A. M. Cassell, J. A. Raymakers, J. Kong, H. J. Dai, J. Phys. Chem. B 103(31), (1999), pp. 6484-6492; (2) M. Su, B. Zheng, J. Liu, Chem. Phys. Lett. 322(5), (2000), pp. 321-326; (3) B. Kitiyanan, W. E. Alvarez, J. H. Harwell, D. E. Resasco, Chem. Phys. Lett. 317(3-5), (2000), pp. 497-503; (4) J. H. Hafner, M. J. Bronikowski, B. R. Azamian, P. Nicolaev, A. G. Rinzler, D. T. Colbert, K. A. Smith, R. E. Smalley, Chem. Phys. Lett. 296(1-2), (1998) pp. 195-202; (5) H. M. Cheng, F. Li, G. Su, H. P. Pan, L. L. He, X. Sun, M. S. Dresselhaus, Appl. Phys. Lett. 72(25), (1998), pp. 3282-3284; (6) B. Zheng, Y. Li, J. Liu, Applied Physics A 74, 345-348 (2002); (7) C. Journet, W. K. Maser, P. Bernier, A. Loiseau, M. Lamy de la Chapelle, S. Lefrant, R. Lee, J. E. Fischer, Nature 388, 756-758 (1997); (8) A. Thess, R. Lee, P. Nikolaev, H. Dai, P. Petit, J. Robert, C. Xu, Y. H. Lee, S. G. Kim, A. G. Rinzler, D. T. Colbert, G. E. Scuseria, D. Tomanek, J. E. Fischer, R. E. Smalley, Science 273, (1996) 483-487; (9) M. Holzinger, A. Hirsch, P. Bernier, G. S. Duesberg, M. Burghard, Applied Physics A 70, (2000) 599-602; (10) G. S. Duesberg, J. Muster, V. Krstic, M. Burghard, S. Roth, Appl. Phys. A 67, (1998), 117-119; (11) J. Liu, A. G. Rinzler, H. Dai, J. H. Hafner, R. K. Bradley, P. J. Boul, A. Lu, T. Iverson, K. Shelimov, C. B. Huffman, F. Rodriuez-Macias, Y. S. Shon, T. R. Lee, D. T. Colbert, R. E. Smalley, Science 280, (1998) 1253-1256; (12) A. G. Rinzler, J. Liu, H. Dai, P. Nikolaev, C. B. Huffman, F. J. Rodriguez-Macias, P. J. Boul, A. H. Lu, D. Heymann, D. T. Colbert, R. S. Lee, J. E. Fischer, A. M. Rao, P. C. Eklund, R. E. Smalley, Appl. Phys. A 67, (1998) 29-37; (13) Y. Feng, G. Zhou, G. Wang, M. Qu, Z. Yu, Chem, Phys, Lett, 375, (2003) 645-648; (14) T. Takenobu, M. Shiraishi, A. Yamada, M. Ata, H. Kataura, Y. Iwasa, Synthetic Metals 135-136, (2003) 787-788; (15) I. W. Chiang, B. E. Brinson, A. Y. Huang, P. A. Willis, M. J. Bronikowski, J. L. Margrave, R. E. Smalley, R. H. Hauge, J. Phys. Chem. B 105, (2001) 8297-8301. (16) U.S. Pat. No. 8,367,035; and (17) U.S. Patent Pub. No. 2011/0147715.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, and methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomer and enantiomer of the compound described individually or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed can be resorted to by those skilled in the art, and that such modifications and variations are considered to be within the scope of this invention as defined by the appended claims.

The following references relate generally to fabrication methods, structures and systems for making electronic devices, and are hereby incorporated by reference to the extent not inconsistent with the disclosure in this application:

| application Ser. No. | Filing Date | Publication No. | Publication Date | Pat. No. | Issue Date |
|---|---|---|---|---|---|
| 11/001,689 | Dec. 1, 2004 | 2006/0286488 | Dec. 21, 2006 | 7,704,684 | Apr. 27, 2010 |
| 11/115,954 | Apr. 27, 2005 | 2005/0238967 | Oct. 27, 2005 | 7,195,733 | Mar. 27, 2007 |
| 11/145,574 | Jun. 2, 2005 | 2009/0294803 | Dec. 3, 2009 | 7,622,367 | Nov. 24, 2009 |
| 11/145,542 | Jun. 2, 2005 | 2006/0038182 | Feb. 23, 2006 | 7,557,367 | Jul. 7, 2009 |
| 11/421,654 | Jun. 1, 2006 | 2007/0032089 | Feb. 8, 2007 | 7,799,699 | Sep. 21, 2010 |
| 11/423,287 | Jun. 9, 2006 | 2006/0286785 | Dec. 21, 2006 | 7,521,292 | Apr. 21, 2009 |
| 11/423,192 | Jun. 9, 2006 | 2009/0199960 | Aug. 13, 2009 | 7,943,491 | May 17, 2011 |
| 11/465,317 | Aug. 17, 2006 | — | — | — | — |
| 11/675,659 | Feb. 16, 2007 | 2008/0055581 | Mar. 6, 2008 | — | — |
| 11/782,799 | Jul. 25, 2007 | 2008/0212102 | Sep. 4, 2008 | 7,705,280 | Apr. 27, 2010 |
| 11/851,182 | Sep. 6, 2007 | 2008/0157235 | Jul. 3, 2008 | 8,217,381 | Jul. 10, 2012 |
| 11/585,788 | Sep. 20, 2007 | 2008/0108171 | May 8, 2008 | 7,932,123 | Apr. 26, 2011 |
| 11/981,380 | Oct. 31, 2007 | 2010/0283069 | Nov. 11, 2010 | 7,972,875 | Jul. 5, 2011 |
| 12/372,605 | Feb. 17, 2009 | — | — | — | — |
| 12/398,811 | Mar. 5, 2009 | 2010/0002402 | Jan. 7, 2010 | 8,552,299 | Oct. 8, 2013 |
| 12/405,475 | Mar. 17, 2009 | 2010/0059863 | Mar. 11, 2010 | 8,198,621 | Jun. 12, 2012 |
| 12/418,071 | Apr. 3, 2009 | 2010/0052112 | Mar. 4, 2010 | 8,470,701 | Jun. 25, 2013 |
| 12/564,566 | Sep. 22, 2009 | 2010/0072577 | Mar. 25, 2010 | 7,982,296 | Jul. 19, 2011 |
| 12/669,287 | Jan. 15, 2010 | 2011/0187798 | Aug. 4, 2011 | — | — |
| 12/778,588 | May 12, 2010 | 2010/0317132 | Dec. 16, 2010 | — | — |

-continued

| application Ser. No. | Filing Date | Publication No. | Publication Date | Pat. No. | Issue Date |
|---|---|---|---|---|---|
| 12/844,492 | Jul. 27, 2010 | 2010/0289124 | Nov. 18, 2010 | 8,039,847 | Oct. 18, 2011 |
| 12/892,001 | Sep. 28, 2010 | 2011/0230747 | Sep. 22, 2011 | 8,666,471 | Mar. 4, 2014 |
| 14/140,299 | Dec. 24, 2013 | — | — | — | — |
| 12/916,934 | Nov. 1, 2010 | 2012/0105528 | May 3, 2012 | 8,562,095 | Oct. 22, 2013 |
| 12/947,120 | Nov. 16, 2010 | 2011/0170225 | Jul. 14, 2011 | — | — |
| 12/996,924 | Dec. 8, 2010 | 2011/0147715 | Jun. 23, 2011 | — | — |
| 12/968,637 | Dec. 15, 2010 | 2012/0157804 | Jun. 21, 2012 | — | — |
| 13/046,191 | Mar. 11, 2011 | 2012/0165759 | Jun. 28, 2012 | — | — |
| 13/071,027 | Mar. 24, 2011 | 2011/0171813 | Jul. 14, 2011 | — | — |
| 13/095,502 | Apr. 27, 2011 | — | — | — | — |
| 13/100,774 | May 4, 2011 | 2011/0266561 | Nov. 3, 2011 | — | — |
| 13/113,504 | May 23, 2011 | 2011/0220890 | Sep. 15, 2011 | 8,440,546 | May 14, 2013 |
| 13/120,486 | Aug. 4, 2011 | 2011/0277813 | Nov. 17, 2011 | — | — |
| 13/228,041 | Sep. 8, 2011 | 2011/0316120 | Dec. 29, 2011 | — | — |
| 13/270,954 | Oct. 11, 2011 | 2012/0083099 | Apr. 5, 2012 | 8,394,706 | Mar. 12, 2013 |
| 13/349,336 | Jan. 12, 2012 | 2012/0261551 | Oct. 18, 2012 | — | — |
| 13/441,618 | Apr. 6, 2012 | 2013/0100618 | Apr. 25, 2013 | — | — |
| 13/441,598 | Apr. 6, 2012 | 2012/0327608 | Dec. 27, 2012 | — | — |
| 13/472,165 | May 15, 2012 | 2012/0320581 | Dec. 20, 2012 | — | — |
| 13/486,726 | Jun. 1, 2012 | 2013/0072775 | Mar. 21, 2013 | — | — |
| 13/492,636 | Jun. 8, 2012 | 2013/0041235 | Feb. 14, 2013 | — | — |
| 13/549,291 | Jul. 13, 2012 | 2013/0036928 | Feb. 14, 2013 | — | — |
| 13/596,343 | Aug. 28, 2012 | 2012/0321785 | Dec. 20, 2012 | 8,367,035 | Feb. 5, 2013 |
| 13/624,096 | Sep. 21, 2012 | 2013/0140649 | Jun. 6, 2013 | — | — |
| 13/801,868 | Mar. 13, 2013 | 2013/0320503 | Dec. 5, 2013 | — | — |
| 14/155,010 | Jan. 14, 2014 | — | — | — | — |
| 13/835,284 | Mar. 15, 2013 | — | — | — | — |
| 13/853,770 | Mar. 29, 2013 | — | — | — | — |

Every formulation or combination of components described or exemplified herein can be used to practice the invention, unless otherwise stated.

All patents and publications mentioned in the specification are indicative of the level of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

We claim:

1. A method for purifying a layer of carbon nanotubes comprising:
   providing a precursor layer of substantially aligned carbon nanotubes supported by a substrate, wherein said precursor layer comprises a mixture of metallic carbon nanotubes and semiconducting carbon nanotubes;
   covering said precursor layer of carbon nanotubes with a thermocapillary resist, wherein said thermocapillary resist is in thermal contact with at least a portion of said carbon nanotubes; and
   applying an electric current to said metallic carbon nanotubes, thereby selectively heating said metallic carbon nanotubes to separate said metallic carbon nanotubes from said semiconducting carbon nanotubes, thereby providing a purified layer of carbon nanotubes comprising at least 50% of said metallic or said semiconducting carbon nanotubes.

2. The method claim 1, wherein said selective heating results from electronic resistance.

3. The method of claim 1, wherein said carbon nanotubes are single-walled carbon nanotubes (SWNTs).

4. The method of claim 1, wherein said carbon nanotubes are multi-walled carbon nanotubes (MWNTs).

5. The method of claim 1, wherein said semiconducting carbon nanotubes do not absorb sufficient energy to overcome the Schottky barrier of said semiconducting carbon nanotubes.

6. The method of claim 1, wherein electric current is an alternating or direct current selected from a range of 0.01 mA to 100 mA.

7. The method of claim 1, wherein said metallic carbon nanotubes and said semiconducting nanotubes of said precursor layer are in electrical contact with a first electrode and a second electrode.

8. The method of claim 7, wherein said step of applying said electric current is performed by applying an electrode bias voltage between said first electrode and said second electrode selected from the range of 0.01 V to 100 V.

9. The method of claim 7, wherein said first and second electrodes are interdigitated.

10. The method of claim 1, wherein said thermocapillary resist comprises a molecular organic species.

11. The method of claim 1, wherein said thermocapillary resist is selected from the group consisting of α,α,α'-Tris (4-hydroxyphenyl)-1-ethyl-4-isopropylbenzene, polymethylmethacrylate (PMMA), polystyrene (PS), poly(styrene-dimethylsiloxane) (PS-PDMS); oligosaccharide-trimethylsilylstyrene, and polyhedral oligomeric silsesquioxane (POSS).

12. The method of claim 1, wherein said thermocapillary resist has a room temperature viscosity selected from a range of 0.5 Pa·s to 100 Pas.

13. The method of claim 1, wherein said layer of substantially aligned carbon nanotubes comprises at least 90% semiconducting carbon nanotubes.

* * * * *